US006444465B1

(12) United States Patent
Wyatt et al.

(10) Patent No.: US 6,444,465 B1
(45) Date of Patent: Sep. 3, 2002

(54) ANTINSENSE MODULATION OF HER-1 EXPRESSION

(75) Inventors: Jacqueline Wyatt, Encinitas; Susan M. Freier, San Diego, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/676,610

(22) Filed: Sep. 29, 2000

(51) Int. Cl.$^7$ .................. C12Q 1/68; C07H 21/04; C12N 15/85
(52) U.S. Cl. .................. 435/375; 435/6; 435/91.1; 435/325; 435/366; 536/23.1; 536/24.31; 536/24.33; 536/24.5
(58) Field of Search .................. 536/23.1, 24.1, 536/24.31, 24.5; 514/44; 435/6, 91.1, 325, 366, 320.1, 377

(56) References Cited

U.S. PATENT DOCUMENTS

| 5,610,288 A | 3/1997 | Rubenstein et al. ....... 536/24.5 |
| 5,914,269 A | 6/1999 | Bennett et al. ............. 435/375 |

FOREIGN PATENT DOCUMENTS

| WO | WO 96/16988 | 6/1996 |

OTHER PUBLICATIONS

Coulson et al., A nonantisense Sequence–Selecive Effect of a Phosphorothioate Oligodeoxynucleotide Directed against the Epidermal Growth Factor Receptor in A431 Cells, *Mol. Pharm.*, 1996, 50, 314.

De Giovanni et al., Antisense epidermal growth factor receptor transfection impairs the proliferation ability of human phabdomyosarcoma cells, *Cancer Res.*, 1996, 56, 3898.

Kraus et al., Isolation and characterization of ERBB3, a third member of the ERBB/epidermal growth factor receptor family: Evidence for overexpression in a subset of human mammary tumors, *Proc. Natl. Acad. Sci. USA*, 1989, 86, 9193.

Kunkel et al., Inhibition of the epidermal growth factor receptor tyrosine kinase by PD153035 in human A431 tumors in athymic nude mice, *Invest. New Drugs*, 1996, 13, 295.

Moroni et al., EGF–R Antisense RNA blocks expression of the epidermal growth factor receptor and suppresses the transforming phenotype of a human carcinoma cell line, *J. Biol. Chem.*, 1992, 267, 2714.

Normanno et al., Growth Inhibition of Human Colon Carcinoma Cells by Combinations of Anti–Epidermal Growth Factor–related Growth Factor Antisense Oligonucleotides, *Clin. Cancer Res.*, 1996, 2, 601.

Rajagopal et al., Epidermal growth factor expression in human colon and colon carcinomas: Antisense epidermal growth factor receptor RNA down–regulates the poliferation of human colon cancer cells, *Int. J. Cancer*, 1995, 62, 661.

Rubenstein et al. Antisense oligonucleotide intralesional therapy for human PC–3 prostate tumors carried in athymic nude mice, *J. Surg. Oncol.*, 1996, 62, 194.

Ullrich et al., Human epidermal growth factor receptor cDNA sequence and aberrant expression of the amplified gene in A431 epidermoid carcinoma cells, *Nature*, 1984, 309, 418.

Wang et al., Delivery of antisense oligodeoxyribonucleotides against the human epidermal growth factor receptor into cultured KB cells with liposomes conjugated to folate via polyethylene glycol, *Proc. Natl. Acad. Sci. USA*, 1995, 92, 3318.

Witters et al., Antisense Oligonucleotides to the Epidermal Growth Factor Receptor, *Breast Cancer Research and Treatment*, 1999, 53, 41–50.

Yoneda et al., The antiproliferative effects of tyrosine kinase inhibitors tyrphostins on a human squamous cell carcinoma in vitro and in nude mice, *Cancer Res.*, 1991, 51, 4430.

*Primary Examiner*—John L. LeGuyader
*Assistant Examiner*—Mary Schmidt
(74) *Attorney, Agent, or Firm*—Licata & Tyrrell P.C.

(57) ABSTRACT

Compounds, compositions and methods are provided for inhibiting the expression of human Her-1. The compositions comprise oligonucleotides complementary to mRNA targeted to nucleic acids encoding Her-1. Methods of using these oligonucleotides for inhibition of Her-1 expression and for treatment of diseases such as cancers associated with overexpression of Her-1 are provided.

26 Claims, No Drawings

ANTINSENSE MODULATION OF HER-1 EXPRESSION

FIELD OF THE INVENTION

The present invention provides compositions and methods of modulating the expression of Her-1. Many human tumors have been found to overexpress this receptor and such enhanced expression has been shown to be correlated with poor prognosis. In particular, this invention relates to oligonucleotides specifically hybridizable with nucleic acids encoding human Her-1. These oligonucleotides have been found to inhibit the expression of Her-1.

BACKGROUND OF THE INVENTION

Her-1, also known as epidermal growth factor receptor (EGFR), is a specific receptor for epidermal growth factor (EGF) and transforming growth factor-α (TGF-α). When these mitogenic polypeptides bind to Her-1, tyrosine kinase activity of the receptor is induced, and this in turn triggers a series of events which regulate cell growth. A number of malignant and non-malignant disease conditions are now believed to be associated with Her-1, particularly aberrant expression of Her-1. Aberrant expression includes both increased expression of normal Her-1 and expression of mutant Her-1. Overexpression of Her-1 is found in many human tumors including most glioblastomas and breast, lung, ovarian, colorectal, bladder, pancreatic, squamous cell and renal carcinomas. Elevated Her-1 levels correlate with poor prognosis in human tumors. Her-1 is also implicated in nonmalignant diseases, such as psoriasis. The sequence of the mRNA encoding human Her-1 is known. Ullrich et al., *Nature*, 1984, 309, 418; GenBank Accession Number X00588; and Kraus et al., *Proc. Natl. Acad. Sci. USA*, 1989, 86, 9193; GenBank Accession Number M29366. The gene encoding Her-1 is also known as ERBB3 or c-erb-B1. Two Her-1 transcripts typically appear on Northern blots, one measuring 10 kb and one measuring 5.6 kb.

A number of inhibitors of Her-1 have been shown to be effective in inhibiting the growth of human tumor cells. Monoclonal antibodies to Her-1 and drugs which inhibit Her-1 tyrosine kinase activity can inhibit the growth of human cancer cell xenografts in nude mice. Normanno et al., *Clin. Cancer Res.*, 1996, 2, 601. The drug PD153035, which inhibits Her-1 tyrosine kinase activity, can inhibit the growth of A431 cells in nude mice, and tyrphostins, which inhibit the activity of Her-1 as well as other tyrosine kinases, have been shown to inhibit the growth of squamous carcinoma in nude mice. Kunkel et al., *Invest. New Drugs*, 1996, 13, 295 and Yoneda et al., *Cancer Res.*, 1991, 51, 4430.

Vectors expressing Her-1 nucleic acid sequences in an orientation complementary to mRNA have been used to study the effects of Her-1 on proliferation of cultured cancer cells. Transfectants of the human epidermoid carcinoma KB cell line expressing Her-1 cDNA or RNA sequences in an orientation complementary to mRNA exhibited restored serum-dependent growth and impaired colony formation and growth in agar. Moroni et al., *J. Biol. Chem.*, 1992, 267, 2714. Human pancreatic carcinoma cells of the PC-7 cell line transfected with vectors expressing Her-1 cDNA sequences in an orientation complimentary to mRNA showed inhibited cell growth, colony formation and tumorigenicity in nude mice. Liu et al., *Chinese Medical Journal.*, 1995, 108, 653. Transfection of human colon cancer cell lines with Her-1 RNA expression vectors producing an oligonucleotide complementary to mRNA caused a reduction in cell proliferation and ability to grow on soft agar. Rajagopal et al., *Int. J. Cancer*, 1995, 62, 661. Human rhabdomyosarcoma cells transfected with a plasmid expressing Her-1 cDNA in an orientation complementary to mRNA had greatly impaired proliferation. De Giovanni et al., *Cancer Res.*, 1996, 56, 3898.

Considerable research is being directed to the application of oligonucleotides complementary to mRNA and other oligomers for therapeutic purposes. Oligonucleotides complementary to mRNA have already been employed as therapeutic moieties in the treatment of disease states in animals and man, and compositions comprising oligomers complementary to mRNA have been shown to be capable of modulating expression of genes implicated in viral, fungal and metabolic diseases. Further, oligonucleotides complementary to mRNA have been safely administered to humans and clinical trials of approximately a dozen oligonucleotide drugs targeted to viral and cellular gene products are underway.

Oligodeoxyribonucleotides complementary to mRNA targeted to Her-1 have been encapsulated into liposomes linked to folate via a polyethylene glycol linker and delivered into cultured human epidermoid carcinoma KB cells. The oligonucleotides were a phosphodiester (P=O) 15-mer complementary to the Her-1 gene stop codon, or the same sequence with three phosphorothioate (P=S) linkages at each end. Both of these oligonucleotides reduced KB cell proliferation by greater than 90% after treatment with 3 μM oligonucleotide in folate-PEG-liposomes. In contrast, free P=O oligonucleotide caused almost no growth inhibition, and free P=S-capped oligonucleotide caused only a 15% growth inhibition, even at this high dosage level. Her-1 expression, measured by indirect immunofluorescence, was virtually abolished in cells treated with either of the folate-PEG-liposome-encapsulated oligonucleotides but Her-1 expression was qualitatively similar to untreated cells after treatment with free oligonucleotide. Wang et al., *Proc. Natl. Acad. Sci. USA*, 1995, 92, 3318.

A 15-mer phosphorothioate oligonucleotide complementary to the translation initiation region of Her-1 mRNA was found to inhibit cell proliferation by over 25% in A431 cells, derived from a vulval carcinoma. This activity, though dose-dependent from 1–25 μM, was not mediated by an antisense mechanism, as demonstrated by a lack of reduction in either Her-1 protein or mRNA after oligonucleotide treatment. In addition, an 18-mer oligonucleotide complementary to mRNA targeted to the same region had no effect even at the highest (25 μM) dose, and neither oligonucleotide had any effect in the two other tumor-derived cell lines tested. Coulson et al., *Mol. Pharm.*, 1996, 50, 314.

The suppression of growth of pancreatic carcinoma cell lines by undisclosed oligonucleotides complementary to mRNA inhibiting the expression of TGF-α and/or the Her-1 has been reported. Hall et al., unpublished data, reported in Hall and Lemoine, Models of Pancreatic Cancer, in *Cancer Surveys*, Volume 16: The Molecular Pathology of Cancer, 1993, p. 135–155.

Rubenstein et al. have reported treatment of established human-derived prostate tumor xenografts in nude mice by intralesional injection of oligonucleotides complementary to mRNA directed against mRNAs encoding TGF-α and Her-1. The oligonucleotides included 39-mers complementary to 18 bases located 5' and 3' from the AUG mRNA translation initiation codon of either TGF-α or Her-1 sequence. The oligonucleotides were phosphorothioated at each of three terminal bases at both the 5' and 3' ends. The oligonucleotides were administered either alone or in combination, with the combination treatment proving most effective. *J. Surg. Oncol.*, 1996, 62, 194. In U.S. Pat. No. 5,610,288, Rubenstein et al. disclose polynucleotides of about 20 to 50 nucleic acid bases, most preferably about 40 nucleic acid bases in length, which preferentially hybridize to the start codon of the mRNA encoding Her-1. A preferred embodiment is a 39-mer including 18 bases complementary to the 5' side of the translation initiation codon. This oligonucleotide inhibited PC-3 cell growth when administered in combination with an oligonucleotide complementary to mRNA targeted to TGF-α. Alone, the Her-1 oligonucleotide gave inhibition of cell growth equivalent to that achieved with an inverted (5' to 3') version of the same sequence.

Disclosed in U.S. Pat. No. 5,914,269 (Bennett, et al.) are oligonucleotides targeting Her-1 and methods of modulating the expression of Her-1 using said oligonucleotides. Three of these oligonucleotides and their analogs have also been used to investigate growth inhibition of SKOV3 cells, a human ovarian cancer cell line. In these studies it was demonstrated that all three oligonucleotides produced a significant reduction in Her-1 expression and protein production as well as in vitro growth inhibition of SKOV3 cells. Witters et al., *Breast Cancer Research and Treatment*, 1999, 53, 41–50.

Rearrangements or deletions of the Her-1 gene resulting in mutant Her-1 protein have been found in some cancers. The in-frame deletion from nucleotides 275–1075 in the Her-1 has been referred to as class I, Type I or Type III mutation. WO 96/16988 (Wong et al.) discloses cell lines capable of overexpressing Type III mutant Her-1, vaccines for inhibiting tumor formation comprising peptides similar to a fusion junction present in mutant human Her-1, antibodies raised against a cell line overexpressing Type III mutant Her-1, and oligonucleotides complementary to mRNA targeted to a Type III mutant Her-1 which decrease expression of a mutant Her-1. In a preferred embodiment, the oligonucleotide complementary to mRNA contains sequences from what were formerly distant portions of the normal Her-1 cDNA. The oligonucleotide must contain the sequence 5'-TACCTT-3'. An 18-mer oligonucleotide containing this sequence was found to downregulate mutant Her-1 levels when given at a 40 µM dose in cultured cells which overexpressed Type III mutant Her-1.

The present invention provides new oligonucleotide compounds complementary to mRNA, as well as other oligonucleotide compounds, and compositions comprising the same together with methodologies for the use of certain compounds of the invention for interfering with translation of selected mRNA targets related to epidermal growth factor receptor.

SUMMARY OF THE INVENTION

The present invention is directed to oligonucleotides, especially those from 12–25 nucleotides in length, which are complementary to a nucleic acid molecule encoding Her-1, and which inhibit the expression of Her-1. In a preferred embodiment, the oligonucleotides comprise at least one phosphorothioate linkage. In other preferred embodiments, the oligonucleotides may comprise at least one 5-methyl cytosine, 2'-O-alkyl or 2'-fluoro modification. Pharmaceutical compositions comprising the oligonucleotides of the invention and a pharmaceutically acceptable carrier are also provided. Further provided are methods of modulating the expression of a human epidermal growth factor receptor in cells or tissues comprising contacting said cells or tissues with the oligonucleotide of the invention. These methods may be performed in vitro, in vivo or ex vivo. Methods of treating an animal having a hyperproliferative disease or condition by administering a therapeutically effective amount of an oligonucleotide of the invention for a time sufficient to ameliorate said hyperproliferative disease or condition are provided. The hyperproliferative disease or condition may be cancer, and in preferred embodiments the cancer is lung cancer, ovarian cancer, colon cancer or prostate cancer.

DETAILED DESCRIPTION OF THE INVENTION

The present invention employs oligonucleotides for use in inhibiting the function of nucleic acid molecules encoding Her-1, ultimately modulating the amount of Her-1 produced. This is accomplished by providing oligonucleotides complementary to mRNA which specifically hybridize with mRNA or DNA encoding Her-1. Such hybridization with mRNA interferes with the normal role of mRNA and causes a modulation of its function. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. The overall effect of such interference with mRNA function is modulation of the expression of Her-1. In the context of this invention, "modulation" means either an increase (stimulation) or a decrease (inhibition) in the expression of a gene. In the context of the present invention, inhibition is the preferred form of modulation of gene expression.

Oligonucleotides may comprise nucleotide sequences sufficient in identity and number to effect specific hybridization with a particular nucleic acid molecule. Such oligonucleotides are commonly described as "complementary to mRNA." Oligonucleotides may also be directed to nucleotide sequences within the genome. Oligonucleotides are commonly used as research reagents and diagnostics. For example, oligonucleotides complementary to mRNA, which are able to inhibit gene expression with exquisite specificity, are often used by those of ordinary skill to elucidate the function of particular genes. Oligonucleotides complementary to mRNA are also used, for example, to distinguish between functions of various members of a biological pathway. This specific inhibitory effect has, therefore, been harnessed for research use.

The specificity and sensitivity of oligonucleotides is also harnessed by those of skill in the art for therapeutic uses. Oligonucleotides have been employed as therapeutic moieties in the treatment of disease states in animals and man. For example, workers in the field have now identified oligonucleotides complementary to mRNA, triplex oligonucleotides, and other oligonucleotide compositions which are capable of modulating expression of genes implicated in viral, fungal and metabolic diseases. Oligonucleotides complementary to mRNA have been safely administered to humans and numerous clinical trials are presently underway. It is thus established that oligonucleotides can be useful therapeutic modalities that can be configured to be useful in treatment regimes for treatment of cells, tissues and animals, especially humans.

It is preferred to target specific genes for attack by oligonucleotides complementary to mRNA. "Targeting" an oligonucleotide to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Her-1. The targeting process also includes determination of a site or sites within this gene for the oligonucleotide interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokayotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Her-1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene). mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Such rearrangements or deletions of the Her-1 gene resulting in mutant Her-1 protein are known to occur in some cancers. Once the target site has been identified, oligonucleotides are chosen which are sufficiently complementary to the target, i.e., hybridize sufficiently well and with sufficient specificity, to give the desired effect.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al., *Acc. Chem. Res.*, 1995, 28, 366.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— backbones, wherein the native phosphodiester backbone is represented as —O—P—O—$CH_2$—). The amide backbones disclosed by De Mesmaeker et al. (Id.) are also preferred. Also preferred are oligonucleotides having morpholino backbone structures, such as those described in Summerton and Weller, U.S. Pat. No. 5,034,506.

In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone. Nielsen et al., *Science*, 1991, 254, 1497.

Oligonucleotides may also contain one or more substituted sugar moieties. Preferred oligonucleotides comprise one of the following at the 2' position: OH, SH, $SCH_3$ F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide, and other substituents having similar properties. A preferred modification includes 2'-methoxyethoxy (2'-O—$CH_2CH_2OCH_3$, also known as 2'-O—(2-methoxyethyl)) (Martin et al., *Helv. Chim. Acta*, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2' deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$ (6-aminohexyl)adenine and 2,6-diaminopurine. Kornberg, A., DNA Replication, W. H. Freeman & Co., San Francisco, 1980, pp.75–77 and Gebeyehu et al., *Nuc. Acids Res.*, 1987, 15, 4513. A "universal" base known in the art, e.g., inosine, may be included. 5-me-C substitutions have been shown to increase nucleic acid duplex stability by 0.6–1.2EC (Sanghvi, Y. S., Crooke, S. T. and Lebleu, B., eds., Antisense Research and Applications, CRC Press, Boca Raton,1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA*, 1989, 86, 6553), cholic acid (Manoharan et al., *Bioorg. Med. Chem. Let.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylaminocarbonyl-oxycholesterol moiety (Crooke et al., *J. Pharmacol. Exp. Ther.*, 1996, 277, 923), all references being incorporated herein by reference. Oligonucleotides comprising lipophilic moieties, and methods for preparing such oligonucleotides are known in the art, for example, U.S. Pat. No. 5,138,045, U.S. Pat. No. 5,218,105 and U.S. Pat. No. 5,459,255, all of which are incorporated herein by reference.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764, incorporated herein by reference.

It is not necessary for all positions in a given oligonucleotide to be uniformly modified, and in fact more than one of the aforementioned modifications may be incorporated in a single oligonucleotide or even at a single nucleoside within an oligonucleotide. The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The oligonucleotides in accordance with this invention preferably comprise from about 8 to about 30 nucleotides. It is more preferred that such oligonucleotides comprise from about 12 to 25 nucleotides. As is known in the art, a nucleotide is a base-sugar combination suitably bound to an adjacent nucleotide through a phosphodiester, phosphorothioate or other covalent linkage.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as diagnostics, therapeutics and as research reagents and kits. For therapeutics, an animal, preferably a human, suspected of having a disease or disorder which can be treated by modulating the expression of Her-1 is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Use of the oligonucleotides and methods of the invention may also be useful prophylactically, e.g., to prevent or delay tumor formation.

The oligonucleotides of the present invention can be used as diagnostics for the presence of Her-1 -specific nucleic acids in a cell or tissue sample. For example, radiolabeled oligonucleotides can be prepared by $^{32}p$ labeling at the 5' end with polynucleotide kinase. Sambrook et al., *Molecular Cloning: A Laboratory Manual*, Cold Spring Harbor Laboratory, 1989, Volume 2, pg. 10.59. Radiolabeled oligonucleotides are then contacted with cell or tissue samples suspected of containing Her-1 mRNA (and thus, Her-1), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of Her-1 for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing an Her-1 gene. Quantitation of the silver grains permits detection of the expression of mRNA molecules encoding Her-1 proteins and permits targeting of oligonucleotides to these areas.

Analogous assays for fluorescent detection of expression of Her-1 can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling, Va.

Oligonucleotides of the present invention directed to Her-1 can be used in diagnostics, therapeutics, prophylaxis, and as research reagents and kits. Because these oligonucleotides hybridize to nucleic acids encoding Her-1, sandwich and other assays can easily be constructed to exploit this fact. Hybridization of the oligonucleotides of the invention with a nucleic acid encoding an Her-1 can be detected by means known in the art. Such means may include conjugation of an enzyme to the oligonucleotide, radiolabelling of the oligonucleotide or any other suitable detection systems. Kits for detecting the presence or absence of Her-1 may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics. U.S. Pat. No. 5,591,721 issued to Agrawal et al. Oligonucleotides with at least one 2'-methoxyethyl modification are believed to be particularly useful for oral administration. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Oligonucleotide Synthesis

Unmodified oligodeoxynucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., *J. Med. Chem.* 1993, 36, 831. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-9-β-O-trifyl group. Thus $N^6$-benzoyl-9-β-D-arabinofuranosyladenine was selectively protected in moderate yield as the 3', 5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2, 2'-anhydro-1-β-D-arabinofuranosyluracil was treated with 70% hydrogen fluoride-pyridine. Standard procedures were used to obtain the 5'-DMT and 5'-DMT-3' phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-(2-methoxyethyl)-modified amidites are synthesized according to Martin, *Helv. Chim. Acta*, 1995, 78, 486. For ease of synthesis, the last nucleotide was a deoxynucleotide. 2'-O—$CH_2CH_2OCH_3$-cytosines may be 5-methyl cytosines, 5-methyl-2'-deoxycytidine (5-me-C) containing oligonucleotides were synthesized according to published methods (Sanghvi et al., *Nuc. Acids Res.*, 1993, 21, 3197) using commercially available phosphoramidites (Glen Research, Sterling, Va. or ChemGenes, Needham, Mass.).

Oligonucleotides having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.*, 1995, 28, 366. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science* 1991, 254, 1497).

After cleavage from the controlled pore glass column (Applied Biosystems) and deblocking in concentrated ammonium hydroxide at 55EC for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}p$ nuclear magnetic resonance spectroscopy, and for some studies oligonucleotides were purified by HPLC, as described by Chiang et al., *J. Biol. Chem.*, 1991, 266, 18162. Results obtained with HPLC-purified material were similar to those obtained with non-HPLC purified material.

Example 2

Cell Culture

Human SKOV3 ovarian carcinoma cells were obtained from the American Type Culture Collection. They were grown in McCoy=s 5A medium containing $NaHCO_3$, 10% fetal bovine serum and antibiotics and routinely passaged. A549 human lung carcinoma cells were routinely passaged in DMEM medium supplemented with 10% fetal bovine serum.

Example 3

Treatment of Cells with Oligonucleotide

SKOV3 and A549 cells were grown in T-75 flasks until 65–75% confluent. The cells were washed once with serum-free OPTI-MEM7 medium (Life Technologies, Inc., Grand Island, N.Y.) and 5 ml of the serum-free OPTI-MEM7 containing 15 μg/ml of LIPOFECTIN7 reagent (a 1:1 liposome formulation of the cationic lipid DOTMA and DOPE, Life Technologies, Inc.) was added. At that time, 300 nM of oligonucleotide was added and swirled vigorously. After a 4–5 hour incubation at 37° C., the solution was removed and fresh maintenance medium containing 10% fetal bovine serum was added. The cells were again incubated overnight at 37° in 5% $CO_2$, after which the cells were assayed for Her-1 mRNA expression or cell growth.

Example 4

Measurement of Her-1 mRNA by Northern Blot Analysis

Total mRNA was extracted from the cells. For SKOV3 cells, cells were washed twice with PBS and 1–2 ml of RNAZOL B7 (Tel-Test, Inc., Friendswood, Tex.) was added. An incubation at 4° C. for 5–30 minutes was done and the cells were scraped into an Eppendorf tube. This solution was frozen at −80° C. for 20 minutes, thawed and chloroform (200 μl/ml) was added. The solution was centrifuged at 12,000×g for 15 minutes at 4° C. and the aqueous layer was transferred to a clean Eppendorf tube. An equal volume of isopropanol was added and incubated at room temperature for 15 minutes. Another centrifugation at 12,000×g for 15 minutes at 4° C. was done. The pellet was washed with 500 μl of 75% ethanol and centrifuged at 7500×g for 5 minutes at 4° C. As much of the supernatant as possible was removed and the pellet was resuspended in 30 μl of double distilled water. For A549 cells, total mRNA was extracted using a guanidinium/cesium chloride extraction protocol as described by Dean et al., *J. Biol. Chem.*, 1994, 269, 16416. Ten μg of this mRNA was resolved on a 1.0% agarose gel containing 3.0% formaldehyde and transferred to a nylon membrane. The membrane was hybridized with a one-way PCR-generated human Her-1 probe radiolabeled with [α-$^{32}$P]-dCTP (Dupont NEN Research Products, Boston, Mass.) generated with the GeneAMP PCR Reagent Kit (Perkin Elmer, Foster City, Calif.), a T7 primer and a human Her-1 transcription template (Ambion, Austin, Tex.). The membrane was exposed to autoradiography film at −80° C. and the mRNA bands quantitated using a densitometer (Molecular Dynamics). Blots were stripped of radioactivity by boiling and then reprobed with a $^{32}$P-labeled control probe which hybridized either to G3PDH (Clontech Laboratories, Inc., Palo Alto, Calif.) or β-actin (Ambion, Austin, Tex).

Example 5

Metabolic Labeling and Immunoprecipitation of Her-1

SKOV3 cells were treated with the indicated oligonucleotides in serum-free, methionine-free OPTI-MEM7 medium for 2.5 hours. The medium was then replaced with methionine-free OPTI-MEM7 containing $^{35}$S-methionine (100 μCi/ml) and 2% dialyzed fetal bovine serum for 10 hours. Cell extracts were prepared as described by Kumar et al., *Proc. Natl. Acad. Sci. USA*, 1992, 89, 6599. Aliquots containing equal amounts of trichloroacetic acid-precipitable counts per minute were subjected to immunoprecipitation with anti-Her-1 monoclonal antibody 528/rabbit anti-mouse IgG/protein A-Sepharose conjugate. Kumar et al., *Proc. Natl. Acad. Sci. USA*, 1992, 89, 6599 and Korutla et al., *Carcinogenesis*, 1995, 16, 1741. Lysates containing equal amounts of protein were also resolved on a 10% SDS-polyacrylamide gel and stained with Coomassie blue.

Example 6

Analysis of Antisense Effects on the Growth of SKOV3 Cells

SKOV3 cells were treated with oligonucleotides ISIS 10563, 12876 and 12877 or the scrambled control oligonucleotide ISIS 12139 as described in Example 3, or left untreated. Cells were then either allowed to grow for 3 additional days in maintenance medium with 10% fetal bovine serum or they were treated again with oligonucleotide at 24 and 48 hours, for 4–5 hours each time. Cells were counted on a Coulter counter at 24, 48 and 72 hours.

Example 7

Synthesis of Particular Oligonucleotides

The following are examples in which methods and compositions of the present invention have been used effectively. The present invention is not limited to these targets or these compositions. In accordance with the present invention, a series of oligonucleotides complementary to mRNA were designed to target different regions of the human Her-1 mRNA, using published sequences (Ullrich et al., *Nature*, 1984, 309, 418; GenBank Accession Number X00588 and Kraus et al., *Proc. Natl. Acad. Sci. USA*, 1989, 86, 9193; GenBank Accession Number M29366). Several analogs of these seguences were also designed. The oligonucleotides are shown in Table 1. Target sites are indicated by source reference (Ullrich or Kraus) and nucleotide numbers, as given in the Genbank listing, to which the oligonucleotide binds.

TABLE 1

| ISIS # | SEQUENCE (5' to 3') | MODIFICATION | TARGET SITE | SEQ ID NO: |
|---|---|---|---|---|
| 10560 | GAGGCGTTCTCCTTTCTCCA | | coding region, Ullrich 2966–2985 | 1 |
| 12878 | GAGGCGTTCTCCTUUCUCCA | 2'-O-propyl | coding region, Ullrich 2966–2985 | 1 |
| 12879 | GAGGCGTTCTCCTUUCUCCA | 2'-fluoro | coding region, Ullrich 2966–2985 | 1 |
| 10561 | TGTCGGCCCCACAGGCTCGG | | coding region, Ullrich 1110–1129 | 2 |
| 10562 | CGCCCGGAGCACTGCTGGGC | | coding region, Ullrich 832–851 | 3 |
| 10563 | CCCCAGCAGCTCCCATTGGG | | coding region, Ullrich 769–788 | 4 |
| 12875 | CCCCAGCAGCTCCCAUUGGG | 2'-fluoro | coding region, Ullrich 769–788 | 4 |

TABLE 1-continued

| ISIS # | SEQUENCE (5' to 3') | MODIFICATION | TARGET SITE | SEQ ID NO: |
|---|---|---|---|---|
| 12876 | CCCCAGCAGCTCCCATTGGG | 5-methyl C | coding region, Ullrich 769–788 | 4 |
| 10564 | CCACGTTGCACAGGGCAGGG | | 5' UTR, Ullrich 645–664 | 5 |
| 10565 | CTCGGCTGACATTCCGGCAA | | coding region, Ullrich 1761–1780 | 6 |
| 12877 | CUCGGCTGACATTCCGGCAA | 2'-fluoro | | 6 |
| 10654 | ATCGAGGCAAGAGCCACCTGA | | 5'UTR, Kraus 18–38 | 7 |
| 10655 | CATGACTCCGCAGAGGGTGAA | | start codon, Kraus 82–102 | 8 |
| 10656 | CGCCGGTCACACTCAGGCCA | | coding region, Kraus 201–220 | 9 |
| 10657 | GCCACAGGGAGCAGGAGTTA | | stop codon, Kraus 4126–4145 | 11 |
| 10658 | GGTTGGGAAAGAGAAGAAAGT | | 3'UTR, Kraus 4319–4339 | 12 |
| 10659 | GAAGCTGAGGAATGGGACTGG | | 3'UTR, Kraus 4373–4393 | 13 |
| 10660 | CACCATGCCCGACTTCCCTTT | | 3'UTR, Kraus 4753–4773 | 14 |
| 12139 | GAGTTCGCGTCCTTTCTCCA | | control | 10 |

All backbones are phosphorothioates. Oligonucleotides for which no additional modification is indicated contain only 2'-deoxynucleotides. Oligonucleotides for which a modification is indicated are modified at underlined nucleosides.

Example 8

Effect Of Oligonucleotides On Her-1 mRNA Levels

Some of the oligonucleotides in Table 1 were tested for their ability to inhibit Her-1 mRNA expression in A549 human lung carcinoma cells and SKOV3 human ovarian carcinoma cells, both of which overexpress the Her-1. Cultured cells were treated with 300 nM of oligonucleotide in the presence of 15 $\mu$g/ml of cationic lipid (LIPOFECTIN7). Total RNA was extracted and quantitated by Northern blot analysis, using PCR-generated Her-1 cDNA probes. Bands were quantitated on a densitometer and normalized to control probe bands (G3PDH for the A549 cells and β-actin for the SKOV3 cells). The results are shown in Table 2 as Her-1 mRNA inhibition (10 kb band) as percent of untreated control. The scrambled control, ISIS 12139 (SEQ ID NO:10), actually gave a slight increase in Her-1 mRNA compared to untreated controls (18% increase in A549 cells, 39% in SKOV3 cells).

TABLE 2

| ISIS # | % Inhibition A549 | SKOV3 | SEQ ID NO: |
|---|---|---|---|
| 12878 | 66 | 22 | 1 |
| 10561 | 75% | 45% | 2 |
| 10563 | 95 | 61 | 4 |
| 12876 | 97 | 66 | 4 |
| 12875 | 77 | 57 | 4 |
| 10565 | 43 | 33 | 6 |
| 12877 | 93 | 61 | 6 |

A reduction in the amount of the 5.6 kb band was also observed after treatment with each of these oligonucleotides.

Three oligonucleotides, ISIS 10563 (SEQ ID NO:4, phosphorothioate deoxyoligonucleotide), ISIS 12876 (SEQ ID NO:4, 5-methyl C) and ISIS 12877 (SEQ ID NO:6, 2'-fluoro) gave the greatest amount of reduction of Her-1 mRNA expression in both cell types. These compounds are, therefore, most preferred, and were further assessed for their effects on Her-1 protein production and cell growth. ISIS 12875 was slightly less potent but is also highly preferred. ISIS 12878 and ISIS 10561 gave greater than 50% inhibition of Her-1 mRNA expression in A549 cells, and are also preferred.

Example 9

Effect Of Oligonucleotides On Her-1 Protein Synthesis

ISIS 10563, ISIS 12876 and ISIS 12877 were added to exponentially growing SKOV3 cells. Cells were metabolically labeled with $^{35}$S-methionine and newly synthesized Her-1 protein was immunoprecipitated. A 90–98% reduction of Her-1 protein production was observed in cells treated with each of these oligonucleotides compared to untreated cells. Cells treated with scrambled control oligonucleotide (ISIS 12139, SEQ NO:10) had a 10% reduction in Her-1 synthesis. This inhibition is specific to Her-1 protein production, as demonstrated by the presence of an identical number of TCA-precipitable counts per minute in oligonucleotide-treated cells and control cells (either untreated or scrambled control-treated). Coomassie blue staining confirmed that proteins other than Her-1 were not affected by treatment of cells with antisense oligonucleotides.

Example 10
Effect Of Oligonucleotide Treatment On Growth Of SKOV3 Cells

Cells were treated with oligonucleotides for 4–5 hours and allowed to grow an additional three days in maintenance medium. Cell counts at 24 hours showed a reduction in cell number of 13–24% for antisense-treated cells compared to untreated or scrambled control-treated cells. Cells treated with repeated oligonucleotide doses at 24 and 48 hours showed a sustained inhibition of cell growth of approximately 30% after 72 hours.

Example 11
Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 12
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 13
Cell Culture and Oligonucleotide Treatment—96 Well Plate Format

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 80% confluency, they were treated with oligonucleotide. For cells grown in 96-well plates, wells were washed once with 200 µL OPTI-MEM™-1 reduced-serum medium (Gibco BRL) and then treated with 130 µL of OPTI-MEM™-1 containing 3.75 µg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 15, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 16, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 14
Analysis of Oligonucleotide Inhibition of Her-1 Expression

Antisense modulation of Her-1 expression can be assayed in a variety of ways known in the art. For example, Her-1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Her-1 can be quantitated in a variety of ways well known in the art, such as immunoprecipitation, Western blot analysis (immunoblotting), ELISA or fluorescence-activated cell sorting (FACS). Antibodies directed to Her-1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 15
Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine, Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 16
Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 100 μL Buffer RLT was added to each well and the plate vigorously agitated for 20 seconds. 100 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 μL water into each well, incubating 1 minute, and then applying the vacuum for 30 seconds. The elution step was repeated with an additional 60 μL water.

The repetitive pipetting and elution steps may be automated using a QIAGEN Bio-Robot 9604 (Qiagen, Inc., Valencia, Calif.). Essentially, after lysing of the cells on the culture plate, the plate is transferred to the robot deck where the pipetting, DNase treatment and elution steps are carried out.

Example 17
Real-time Quantitative PCR Analysis of Her-1 mRNA Levels

Quantitation of Her-1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1× TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Org.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human Her-1 were designed to hybridize to a human Her-1 sequence, using published sequence information (GenBank accession number X00588, incorporated herein as SEQ ID NO:17). For human Her-1 the PCR primers were:

forward primer: GCGTCTCTTGCCGGAATGT (SEQ ID NO: 18)

reverse primer: GGCTCACCCTCCAGAAGCTT (SEQ ID NO: 19) and the PCR probe was: FAM-CCACGCATTCCCTGCCTCGG-TAMRA (SEQ ID NO: 20) where FAM (PE-Applied Biosystems, Foster City, Calif.) is the fluorescent reporter dye) and TAMRA (PE-Applied Biosystems, Foster City, Calif.) is the quencher dye.

For human GAPDH the PCR primers were:

forward primer: CAACGGATTTGGTCGTATTGG (SEQ ID NO: 21)

reverse primer: GGCAACAATATCCACTTTACCA-GAGT (SEQ ID NO: 22) and the PCR probe was: 5' JOE-CGCCTGGTCACCAGGGCTGCT- TAMRA 3' (SEQ ID NO: 23) where JOE (PE-Applied Biosystems, Foster City, Calif.) is the fluorescent reporter dye) and TAMRA (PE-Applied Biosystems, Foster City, Calif.) is the quencher dye.

Example 18
Northern Blot Analysis of Her-1 mRNA Levels

Eighteen hours after antisense treatment, cell monolayers were washed twice with cold PBS and lysed in 1 mL RNAZOL~ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Her-1, a human Her-1 specific probe was prepared by PCR using the forward primer GCGTCTCT-TGCCGGAATGT (SEQ ID NO: 18) and the reverse primer GGCTCACCCTCCAGAAGCTT (SEQ ID NO: 19). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 19
Antisense Inhibition of Human Her-1 Expression by Chimeric Phosphorothioate Oligonucleotides Having 2'-MOE Wings and a Deoxy Gap In accordance with the present invention, a series of oligonucleotides were designed to target different regions of the human Her-1 RNA, using published sequences (GenBank accession number X00588, incorporated herein as SEQ ID NO: 17, nucleotides 1-163586 of GenBank accession number AC006977, incorporated herein as SEQ ID NO: 24, GenBank accession number U48722, incorporated herein as SEQ ID NO: 25, and GenBank accession number U95089, incorporated herein as SEQ ID NO: 26). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human Her-1 mRNA levels by quantitative real-time PCR as described in other examples herein. Data are averages from two experiments. If present, "N.D." indicates "no data".

TABLE 3

Inhibition of human Her-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 122105 | 5'UTR | 17 | 11 | ggctagctcgggactccggc | 44 | 27 |
| 122106 | 5'UTR | 17 | 37 | tccggtctgggcggcggcgg | 39 | 28 |
| 122107 | 5'UTR | 17 | 96 | ggttgtggcgttggcggcga | 49 | 29 |
| 122125 | Start Codon | 17 | 179 | ggagggtcgcatcgctgctc | 42 | 30 |
| 122126 | Coding | 17 | 262 | tggcaaactttcttttcctc | 69 | 31 |
| 122127 | Coding | 17 | 379 | tgcacataggtaatttccaa | 54 | 32 |
| 122128 | Coding | 17 | 412 | atggtctttaagaaggaaag | 40 | 33 |
| 122129 | Coding | 17 | 417 | cctggatggtctttaagaag | 16 | 34 |
| 122130 | Coding | 17 | 422 | cacctcctggatggtcttta | 30 | 35 |
| 122131 | Coding | 17 | 448 | ttgagggcaatgaggacata | 53 | 36 |
| 122132 | Coding | 17 | 628 | gggttgttgctgaaccgcac | 58 | 37 |
| 122133 | Coding | 17 | 754 | ttgggacagcttggatcaca | 23 | 38 |
| 122134 | Coding | 17 | 792 | tctggcagttctcctctcct | 70 | 39 |
| 122135 | Coding | 17 | 817 | tgggcacagatgattttggt | 38 | 40 |
| 122136 | Coding | 17 | 869 | gttgtggcagcagtcactgg | 50 | 41 |
| 122137 | Coding | 17 | 1039 | caggtggcaccaaagctgta | 22 | 42 |
| 122138 | Coding | 17 | 1227 | tagcatttatggagagtgag | 48 | 43 |
| 122139 | Coding | 17 | 1396 | caagcctgaatcagcaaaaa | 73 | 44 |
| 122140 | Coding | 17 | 1401 | caggccaagcctgaatcagc | 51 | 45 |
| 122141 | Coding | 17 | 1477 | gaaaactgaccatgttgctt | 47 | 46 |
| 122142 | Coding | 17 | 1541 | atcacttatctccttgaggg | 63 | 47 |
| 122143 | Coding | 17 | 1606 | agtttttccagtttattgt | 36 | 48 |
| 122144 | Coding | 17 | 1741 | gagacgcagtccctgggctc | 56 | 49 |
| 122145 | Coding | 17 | 1879 | caggtgatgttcatggcctg | 27 | 50 |
| 122146 | Coding | 17 | 1924 | atgtagtgggcacactggat | 36 | 51 |
| 122147 | Coding | 17 | 2272 | gcttggttgggagcttctcc | 53 | 52 |
| 122148 | Coding | 17 | 2317 | actttgatcttttgaattc | 46 | 53 |
| 122149 | Coding | 17 | 2374 | tcaccttctgggatccagag | 65 | 54 |
| 122150 | Coding | 17 | 2378 | tttctcaccttctgggatcc | 64 | 55 |
| 122151 | Coding | 17 | 2425 | ggagatgttgcttctcttaa | 43 | 56 |
| 122152 | Coding | 17 | 2652 | ccaagtagttcatgcccttt | 44 | 57 |
| 122153 | Coding | 17 | 2731 | tctgtgatcttgacatgctg | 29 | 58 |
| 122154 | Coding | 17 | 2737 | ccaaaatctgtgatcttgac | 62 | 59 |
| 122155 | Coding | 17 | 2742 | ccagcccaaaatctgtgatc | 62 | 60 |
| 122156 | Coding | 17 | 2748 | gtttggccagcccaaaatct | 44 | 61 |
| 122157 | Coding | 17 | 2827 | aaaattgattccaatgccat | 68 | 62 |
| 122158 | Coding | 17 | 2907 | gcttggatccaaaggtcatc | 42 | 63 |
| 122159 | Coding | 17 | 3085 | cgggccattttggagaattc | 39 | 64 |
| 122160 | Coding | 17 | 3130 | tgcattctttcatcccctg | 68 | 65 |
| 122161 | Coding | 17 | 3135 | gcaaatgcattctttcatcc | 62 | 66 |
| 122162 | Coding | 17 | 3311 | agccacggtggaattgttgc | 30 | 67 |
| 122163 | Coding | 17 | 3508 | ggctgattgtgatagacagg | 48 | 68 |
| 122164 | Coding | 17 | 3688 | tgctggtagtcagggttgtc | 47 | 69 |
| 122165 | Coding | 17 | 3693 | agtcctgctggtagtcaggg | 52 | 70 |

TABLE 3-continued

Inhibition of human Her-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 122166 | Coding | 17 | 3759 | ggtattctgcattttcagct | 39 | 71 |
| 122167 | Stop Codon | 17 | 3808 | ctccgtggtcatgctccaat | 69 | 72 |
| 122168 | 3'UTR | 17 | 3949 | ttcctggctagtcggtgtaa | 32 | 73 |
| 122169 | 3'UTR | 17 | 3952 | tacttcctggctagtcggtg | 47 | 74 |
| 122170 | 3'UTR | 17 | 4026 | gatgcgtttctgtaaatgct | 44 | 75 |
| 122171 | 3'UTR | 17 | 4114 | aaaaatcctcacatatactt | 63 | 76 |
| 122172 | 3'UTR | 17 | 4149 | agcgacaatgaaaaactcca | 67 | 77 |
| 122173 | 3'UTR | 17 | 4162 | agtaaaaatcaatagcgaca | 64 | 78 |
| 122174 | 3'UTR | 17 | 4218 | actcagggtagcaagtgcta | 44 | 79 |
| 122175 | 3'UTR | 17 | 4328 | ttggatctttagtgttttgc | 35 | 80 |
| 122176 | 3'UTR | 17 | 4398 | gcttatcctactgtacctgc | 47 | 81 |
| 122177 | 3'UTR | 17 | 4512 | gaaaccactggtccatcagt | 44 | 82 |
| 122178 | 3'UTR | 17 | 4632 | agttattatttgatgtgtca | 29 | 83 |
| 122179 | 3'UTR | 17 | 4787 | ctatgccccaaaggacctga | 65 | 84 |
| 122180 | 3'UTR | 17 | 4839 | ggtgatggctaaaggagatt | 48 | 85 |
| 122181 | 3'UTR | 17 | 4877 | tcttccataagtaacacaaa | 67 | 86 |
| 122182 | 3'UTR | 17 | 4994 | gcagagacactttttgtgtg | 50 | 87 |
| 122183 | 3'UTR | 17 | 5082 | tcacactactcataatgcta | 68 | 88 |
| 122184 | 3'UTR | 17 | 5214 | tagctgaatcttccaatctt | 49 | 89 |
| 122185 | 3'UTR | 17 | 5264 | ccagtcaggttacagggcac | 61 | 90 |
| 122186 | 3'UTR | 17 | 5382 | gactgaacataactgtaggc | 75 | 91 |
| 122187 | 3'UTR | 17 | 5505 | atatagttttattttcattg | 55 | 92 |
| 122188 | Intron | 24 | 97770 | ggtcctgagagcagaccggg | 70 | 93 |
| 122189 | Intron | 24 | 111798 | aggtcctgaaaccggagagg | 48 | 94 |
| 122190 | Intron | 24 | 129827 | gcaagataaaagagttctgt | 41 | 95 |
| 122191 | Intron | 24 | 132873 | aaatgttaacagtgcagatc | 36 | 96 |
| 122192 | Exon | 24 | 134761 | gcatcttaccaggcagtcgc | 48 | 97 |
| 122193 | Intron | 24 | 135975 | gttccactagtgtgggaaaa | 25 | 98 |
| 122194 | Intron | 24 | 137320 | tgacctcagacaatccagcc | 58 | 99 |
| 122195 | Intron | 24 | 153946 | gtttggaaacatccaaaatg | 56 | 100 |
| 122196 | Intron | 24 | 155828 | aagttggtagaaacacaggc | 72 | 101 |
| 122197 | Intron | 24 | 159960 | aagtagtaaacgtgcaccgt | 50 | 102 |
| 122198 | 5'UTR | 26 | 100 | gggacccaaggccactcccg | 47 | 103 |
| 122199 | 5'UTR | 26 | 133 | gaatgcgaggaggagggagg | 6 | 104 |
| 128453 | 5'UTR | 25 | 108 | aggtggcctgtcgtccggtc | 57 | 105 |
| 128454 | 5'UTR | 25 | 193 | ccgatcaatactggacggag | 78 | 106 |
| 128455 | 5'UTR | 25 | 203 | tccggctctcccgatcaata | 81 | 107 |
| 128456 | Start Codon | 25 | 229 | gcatcgctgctccccgaaga | 85 | 108 |
| 128457 | Start Codon | 25 | 244 | ccgtcccggagggtcgcatc | 56 | 109 |
| 128458 | Coding | 25 | 313 | ctttcttttcctccagagcc | 52 | 116 |
| 128459 | Coding | 25 | 328 | tcgtgccttggcaaactttc | 0 | 111 |
| 128460 | Coding | 25 | 338 | agcttgttactcgtgccttg | 51 | 112 |
| 128461 | Coding | 25 | 352 | tgcccaactgcgtgagcttg | 76 | 113 |
| 128462 | Coding | 25 | 362 | tcttcaaaagtgcccaactg | 47 | 114 |
| 128463 | Coding | 25 | 371 | agaaaatgatcttcaaaagt | 24 | 115 |
| 128464 | Coding | 25 | 386 | atcctctggaggctgagaaa | 46 | 116 |
| 128465 | Coding | 25 | 398 | cagttattgaacatcctctg | 72 | 117 |
| T28466 | Coding | 25 | 409 | ggaccacctcacagttattg | 64 | 118 |
| 128467 | Coding | 25 | 419 | aaattcccaaggaccacctc | 56 | 119 |
| 128468 | Coding | 25 | 429 | ggtaatttccaaattccaa | 67 | 120 |
| 128469 | Coding | 25 | 443 | ttcctctgcacataggtaat | 67 | 121 |
| 128470 | Coding | 25 | 461 | aagaaggaaagatcataatt | 6 | 122 |
| 128471 | Coding | 25 | 486 | accagccacctcctggatgg | 77 | 123 |
| 128472 | Coding | 25 | 497 | atgaggacataaccagccac | 64 | 124 |
| 128473 | Coding | 25 | 513 | cactgtgttgagggcaatga | 59 | 125 |
| 128474 | Coding | 25 | 530 | tccaaaggaattcgctccac | 74 | 126 |
| 128475 | Coding | 25 | 540 | ctgcaggttttccaaaggaa | 33 | 127 |
| 122476 | Coding | 25 | 551 | cctctgatgatctgcaggtt | 61 | 128 |
| 128477 | Coding | 25 | 584 | gctaaggcataggaattttc | 72 | 129 |
| 128478 | Coding | 25 | 598 | agttagataagactgctaag | 63 | 130 |

TABLE 3-continued

Inhibition of human Her-1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 128479 | Coding | 25 | 619 | gtccggttttatttgcatca | 38 | 131 |
| 128480 | Coding | 25 | 629 | agctccttcagtccggtttt | 69 | 132 |
| 128482 | Coding | 25 | 641 | ttctcatgggcagctcctt | 66 | 133 |
| 122484 | Coding | 25 | 657 | caggatttcctgtaaatttc | 64 | 134 |
| 128485 | Coding | 25 | 710 | atgctctccacattgcacag | 52 | 135 |
| 128487 | Coding | 25 | 728 | actatgtcccgccactggat | 69 | 136 |
| 128489 | Coding | 25 | 763 | agtccatcgacatgttgctg | 53 | 137 |
| 128495 | Coding | 25 | 774 | gtggttctggaagtccatcg | 47 | 138 |
| i28499 | Coding | 25 | 791 | ttttggcagctgcccaggtg | 25 | 139 |
| 128500 | Coding | 25 | 801 | tggatcacacttttggcagc | 51 | 140 |
| 128501 | Coding | 25 | 819 | gctcccattgggacagcttg | 50 | 141 |
| 128502 | Coding | 25 | 836 | tctcctgcaccccagcagct | 48 | 142 |
| 128503 | Coding | 25 | 851 | ttctggcagttctcctctcc | 77 | 143 |
| 128504 | Coding | 25 | 867 | gatgattttggtcagtttct | 43 | 144 |
| 128505 | Coding | 25 | 882 | gcactgctgggcacagatga | 36 | 145 |
| 128506 | Coding | 25 | 909 | gggggacttgccacggcagc | 16 | 146 |
| 128507 | Coding | 25 | 920 | cagcagtcactgggggactt | 52 | 147 |
| 128508 | Coding | 25 | 941 | cctgcagcacactggttgtg | 57 | 148 |
| 128509 | Coding | 25 | 978 | gcagaccaggcagtcgctct | 67 | 159 |
| 128510 | Coding | 25 | 1017 | gcaggtgtccttgcacgtgg | 58 | 150 |
| 128511 | Coding | 25 | 1028 | atgagtgggggcaggtgtc | 23 | 151 |
| 128512 | Coding | 25 | 1039 | ggttgtagagcatgagtggg | 41 | 152 |
| 128513 | Coding | 25 | 1049 | tacgtggtggggttgtagag | 2 | 153 |
| 128514 | Coding | 25 | 1060 | catccatctggtacgtggtg | 67 | 154 |
| 128515 | Coding | 25 | 1070 | tcggggttcacatccatctg | 66 | 155 |
| 128516 | Coding | 25 | 1091 | gcaccaaagctgtatttgcc | 74 | 156 |
| 128517 | Coding | 25 | 1104 | cttcacgcaggtggcaccaa | 28 | 157 |
| 128518 | Coding | 25 | 1115 | cggggacacttcttcacgca | 74 | 158 |
| 128519 | Coding | 25 | 1139 | ccgtgatctgtcaccacata | 65 | 159 |
| 128520 | Coding | 25 | 1157 | caggctcggacgcacgagcc | 15 | 160 |
| 128521 | Coding | 25 | 1167 | tgcggccccacaggctcgga | 73 | 161 |
| 128522 | Coding | 25 | 1180 | ccatctcatagctgtcggcc | 74 | 162 |
| 128523 | Coding | 25 | 1205 | ttacacttgcggacgccgtc | 63 | 163 |
| 128524 | Coding | 25 | 1221 | aggcccttcgcacttcttac | 62 | 164 |
| 128525 | Coding | 25 | 1233 | cactttgcggcaaggcccctt | 69 | 165 |
| 128526 | Coding | 25 | 1245 | tattccgttacacactttgc | 70 | 166 |
| 128527 | Coding | 25 | 1260 | aaattcaccaatacctattc | 45 | 167 |
| 128528 | Coding | 25 | 1270 | gtgagtctttaaattcacca | 70 | 168 |
| 128529 | Coding | 25 | 1292 | atattcgtagcatttatgga | 11 | 169 |
| 128530 | Coding | 25 | 1313 | gtgcagttttgaagtgttt | 58 | 170 |
| 128531 | Coding | 25 | 1326 | gccactgatggaggtgcagt | 82 | 171 |
| 128532 | Coding | 25 | 1352 | aatgccaccggcaggatgtg | 32 | 172 |
| 128533 | Coding | 25 | 1370 | gtgaaggagtcacccctaaa | 73 | 173 |
| 128534 | Coding | 25 | 1386 | cagaggaggagtatgtgtga | 55 | 174 |
| 128535 | Coding | 25 | 1401 | cagttcctgtggatccagag | 80 | 175 |
| 128536 | Coding | 25 | 1412 | ttcagaatatccagttcctg | 62 | 176 |
| 128537 | Coding | 25 | 1422 | ctttacggttttcagaatat | 35 | 177 |
| 128538 | Coding | 25 | 1433 | cctgtgatttcctttacggt | 81 | 178 |
| 128539 | Stop Codon | 25 | 1452 | tgtgataattcagctcaaac | 39 | 179 |
| 128540 | 3'UTR | 25 | 1479 | aaaacactgatttcccattt | 42 | 180 |
| 128541 | 3'UTR | 25 | 1491 | agttctctctctaaaacact | 58 | 181 |
| 128542 | 3'UTR | 25 | 1525 | ttttattccaagggaacag | 46 | 182 |

As shown in Table 1, SEQ ID NOs 27, 28, 29, 30, 31, 32, 33, 36, 37, 39, 40, 41, 43, 44, 45, 46, 47, 48, 49, 51, 52, 53, 55, 56, 57, 59, 60, 61, 62, 63, 64, 65, 66, 68, 69, 70, 71, 72, 73, 74, 75, 76, 77, 78, 79, 80, 81, 82, 84, 85, 86, 87, 88, 89, 90, 91, 92, 93, 94, 95, 96, 97, 99, 100, 101, 102, 103, 105, 106, 107, 108, 109, 110, 111, 112, 114, 116, 117, 118, 119, 120, 121, 123, 124, 125, 126, 127, 128, 129, 130, 131, 132, 133, 134, 135, 135, 136, 137, 138, 140, 141, 142, 143, 144, 145, 147, 148, 149, 150, 152, 154, 155, 156, 158, 159, 161, 162, 163, 164, 165, 166, 167, 168, 170, 171, 172, 173, 174, 175, 176, 177, 178, 179, 180, 181 and 182 demonstrated at least 30% inhibition of human Her-1 expression in this assay and are therefore preferred. The target sites to which these preferred sequences are complimentary are herein referred to as "active sites" and are therefore preferred sites for targeting by compounds of the present invention.

Example 20

Western Blot Analysis of Her-1 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to Her-1 is used, with a radiolabelled or fluorescently labeled secondary antibody directed against the primary antibody species. Bands are visualized using a PHOSPHORIMAGER™ (Molecular Dynamics, Sunnyvale, Calif.).

What is claimed is:

1. A compound 8 to 50 nucleobases in length targeted to a nucleic acid molecule encoding epidermal growth factor receptor and comprising at least an 8 nucleobase portion of SEQ ID NO: 27, 28, 29, 32, 33, 36, 37, 39, 40, 41, 43, 44, 45, 46, 47, 48, 49, 51, 52, 53, 54, 55, 56, 57, 59, 60, 61, 62, 63, 64, 65, 66, 68, 69, 70, 71, 73, 74, 75, 76, 77, 78, 79, 80, 81, 82, 84, 85, 86, 87, 88, 89, 90, 91, 92, 93, 94, 95, 96, 97, 99, 100, 101, 102, 103, 105, 106, 107, 108, 110, 111, 112, 114, 116, 117, 118, 119, 120, 121, 123, 124, 125, 126, 127, 128, 129, 130, 131, 132, 133, 134, 135, 136, 137, 138, 140, 141, 142, 143, 144, 145, 147, 148, 149, 150, 152, 154, 155, 156, 158, 159, 162, 163, 164, 165, 166, 167, 168, 170, 171, 172, 173, 174, 175, 176, 177, 178, 179, 180, 181 or 182, wherein said compound inhibits the expression of said human epidermal growth factor receptor.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of human epidermal growth factor receptor in cells or tissues comprising contacting said cells or tissues in vitro with the compound of claim 1 so that expression of human epidermal growth factor is inhibited.

14. A compound 8 to 50 nucleobases in length targeted to a nucleic acid molecule encoding human epidermal growth factor receptor and consisting of SEQ ID NO: 30, 31, 72, 109 or 161.

15. The compound of claim 14 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 14 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of human epidermal growth factor receptor in cells or tissues comprising contacting said cells or tissues in vitro with the compound of claim 14 so that expression of human epidermal growth factor is inhibited.

* * * * *

```
                         SEQUENCE LISTING

<160> NUMBER OF SEQ ID NOS: 182

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
gaggcgttct cctttctcca                                                   20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
tgtcggcccc acaggctcgg                                                   20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
cgcccggagc actgctgggc                                                   20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
ccccagcagc tcccattggg                                                   20

<210> SEQ ID NO 5
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 5
ccacgttgca cagggcaggg                                                   20

<210> SEQ ID NO 6
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 6
```

-continued ctcggctgac attccggcaa                      20

<210> SEQ ID NO 7
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 7
atcgaggcaa gagccacctg a                    21

<210> SEQ ID NO 8
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 8
catgactccg cagagggtga a                    21

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
cgccggtcac actcaggcca                      20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
gagttcgcgt cctttctcca                      20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
gccacaggga gcaggagtta                      20

<210> SEQ ID NO 12
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 12
ggttgggaaa gagaagaaag t                    21

<210> SEQ ID NO 13
<211> LENGTH: 21
<212> TYPE: DNA
<213> ORGANISM: Artificial Sequence

```
<220> FEATURE:
<223> OTHER INFORMATION: Antisense Oligonucleotide

<400> SEQUENCE: 13
gaagctgagg aatgggactg g                                              21

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 14
caccatgccc gacttccctt t                                              21

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
tccgtcatcg ctcctcaggg                                                20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
atgcattctg cccccaagga                                                20

<210> SEQ ID NO 17
<211> LENGTH: 5532
<212> TYPE: DNA
<213> ORGANISM: Homo sapiens
<220> FEATURE:
<221> NAME/KEY: CDS
<222> LOCATION: (187)...(3819)

<400> SEQUENCE: 17
gccgcgctgc gccggagtcc cgagctagcc ccggcgccgc cgccgcccag accggacgac     60
aggccacctc gtcggcgtcc gcccgagtcc ccgcctcgcc gccaacgcca caaccaccgc    120
gcacggcccc ctgactccgt ccagtattga tcgggagagc cggagcgagc tcttcgggga    180 gcagcg atg cga ccc tcc ggg acg gcc ggg gca gcg ctc ctg gcg ctg       228
       Met Arg Pro Ser Gly Thr Ala Gly Ala Ala Leu Leu Ala Leu
         1               5                  10 ctg gct gcg ctc tgc ccg gcg agt cgg gct ctg gag gaa aag aaa gtt     276
Leu Ala Ala Leu Cys Pro Ala Ser Arg Ala Leu Glu Glu Lys Lys Val
 15              20                  25                  30 tgc caa ggc acg agt aac aag ctc acg cag ttg ggc act ttt gaa gat     324
Cys Gln Gly Thr Ser Asn Lys Leu Thr Gln Leu Gly Thr Phe Glu Asp
             35                  40                  45 cat ttt ctc agc ctc cag agg atg ttc aat aac tgt gag gtg gtc ctt     372
His Phe Leu Ser Leu Gln Arg Met Phe Asn Asn Cys Glu Val Val Leu
         50                  55                  60 ggg aat ttg gaa att acc tat gtg cag agg aat tat gat ctt tcc ttc     420
Gly Asn Leu Glu Ile Thr Tyr Val Gln Arg Asn Tyr Asp Leu Ser Phe
     65                  70                  75
```

```
-continued tta aag acc atc cag gag gtg gct ggt tat gtc ctc att gcc ctc aac      468
Leu Lys Thr Ile Gln Glu Val Ala Gly Tyr Val Leu Ile Ala Leu Asn
         80                  85                  90 aca gtg gag cga att cct ttg gaa aac ctg cag atc atc aga gga aat      516
Thr Val Glu Arg Ile Pro Leu Glu Asn Leu Gln Ile Ile Arg Gly Asn
 95                 100                 105                 110 atg tac tac gaa aat tcc tat gcc tta gca gtc tta tct aac tat gat      564
Met Tyr Tyr Glu Asn Ser Tyr Ala Leu Ala Val Leu Ser Asn Tyr Asp
                    115                 120                 125 gca aat aaa acc gga ctg aag gag ctg ccc atg aga aat tta cag gaa      612
Ala Asn Lys Thr Gly Leu Lys Glu Leu Pro Met Arg Asn Leu Gln Glu
            130                 135                 140 atc ctg cat ggc gcc gtg cgg ttc agc aac aac cct gcc ctg tgc aac      660
Ile Leu His Gly Ala Val Arg Phe Ser Asn Asn Pro Ala Leu Cys Asn
            145                 150                 155 gtg gag agc atc cag tgg cgg gac ata gtc agc agt gac ttt ctc agc      708
Val Glu Ser Ile Gln Trp Arg Asp Ile Val Ser Ser Asp Phe Leu Ser
        160                 165                 170 aac atg tcg atg gac ttc cag aac cac ctg ggc agc tgc caa aag tgt      756
Asn Met Ser Met Asp Phe Gln Asn His Leu Gly Ser Cys Gln Lys Cys
175                 180                 185                 190 gat cca agc tgt ccc aat ggg agc tgc tgg ggt gca gga gag gag aac      804
Asp Pro Ser Cys Pro Asn Gly Ser Cys Trp Gly Ala Gly Glu Glu Asn
                    195                 200                 205 tgc cag aaa ctg acc aaa atc atc tgt gcc cag cag tgc tcc ggg cgc      852
Cys Gln Lys Leu Thr Lys Ile Ile Cys Ala Gln Gln Cys Ser Gly Arg
            210                 215                 220 tgc cgt ggc aag tcc ccc agt gac tgc tgc cac aac cag tgt gct gca      900
Cys Arg Gly Lys Ser Pro Ser Asp Cys Cys His Asn Gln Cys Ala Ala
            225                 230                 235 ggc tgc aca ggc ccc cgg gag agc gac tgc ctg gtc tgc cgc aaa ttc      948
Gly Cys Thr Gly Pro Arg Glu Ser Asp Cys Leu Val Cys Arg Lys Phe
        240                 245                 250 cga gac gaa gcc acg tgc aag gac acc tgc ccc cca ctc atg ctc tac      996
Arg Asp Glu Ala Thr Cys Lys Asp Thr Cys Pro Pro Leu Met Leu Tyr
255                 260                 265                 270 aac ccc acc acg tac cag atg gat gtg aac ccc gag ggc aaa tac agc     1044
Asn Pro Thr Thr Tyr Gln Met Asp Val Asn Pro Glu Gly Lys Tyr Ser
                    275                 280                 285 ttt ggt gcc acc tgc gtg aag aag tgt ccc cgt aat tat gtg gtg aca     1092
Phe Gly Ala Thr Cys Val Lys Lys Cys Pro Arg Asn Tyr Val Val Thr
            290                 295                 300 gat cac ggc tcg tgc gtc cga gcc tgt ggg gcc gac agc tat gag atg     1140
Asp His Gly Ser Cys Val Arg Ala Cys Gly Ala Asp Ser Tyr Glu Met
            305                 310                 315 gag gaa gac ggc gtc cgc aag tgt aag aag tgc gaa ggg cct tgc cgc     1188
Glu Glu Asp Gly Val Arg Lys Cys Lys Lys Cys Glu Gly Pro Cys Arg
        320                 325                 330 aaa gtg tgt aac gga ata ggt att ggt gaa ttt aaa gac tca ctc tcc     1236
Lys Val Cys Asn Gly Ile Gly Ile Gly Glu Phe Lys Asp Ser Leu Ser
335                 340                 345                 350 ata aat gct acg aat att aaa cac ttc aaa aac tgc acc tcc atc agt     1284
Ile Asn Ala Thr Asn Ile Lys His Phe Lys Asn Cys Thr Ser Ile Ser
                    355                 360                 365 ggc gat ctc cac atc ctg ccg gtg gca ttt agg ggt gac tcc ttc aca     1332
Gly Asp Leu His Ile Leu Pro Val Ala Phe Arg Gly Asp Ser Phe Thr
            370                 375                 380 cat act cct cct ctg gat cca cag gaa ctg gat att ctg aaa acc gta     1380
His Thr Pro Pro Leu Asp Pro Gln Glu Leu Asp Ile Leu Lys Thr Val
```

-continued

```
            385                 390                 395
aag gaa atc aca ggg ttt ttg ctg att cag gct tgg cct gaa aac agg    1428
Lys Glu Ile Thr Gly Phe Leu Leu Ile Gln Ala Trp Pro Glu Asn Arg
    400                 405                 410 acg gac ctc cat gcc ttt gag aac cta gaa atc ata cgc ggc agg acc    1476
Thr Asp Leu His Ala Phe Glu Asn Leu Glu Ile Ile Arg Gly Arg Thr
415                 420                 425                 430 aag caa cat ggt cag ttt tct ctt gca gtc gtc agc ctg aac ata aca    1524
Lys Gln His Gly Gln Phe Ser Leu Ala Val Val Ser Leu Asn Ile Thr
                435                 440                 445 tcc ttg gga tta cgc tcc ctc aag gag ata agt gat gga gat gtg ata    1572
Ser Leu Gly Leu Arg Ser Leu Lys Glu Ile Ser Asp Gly Asp Val Ile
            450                 455                 460 att tca gga aac aaa aat ttg tgc tat gca aat aca ata aac tgg aaa    1620
Ile Ser Gly Asn Lys Asn Leu Cys Tyr Ala Asn Thr Ile Asn Trp Lys
            465                 470                 475 aaa ctg ttt ggg acc tcc ggt cag aaa acc aaa att ata agc aac aga    1668
Lys Leu Phe Gly Thr Ser Gly Gln Lys Thr Lys Ile Ile Ser Asn Arg
        480                 485                 490 ggt gaa aac agc tgc aag gcc aca ggc cag gtc tgc cat gcc ttg tgc    1716
Gly Glu Asn Ser Cys Lys Ala Thr Gly Gln Val Cys His Ala Leu Cys
495                 500                 505                 510 tcc ccc gag ggc tgc tgg ggc ccg gag ccc agg gac tgc gtc tct tgc    1764
Ser Pro Glu Gly Cys Trp Gly Pro Glu Pro Arg Asp Cys Val Ser Cys
                515                 520                 525 cgg aat gtc agc cga ggc agg gaa tgc gtg gac aag tgc aag ctt ctg    1812
Arg Asn Val Ser Arg Gly Arg Glu Cys Val Asp Lys Cys Lys Leu Leu
            530                 535                 540 gag ggt gag cca agg gag ttt gtg gag aac tct gag tgc ata cag tgc    1860
Glu Gly Glu Pro Arg Glu Phe Val Glu Asn Ser Glu Cys Ile Gln Cys
        545                 550                 555 cac cca gag tgc ctg cct cag gcc atg aac atc acc tgc aca gga cgg    1908
His Pro Glu Cys Leu Pro Gln Ala Met Asn Ile Thr Cys Thr Gly Arg
    560                 565                 570 gga cca gac aac tgt atc cag tgt gcc cac tac att gac ggc ccc cac    1956
Gly Pro Asp Asn Cys Ile Gln Cys Ala His Tyr Ile Asp Gly Pro His
575                 580                 585                 590 tgc gtc aag acc tgc ccg gca gga gtc atg gga gaa aac aac acc ctg    2004
Cys Val Lys Thr Cys Pro Ala Gly Val Met Gly Glu Asn Asn Thr Leu
                595                 600                 605 gtc tgg aag tac gca gac gcc ggc cat gtg tgc cac ctg tgc cat cca    2052
Val Trp Lys Tyr Ala Asp Ala Gly His Val Cys His Leu Cys His Pro
            610                 615                 620 aac tgc acc tac gga tgc act ggg cca ggt ctt gaa ggc tgt cca acg    2100
Asn Cys Thr Tyr Gly Cys Thr Gly Pro Gly Leu Glu Gly Cys Pro Thr
        625                 630                 635 aat ggg cct aag atc ccg tcc atc gcc act ggg atg gtg ggg gcc ctc    2148
Asn Gly Pro Lys Ile Pro Ser Ile Ala Thr Gly Met Val Gly Ala Leu
    640                 645                 650 ctc ttg ctg ctg gtg gtg gcc ctg ggg atc ggc ctc ttc atg cga agg    2196
Leu Leu Leu Leu Val Val Ala Leu Gly Ile Gly Leu Phe Met Arg Arg
655                 660                 665                 670 cgc cac atc gtt cgg aag cgc acg ctg cgg agg ctg ctg cag gag agg    2244
Arg His Ile Val Arg Lys Arg Thr Leu Arg Arg Leu Leu Gln Glu Arg
                675                 680                 685 gag ctt gtg gag cct ctt aca ccc agt gga gaa gct ccc aac caa gct    2292
Glu Leu Val Glu Pro Leu Thr Pro Ser Gly Glu Ala Pro Asn Gln Ala
            690                 695                 700 ctc ttg agg atc ttg aag gaa act gaa ttc aaa aag atc aaa gtg ctg    2340
```

```
                                                              -continued

Leu Leu Arg Ile Leu Lys Glu Thr Glu Phe Lys Lys Ile Lys Val Leu
            705                 710                 715 ggc tcc ggt gcg ttc ggc acg gtg tat aag gga ctc tgg atc cca gaa      2388
Gly Ser Gly Ala Phe Gly Thr Val Tyr Lys Gly Leu Trp Ile Pro Glu
720                 725                 730 ggt gag aaa gtt aaa att ccc gtc gct atc aag gaa tta aga gaa gca      2436
Gly Glu Lys Val Lys Ile Pro Val Ala Ile Lys Glu Leu Arg Glu Ala
735                 740                 745                 750 aca tct ccg aaa gcc aac aag gaa atc ctc gat gaa gcc tac gtg atg      2484
Thr Ser Pro Lys Ala Asn Lys Glu Ile Leu Asp Glu Ala Tyr Val Met
                755                 760                 765 gcc agc gtg gac aac ccc cac gtg tgc cgc ctg ctg ggc atc tgc ctc      2532
Ala Ser Val Asp Asn Pro His Val Cys Arg Leu Leu Gly Ile Cys Leu
            770                 775                 780 acc tcc acc gtg caa ctc atc acg cag ctc atg ccc ttc ggc tgc ctc      2580
Thr Ser Thr Val Gln Leu Ile Thr Gln Leu Met Pro Phe Gly Cys Leu
785                 790                 795 ctg gac tat gtc cgg gaa cac aaa gac aat att ggc tcc cag tac ctg      2628
Leu Asp Tyr Val Arg Glu His Lys Asp Asn Ile Gly Ser Gln Tyr Leu
800                 805                 810 ctc aac tgg tgt gtg cag atc gca aag ggc atg aac tac ttg gag gac      2676
Leu Asn Trp Cys Val Gln Ile Ala Lys Gly Met Asn Tyr Leu Glu Asp
815                 820                 825                 830 cgt cgc ttg gtg cac cgc gac ctg gca gcc agg aac gta ctg gtg aaa      2724
Arg Arg Leu Val His Arg Asp Leu Ala Ala Arg Asn Val Leu Val Lys
                835                 840                 845 aca ccg cag cat gtc aag atc aca gat ttt ggg ctg gcc aaa ctg ctg      2772
Thr Pro Gln His Val Lys Ile Thr Asp Phe Gly Leu Ala Lys Leu Leu
            850                 855                 860 ggt gcg gaa gag aaa gaa tac cat gca gaa gga ggc aaa gtg cct atc      2820
Gly Ala Glu Glu Lys Glu Tyr His Ala Glu Gly Gly Lys Val Pro Ile
865                 870                 875 aag tgg atg gca ttg gaa tca att tta cac aga atc tat acc cac cag      2868
Lys Trp Met Ala Leu Glu Ser Ile Leu His Arg Ile Tyr Thr His Gln
880                 885                 890 agt gat gtc tgg agc tac ggg gtg acc gtt tgg gag ttg atg acc ttt      2916
Ser Asp Val Trp Ser Tyr Gly Val Thr Val Trp Glu Leu Met Thr Phe
895                 900                 905                 910 gga tcc aag cca tat gac gga atc cct gcc agc gag atc tcc tcc atc      2964
Gly Ser Lys Pro Tyr Asp Gly Ile Pro Ala Ser Glu Ile Ser Ser Ile
                915                 920                 925 ctg gag aaa gga gaa cgc ctc cct cag cca ccc ata tgt acc atc gat      3012
Leu Glu Lys Gly Glu Arg Leu Pro Gln Pro Pro Ile Cys Thr Ile Asp
            930                 935                 940 gtc tac atg atc atg gtc aag tgc tgg atg ata gac gca gat agt cgc      3060
Val Tyr Met Ile Met Val Lys Cys Trp Met Ile Asp Ala Asp Ser Arg
945                 950                 955 cca aag ttc cgt gag ttg atc atc gaa ttc tcc aaa atg gcc cga gac      3108
Pro Lys Phe Arg Glu Leu Ile Ile Glu Phe Ser Lys Met Ala Arg Asp
960                 965                 970 ccc cag cgc tac ctt gtc att cag ggg gat gaa aga atg cat ttg cca      3156
Pro Gln Arg Tyr Leu Val Ile Gln Gly Asp Glu Arg Met His Leu Pro
975                 980                 985                 990 agt cct aca gac tcc aac ttc tac cgt gcc ctg atg gat gaa gaa gac      3204
Ser Pro Thr Asp Ser Asn Phe Tyr Arg Ala Leu Met Asp Glu Glu Asp
                995                 1000                1005 atg gac gac gtg gtg gat gcc gac gag tac ctc atc cca cag cag ggc      3252
Met Asp Asp Val Val Asp Ala Asp Glu Tyr Leu Ile Pro Gln Gln Gly
            1010                1015                1020
```

```
ttc ttc agc agc ccc tcc acg tca cgg act ccc ctc ctg agc tct ctg      3300
Phe Phe Ser Ser Pro Ser Thr Ser Arg Thr Pro Leu Leu Ser Ser Leu
        1025                1030                1035 agt gca acc agc aac aat tcc acc gtg gct tgc att gat aga aat ggg      3348
Ser Ala Thr Ser Asn Asn Ser Thr Val Ala Cys Ile Asp Arg Asn Gly
    1040                1045                1050 ctg caa agc tgt ccc atc aag gaa gac agc ttg cag cga tac agc          3396
Leu Gln Ser Cys Pro Ile Lys Glu Asp Ser Phe Leu Gln Arg Tyr Ser
1055                1060                1065                1070 tca gac ccc aca ggc gcc ttg act gag gac agc ata gac gac acc ttc      3444
Ser Asp Pro Thr Gly Ala Leu Thr Glu Asp Ser Ile Asp Asp Thr Phe
            1075                1080                1085 ctc cca gtg cct gaa tac ata aac cag tcc gtt ccc aaa agg ccc gct      3492
Leu Pro Val Pro Glu Tyr Ile Asn Gln Ser Val Pro Lys Arg Pro Ala
        1090                1095                1100 ggc tct gtg cag aat cct gtc tat cac aat cag cct ctg aac ccc gcg      3540
Gly Ser Val Gln Asn Pro Val Tyr His Asn Gln Pro Leu Asn Pro Ala
    1105                1110                1115 ccc agc aga gac cca cac tac cag gac ccc cac agc act gca gtg ggc      3588
Pro Ser Arg Asp Pro His Tyr Gln Asp Pro His Ser Thr Ala Val Gly
        1120                1125                1130 aac ccc gag tat ctc aac act gtc cag ccc acc tgt gtc aac agc aca      3636
Asn Pro Glu Tyr Leu Asn Thr Val Gln Pro Thr Cys Val Asn Ser Thr
1135                1140                1145                1150 ttc gac agc cct gcc cac tgg gcc cag aaa ggc agc cac caa att agc      3684
Phe Asp Ser Pro Ala His Trp Ala Gln Lys Gly Ser His Gln Ile Ser
            1155                1160                1165 ctg gac aac cct gac tac cag cag gac ttc ttt ccc aag gaa gcc aag      3732
Leu Asp Asn Pro Asp Tyr Gln Gln Asp Phe Phe Pro Lys Glu Ala Lys
        1170                1175                1180 cca aat ggc atc ttt aag ggc tcc aca gct gaa aat gca gaa tac cta      3780
Pro Asn Gly Ile Phe Lys Gly Ser Thr Ala Glu Asn Ala Glu Tyr Leu
    1185                1190                1195 agg gtc gcg cca caa agc agt gaa ttt att gga gca tga ccacggagga       3829
Arg Val Ala Pro Gln Ser Ser Glu Phe Ile Gly Ala
    1200                1205                1210 tagtatgagc cctaaaaatc cagactcttt cgatacccag gaccaagcca cagcaggtcc    3889
tccatcccaa cagccatgcc cgcattagct cttagaccca cagactggtt ttgcaacgtt    3949
tacaccgact agccaggaag tacttccacc tcgggcacat tttgggaagt tgcattcctt    4009
tgtcttcaaa ctgtgaagca tttacagaaa cgcatccagc aagaatattg tcccttttgag   4069 cagaaattta tctttcaaag aggtatattt gaaaaaaaaa aaaaaagtat atgtgaggat    4129
ttttattgat tggggatctt ggagtttttc attgtcgcta ttgattttta cttcaatggg    4189
ctcttccaac aaggaagaag cttgctggta gcacttgcta ccctgagttc atccaggccc    4249
aactgtgagc aaggagcaca agccacaagt cttccagagg atgcttgatt ccagtggttc    4309
tgcttcaagg cttccactgc aaaacactaa agatccaaga aggccttcat ggccccagca    4369
ggccggatcg gtactgtatc aagtcatggc aggtacagta ggataagcca ctctgtccct    4429
tcctgggcaa agaagaaacg gagggatga attcttcctt agacttactt ttgtaaaaat     4489
gtccccacgg tacttactcc ccactgatgg accagtggtt tccagtcatg agcgttagac    4549
tgacttgttt gtcttccatt ccattgtttt gaaactcagt atgccgcccc tgtcttgctg    4609
tcatgaaatc agcaagagag gatgacacat caaataataa ctcggattcc agcccacatt    4669
ggattcatca gcatttggac caatagccca cagctgagaa tgtggaatac ctaaggataa    4729
caccgctttt gttctcgcaa aaacgtatct cctaatttga ggctcagatg aaatgcatca    4789
```

-continued

```
ggtcctttgg ggcatagatc agaagactac aaaaatgaag ctgctctgaa atctccttta      4849
gccatcaccc caaccccca aaattagttt gtgttactta tggaagatag ttttctcctt       4909
ttacttcact tcaaaagctt tttactcaaa gagtatatgt tccctccagg tcagctgccc      4969
ccaaaccccc tccttacgct tgtcacaca aaaagtgtct ctgccttgag tcatctattc       5029
aagcacttac agctctggcc acaacagggc attttacagg tgcgaatgac agtagcatta     5089
tgagtagtgt gaattcaggt agtaaatatg aaactagggt ttgaaattga taatgctttc     5149
acaacatttg cagatgtttt agaaggaaaa aagttccttc ctaaaataat ttctctacaa     5209
ttggaagatt ggaagattca gctagttagg agcccatttt ttcctaatct gtgtgtgccc     5269
tgtaacctga ctggttaaca gcagtccttt gtaaacagtg ttttaaactc tcctagtcaa     5329
tatccacccc atccaattta tcaaggaaga aatggttcag aaaatatttt cagcctacag     5389
ttatgttcag tcacacacac atacaaaatg ttccttttgc ttttaaagta attttttgact   5449 cccagatcag tcagagcccc tacagcattg ttaagaaagt atttgatttt tgtctcaatg     5509
aaaataaaac tatattcatt tcc                                              5532
```

<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
gcgtctcttg ccggaatgt                                                   19

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
ggctcaccct ccagaagctt                                                  20

<210> SEQ ID NO 20
<211> LENGTH: 20
<212> TYPE: DNA
<213> ORGANISM: Artificial Sequence
<220> FEATURE:
<223> OTHER INFORMATION: PCR Probe

<400> SEQUENCE: 20
ccacgcattc cctgcctcgg                                                  20

<210> SEQ ID NO 21
<211> LENGTH: 21
<212> TYPE: DNA
<213> ORGANISM: Artificial Sequence
<220> FEATURE:
<223> OTHER INFORMATION: PCR Primer

<400> SEQUENCE: 21
caacggattt ggtcgtattg g                                                21

<210> SEQ ID NO 22
<211> LENGTH: 26
<212> TYPE: DNA

```
<213> ORGANISM: Artificial Sequence
<220> FEATURE:
<223> OTHER INFORMATION: PCR Primer

<400> SEQUENCE: 22
ggcaacaata tccactttac cagagt                                        26

<210> SEQ ID NO 23
<211> LENGTH: 21
<212> TYPE: DNA
<213> ORGANISM: Artificial Sequence
<220> FEATURE:
<223> OTHER INFORMATION: PCR Probe

<400> SEQUENCE: 23
cgcctggtca ccagggctgc t                                             21

<210> SEQ ID NO 24
<211> LENGTH: 169998
<212> TYPE: DNA
<213> ORGANISM: Homo sapiens
<220> FEATURE:
<221> NAME/KEY: exon
<222> LOCATION: (1208)...(1472)
<221> NAME/KEY: intron
<222> LOCATION: (1473)...(124390)
<221> NAME/KEY: exon
<222> LOCATION: (124391)...(124544)
<221> NAME/KEY: intron
<222> LOCATION: (124545)...(125409)
<221> NAME/KEY: exon
<222> LOCATION: (125410)...(125595)
<221> NAME/KEY: intron
<222> LOCATION: (125596)...(128711)
<221> NAME/KEY: exon
<222> LOCATION: (128712)...(128848)
<221> NAME/KEY: intron
<222> LOCATION: (128849)...(133400)
<221> NAME/KEY: exon
<222> LOCATION: (133401)...(133469)
<221> NAME/KEY: intron
<222> LOCATION: (133470)...(134652)
<221> NAME/KEY: exon
<222> LOCATION: (134653)...(134773)
<221> NAME/KEY: intron
<222> LOCATION: (134774)...(136116)
<221> NAME/KEY: exon
<222> LOCATION: (136117)...(136261)
<221> NAME/KEY: intron
<222> LOCATION: (136262)...(137936)
<221> NAME/KEY: exon
<222> LOCATION: (137937)...(138053)
<221> NAME/KEY: intron
<222> LOCATION: (138054)...(138637)
<221> NAME/KEY: exon
<222> LOCATION: (138638)...(138766)
<221> NAME/KEY: intron
<222> LOCATION: (138767)...(138864)
<221> NAME/KEY: exon
<222> LOCATION: (138865)...(138940)
<221> NAME/KEY: intron
<222> LOCATION: (138941)...(139765)
<221> NAME/KEY: exon
<222> LOCATION: (139766)...(139860)
<221> NAME/KEY: intron
<222> LOCATION: (139861)...(142245)
<221> NAME/KEY: exon
<222> LOCATION: (142246)...(142445)
<221> NAME/KEY: intron
<222> LOCATION: (142446)...(143605)
<221> NAME/KEY: exon
<222> LOCATION: (143606)...(143738)
<221> NAME/KEY: intron
<222> LOCATION: (143739)...(145838)
<221> NAME/KEY: exon
```

<222> LOCATION: (145839)...(145931)
<221> NAME/KEY: intron
<222> LOCATION: (145932)...(147385)
<221> NAME/KEY: exon
<222> LOCATION: (147386)...(147544)
<221> NAME/KEY: intron
<222> LOCATION: (147545)...(153274)
<221> NAME/KEY: exon
<222> LOCATION: (153275)...(153321)
<221> NAME/KEY: intron
<222> LOCATION: (153322)...(155088)
<221> NAME/KEY: exon
<222> LOCATION: (155089)...(155231)
<221> NAME/KEY: intron
<222> LOCATION: (155232)...(156025)
<221> NAME/KEY: exon
<222> LOCATION: (156026)...(156151)
<221> NAME/KEY: intron
<222> LOCATION: (156152)...(156826)
<221> NAME/KEY: exon
<222> LOCATION: (156827)...(156928)
<221> NAME/KEY: intron
<222> LOCATION: (156929)...(163399)
<221> NAME/KEY: exon
<222> LOCATION: (163400)...(163586)

<400> SEQUENCE: 24

```
ttgctcccct tcagagacag caaagggcag gtctgtagct tcacttactt caggattgtg      60
attttttgaca gagccgagag atcagggttg ttgaaccagg cctgaaggtc ctagtgaatc     120
tcgtgaagag aggagggtc tggctgtaac atggacctag aggacatttt tactgcagga      180
gaaggaacag tggggatggg gtggacttgc caaaggaata tagctcaagt tcctgcagcc     240
caaaaaagct cagtttcttt tggccaaagc ttccgcgagt ttccctggca tttctcctgc     300
gggagctaca ggggcagtgg gacacttagc ctctctaaaa gcacctccac ggctgtttgt     360
gtcaagcctt tattccaaga gcttcacttt tgcgaagtaa tgtgcttcac acattggctt     420
caaagtaccc atggctggtt gcaataaaca ttaaggaggc ctgtctctgc acccggagtt     480
gggtgccctc atttcagatg atttcgaggg tgcttgacaa gatctgaagg accctcggac     540
tttagagcac cacctcggac gcctggcacc cctgccgcgc gggcacggcg acctcctcag     600
ctgccaggcc agcctctgat ccccgagagg gtcccgtagt gctgcagggg aggtggggac     660
ccgaataaag gagcagtttc cccgtcggtg ccattatccg acgctggctc taaggctcgg     720
ccagtctgtc taaagctggt acaagtttgc tttgtaaaac aaaagaaggg aaaggggaa      780
ggggaccctg gcacagattt ggctcgacct ggacataggc tgggcctgca agtccgcggg     840
gaccgggtcc agaggggcag tgctgggaac gcccctctcg gaaattaact cctcagggca     900
cccgctcccc tccatgcgc cgccccactc ccgccggaga ctaggtcccg cggggccac       960
cgctgtccac cgcctccggc ggccgctggc cttgggtccc cgctgctggt tctcctccct    1020
cctcctcgca ttctcctcct cctctgctcc tcccgatccc tcctccgccg cctggtccct    1080
cctcctcccg ccctgcctcc ccgcgcctcg gcccgcgcga gctagacgtc cgggcagccc    1140
ccggcgcagc gcggccgcag cagcctccgc ccccgcacg  gtgtgagcgc ccgacgcggc    1200
cgaggcggcc ggagtcccga gctagccccg gcggccgccg ccgcccagac cggacgacag    1260
gccacctcgt cggcgtccgc ccgagtcccc ggctcgccgc caacgccaca accaccgcgc    1320
acggccccct gactccgtcc agtattgatc gggagagccg gagcgagctc ttcggggagc    1380
agcgatgcga ccctcgggga cggccggggc agcgctcctg gcgctgctgg ctgcgctctg    1440
cccggcgagt cgggctctgg aggaaaagaa aggtaaggc  gtgtctcgcc ggctcccgcg    1500
ccgccccgg atcgcgcccc ggaccccgca gcccgcccaa ccgcgcaccg cgcaccggc      1560
```

```
tcggcgcccg cgcccccgcc cgtcctttcc tgtttccttg agatcagctg cgccgccgac    1620
cgggaccgcg ggaggaacgg gacgtttcgt tcttcggccg ggagagtctg gggcgggcgg    1680
aggaggagac gcgtgggaca ccgggctgca ggccaggcgg ggaacggccg ccgggacctc    1740
cggcgccccg aaccgctccc aactttcttc cctcactttc cccgcccagc tgcgcaggat    1800
cggcgtcagt gggcgaaagc cgggtgctgg tgggcgcctg gggccgggt cccgcacgtg     1860 cgccccgcgc tgtcttccca gggcgcgacg gggtcctggc gcgcacccga ggggcgggcg    1920
ctgcccaccc gccgagactg cactgtttag ggaagctgag gaaggaaccc aaaaatacag    1980
cctcccctcg gaccccgcgg gacaggcggc tttctgagag gacctccccg cctccgccct    2040
ccgcgcaggt ctcaaactga agccggcgcc cgccagcctg gccccggccc ctctccaggt    2100
ccccgcgatc ctcgttcccc agtgtggagt cgcagcctcg acctgggagc tgggagaact    2160
cgtctaccac cacctgcggc tcccggggag gggtggtgct ggcggcggtt agtttcctcg    2220
ttggcaaaag gcaggtgggg tccgacccgc cccttgggcg cagaccccgg ccgctcgcct    2280
cgcccggtgc gccctcgtct tgcctatcca agagtgcccc ccacctcccg gggacccccag   2340 ctccctcctg ggcgcccgcg ccgaaagccc caggctctcc ttcgatggcc gcctcgcgga    2400
gacgtccggg tctgctccac ctgcagccct cggtcgcgc ctgggcttcg cggtggagcg     2460
ggacgcggct gtccggccac tgcagggggg gatcgcggga ctcttgagcg gaagccccgg    2520
aagcagagct catcctggcc aacaccatgg tgtttcaaaa tggggctcac agcaaacttc    2580
tcctcaaaac ccggagactt tctttcttgg atgtctcttt ttgctgtttg aagaatttga    2640
gccaaccaaa atattaaacc tgtcttacac acacacacac acacacacac acacacacac    2700
cggattgctg tccctggttc aagtgtgcca agtgtgcaga cagaacatga gcgagtctgg    2760
cttcgtgact accgaccata aacccacttg acagggaaa catgccttgg aaggtttaat     2820
tgcacaattc caaccttgag ctgcgcgggt tccaagagcc aggcccgtac ttgctgttga    2880
tgtcattggc ttggggagtt ggggtttggt gcccagcgcg gtcgttgggg gaggggcaag    2940
gcatagaaca gtggttccca gaccttgctg cacattggaa ttacctggga ttaaaaaaaa    3000
aaaaatcaaa acaaaaacca gtgtctggct cccgccccca gacattctga tttaattggc    3060
atggggcaag acctggactt gggatttttt ttaatgctct tcatgtgatc tgttgggcag    3120
ccagatttgg ggatcactag acggaagaag gattgttaaa gtctccggag atgttacttg    3180
ccaatgctaa gagctctttg aggacatctg gaattgttac aatattgcca aatataggaa    3240
agagggaaaa ggtagagtgt gattccaata ataaaggatt ccgcttttca ttgaaggaac    3300
tggtggaaag gtttcttctc tgctgagcct gcaggcccgt cctgcctgcc tggggtgccc    3360
gggagacgcg ggcctgctcc ggagactgct gactgccggt cctgttagtc aggtgtcagc    3420
cctgtctctg ccgaagagac tcttctcttt attttaaatt aaaccctcag agcaccacca    3480
aagcatcact tttctccctc cattggtgtt ctcattcttt gatgttactt gtttgaacac    3540
cactattagt agttggagat ttgttcctga gaaaaatata aataccactt aatttgcctg    3600
tttgtcccgc attcactcaa aacagaatgc tcctgaagac aagagagaga gtaggagaac    3660
agacgctatt ccattacagt aacataaaag actggatttt caggggcaaa ttattaaaat    3720
aggagatgag ctcttttaac agaaatttgt ttaaggcctg tgtctatcaa attcagtgga    3780
ttttattcaa gatgcacttt gtttagtggg agttttgttt ggttctggga catgctaact    3840
tctagacttg ctgctcttag aggtaatgac tgccagacac catttcatga gtcctaatcc    3900
```

-continued

```
ccacattaag cataagaggt gcacactctc ctcctatggg ggaaactgag gtacgaagaa    3960
ctaaagtgac tttcccacag ctggtgggag gcagacggga aattcacacc aggggcttcc    4020
aactccagat ccctctctca acttccaaac tccactgcct tgtccgagtt ctggtttcag    4080
gagatccaaa tcaggtgtgt gcaaatgtct aatgtcagag ctggcaaggg gaaagggccc    4140
agggagccgg ctcatgacga tgagcctgtc tgaagcttca acgcgggctg tccggcagtc    4200
tgcattcctg ccgagttcct cagccctctg ttgggtcacc ttccatagag gcagcttagt    4260
cctcagttca gtgagcatgg agtggagact gcttgagggg tgctgagcaa agccctgcct    4320
cttacaggat gaaggtgctc tccagaaggg acactggaaa gtattccaag gcgagtcgaa    4380
ttcccaactg agggagcttt gtggaaataa gcccgcccag ccccacttct ggagacgttc    4440
ccattcagta ggtccgagct gtcttaaaga gaaaccaaag tggggatatt aatggtatcc    4500
aaagtgagat ctaccccacc ctccctcctc aaaggaggtc agatcaagaa agcccaagcc    4560
cggcctggca attgggacct ttcttctcac tccagcccag ggtgaaggtg gacaagtcac    4620
tttgaccctt caggcttctg agctgttgtt tctgaattca gtgaatattt actgagtgca    4680
tagaatatgc tagatattct gggctaaagg ttgaaggggg ggtgagtttt aagggtttct    4740
gctcttgctt ccagattgct ttcaaatctg gaaaggacac cagtggtttg tgtgttagac    4800
ccacactgcc gtagcacaga atacaagaaa ctggctgaga gctccaatag gcttttaaca    4860
gtaatttctg gcttcacgta tttagtttca taactcatga ttttcaaaa acttctggtt    4920
tgaagacacc gattgccgaa agtccattgt gctgcataat tacacttggt ccacgtgaca    4980
gcactaacat gttctgaaat gttttttagaa gtagtctcag caaagatgaa ggattcctcc    5040
ctgtttgaaa agaaaatatt ctttgttttt tctttgatct aagctctaag actagcagct    5100
agcatctgaa acttttttga cgagagtgac aaaccaactc taatattaaa ggcaattgat    5160
gattatgggc actgaaggga aggtaacccc aggctggtgc cccggaatag ggatgggtca    5220
caatgttgag gacatttcgc ctgttgcaga acccacctgc aacacagtgt ggcccttgcc    5280
atgtgacttg tgtgtgtgcc tgtgtgtctg tgtgtgcgtg ttttaatttt gacttcataa    5340
gtactctagt tatgagctta tttaacattg ggttttacta ataggggtat gtgttgagaa    5400
aatttcaaag ttttagaata tggttcaccc acatgttgct tccctgtaaa tataattttt    5460
aaaaccagat tctgggccgg gcatggtggc tcacctctat aatcccaaaa cgttgggagg    5520
ccgaggcagc gaatcatga agccaggagt ttgagaccag gctgaccaac acggtgaaac    5580
ccagtctcta ctaaaaatac aaaaaaaatt agctgggcgt ggtggcaggt gcctgtaatc    5640
ccagctactc aggaggctga ggcaggagaa ttgcttgaac ccaggaggca gaggttgcag    5700
tgagccaaga tcgcaccatt gcactccagc ccgcgcgaca gtgtgagact ccatctcaaa    5760
aaaaaaaaaa aaaaaacaga ttctgttcct cagatccatt ccattttgt tttccttat     5820
cacttatgga catttgaaat tatggtaata acattgtta gtctcagtta attattactg     5880
gtttattctt gaaccactaa tccatagaga atagagtgta aatcttaact tgttcctgta    5940
ggccatcccc attaaacatc atagtgtttt ctcattcgtt ctttttcgtt ttcctcctac    6000
aggaatgaat tttctaagaa aattccagca gttggctctt tggacgacat ctctagattg    6060
tcctccattg ggcccatagg cacaagctgg ccagtttgaa tttgggcaag aatccaggca    6120
ttggaactta ttcaaataac tagttttgcct gtaattttca cttttcaga gtcatctgat     6180
aaagctttct tgctacacat ttagatagat acactcaatc cagttgtcta gaaagttccc    6240
tgagccagct gggagcagga ggggtagttg gggccaggaa tattgggggt gtgtttactg    6300
```

```
agcccctaga aagtaagtgc tagatttgac atttcaatcc ctgaaggccc tgaagttcag    6360
tatcaaatga ctggtcctgt ggactgagca tctgtgaatt gcatatgctt agagtaaatt    6420
ttactcctac cagtttcagc agcttgcttt agcaagcagt atggaaacac taacatgggg    6480
gagtagaatt tctctctctg atccaagttt tatctcattc tggtgggttt tcaaggagag    6540
actcggagtc caagtgtcct ttctgaatat atctggaact tctcattaac aaaagactca    6600
agttataatt taggggacaa ggcacccaat gagaatgcct tgcaggcagc cctaagtaca    6660
cctgcaatta caccattact agcgcggcag cacacatggc cctgacttag tttaaataat    6720
tacgtaagtc aaccatgatt gtttgccctt tgcatagaag ggcaagtatt ggtacctgtt    6780
acaacttagg cttttttttc tttatgtttg agccatgatg agtgatttac actgttgcat    6840
ccatatgttg agatgtaaga ataaattaga cttggtaatt gcccttaagt gtctggaagt    6900
caactgggga aagagagcta gagataataa gtgtgaaaca atgtcacaga atcaatgacg    6960
gaactcttcc caggacaaag gatgactttt gagttcagtc tttgcctttta attctacatg    7020 gggaggagag cacgtttagc cacaaatgga agggattact catttgagct atttggttat    7080
atgattattt ccccagagaa taggatgtgc agggcattac acaagcagtg ccaatagcag    7140
caaagttctt gagagtgcta gtaattcaaa tggcaggaag agaaggaata aatggtaagg    7200
ctacctacag ttcacagaga gctccatcct cactgtggct ttggattttg tcctgtgtga    7260
aagagaagtg actgtgaact gacatgctgt gtttggtgtt ttagaaagat ggctgcagca    7320
gcggtttggg gaatggactg caggagtggc attggaaaca ggaaggttca tgactattgc    7380
cagagacaga ggatgaagca ggagcaagga agattcagga caggggactc cggggctgat    7440
caggaggcag aactggttga taagtatatg tagcagcata agaaagaaag aatcccagat    7500
tgacacccag gcttctcact tggaagcctg gatagatact gaatgcaatc acaaaggctg    7560
ggaagtcaat gggactgcag ggaagggaag ggaagggagg agaagaggaa gggcaggagg    7620
gtccaatatc aatattcagc ttttagatgt gttgagcttg aagtgctcag atggagaagt    7680
ccaggaggca gtagaatacg gtggtccaga gcacaggaga gcaatgtggc ttgagttgtc    7740
atttgctcac atatttccgt gtcagttact tgtcttagat cacagaacaa gttctccctct    7800 cacagtttcc tggctccacc tgtctcatgc tcaccgtcag catcgaaatt gagccacacc    7860
aggggtcctg gataccagct tctctctagg tgaggctgct atagtcagca gctgattagt    7920
tgcagttatc agcaactggt aatataatat attgtgcata taagtgtacc agaagtcatg    7980
tttatatatt gctgcaaata ctcggaatgg ggatctcttg ttccctgctt aagaccacat    8040
cacattactt ggttttgtac gctagtggct gaaccaaaaa aagtaggaga tgatttttt    8100 tctttttttct taaagcagta gcttttgaac cttgaccatg cttctaaacc agctgagggg    8160
cttttgaaaa agagggtgcc ttactgtgcc ccagaccagg acaatcagta tttctgggga    8220
atggagcctg gcacacacac atttcttaaa gctcccttgg caattctgag gagtggatta    8280
catgttgtat gtagctcgta acgaaagaaa tcttgtctttt gctctcagac ccccatttct    8340
tactcatctc atgagctcct tcgagatcca gaaacagttg catatttcat tagtaaatca    8400
gttccagagt cacattttat ttcacaagtt agtccattaa aagtttcctg cagtgaggaa    8460
atagccagaa agaacactcc accctcctc ctttttataa ctatagggtc tggctcgaca    8520
gagcaggagc atcgccatct tggacaagcc cctcattcta aagttcacct taataaaaaa    8580
ctgcctaaat tcaaactgca tcagcctaat ggctaaggtc agcatgacca taaaccacaa    8640
```

```
ataacatctc caaccggaaa cattcgaaac tcctcctcga ccagagacat gctagtcccg   8700
agataacccc cctccagcag ggaagatgcc agtctcggga taacctctct ctggccggaa   8760
agatgcctgc cccaagataa acttgcctcc tcccagagat attccaaccc tgccataaaa   8820
cttctccctc aaacaggaac attccaaaat tctgataatc tccctcaccc taaaaccaat   8880
atatactcct agtctgtaag agaaagcgct cttgaccaaa attcaccagg agtgcctccc   8940
aggttttaac taaagaaaac ctctctttaa ctgccaaaaa aaaaagggga aaaaaaaaag   9000
ctttctgcag tggcttttcag cgggcccagc atggcagcag cacctgagaa cctgttggag   9060
atgcacactc ttggacccca ccctggcctc tgagtaagac actggaaggg caggccccgg   9120
tctgtgcaca caagtcctca gggagattct gactgatgca tgccagattt tgagaactgc   9180
tgatatactc caggcacatc gcatgctggg atctagatac accaagggaa caaataact   9240 gcacttgtcc tctgaggacc gacttacctt ttggaagggc tgagaaagag agacacatac   9300
aagatcactc cctgtaatgc aatgttttat aacagatgtg atttgggatt tcagtgggag   9360
cccaaaagag ggactgacta attcagcctc tgtgacaagg ggagtttctc agaaacagaa   9420
tgcttagctg ggcctccagg cacagggaca ggaatgagga aatacttgta ggccctgtgc   9480
tccttcagca aaaccctcag tttcttgtta ttttttataaa tgcaaacatc ttattaaagt   9540
agatgctaag gcattagaat ttcctgcttt attttttctaa atgaccatga ggaaacctgg   9600
aatgtcaaag ataaagtgca acacattctg catttaaaaa ttaaaatgat cctttttaaa   9660
agtagcaacc agatgtgaaa aattggactg gagtccaggt tatagttgat agctttaact   9720
ttctccccaa cagcaacagc acaatttttcc ctaaaatgtg ttatgaataa gtaaaatgac   9780
tacttcacat cctttaactc ttcctacaga aatctaagag agaaatgaaa caaaagtttg   9840
cacagttcta gacacgataa atacatgtga aatcacacaa ctcagaaaat gtcccttaaa   9900
ttaattgagc cattggtact tgtgaattag aagagacatc tatgttctga tccactgttg   9960
aaagctgtac aatgttacct atttatttgc agacatcctt tggaaacaaa taggtagatt  10020
tgcaacaaat aaagagtgga gtacagctgc tgacattacc ttgtatattc atgccttttat 10080 gtaaaaaaaa aaaaaaaaat atatatatat atatatatat atatatatat atacacacac  10140
acacacatat ggaggtaaag accactgctt gctttgcagt tgttttaaga gcattcatga  10200
aggattttat tttataagca gaaatgtgat atctgacgat tttaccacta catgcttgca  10260
ggccagtgca cagcagatga cgtcatgatt gttttagcag tcctatcgtt ttacttatga  10320
tgtcattaca acccctttgct aaaatttctt tccttttactc caggttttgg ataaaattga  10380
tgcattgcac atagtctctc tgataagaca aactggcatt tgtatgtgaa aaactgtgca  10440
tgttttagtg tctctgctga tactcaaatt atccattatt ttagtgctgg aataaaaaca  10500
aaccacttag tgaatttgtg caggtcctta aggacaggca aaggtgtcct gagattttct  10560
gatcattgta taccaaattt tagaaacttt ttcaaaaaca ttttttttaat ttcaaaaacc  10620 tggttttgtt tatttaccag caatcattga atacctgaaa gctttcagga gattttatta  10680
caatggtttc tattcactta caaaattatc tcctagttca ttctcataca ctgtaagcca  10740
ttgtaaatgc ttcaaattgt gccgaacaag ataaactaga caaactattt taagtttgtt  10800
ctagtgctaa cttgcaagat ctaatggctc caactagatt ttttaaaataa agtatatttt  10860 aatatattat tagaaagtta agcaattatc tgtttatagg taacaaaaac cctggaaccc  10920
caatgtcaga tgtcatccac ttttgattaa gtccaaacat atgacagata aacaaaagat  10980
ggttggctgg gctcagtggc tcatgcctgt aatctcagca ctttcagagg ccgaggcggg  11040
```

-continued

```
cggatcacaa ggtcaggagt ttgagacttg cctgaccaac atggtgaaac ccgcctctac    11100
taaaaataca aaaaaaacag ctgggtgcgg tggcacgtgc ctgtagtccc agctactcag    11160
gaggctgagg caggagaatc acttaaacct ggaaggcagg ggttgcagtg agctgagatc    11220
acaccactac actccagcct aggcgacaga gcaagactca gtcaaaaaac aaaaaaaaag    11280
tggtcattgg agaattattg tgtcacctgt tgttttttaa tgtactaatt ttgagaggct    11340
tttaaataga gtgcactata gaactttttc ttggcttcaa tttgctacaa tgttaataga    11400
gaatcagaaa ccttatcctt atagatgttt cttgattttt ttaatttctg gtgacattta    11460
tgagtgagaa tagtgtattg ccctgttttc tttcttactc cccttctttc ttccttcctt    11520
gctttctttc ttcttccctt ccttcttttct cttcctcgct ccttcttttt tacaagctgt    11580
tatgaattag ccttcacaga gaaagaaaaa ttttttataaa taactggaaa tgaaactttg    11640
caaaggactg cagatgaaaa actttgtcaa atgactgtaa aaatatacta tataatttc    11700 aaaagttaga aagtaccaaa cacactcagt attcatggtt atacaagtat gcatacacat    11760
gtattgctcc ctgaaaagtg gtgttgttaa gggagttttt cttagtacgc ggcttaacat    11820 attttttttct gtaatttgtt gttagttata atggggagag aaaacaggtt agagtctccc    11880
ctctcagttt caccttccat aaaacagcta aactagacga tcgtcagact ccttccagct    11940
gaaaacatct gtaaaattaa aaacaaatct aaatgtatgc aagatatgta tttaaacatg    12000
ctggtaataa gtgtgctgtc cctataattt agatgctaaa acattgatgt cataataata    12060
acaacacctc gcatttgtac agcacctcat agtttacaca atgccttaac attcttctct    12120
ctcagcctcc tacaacccca caggattggg atagctttcc agattgggag gtgagggacc    12180
caggctcaga gcgattctgc tgttgtccgt aatcaccagg ctggtgatca gtgggcactg    12240
ggtgctctcc tgctacacag cactgtctct caacatgcag gtcaaggtta cttattcctc    12300
cttcaagacg tcattgggtt ttttagctat ggatgcccca tcacttttag ttctatttgt    12360
gaatcaaagg ctaaataaag tattcctcaa aatttgttat acttctgtta ctaatgctta    12420
atgtccctca caatttctgt atatttctgt gtatttctgc tctgttttgg ttccttttccc    12480 aggtttcttt tttgttatga agtagttttt agactcaagt ctcttctgta tgtgttataa    12540
ctgcccattc cataagatac agggcagtga atttgtgagc cttgaaaata tttactttag    12600
aaatgagaag tatgactttt caacgttgtg tcatcaactt ctgtaaattt tccagaccta    12660
taaatacttg cagaaaaaaa atgaaaggag aaggcaactt gatttagcag ttgggtcagt    12720
tagcaatgcc tatggcaagc tgtagtaatt cccttacata gatttgtaag actcatttct    12780
atgatttaaa tgaaggcata cacttaacct ctttagggtg tgaaacagct tttacaaaaa    12840
gagacaaact taagaaacag tgtggccctc caagagtgtt cattttccat atcataccat    12900
ttgtaataag ctattctggc tgggattac ttgcaagcat tggcttttaa gaagagatgg    12960
tttcacacat caaattattc acttggaggc actttctggg ttgaaggaat ggaatggaga    13020
gtgcggcagt gagtagatct ctcagtgacg gtgatgtgcc tctcccagaa gaaatttcaa    13080
aatgcagtgt tcattttcct ccacaagaaa ggaagaaact gttttgttat tgtttattcc    13140
taacatagtg gaaactttc agtactctgg cagaaatttc ccaaaagcaa ttttctattt    13200
catgattata aagtagcaaa ggaaaaagtc ctgcactcca gctgagcaat ggatctccag    13260
ttgttatcta ggtgctgcag gtttagagag gattgccagg agaacacatc gattttcag    13320 gcctgtgatg acgtatctct tgttgaataa gtaaaccctt ccagtaaaca gacagttagt    13380
```

| | | | | |
|---|---|---|---|---|
| atattgattt | cagggtggct | ttagccactg | aacctgtaag | tcttgcaaag | gttacttggg | 13440 |
| caaaagcatc | attattttac | cttcagtcaa | caaaaatcta | cctggccaag | gcagaacaga | 13500 |
| aagttcagca | atttgatgaa | gtgggacaac | atgaagaatc | aggtgagttg | cctacttttt | 13560 |
| cacttcactt | tccaccttta | gagattcttg | tttagatgca | gagtagtgac | gtgcctggtg | 13620 |
| tcagggagag | agttgaatga | gaaaagtccc | agaagggcag | aagacttggg | tgattatctg | 13680 |
| agtccatctt | tccttatcac | atgacagagt | tcttgaagtc | ttggctagga | attctaggct | 13740 |
| tttagattct | ttgggcaatg | gctactaaat | gttcataatg | ttgctcagtt | gcaaaaacaa | 13800 |
| gacattcaaa | ctatagccag | ggagataagt | agtcacgaac | tcaaggccta | aattctgctg | 13860 |
| atggagccga | tgagaattgg | gtgctaaggc | aaagagagtt | gccaatatta | tattcttcgg | 13920 |
| ggttttttgt | ttttattcgc | attttggaaa | aggaaaatat | tagcattcct | ctgacttaat | 13980 |
| attgagaaga | cattgggcac | tcttttttcct | cccacacttg | tcttctttca | ctaggtgaca | 14040 |
| agggaagagg | tagcatgagg | tggtggtcac | aggtgagagg | ggctgttgtg | agcacaggca | 14100 |
| tgttgactgc | acattggtca | cctagtagaa | gttttgcagg | cttggtgact | tctgaacact | 14160 |
| gttttcaagg | ttgattttta | gttgagagaa | cctctaggta | ccacgtaatg | ttattaacag | 14220 |
| tagtactgat | ctcacaatcg | ccctatgtcc | cattcacaag | atgttctgcc | aagccataaa | 14280 |
| aggcccagtt | aagtttaaga | gaagtctcaa | aagtaacaga | tgataactaa | ttaataccca | 14340 |
| gtgattttga | aatgtagaca | tcaaacatac | caattcagtg | gtatcatcct | tagaggcaga | 14400 |
| cagaggatga | ttaaatcatt | cagcccatct | ctgtctgagg | acgcagctta | gcacagcatg | 14460 |
| gtggaggcta | aatgggcctt | aagggaaaaa | atgatatctg | aagatgcaat | ttatttcaaa | 14520 |
| aagagtttgc | tcccgtgaat | tttcactctc | tatgtagaac | ggcaccagca | cacacttttc | 14580 |
| ctgagccttt | gcatgtgtgg | caggcagcgg | cctggcatcc | tggggaactg | aatgaggacg | 14640 |
| cagatgaccc | ggacgtgttc | acagtttgac | acatctgact | cccagatcag | ggacagctag | 14700 |
| ctttgctggc | tggttaagtt | gatgattcca | tctttgcctg | gttctctgac | tgtctcatgc | 14760 |
| tttctgttat | tactatttg | cagcagatat | ttctgctcat | ttttcaatca | tatatgcatc | 14820 |
| ctggatggca | tagagttgat | tctcctaaca | aatcagtgtc | cctttgtatt | tttttctggc | 14880 |
| cataagatag | aatatatatg | tcatttatta | aaaatggaga | aaatgttcag | gagtttcttg | 14940 |
| actcagagag | ggaaaaggga | tactcagggc | acttttttcag | ccaggaattt | actacctttg | 15000 |
| cagggtaaag | gggactcacc | acgctggaag | tcaaaataag | ccaccagtgc | caagtgttca | 15060 |
| aagcccttag | aatcacaatg | ctcttaaagc | aaagtcttca | acaatgcttg | aaaacttcca | 15120 |
| ctggttctca | gtatgtccaa | aattgtcatg | tctatgaatg | attttctcaa | tctgaaaatt | 15180 |
| tttatagcag | gctaaagaat | gagataggtc | agtgtgattc | tagaactaat | cattaacatt | 15240 |
| caatagatga | ctattttatt | ctagaaaaag | cagcaacttt | ctatttactc | tctattttga | 15300 |
| gggtaaattc | tctgtaagta | gaaaaagcaa | aatgtggaca | tgggactaac | atatgaatat | 15360 |
| acaaagcaaa | tgtaccgaaa | aaatcttaag | acctgccttg | tggtgttttt | tgttttgttt | 15420 |
| tgttttcatt | aaagtgactt | gttagcctct | tgctccctgt | gaagcacagg | gaggtgacgt | 15480 |
| gatgtgcaca | gggcagactc | tgccatatgc | cctggccttg | aactcagggc | cccctgggga | 15540 |
| ctgcagggga | tgctggccat | gctgagcaat | gcctgtgggt | gtcagtttcc | tcatctgcag | 15600 |
| aatgagggta | ggcctggtgc | ttatttcata | gggtcgcaga | ggggattcag | tgacagggtg | 15660 |
| gtgtagaggc | tggagcgtgc | cccatgtgtg | cacgacagcc | ttccaactag | gggaggcggg | 15720 |
| cctgggctct | caccagagag | cctgtgttct | ccatggctac | atgactttgc | cccagacgtc | 15780 |

```
cttcccgtgg tctggaccct gggaagtcgc caagagccag acaggagaaa ggctccactt   15840
ggctctcctc tttggtgacc atcccttgcc tccatggcgg gactctcagg tgacatccca   15900
ccaaccctca ctttgcttcc ctggtgggtc tcactttccc tcaagagtgt tgctttttg    15960 tttcctgcat agtcctgggc cagttttgat aaccctcttc atttcacttc agaaaccctg   16020
atgatttctt cctgtgctct ttttacctta ggacttttac tatgacgact gtgactggcc   16080
catttcttgt ttttttctc ttgctctgct ttctccccca tcatcactaa agcagacatg    16140
gcaatgatgg ccatgcacac tttccaaggg tccagctgta gatcttcatg gttccccagg   16200
tgcctggacc atcttgtgag gagggaggca acacaccct gcctggagca cttggcccctt   16260 tcggcaatgt tttggcttcc tcaagtgaga aagaatgga tttgtattcc ccctctgcat    16320
tattgttttt gttttgtttg tttgttttgt tttgtattga acagagtct cacttttttc    16380 cccaggctga agtgcagtgg cccgacctcg gctcactgca acctccacct tccgggttca   16440
agtgattctc ctgtctcagc ccctgagta gctgggacta caggtgcccg ccaccacacc    16500
tgactaattt ttgtatgttt tgtagagaca gggtttcacc atgttggcca ggtgcccatt   16560
attatttgat ctggaattaa ctgagctact gcaggaattg cttgattcac tgatgactgg   16620
tgttgagcca gtacacaccc acacccaagg actgtgactg tcttctgagg tccatcctca   16680
gaaattcctg tctcttcacc tagtgtgtaa taaggcctgc gcgtgttata tggaactgta   16740
aaaaatgcgc caaccatctg tccttcctct ttatctgatt acttatcatt gttctctaag   16800
ttgcaagtta atagactgat cataaattaa tgcatgctgg agacttgctg tttcctacta   16860
gcagcatata aaagttattt ttaaagttgt tttaaatctg tgagtaaaaa taaattgctt    16920
tgctgcaaga acaccaaac atggaaaagc taacggttca aagttaataa tttatcttat    16980
ggacatcact agtggcatag ttgctttaaa cagtgagagg atttaataga tatttgattt    17040
gcaagtggga tgaagggtgg tctaaccttt gtcctgtgtt taccttccat gagatcctag   17100
aggttgtaca gcacagtagt ggcatgtgac acacttgaga gtgcctgttc tgtttggaaa   17160 cctggaaaact atgaagggaa gtggccttcg agcttaacac ataagacttg ggaggcaaaa   17220 cctttattc tctttaaata ttcactttag gataagcatt ttttaggtg ttaggaacag     17280 ggaaaactgt gtggttagga aggaagaaag aagaaagtta actgttgtac attccctagg   17340
taatgttttt aagcattgtt attcacttt aaaacacatt ttatttattt ggacttaata    17400
ttttgatctt attttttcaa tttctttaa tttaacagac aggatgagtt tttttatagt    17460
tgtattactt agaaattata ctaaaaatgg ccgagtgtgg tggctcacac ctgtaatccc   17520
agcactttgg gaggccaagg caggtggatc acttggatca cttgaggttg ggagttcaag   17580
accagcctgg ccaacatagc aaacccccgt cttcactaaa aaaaaaaac aaaaaaaaa     17640 ctagccacgc atggtggcag gtgtgcctgt aaccctatct actagggaga ctgagacata   17700
agaatcactt gaatccagga agcagaggtt gcagtgagca gagattgcac cactgcactt   17760
cagcctgggt gacagagcaa gactctgtct cggaaaaaaa aaaaaaaaag gataaagaaa   17820
tcatactaaa aacaaaacag aatgctgacc accttataga aatagaaata gtggtttgct   17880
gtgatagcaa attttcttgt taactttta ttttaaaga attgcacatt cacaggaagt     17940
tgcaaaaaat ctactgggag gtcctatccc ccttccccca acctcctcca gtagtaacat   18000
cttagtagca aagttttgta tatttatttt gatatcatta tctaagtttg acatcattat   18060
ctaatattaa cctaagccaa aagcccacta ttttaattat ctagtgatgc agtgttatag   18120
```

-continued

```
aactcatagc ctttcacagc attatttgga agttaatttt cttaagtgaa atgttttgg    18180
tctttaaggt ttggaggcca tggaggcatg aggagaaatg ggatgaggga gagagagcta    18240
agatagataa agacagagat ggggagatcc actgattcgt tgaacaaacc agatacttcc    18300
ttatagtttt tggattaact tacatgagct aagtttatat tctgttcaga tcacaagtgg    18360
tcaagtttgt gtgtgtgtgg ggggggggg gtgggtgtgt gtgtgtacca ctctacccat     18420
cctatattta ttgtcctgta tttggtctgt tctgccttct ttattttcag gataggtgtc    18480
ctaaatgagg gtctttggaa agctggtgag gccatgttgc ccgtttcagg tgttccgtgc    18540
tcaaatgtat tcatttcttg aaaaattcag ggagtgcaca cttttgtaca ttttcctatg    18600
tgtatatgat accattatat aaatcttaaa aatatatatg gttcacctga atccccagcc    18660
atttggtaga aagatagaa aacctacaga ggaggctaag atttttattag aaaattcagc    18720
ttctcgacgg aggtattggc tttaaagtca aggcaatgca tctattcttt cttttgatat    18780
aactagctaa aagatctctt aaattcaaag tggccctcat cttactgtta ctgcaattta    18840
ctcttaatta caaattatat aaaaatggt tttgaaatac tgtagcgaca aagtaacata    18900
cctctgctcc attacacaga taaaacctct aaggaacacc tcctctctta acaggcatta    18960
accaactgca gaaactgcag aaggacaggg ctatttggga ataacacagc tcccttcctt    19020
gtctgttccc tcccattgtc aggcttctgt ggagccatat tcagagcaac ataggaggg     19080
ggaagagaaa atcaaccct tggtgaagga aagctcccaa ttcacagagc aaacatgggt    19140
actcttgttt gtgggagctc ccagggcctc ccagctcacc gagcattctg agccctgatc    19200
cttacactaa ttgtattatg caaccataaa tgatgtctgc tgtaccagcg gggacagttt    19260
attttaatag attggtataa cttggcagaa tcttatctgc atgtttcatc ttggattttt    19320
agctcaattc aactcaatag gcatgtgtca aatgtctact gcagactgag cactgaaaag    19380
ctgctgggta caggggttaca tggatagaaa acgtagcctc tgaccccta ggagcctgta     19440
atccagatcc ccattctttc catcccattc tcccaagcaa gaatttacct aatgtggttt    19500
gcgagaattt aagagctgga aaggtggtca cgagaagccg gaatgggttc gctaaaatgt    19560
gtctatatga ttaagcataa cgtagctttg cagcactctt cacagcttcc tcagagcctt    19620
ccgcacgcgg tgtctcattt gaatactgt gtgaggatag cctcatacccc ctcagtgagc    19680
tcttcatgga gtgatgcagt agacagcaag cctcacactt ctatgctcac ggaagaccaa    19740
atttgccttg aaaatcttt atagtctctt cacatttcta agttgacatc aaaaatcggt    19800
taccataaaa tcctaatagt tgaagagatg taatttcaat tatttggtaa acctgacctt    19860
cattgtcaaa gcaattagtc aactcagatt tactttctcc cagataatag attctgactt    19920
ctttttttct gattaaaaaa cttaacacct tcctcaggag atctatctca gttctgaatg    19980
ctgattctaa ctaagaagga tatttggcta catgctggga agaggggtac tgaggcacgc    20040
cgcgattcca ctccagcatt tccagttagt cgggtgcctc tgcactcccg tgttccggc     20100
gcccagttag ttgtgtactc tgggctgtcc ctatactgga gtcctaaaac acttacgact    20160
gcagataggg ggaggttttt caaaaccttg gtctgaaaag ccatagaagg gagataggaa    20220
agcgggggg tggagccaca gtacattcag gtggatccgt ttttggaaat agtacaaact     20280
ggaggtgaaa ccctggaaat tgatctgtcg ttcacatgct tcatgccgag tccttgtgga    20340
cccacagaga cacactcgcc ccagtttgaa ggctgctaac ttgattctga ggacaccagt    20400
gaggtggtag tgtgcaaatg atgtgtgagg aaactttgga ggagtctcac cctgcctgga    20460
gcacgtggcc cctaaaacag cgcagcctcc caaagacaga agatgtggac tagtgagaag    20520
```

```
ccaggtatgg tgactgctgc tggatgaagc ttgtcccacc agaggctcgc ttgtttcatt   20580
gagcacctac tgtgtgcttg tgggatgcaa acacacgtgt ggtccctgcc ctcaggttaa   20640
taggcagggg tggaacagtt atgaaactgc tctaaagtca ttttctcaaa ctgggagtga   20700
caaatgtatc cacttggaaa agattgagaa ttttataaga ttttttaaatt tttgtttatt   20760 cacattgagg agaatctaaa ttcttttgaa cttatgtata gatttcacca ttttatagta   20820
ataaatcagt cctcctgtgt gtgtgtgtgt atgtgtgtgt gtgtgtatgt aaacctcacc   20880
ttgcaatatt attattttaa atagccactt gcatcttaag gaaattaaga ggacaaaaga   20940
aaagctgctg ttttgtatgt atccacatat ttaccagctg cttccctgcc ggcaggtgct   21000
ctggttctgc actgcctgtt gtcccttgcc tgaaaatggt tgcctccaat attttgctca   21060
gttttctgat tgtttacagt ggcagaggag ggtagatctg gtaccagtta gtaattgcca   21120
gaggtggaag tctgtggatg aaatttgtat aacatggaac gttagttcca cagttaatgc   21180
tactcaattg gaacccatgg aaattatttt ttggtgaaaa gggcccatgc gttatgaaat   21240
ttgagatcca tcactttaag tgaatgtagg ccctggatac agtgggagct cagaagagca   21300
aatcagttgg tcaccttgct caacgtattt tactaagggc atcagtaagg ctttctatga   21360
cctgctcctt caatgcttgg ttgacatttg gggagcaaaa ataaactaag gattctaagt   21420
tctgtcctgt gatgctgtaa ggggaatctc aaacctctag gtggaggagt gcagagatga   21480
ccaggatggt ggaagcctgc aggagagctg aacacctgaa gacacccagt gggaagacca   21540
ggacctttaa cgcccatatc tgctgctcaa gactggcaga gagaagaggg tttgtgatga   21600
gaaaaggtgg tgaaaggcac aaggaggcac agagcatgtc aggtcccata tcccaaaagg   21660
aatgtgcttg ggtgagggag agctcctcca tggctggagg cattcagaga ccaggcagtc   21720
gcttgtgggt ttgtgattag agtgaggttc ttttataaag gggagtgagaa gagaaggtct   21780 gtggatactt gagtgtatcg gtaattaaga aataaattgt gtacatccca tttctttcca   21840
cattttcctg ggctgtcaca gtggctgcaa agaaagcagt ccgtgaactg aactgtgatc   21900
ccagacaggc aagcacacca ggaatctctt ctcagctgtt gataatgagg gagcgctggg   21960
gagagaaatg gggtccctctt tgagtttcct ctgtgccgat acctttctct ttgttaaaac   22020
agctaattaa acactgaagc agtatagctc tcttactata cactggtagt catagttctc   22080
ttactgttct cttcactgac agttctctta ctatacactg atggtgacgc agaaattcag   22140
aattccccgc atgtgtcccg gtttgaaagc cactgtgctt tgctgtggat taggatcaga   22200
cagttgagtc ttgttccaac aaggaaagtt gcttattgga aagttttgct gcagggagcc   22260
ttgagttctg catcaggctt ggaagtgggc tctgtggagg tcagaaggag gatcccccac   22320
ccgcagcctc aagaaaaata tgaaagtgg attatgcctc tgtagctata ttgcctataa   22380
actttctgca gaatgacagt attcatatcc tacattttt caaagcgata ttaatcctga   22440
gacctgcagc taaagtcaag tagaatttag ggataattaa taggaggaag gtggggttgg   22500
aagatctgca tgattatagt cctctgatat aactggaaaa ttctttccat tagcaaggag   22560
ctttggttaa tataaaatgg acagattaaa cctaggcaat ttattttact cattgctgta   22620 ttttttatttc agagctggtt gaaaatatta caaagtaata ttttaaagtg cttatctaaa   22680
ctcttactct gcattttatc attgggttat gaaatgactg gggaaagact ttcttgctt    22740 ttatttctca gtgtctactt ataaacatgt tttttgaact actgttttg tgacaacatg    22800 ccttttttccc agaaaatctc aggttaacat taaataggca ctggatgttt atctgatctt   22860
```

```
gtttatagaa acacaagaaa attttaacct tgtatatact ttactcaatt aactaggtaa    22920
gaggtcattg aaacatttag aattccactc tacatttcaa taattatcag gtgaaagcta    22980
ctgcatctac atcagaagat gtttgtaatt tatttaagaa taaaattagc tatgcaagaa    23040
atagtatgtg gagtcctatg tggaaatcac agaaaccctg acaacttgat gatctttccg    23100
caagctaaaa atatcactct ggatcacagc agtagaggac tctgtaaatt taatctgtgt    23160
gtctcctgta aataagtgca ttagcagtac acaggtggtg tcagagtcag tgatgatgga    23220
tagaaattct acataaaatc caggctcagt ggctcatgcc tttaatccca gcactttggg    23280
agtctgaggc gggtggatca cctgaggtca ggagttcgag accagcctgg ccaacatggc    23340
aaaacctcgt ctctactaaa aatacaaaaa ttagctggat gatggacat gcctgtaatc    23400 ccagctattc gggaggcgga ggcaggagaa tctcttgaac ctgggaggta gaggttgcag    23460
tgagccgaga tcacgccatt gcactccagc ctgggcaaaa gagcgacact ccatcgcaaa    23520 aaaaaagaa gtaagaagtt ttacataaaa acgtggagtg agcccaaggt gccatttatc    23580
cagcccatac acatcgtacc atgtacagag tggacaccag ataaatacat tgactgcatg    23640
ccacaaacat atatatgtag gcaccgttgc attcaaatac acatctgcag ccctaacaca    23700
tctttatttg ctaacgagca tcaatgtatt taaaaacaaa catgttttaaa ctagtgaatg    23760 attagattat aatgatctta attcataagt tttctcattg gccttttgta tacttcaatt    23820
gtaataccta gaaaaacagt tatgtccaaa ggagtgaata ggccttatct gaaacaggtg    23880
agcgtgacaa gtgttttctt acttatttta cttttcagat aattcatcct taagtacat    23940 tagtttaaaa gtactgttta aggaaacagt acttggatta aaacttgaat cattgttaag    24000
gaaaactata ccttaacttc atgtaatcac aattaaacct cttcatatag aaggatctaa    24060
gaattttctg cagcattcac cagcaccaaa aagctcagag acatatattt ctttctctgt    24120
atatgtattt taaattcaag ttagtataaa ttgacaggca ggtcagagta atatatgatc    24180
ttctgagtcc ccttagtaat taaagaaat gattattttt gcatgaaata tgataaagtg    24240
attttaagtg cctgataaaa agtcttaacc atgacaacca ttaaagatta catcaaagaa    24300
aaataagttt gactttcatt taccttggaa acagctatta actggtaacc tcaagaaaca    24360
ccatgaagag tcagtttgct ccacacatgt cttgtaaaag tcaaataact ggtggttatc    24420
cagtaatgac aagaggtaga agttacatcc ttgctgtctg attgaacctt cccagagctg    24480
gcacaaggct gggaagacca taggtgctaa atgaggaact acttaaagaa agaaaatgga    24540
atttcacgga caagaaaatc catgtccatt tggttctgtg acccacatcc tttgtatcct    24600
atgctttttt acacttggta catggttgca agattgcccc tgttttctac ttatagttcc    24660
atgcagcatg gatgtgggaa aaagtctcct ctgcaaaggg ggttaatgca ggtcactcta    24720
cgtatgtgca cgaggtcgtt ataaagctcg aaaatatggg ctcaccaacc aggtgatttt    24780
tttaattatc caaccagaag acataacata taggggaatc aaaagaaatc tctgagtaaa    24840
ataatgataa caggtcaaac tttgcggtcc cacgtgaggc tggagatgcg tattgtcttg    24900
actttgcatc tacaagttta acaaatgatg ctttctcagt ttacctctgg aaatggaaat    24960
tagcattgca aatgacttca tgaggaggta gaagctatct gtgaatttcc tttcgctgtg    25020
tttacgatag actctcacgt ctagatgtgt catgtattat gttaaattgg tatgtcttga    25080
agttataaag cacagccctc tataagtata tatattccac ctctttcaaa tcggatggta    25140
cctatccttc aaactgctat ttaatgactg tctgctatgt tcaaggcact gctctcaatg    25200
ttaatacttg atgagatcgg gcgcgttcaa ggtggcatgg ccgtagactc aatgttagta    25260
```

```
tctgaaatat ggcctacgag ctgagttgtg aatcaagtta atagattttc ggaatgttaa    25320
ggtctaaacc agtagctctt aactgagaca atcctgtcct catctcacct gggagacatc    25380
tggcaatgtt tggagaacct tttggttgtc acactggggc atctagtgag tagaggtcag    25440
ggatggtggt aaacaagttt ttttgtttgt ttgttttgtt tttgagacag agtctcactt    25500
tgtcacccag gctggagtgc agtggtgtga tctcagctca ctgcaacctc tgcctcctag    25560
gttcaagcaa ttcttatgcc tcagcctccc aagtagtagc tgggattaca ggtgtgcacc    25620
actacactca gctaattttt gcattttttag tagagacggg gttttgccat gttggctagg    25680
ttggtctcga actcctggcc tcaagagaac cgccccttc ttggcctccc aatatgccgg    25740
gattacaggt gtgagccacc gtgcccaggc taacattctt taatgcatag gacagccccc    25800
accatacaga ggaatcccca gcccagaatg ttaatagttc taaggttgag aaacccaagg    25860
ttaagccaag tcaacttatc tatcttcttt aaaattgcat aagaatgcag tcctgttctt    25920
cattcctctt gctttgcagt taatgatcct ttgcctggac tttctaagtg cccagaagag    25980
caacagccag catgcaggat ggcattcctg accagttgca cttggcctag cattccaacc    26040
tcacctgcct cagcttgttc aacctgaaaa cctaccaagt gaaagcaaga gccacgtgaa    26100
gacgccttag ttatatgcac ccacccagac acttgctcag aaaggaatca gtggggcccct   26160 ggccttagaa actggctcct tcactgctgt agaaacaaca taaatttaac ataaaacacg     26220
tgcttttctt ttttcttctt actttttcct gtcttggcaa tgcaaggatg ccattaggta    26280
aagaaatcct tcaccacact aatcctgcag agccagaaga gaaaccagct tgttctaacc    26340
cagctttgtc atggagagaa ggcagctgct ccagtctgaa ctattctttc ttttggtagc    26400
agcctgccca agggtgaaag tgtgtttaat agtttgaatt acacaagtga acagtaaatg    26460
tatgcctgtt tctgctttat gggactttga aataatgttg tttgtgccaa ggttttagat    26520
tactatacct aacaacctag aaaaagaaat gaaaggaag ccttctgcca ggcagaggtc      26580
actacgggcc tggagctggg cacctgactc agcagctgcc cagatcccca gagctgagaa    26640
gtcaccatgc atttgtggtg cttcgagcga gttaccagag tcctggaaca gagcagcaca    26700 cctgcgggt gtccccttgg catttgggca gggcaggtga ccaagggtct tgttggaact     26760
gaagtccagc ttgaaaagca aatctggttg tgagctagag tccagtaaca cttgtttccc    26820 gccgccccc gcataactcg tgtgtcctaa aatacaataa tttcttgaac ttcagtcact     26880
tatgcctata agcgggcata caacagggc acaataaatg tttgttaagt gaatgaattc      26940
tttcagaact agatgggatc ttagtccaac tctcttatt aacgaggtcc acagaggttc      27000
tgcgattgtc taagaaagaa ggctgtgttc atggcctttg ttgtttacgt ggccctgtga    27060
ttctcttggc tccgtgaaag tcctgatgca gacattccgg ccatctagaa aggcatgcag    27120
acaagccatc cagctggcat gatcctgagt ccagctttct ttaaaagagc ttccaaaact    27180
gcttaagctt tgactgcaca aaacctgcat cacctccagt tgagaaactc aagagaataa    27240
gtaagttatg gagttggaga ccccagctta actactagtt ttaaaatagt gaaatcaaca    27300
ttttcaaatc tttgacttca ctaagattta ataaagttta ttaatcatat attatgagtt    27360
attgctctct ctttatgtct gtaatgcagt tgctcctctc tgtataaatt aataagtttt    27420
agagatccaa aatgagaatt ttaaaataaa ttacgtatat tttaatcaag tttaatttga    27480
ctatatccag ctaaacaatt gattgaactt cacttgcttt tctatgacag gtttttttgtt   27540 cttagtaaaa gaccccagtt ttctcacttg tgaacagaag gggttagact tcatgacagc    27600
```

```
taaggttcct tccgtctcta acaaaagtgg cctgaagaga ggcttctaga ctatactcac    27660
ggtgggttct tgggacctca gagtcagctc catcacttaa gtggctgtgt gattgagtgg    27720
agacacctca atctctttgt gcctcagttt cctcacctgt cgagtgtcaa catgatggca    27780
cctaaagctg ttgagacttc agaaaggtaa tgtgtgaaaa gtgaaaagtg cctggcatcc    27840
aggaagtact caataaatac caactatttt attgctgcag ctgttcttat agatgtgatt    27900
tctagaacat tgccttctaa tagggtagcc atgggccaca attgttggct gttcggtgtt    27960
tcacatatgg ttagtccaaa ctaagatgtg ttgtgagtct caaatacaca ctggattgtg    28020
aagacttagg acaaggaaaa caatgttaat aaaatctcat tgataacttt taaattaatt    28080
acatgttgaa atgaaaatat ttgggacata ttgagttaaa taaaacagga gattaatttc    28140
ttctgtttct ttctacttttt tttattagtg tggctactca aaaatgtgac attatgtatg    28200
catctcgtat tacatttcta ttggacagca gcgctctaga cagtactatg ggtagtatct    28260
gtggggaggt tctcagaaac atgtcgcatg ctctttttaga accttaaagt attcctagtc    28320
tcctctactt ccagcccttg gctcttgggc ctcagtcttt ttacttttgc ggctgtgttt    28380
ctctgaaggc ttggcattag tagattgaaa agaataacca tctagggaaa tgtgaattca    28440
gtttctttct gacattctgc tctctacaag gggatattat gtacacataa acctacttcc    28500
aaaataatga agtgaggcct aattccttac tcttcagaga gcccactgtg gaagtgtcac    28560
tgaccttgtg tatgggctgc ccttcatggc tctgggagtc attataaagg gcagcatttg    28620
gcgtggtgcg tcctaagcca gtgttttctcg gctctgttcc ttagacatgt gttagtgtta    28680
atagatgttc ttgaaaaaaa aaaaaaaaaa cagcattctg aggtcaaaca tgctcagaaa    28740
gcttggaatc tgcactacgc ttctcgtaca catttcatat taaagatttt ggaaagtcct    28800
gcaatacaga gccctgtcta atattgccac aacccacaat tgctcaaatg taaatagatt    28860
tgagtttatt cacattcaga tcacctctta aggccccacc tcccaatgct gtcacaatgg    28920
caattagatt tccacatgag ttttggaagg gacattcaga ccacagcagg ggaaagcagg    28980
gtacttgctg ctttgcaagt gtgtccacat ctaattaata gtacagttct tactcttggt    29040
gtgtccggtg atattaaaaa ttaatgtgcc ttatttagat aagtaacata aaaatcacaa    29100
aatgtatgcc ttagatttat atgtatttat aactagtcta tttcctgaaa acagttgaga    29160
caccttgtaa aagttaccgg tacgataggg ccattccaac aaagctgtaa agtggtgata    29220
acacagtcat aaagaagagg agatagctct gggagaaaag gtggcccaga aaccagctct    29280
gagcctcatg gctgcaggca aggtctgcag gttcctggtc ctgattgcag gccatttgct    29340
gccttgagtg gtggttacac aaggccagcc ctggggtat cacccagaac acctagtaca    29400
cgaatttcag tttagaggac gaagcattac tggagtattg ttatgcagga aaacttttttc    29460 ctaaaaatgc cctgaaaaga gagtagccta atgcattcaa tcaaaatgtt tttaagtgga    29520
aaacatattg tgtgtacttg atctggcctg ctgcttttaa aagattaaaa ctgggactgg    29580
gcatggtggc tcacacctgt aatcccagca ctttgggagg cagaggcagg tggatcacct    29640
gaggtcaaga gttggagacc agcctgacca agatggtgaa accccatgcc tactaaaaat    29700
gcaaaaagtt agccaggctt ggtggcgcat gccggtaatc ccagctagtt gaggggctga    29760
ggcaggggaa tcacttgaac ctgggagccg gaggttgcag tgagctgaga tcgcatcatt    29820
gtactccagc ctgggcaaca agagtgaaac tccatctcga aaacaaacaa acaaacaaaa    29880
aaacactggg gccaaagaac tctgtgtgct gtatcaccta accacatttc atgacacggc    29940
tagagaagaa tcatgcaaat aaaaatttcc aacatgttcg taaactggga aagtatttca    30000
```

-continued

```
ctggggagtg agcagaaaag taatactata acctctatat ctagacaaat gtgaattcag   30060
tttcacatat aaatatataa gtgaaaaaat atataaatat aaataatatg aaataatggt   30120
tatctcacca cttctacat cttttgtgaa tattttatag tgctcaaata tattagtgca   30180
ctagtatatg tacattacat taaataacta atcatttatt aggaggatgt gcttgttttt   30240
tgctaataaa gatgataata aaaaaatcct tagacccccc ctcggtttgt tttcagttag   30300
gaattaggga tatttataag aatatctta aatgacacat gccttgctct gggacgaggc   30360
atctgcatgg gtgacacata tgtgttgtgt gtacaggctc ccagcatttc cagggccctg   30420
ctcagaatgt aggccttact gattcttaca gagttacaag cgctggtgag gttggcgaag   30480
tttaggtaaa cacagctggg aatgccccat ggcctctggg tgactttgga catcactgaa   30540 ctttacccttt agagatgcat acctgcatct tttttaccct gatagggcct tccatgatgc   30600
tttcaaagtg tttttgtctg cttttcggtt aatagacttt cacagtagcc aattgaatat   30660
attggttaaa tgcatctctt tatacacaga ctggattcaa actgaggttg tgtctctccc   30720
tggctgtgtg acgttgggta tgatccaagt gtcagattac tcaacttcaa aatgaggaca   30780
gagcctttcc cttctagggc tgccaggaac attgaatgag agagtgctgg cagcttagta   30840
caggtgttca ttgctcttgt atggtactgt ctgtggcacg gctagataaa atacagtagc   30900
cactgattca aatttcaact gaggagtaaa ataaactgaa taacttagaa aagttttctt   30960
cttttgaatg actctaagaa tttaaggagc atgtgagtgt tgatggctct aaaagggtaa   31020
cagagcccaa ctagctcagt tctcagcatg aaaatagtca tatggcacag actcagtgga   31080
gtgggtgcac ttcaataact ggaagcacag atgccctaca gcagcatcaa agatggcact   31140
ctaaactact ttcaatcctt taaaataaat ggaaacgcac atttagtatg catatgacaa   31200
cacgaaggac ttcgattttg ctgatgcaat acagttttac aggatttttt atactcaaat   31260
tagtaaaatt ctgtattgca tccaaattat aaattataat atcatctaga ttggacatag   31320
gaataacgac cactggtatc tgcccagaaa gctctaccgc ctgttttataa gctcctgcag   31380 gagacacaaa aagaagagaa tttgaatata acttgaaatg accgtaatct cctgccccaa   31440
ctcatttcat taccaaaccg cctctttctt cattatttct cctgaagcac aaatctatag   31500
agaactcagc tgccagtctc tcccactgca ctcagcagtg aaagggttag gcctaggctt   31560
ttcaaacaga ccagtgcttg tatcagcccct taaacatctc tggagaagga atgggatcc   31620 ttctttggta attcattttt gacagttggg gattaggtgt tctgtatctg gggggccttg   31680
ctgtcttctc tcctcctcct cccactgcag accctctcct cccctcccct ctccagctct   31740
ctgatgactg cttcatgctc cttccacctg aggactgcca gcacagccta ttgcaggaac   31800
agccaatgag gggctggctg tgctcttta tttataaaat tataaactca agcaaaatct   31860
agactatgtg tccccaagat cagaggagca caaatccctt gcttacagat tgcatggggg   31920
gcacattctt taaaattggt ccctgatcta gactctagcc tgagaatcat ctttaagttc   31980
agaatttcca ctcatgacct cacatctgtg ggctcccaca ttgtcttcca aaacacacat   32040
ggcatctggc atcaccttca cccccaccct cagagcctca tctccctgca ggtagatagt   32100
caaggcaacc tcttcactct tctgccaagc ctcctctcct cagctcttcc cttcctctct   32160 cttttttgaaa atattttaa ttgtggcaaa atatacacaa cataaaattt accatcttaa   32220
tcatgtataa aagtggagtt cagtggcatt aaatacattc acgttgttct atagccataa   32280
acaccattca tctccagagc tcctttcatc ttgcaaagct gaaactctgt ccccattaag   32340
```

```
caatggctct gttttcctcc gttcccccag cccctggcca ccatcctcag ttttctgtct    32400
ctgtgagttt gattactcta agcacctctt ataagtggat catacaatgt atctgtcttt    32460
ttgtgactgg cttgtttcac tttccataat gtcttcaagg ttcatccacg ttgcagcata    32520
tggcagaaca tctgtccatt tccaggctga atggtactct tttgtacgtg tggaccacat    32580
ttcatttatc cattcatcca cgggagggca cttgggttgc ttctgctttt tagctattgt    32640
gaataacgct gctatgaaca tagctgtatg cctttgtctt ttaaagccca aatctgatca    32700
agtcactccc cagcttaaaa ccttccactg ctccccagca gtgggataaa ggccagtctc    32760
ccctgtaggt ctctcccgcc agccctgctc agtcttcttg cttgtcatcc ttggctaggc    32820
cttgcattgc catagccctc tgcctctgtt cacgctctct catcttggag catgagcctt    32880
ccatcatctc taccagatga actctcattt cttctttcaa aaataaaaa acccaaaaaa     32940 cccagagatc ccaactgtcc tggtgtctgc atagtctgca gcacacgccc cctccatggc    33000
ccttcctcca taagcagaat cactcctcac tgttcctgca gcacctcctg tgtgcccaca    33060
cagctgtcct gcggtgggct gtgtgtgtga gtgtgccccc tctaggacct gagctccttc    33120
tggagggtgg gcacagcatc cattcattct gggaatcctg gtcggcacca tgctagaact    33180
tctgcaagtg agtgcctttg gtgctggccc atgggagagc tgttggtaag catactttt    33240 gcagattcca gttgctgctg aggttgttgc tctttgcaca agtttcttct agtcaccagt    33300
gaagtgacat gtgtggcagg catggcccag ggaggctttt tcataaagaa gaggttgaat    33360
cttttgggct gtggtttgaa tatgtccctc aagcttatgt gttggaaact taatcccaaa    33420
tgcaatagtg ttaggaggtg gggcctaatc acaggtgatt aggtcataag gctctgccct    33480
catggatggc ttaacatgtt tagtgaggca gtgggttagc tattgtgaga gtgggcttgt    33540
tagaaaattg agtgcagccc cctcttgctt gctggctacc atgctctctt gcttttctgc    33600
cttctgccgt ggggtgacac agcaagaaga ccctccccag atgctggcac catgccctgg    33660
gactttccag ccttcagaac cacgagccag acaaatttct tttctttata aattacccag    33720
tctgtggtat tctgttatag aaacacaaaa tggactaaga caatcttctt tcatcaagtt    33780
agggtaccaa cctttaaaga ctgccagtcc aaggttaaag gaaacttttc aagagcagtc    33840
caaacatgat ctggccctca gctactctcc agggtcatgc caccctatca cccactggct    33900
cacacagacg ctgaccactg cttagtttct caaactgaag ttttcctcct cagagctttt    33960
gcaaaacctt ttcttttgcct ggaaaactcc ccccacaaat ctttagttgt aggttccttc    34020
tcatcttgca gaattattag tttgctcttc aaatagtctc tccagctaga ctatcaactc    34080
caggagggca gagttcttct tcgcttcctt cacccatgtg cccactgagt ccagaactgt    34140
atagcagttt gattgaaaaa atccacaggg tggaggatga gaggaccctg gatcccagcc    34200
tcacagcctc ttacttcacc tgtgtgattt tggtcaagtc ctttattctt cctgggcttt    34260
agttttccct tatctaaaat atgagaaaag ttccctctc ctgggtattc tgggagactc     34320
atgtaaaagg cactgagcca gtgcagcaca tctatgacca ggaagggtca gcttcctgcc    34380
ttgcatgaga cacacattcc cttcttcatg cacagttatt catgagttaa atatgtattg    34440
agaagtgggt tctcaggaga tgatgcatcc acagcattgt ttgtatgcct ctgtctttga    34500
tgtccctgcc tgagtcgccc actttagagc ccttctgttc ttcagaaacc agacttttct    34560
ttcaatagtt tcagtaatca atcgatcaat caatcaacca atcaacagtg ataataatca    34620
tgagtgagcc cctgccgtg ctggctgtgt cctgctgaag gcacactaag tgctgccctt     34680
cccagaagcc tcaggaagct tgcgaagctc aggtgcatgg atgcctggtg gaatgaggaa    34740
```

```
gggatgcagc caggtagaga aatgccctgc catcacttgc atcagcatct gtgaagagct    34800
ggccaggctt ttgctcacag tggttgacac agtcaaggag caagggcccc gtaggagagg    34860
ggagtcaagg gctccgggtg ggaatggagc tgggggctga tgctggcttc tggagcactg    34920
taatgtgact gagaaaggtg aaggagccgt tctgaaaaag aagaaggcag gagctcgcac    34980
agctcttgac tcatcttgac ttcttttttcc tgcttcatcc aagcaggtcg actctctcgt    35040
gatctcagag acagagtgaa gtcatgagtg ggaggggagc acagaaaata agaccttgat    35100
tcccagcatt gggagactcc ctgctcccct gagtctcgga aaatagcacc cttcaaatgt    35160
tttagggatc cagatttgat gaagagatgt tattttggct tttagattct taggagagat    35220
ttgtctttct caggtcagga agaaaatgct gcccgctgca cattcttcgg acagactct    35280 tttaattatt actagtttaa tgtatgtttt gcttagttaa ggaaaacccc tgtggtttct    35340
tgacgtgctt cagtattcta actcacagct gattcagttc aggggctgg ggagatgtcc    35400 tcgacctctg gaaggaggg tgcatctcta gaaataaggc taagtatgcc actgacactg    35460
tctgcataaa cgtgtgtgat ctcaggtcca aaggatgggg cctggtctaa gccagggacg    35520
tgggaaatca ttttcctgtg gcaacttgtg aagaccattc tgtgaccttg gtgtctctgg    35580
gccttctctt agattttcta agttggctag tcagtggagc tgccatccct cctttgccca    35640
tgttctactc ccagagttcc tccaagaaat tgcggagcaa tgcctgtttc atgagagctg    35700
agtttgctgt gtcttccact tagaaacaac actgtggacc aggaggacac acagctccca    35760
gggccatcac cacacaaagt gaaggctggt gaatccgagg cttctagccc ttgccgggcc    35820
aggcccgcag cactccgctc cccaacccag ccgctgcttt gtcgcaggaa cctcagcagg    35880
gcagggtgtt tcctaggagg acatccgatt cccagccatt cctttcagtg aatcacctga    35940
gctcacattc ttttttcttt tattttttgaa gctcttagcc aatctgcttc gcgatgaacc    36000
agttttgctt gaagcagaca aacccgattg tcaggagaca gtgatgattt cttcagtctc    36060
tgaggaagag ttttcatttt ccccaattcg caaaaaagt caggtccctc cctccctccc    36120
tctccgtaga atatttttcca tgtgtgttaa caatggctga gcgtggtaga tgccaggaat    36180
ttctgtcaac cctcaaagag gaaagccctg cctaatggtc tgcccgttct tgttcactcc    36240
ctgccccagg ctccccaccc gccttctttc tggaaggtat aaaggctcct gcttatacct    36300
ggcactgcac gcttcgctcc ctctgatctc ctgactgtca tgcccagtgt ctcagcctat    36360
cattctacct ctaactcgac cttgagtgac cttgagcaag tttctcagga ttccacctcc    36420
aagtcactct ccctttggga tatgcagcac taagttaagc ttgcctggaa aacatcactt    36480
gaagctggaa aaccactttt aacacagcgg gaaaagctat ttgttcagac aggagtgggg    36540
tgggtctggg cagagcactg ctctaacttg gccatgccgt ggcagcagct cctttaatgc    36600 cacttttttcc tggcgcgccc gcggggcctg gagctcagaa agaggggaac gctccctcgt    36660
ctctcaacag ttgctccaga caggtcagca acatggaat tcagaatgtt cattaaacac    36720
tggctgtgtc ttttgtgttc aaaagcaaga cactctctct gaaccatggc cccacagaga    36780
gtgcagaatg tgtgaaacct gccgggaagg tctggacccc ttgcggggca gtgggcagca    36840
ccgtgcctcc gttcacacca ctcacatggc tgtgcctctg cttccttctg gcatggctgc    36900
ttcttcctca ggtctcaacc atctccctca gatgctcttt cccatgtttg tggctacagg    36960
tccccgtgac ctgcagaggc agagcactca ccagcagccc agcctcgttg cgcacccatg    37020
tttgcatttg caggccctag aaccactcca agctccgtgt ggcgagatgc accctcctgc    37080
```

-continued

```
ccttcactgg ggagctgccc tcctgttcac agcggcacct gagtcacaca tctggagcca   37140
tcctggactg cctcatttcc ccgatggggg gtttccctga cttcatccat cctgtctttt   37200
gggtccccat aataactgac atgggtcggc ccgtaccagc ccctgtgaga agggctttaa   37260
ctgccttccc acccctgct catcttagag tctctctata gtgctgctga aagaatctct    37320
aaatcagtgg ttctcaacct cagccgcaca ttgagaatca cctgggaccc ttaaaaaat    37380 cttaactctt ggtccaagaa ttctattaca atcggtctgg gatgggccc tacaggtatt    37440 tttttaaagc tctccagttg gtaatgcata gctagagttg agtatcgctg ttctaacgtg   37500
cagatctggt catgttacca gccttttagg tggtcttctt tggctttctc tatctaaagt   37560
tcaaaaccga acatgtgcgc attcagtgca cccattttca actgtgcatt aacacattca   37620
gcccaccagc aagatttatg aaccattttc tgctgttgta tataacatat catatgcata   37680
atggcatagg ttattgtttt cttcaaaata tatgagatgt gagtccttct acgaactgac   37740
tcacactgat tgcccaactt cctctctcga ggtctcatcc tctttccctg cagccgtctc   37800
cctcttgcac gcacacacac acacacacac cacacacaca cacacaccac acacaccagg   37860
gtcgatgcca tctaccctgg acttcatctt gaactccttc gagtgtgagt cattactcct   37920
ttgtgcacct ctgctttctc ttctcaagat gttcacctgc ttgaggtcag ttccttgagc   37980
gtcttccact tgccatgttc accacagtgc tcaacatgcc tgaatgcatg gatggcgact   38040
tctcagatcc tcagtctcct catctgggta ataaggcatt gggttggcgg gtccatctgg   38100
tttcttccag ctctgagagt gcatttgctc tgtgattcat tcgttccaca acacttcacc   38160
aattaaagag agggtacaaa aagtgaacat ccttggctcc cagcagatgc tcctcaaaac   38220
ctgaaaaatc agataggtga gggaagattg aatgaaaggc ctcttatgat tctgcagcaa   38280
ttttggtggt ttaagaactc tatggaaaaa tcatcagtat ttctggaatt gaagtaaaat   38340
ggatagtgag cctctgtgta tgtgaaggcc cgcatctgga acatgaaaga acctgtctga   38400
tgtgttctag tcaggaaagc aggtagccaa tactatttat agaatttaca gaaactgaag   38460
attttgtttc tactgatttt caaaatagta ttatgtctga ttttttttcct cagaaatata   38520 cttcctgctc ttctcaacaa actcatttga aaatatgatt agaacatgat agaattttac   38580
tcatttgcca actgcggttc ccatttcaca tattgttaga attctgcatg gtggctttgc   38640
cctttaacca ctaactgata aatgatgtag ttagctttta aatgtgtgga aaaatataat   38700
ttcaggttca accataggtc agaagtacac gtgttttgtt agtctatttg tctctcagtc   38760
atctcatgga aaattctcag cttttggtat ggaaataatt ttcttgaagg caatatttgt   38820
tgagtgactc acggaatgaa aaacgccagt tgcgtaagtg tgaaaaagat ctgggtgttt   38880
tcattggatc caaattccac atgagccaac aacagcgtgg tgtggaggct ggagcacatt   38940
aataagaaca gtgtcctaaa ttcaggaggt aatgctctgc ccatgccctg tgcagctcag   39000
acggtgtgtg cagtgcagta tgtaacccag ggcacatttc agggggccac agggagctgc   39060
agcttgtaag gtggagtgca gccaacagag cagagagtca gaatccccgc agagtggttg   39120
aaggcacaag gatgcgcagc aaggaagaca gacttatagg tggtgcgact gccatcctct   39180
ggtactgaag gtgctatcat ggagggaggg aagtagattg accctcctgg ctccagagta   39240
cggaactcag acaaacggtc agaagcttac agggaggcca attttggatc aactttaaga   39300
agaatttttt aaaagctaga gcaatcctaa aatggaattt gctctttata aagttgcgaa   39360
tgcctcaccc tggaattgct taagcaaagt tgggacgggc agttgtgagt aatctccttt   39420
ccaatccata cccgcaatca ccagaaacgt ggacttccct gacactgagc acctcttaat   39480
```

```
taagcatctc ataagtgaac aaaacccagc ccttcaaaga agtcactttta tttatgtgtg   39540 ggtctgcagc ttggattct tgataatgtt aaataaaact ccatctactc ttccacaaac    39600
acttcaagaa acctaagact tttggccaga gtaacaccga ggtttgagag aaaggatatg   39660
tgtgtgagag gtgtggtttc attagaacat attatttgac ttcatgttga atcaacactt   39720
ttgtgcaaaa tgcagtttta ccagcctctt tccttgtttt ggtcacataa tttaacttaa   39780
cattctcggt acttgatttt ctaacataaa atgggattga gaggggaatt ttgaagttcc   39840
catggtctgt cctctacatt ctgacagctc attatctctg cggtattgtt ctcacattta   39900
agtgaggtta gcggaggcag aggcctctca ggcctgaaga tagcctctgt tttcagggaa   39960
atactagact gtgagatctg tgacactgaa gcactaagtt catctcacaa aagcaacgtg   40020 ctcttttttaa atggttgatc aaagttactt tcaaaggaa gtgttagttt ttgttattag    40080
ccgaaacaag agctgcttta atgtagtata tttaaaatca tatctcaatt aagatgttat   40140
tcaaatacta tttgacccac caatctcatt actggatata tacccaaagg aatagaaatc   40200
attctattat aaaaacacat ggctgggcac agtggctcac gcctgtaatc ccagcatttt   40260
gggaggccga ggcgggtgga tcacgaggtc aggagttcaa gaccagcctg gccaagatgg   40320
tgaaacctca tctctactaa aaatacaaaa attagccagg cgcggtggca ggcacctgta   40380
atcccagcta ctcggaaggc tgaggcagga aaattgcttg aacgcgggag gcggagtttg   40440
cagtgaacag agatgaagcc actgcacttt agcctaggtg acagagcgag actctgtctc   40500
aaaaaaaaaa aaagaaccac ttgcatatac actattcaca atagcaaaga cgtggaatca   40560
acctaaatgc ccatcggtga tagactgcat aaagaaaatg tggtacatat ataccacgaa   40620
atactatgca gccataaaaa agaacaagat catgtccttt gcggggacat ggatggaact   40680
gcaggtcatt atccttagca aacgaataag aaaagaaaac aaaataccgc atgttatcac   40740
ttataagtgg gaggtaaatg atgagaacac aaggatacac tggggcctac ttgagggtag   40800
agggttgaag ggagagaagc agaaaaaaata actattgggg tactaggctt agtaccaggg   40860
tgacaaaata atctgtacaa caaactacta tgacacaagt ttacctgttt aacatacctg   40920
cacatgtacc cctgaactta aaaaaatttt taaaagatg ctatgcaata aaattctcaa    40980
ttaagaattt aacttggtaa atgttcattt aatgatctaa aaatatgtgt ctggatggct   41040
ctagcaaaaa aataaataat aagtttctca gagatggtaa ggctgaaata aatggggaaa   41100
aatctgaatt gtaatccttt ttctgttgga cctggtgttg gggtttcaca cttgtgggtg   41160
aatgtgggcc tcctgtgagc accagcacaa aagactaaac tgaacaaaag attaaatgtc   41220
acctctaaaa ttctgtgcaa caagacttcc agccacagaa tgtgcaactc agatttccaa   41280
gtaaaaacac accaggaagc agatcttaga tctctgttat ctccttggca ccagctggta   41340
ttcatcctca atgctagcta gagttgaaat aaagagtgaa agaactttct cttttattac   41400
ttaataaact tccttttttg agctgtttta ggcttacaga aaaattgagt ggcagtttca   41460
gggagttcca gcacggcccc tgtttctttc tcatggtccc tgcaggtttc ccctattatt   41520
aacgtctgtc attagcatgg cacatttgtt acaattaatg agccaatatt gatacattat   41580
tcactaaagc ccacaggttg cgttaggggt cattcttggt ggtgtacgtt cttcaggtct   41640
ggacaaatct ataatgacat gcattcacca ttactatatc acgcagagtc gtctcctggc   41700
cctacaagtc ccctccttcc ccacctgctc actcctcctt cccaccctcc ccaaactgtg   41760
gcaaccattt aacttttgac tgaatggatt tattcttatt ctgccttatt gtatgtacac   41820
```

-continued

```
catattttaa taagataaaa taatagtcta tagtagactt ctgtaaatac tcaatgaata    41880
aatacttgca tgaatgcagg aaaaatcaat cagtcttgca ggatttctta tgcgttacat    41940
cgtccttata agaaagcagt cattctcacc gagatgtgct gagcagatac tggacatgtt    42000
ctgacccaga taagggctgg gtggaagtag ggctggagac acagagaccc agtgccaact    42060
tccaggacct cggaagaact gaaggcagag aggtcctctc agtgtggact gggcctctgc    42120
tggcagccac cagcgggcac agagctgatg tgtgttatgc cacgtgggga aaacctacag    42180
acgattctga gaaggctca cagggacacc ctctgcccct aaaagaacaa tttaactcta     42240
atttatttct gtcactctgc attttctgac cttttcccaag tgtacagttt tatatgcatt   42300
taactgccaa attgtcatgt gagattatat ggttatattt cattaatata ttctagtttg    42360
ttcagctgtt cttactgggt gaatttgtgt ggtttcctga cattttttgtt tttagtagtg   42420 cctcagtagt tttatacata attacgtttc ccttctggat tatttcctta gtatctagtt    42480
caagaagtga aatcgctgga ttcttgtggt aaattttttga atttcacagt ataatgctga   42540
ttttctcaaa gtctcacatt ctaagaaagt ataatgaggc aaaacaaaca acaaacatct    42600
taagttgatt ttttcctagc atcttttcct tccatctttg cttgtagaat ctagactatt    42660
tcatgaaccc aagatataat cagtatcctt cttcagtatg gccaaagtga gtttctcatt   42720
attttacctc cccttcagga aatgacttttt catcttgtgt tttgggagcc atagatggtt  42780
ctgggcagga aactggcttt ggatagaccc agcatgtaga tggctatttg gccttgctcc   42840
cagtataacg atgcagttcc ctgtgaaagg gtatgagtag gttttggggc tctggatacc   42900
gtgtggcctg aagagacaag ggctcaatgc caactctgcc tgtttccaac tgtgtaacca   42960
tgtgagcgtc aaaaatcatg gacgtgctct ggttaacact gagtgggagc tcaacaaatt   43020 attatttta attgttactt ggacatggcc aagttgacta cactttatgt tctgctacct    43080
gccagtctga aagtgacgcc acagaaggtg aaccgcatgt tgggagatgc tcctcatctg   43140
cttaaatgag gtgcaaacac agcccatgcg cctgctcttc atgactgtat ctgtaccagc   43200
aatatttgta ttggcaaatc acatgcccca gtgggaacta cttaagggga attcaatgga   43260
tttcattcct tttatgtaat tggccactta gtaatagacg tgtaggtctc ttgtgtggat   43320
aaggattctg cctttttatgt aagatatgtg ttgcaattca gctttcaggt cccagccccg   43380
ggaaggctcc aggccttcac aaactggccc acccacgaga aggaaagcaa ttgtccaaat   43440
gtgggtagct tttcttccca ctgttgtcag ctgcttccaa ttagccccca tatacataat   43500
cccagtttgt gtctgtatca gtacaattct cccatgtcaa tgtgaatttt aagccacaga   43560
gggaaagggg acagagaata tgctttcatt cagctctcct cgtctcacac ctcttgccct   43620
gcatgcattt ctttgctctg attaaacgag catttttataa gccacatttg ctgtgtgaaa   43680
ggcaaagtct tccctcccac ggatgacggt ctccagggat gtgtgtgtgt gtgtgtgtgt   43740
gtgtgtgtgt gtgtgtgaga gagagagaga gagagagaga ctgtaaacat atatctctgt   43800
gaaacttcat tttccatatg tgaattttttg gaaccgagac aaatgaaact tagctaaaag   43860
atgggaaagg tagactgact ctgacttaat ctacttaacc taccaggcaa tttataactt   43920
gatggcctaa ttttttgcagc acccagaagc aagcctgttt cagcacgggca aaggctcagc   43980 tgctaagtgg gcagcattgt tggaggtgag cagcttaggc tgactgttca tcaaaggacc   44040
aagcgcttga ggtcgctcca tcgctggagg ccagagtggg gagggccatt taactgctca   44100
aggccatgga actctactgt cagtttcagg gaaatttggg accctggagc acaaaccaaa    44160
actccaatta accaggagag gaactcgatc cccaggagat aagtgaagag taagaagtct   44220
```

```
atctttagaa acaagagatg tccaaggcta gaaagatggg gaaggagggt ggaactgttc    44280
tggaagtggg tctcaatctc agcaccagca gctctcaaga ctttctagag aaggaaactt    44340
catttctgaa ttaaaattag tcttcaatga catggcaggg atttcggcac actctcttgc    44400
gtcataggcc actgtgttgg aggcaggagt gttggctttg gaggcataga gattaaaatt    44460
agagtaacac gtgagcactg aaaaggttaa acagtagaga catggaggac tcccgacccc    44520
catgtacccc tttcttaacc ctttaattaa gatcacagcc ctagaaatag cttgcaaaat    44580
aattaactac tgatcattta taccttagtg cttctgtgag catgttttct cttttcattgc    44640 tgctcatctg catggaaaaa tgtgcatggg tttctgaata taactccatg gtgcttgctt    44700
ccattatatt tgtgccattt ggatcataac tgataagcaa ccaaagagtc ccatattact    44760
gcacgttccc atcgctattt tatgtgaagg tggtcctggg ggctgttctg aattctcagt    44820 ttccttttttt cccctcccca gttctttgaa aatatcagaa acggacttgt ggcatctttg    44880
aaaagctact taaaatgtgc tgctgtgctc tgaacttgaa aatgtgcttt taatacaaag    44940
tttgtgcagc ccttgctgct catacgagat gaatcttacc atgtggtgga tgcccgtctc    45000
atgccaggca ctgtgctcta agcccattgg tttatttcag tgcttgaaat tggctttcga    45060
gagaggcacc acgttccct ttttacagga gaggaaacac cagaggatca gagatggaga     45120
gtctttctcc acaaactcac agaccccaaa ggcaagctca gggttgtcag cttccaaagt    45180
ctgcctgctc caggacctca tgttgcatct ccattctctt cactgagggt caaatggaaa    45240
gaacacatgg gggtcaagtt tcagaaaata agagaaatga agaaatatgt gcccggaagc    45300
aagaacgacc gacctcatta aactggctcc cttcacctcc tctcacatct ttttctgcct    45360
tttggccaag ttttctctcc cccgcatttc ctccttgatc tcgtttgaat cctcttccct    45420
ggtgaagtca tttaggttca ggctcttatt ttactttggt ccataattta gatcgaacca    45480
catgtgctga tgtgattgaa acgatgtgga attctctgga cagagataga attatggagg    45540
ggttagtgtg tgtgtttaag attaaaagac caggtgtatg ggaggaaata taatgaacaa    45600
aaaatagtat tttaaatgaa tactaaactt gcactcatgg aaaaagttct cttcccatga    45660
ggttctcgca aagcatttta ccatcagcac acgcagtttt tctcagtttt ctgagatggg    45720
gccatcttga atccaacaga caacacacag catcagccag actaacacaa aggacgtcat    45780
gggcatggac gtaaatactg gtgtcaacac taggtctgca cctcgagagg agtgagcaa    45840 aaggatggag tggcagatga aggtatgctg ttcagaaagg aggcagaaat gaaggaaga    45900 ccatcagtgc gctccacagc ttgaggaccg tcctggaggg caaatgccag ctgctcactt    45960
ctgaaaagaa aaattccagt gaaatgagta cagtcattct taggattact cacttgatac    46020
tgtgtatgtc tcttcttggc ttctcatctc cacacaaaac cctcaggtgg taaaaatcta    46080
attaaaaaaa ttatataaag tcttgtagat ttattagcct gaacataata gatttttttt    46140
aagcacgtta agtcttccat ggactaaaag aaaacttgta aacctaagag aacctctatt    46200
tttgatatac aaaataatac atttccttaa actatgatct tgatactaga attttaatta    46260
aaaaatacct gcagtttata tgcaaagtta tagattaatg cttaaaaata ggttgtatgt    46320
agtatccaca ggtcatgttt gactgtcaaa tagatgtaat tttaattcat aataattgtg    46380
tcgtgttctt ccccactaga agccaattat gcaagcttca ccattcacac atggaaaata    46440
atttaatgga gtactcattg caatttcact tatccagaat tggctgttgt tctcagagca    46500
gcttgtgttg ccttgttaag gagaatatgt tagtatccag acatccagaa aggatccttt    46560
```

```
actgtttcag agtccatttt ccccactttt gaaatacaca cacaaacacc cattcatgca    46620
aaccaaacag agattgtaaa gtgattccac tgacatttat gcacttcttt tttctctttg    46680
gttcttcaaa ctctcagtca gtgcgcattt actcttaatt tagatacggt ttaaacctaa    46740
ttagaaacca gaagctcttg tatttccaca aaggattatg acagcccaa gaaaagatag     46800 tgaaaccatt atataacaag ataaaggctt cttaacaata caaggatgga ttttctcatt    46860
gatcttagcc ttctgaattt tagaaattgc catttcaaag tctaaaacaa aggaaaatca    46920
gggaataaaa gaatggtaag tagacacaaa cctactggct ccatcatttc tgttttagca    46980
aataacctgc cacatatacc aatagcccaa gagatgggca tgtccctgca tttcctggtc    47040
aaggtgacaa cactgcgtcc tcctggaaga ggtctgccac tcaccatacc acaaaccaaa    47100
tataataaaa tcagaaggca cactatagtg aattttttag aggcatgtat tgaaaagcat    47160
ctcaaaaagc attctcgaag cttccagaag tcaactcaag ttatctgaaa agtgacactt    47220
ttgatgattg ctcgcttaat actgggagag ccagatgaag attcctcccc acttcctcag    47280
atgtgcaact ctggaatttc ttagtgttac tggagattcc tgctgcattc tgggccttta    47340
atgcataaac actgagatgt tctaaggaaa ttactcccta gggaggagag gggtggacga    47400
ggagtaagct tgctggtga ctcatgcgct gtgtggaaac tccctgcaca agtgagctgc      47460
gcagggtgag tctaaagggt taatgcactt tcaaaagcct ctaatttgtt attccagaag    47520
agtaatttac tcactagaag tatctgggtg gctactaaca catttgtgtc tttaaaaga     47580 tcagttttat tttaagatta aaaatataaa gcaagagctg gaaagtcact aaaaactgac    47640
agccagtttc ccattttcaa gagtatttat taaaaggttc tggttgcaga aggaataaga    47700
aatggcttga gatcatgaca cagtgaatca tgttgtaaac atgttagcta tggctgtgaa    47760
ttcaaccagc gatgagttca agcgtcccca gaaggtgttg ggggaattag ggacatggct    47820
gtgtttcccc agagaaaagt ggccatttta ctttccctct tcactaacat gcttttgaca    47880
tgcatggcag agctgaaggc aaggggaagg ggacaacata gtaagtgact aagtggcttt    47940
tttttttttt tttttgccaa gtgaagctga gtcatatggc ctctgtcatt ccaaaactat    48000
tctctacggc tgcattcctt tcgctcttgc cttcctttag aaccctggag aaggcctcct    48060
gaagcctggc cctattatgt atcctgacaa agataaactt ttccaaaaag ctgcatgttg    48120
tttctagcac agttttcct cgcagtgact acgtgatgaa agtaccatgc agaggaggtg      48180
tctgactgag gcgttcgtgg tgtgtgacag agtcccctgc acaggacagc cgcactcccc    48240
tcttgcgtcc tttcctccca tgtttgcaaa gcctcttcc ctgtcagcag ggggtgttct      48300
ggcagttgac atttctgaaa actacagcct acattttaa aaaatccagt aagtgaaaac      48360
taaaaaatta ataccgtggt cataatagtg tggcatttga taactaatga ggcactgtcg    48420
tgccagctat tattttcaga catttacagt ccttttttaa atacaaagaa atatttggtg    48480
tgaaatgttc cccgggagct ggtgcaagca gaggcgacag ggcaagggag cttgggttgt    48540
agcctcgaat tcctccggcc agggctaccg tcagcctgcg gcacacaagt aaatcaaata    48600
taaaaccaaa atttctgtaa gcaaatcagt ttctaactca ctgtaacgaa ttatctttcg    48660
cacatcacag aggcatctct tttcactgtc gagtttggtt tgcttggtta caaaaagggc    48720
agttcaaaag ctttggttgc tattgtgaaa gtcagctgaa ttccttccac cgtgctgggg    48780
tggggtgggg ttcacgcagg ttctcttttg tcaccagggg tgctgtggat tcacaagtaa    48840
gcaagaggct cctcaggtca agcctctggc tgctcccctga ggtcagctgc ctagcttctc    48900
ctcctctgag atagacggga acaaagtctt tgatgtgtgc atttctcaag cttgacaatg    48960
```

```
atacagctac ataaaaaccc atgatttcat atagatattc caaaacgtaa aagtaaacca   49020
tgcatccaca gagacatgga attacagaac tggatgctga gctggtcact tgggaggcag   49080
gcgtccttgc cattggttta tgcctcagcc ccaccatgca gtggctggcc aggtgaccta   49140
ggccagtcct gcatcctcgg ctcctcacct gcctggtggg acagtgacat ctctcctgca   49200
gcactgctgt caggtgagg gaggtagggc gcagtttcag aaaaccattg ggctgcacct   49260
gcgtgagcac agctgcagga gcaaaagtca gaaaggtcag caaaggattt caggagcaaa   49320
ggtcagaaga aaccctcaag gtggttgtgt ctgcaggaaa gtgctgtcgt ctcctgcaat   49380
gctttcaaga ctattcagaa gcacagtgtg aagggagagc cggagcccat ggggaaatga   49440
ctccagagtg ttccacgtgt tggaaggcat ctgttggaaa acggacattc aagcaaatag   49500
ttgcctgcat agacaacgca gaatgactgg gaaagcccca acaagttacc tactggtaaa   49560
tgaggtgaga agcttaaagt gagaaccccca ttgctgcctc tttttcactt taaaaacatt   49620
taagttttga attatggtaa aatacacgta agatttacta ctgtaaccat ttttaagtgt   49680
acggttcagt agtgttaagt atattcacat tgctaaggaa ccaatctgct acttttgttt   49740
attaattttt tcctgagggg aaatattttt aaattttaaa atatttaatt gacaaataaa   49800
aattgtgtat attcaaggtg tagaacatga tttcatatgc acgtacattg tatactcatt   49860
accacaatca aagaaattaa cacatccaac ccacccatag ttgccattgt gtgtgcgcgg   49920
atgtgcgtgt atgtgtgtgt atgtgtgcac gtgtgcgcct gtgtgtgtct gtgtgtctct   49980
gtgtatacgt gtgtgtacat gtgtgtacgt gtgtgttcct gtgtatgtgt gtctgcgcac   50040
gtgtgtatgc atgtatatgg gtatgtgtgt acgtgtgtac gtgtgtgtgc atgtgtgtat   50100
atgtgtgtct gtgggcacag gtgtgcctgt gtgtatgtgt atatgtgtat gtgtgtacat   50160
gtatgtacgc gtgtgcatac gtgtgtgtgt gtgcacaggt gtgtatgtgt gtgcctgtgt   50220
gtgtgtgtgc atgtgtggtg gggacactaa aaatctctca tcacctttt agtcaaaaga   50280 acagttgttt tggtttggct cttctgtttt aaaatatcag aacaataata atttcccaca   50340
gacaaaatcc tcaatcctca ccatccttct atttcctata ttcatcataa acttcatgct   50400
tgatgttgaa attgttttct gaaaatagag aatacaaaga ggagatttta aaatgtcagt   50460
ggcagcccca cactcctttt taatcttatt tcctgatatc ttgagtttac ttggacgtag   50520
agttttcctt gactatggtt atttctggta gtagcagctc cagattaggc aatggttttc   50580
ttcagagata gcttagagtg agccccagaa caaggtcaat gcgaagattg cttgtgtctg   50640
cgtgtccagg gcacagtgat cctcatcact agccgggggg ctccgtgagg atctgctcct   50700
ggtcgtttct gttctgtatc ttctctgcag cccttactga agccgttacc aactggcaca   50760
attcaattcc tactgtaccc atcatgcaca gatggctgaa gtattgagaa cgctccagtg   50820
accgggaggc aatagtctgt ccacatctaa gaacacactt ggaataacct tagagaagag   50880
agagagagag agaatgcatg gttagtaggt tatcaaactc ctatgacttt tcacaggaaa   50940
agccctcatc cacaccaact ttaggaatgt gtagaaagaa gggtcaggga caggggtgag   51000
tggtgggcag agcagttgga gggcacaggg aaaaggcatc tggtcatgta tttggagtag   51060
gaggtcttgc tttactattg aattgcaggg acactttggg aacagtgttc acttcttttt   51120
gcaaccattt cttcagagaa aagtcatgat actcaagtct tcttacaaag cagtttgagg   51180
ctttgagtac cagactgatt acagagatga gtatgaagca ttattgtagt attttttaagt   51240 gaaattcact aaatgcaaat aaacctagca aatgctctat ggttaatttt tttctaaaat   51300
```

-continued

```
tcagataatt aagacaattc attctcctga aactgctgtt catgtaaaaa ggaattttat   51360
cgaggtggcc cttgagtgcc aaacagcctg tcctcagctg caaaatgagt cgttgatgat   51420
cctccagcaa gggatacttt ttagctcgtg tggtgattgc tgcacacggg atatgtgcag   51480
caagtatctg ctgagctaat aataaacagc ctcagacaga aagacagtgg gcacaaggtc   51540
atgcttaaaa agacccttg ttctactgca tcccagctcc ccaccatggg gcctcacagg   51600
ccctggtgac caagcacatc agacctggtt cttgctcagt cctgggagcc acagaaccca   51660
gcacgtactt taccccaag accagactcc agcttggctt ttgtcctcct ctccaggatt   51720
ggtgacctcc taggtcgtga agctgtgatg agcaaagaca cactcctctc cattctccca   51780
acttcaggtc cctttgacag tgtcagcagg catttaaata gcagaccacc cacagcaggg   51840
ctggtagatg cagtgaactc aggaagatgc ctgcatagac tctagtgtta aagacagaat   51900
ccttacaagg aacccccata gttacctaac tgctgtctcc agtggtcata gaagtgtgat   51960
aacccactaa tcatcattct ctgtctctct gtctttctca tacacactta cacacacata   52020
cacacaacct tgttgcttaa ttttcagaga gtctactttc agaaaagcct tcaggaatac   52080
atcatgtaca aaactgagaa attacctgaa gtatctttaa atttagtaaa aagttgcatt   52140 gtttttgaa catcacactt gaaaagtaca tgaatacaaa catacttagg aaaaaaagct   52200
ttaattaatt taaaaggag aacaatgcta tatgctgtat cccacctttc tctgaatgtt   52260
acattttctc ccctatccca ggctgcatct aagaaaactc agagggaata tgctatctat   52320
cttttccgag caatgaaagc tctgggtttt ttccttgctt ttcagggcac aatacttctc   52380
tttcttcctg gttagacagg ataagttctg agtcccctgg tatcatcagc ttacttcttc   52440
tctgttaaat attcacaaaa aatcactaac tttcatgcct cagcaaacct ccactgccta   52500
aaatatagtg aggtcattca tcttcggaca aattgcccca actacggtgg gaaaagaacc   52560
aatgtgttgg actatttatc taattttgt ttagttcggg gatacaaata aatgcataga   52620
tacatacaaa catgcgtaca taatagcagc agcagcctgt gaaacattga caagacctgg   52680
agttggaaga ggactttgcc atcctccagt ccaacagttg cctgtcacag attagacgac   52740
tgggatgtgc gcaggcgatt atttgcaaac ggccctgagt cccccagttt atgtcttaat   52800
tcgcagccag ggctgattgt agaagcaaat ttgcaaacat gtgcaagaag aaatcacaca   52860
tcctagagct tggatttcct cgtttcttgc tatttctatc cgtagacaga accattgctg   52920
agctgttaaa tttgtctcct tcccctatac cagtcttgaa aaaggaaagg aagtggagca   52980
aagaaaaaga aattaataaa gccggcagat cctaggagaa tcttatttaa tccaagcttt   53040
gtaaagtttt gctttattcc atggcaacat gggtatacac atcccaccgg ctgtttcagt   53100
ggctcagagc aggtaaggcc tgtgccaaac gccgctagca ggaggaacaa cgtggagaca   53160
gccccagagg tggaacgttg gcccttctgt ggctccggtg tctcaggacc tcctaaaagc   53220
ccagccctga cactgagcaa gtttccacca ctgttaggaa gaagtagaaa ggaatttgga   53280
gggttggtgt tactgttcaa gagctggaag gcttctgccc ccattcccat tccattaatt   53340
gcgtgaggta gagaactcat agaagatagg aacacatatg ctgatttcca aaattgcctt   53400
tgtatatttt cacgtgaaga ctttaggggc aaaagaaaag aagcaagcat ttgaatatg   53460 tgtttcaatt tgccttctgt tatataaaat tgtattttgc ctattctttt ttcattattc   53520
ggaaccttca agaaataaat taagttctct caaaaatgtg tttttgaaa agaggactaa   53580 aacagatggc ctggctgtgt taaacacagg gaccagacca gcacccacct ctccacctgc   53640
cctgccttca ctggcagaat tgtgatccat catgttctct gttcaatgtc atcatccctt   53700
```

```
tcagagcatg ggtctcttcc tttctaggca gtcttaccag gatgcatggg tgtgcctgcg   53760
taggcacacg cacagctccc aaggactcta aaaaaagata ttttctgct tatatactaa    53820 taatatgtta gagatttatg tttcaaatta gtacagaatc acatggttct ctccaaatta   53880
tatttgagag agaaagaata gaacaaaatt tattttacaa aaatactcag tacatttagg   53940
gcatatacaa agatgttcca gaatgtagct tatctcttta aagacaatta acacagtttc   54000
tgggcaaggc aaggcaaaat attcagtaac ttagcaacac caacagaaga cagccaatat   54060
tgcagcacat ttttctcttg gattgggtca gagagtactg cagagaaaat ggagtagaga   54120
gacctgaaat actttcgcac acactgtggt cagtgcagcg tccactgtgt gccacagtaa   54180
tactagaaac tccctggtta ggccttggaa tccagctctc atttcgtatg tgacctgcag   54240
ggaagtaagt taaatgcaca cgttttatca agttcaaatg caaacttaat tttaaatgta   54300
tgcaacatca gtttaagcgt tgtagctatt actagcaatt gtacctatta ctagtctgta   54360
ctctgcacaa ctttggagta tactgcctac tcaaggtgga ttttagagct ctatttgtgg   54420
cattatatca cggacaaaag cacgttcatc agagtcagag gaatgtggtg caaatcccag   54480
ctgtcccact taccagctgt gggacttgag taagctcctg aagcagctgc acctgcattt   54540
tctggtgggc accatggagc tgtcagcagt gctttcctca gagggctgcg ggctggatga   54600
ggtttgctgg tgcatgtgaa gtgtcaatca ttgctctcat gagtggtgat gctgatgccg   54660 ttccctttt tagggaagtg attttcccctt acaaagttac caacagtttc atgttggccc   54720 attttctat taattgtttc cactaatagg accaacagtg gtagtcccat cattttatta   54780
ctgcttgtcg tagcacaagc agttgcttca ttgtgtttag ataaatattg acggctgctt   54840
ttaacagtct gctgttttgt ctccttttga ggtccttaaa gtaatcctta aaaagatagt   54900
gcagatggaa agatgtctgg agtcagtgaa cctgccttct ttcctgtgtg cttgtcagtt   54960
tctaaaatgc catacacaaa ggactttcat gatttctttt taggtacatg attacagttc   55020
aattcacttc actgtctgga aaatttcctt ataatcagga tgaaatttct catgttagcc   55080
tttcacattt cactactttt agataaggaa ttctcaggct ttgctatatc tgactgctct   55140
tggaggctga gcttttggct aactacctga ctactttgtc gtttctcttc ccttggaatg   55200
aagcaaatat ctaacttctc actcattgtt tctgctattt taccatttag tcatctgtga   55260
tttttctaaa tactgaaaga cttccctcaa ttcaaactat gtgccggatc aaggaaaggg   55320
cagttggata ttgcagacag catagtgcaa ttgtgaagag tgtctgctta ccagccacgc   55380
tgccttgcac aagttatcaa gcctctcaac ccacttcctc aatctgtaaa ataggtatga   55440
gtgtaggacc ttcccagggg attttttttgt gactatagaa tgattctcag aagactttca   55500
ggcagtatgt gggtgaggca catgctggaa aggcttctgc aggtgcagtg atcaatgctt   55560
ttctcagtgt gtacatccca taatacagac acgttaccag aaactcccta gccaggactt   55620
tgattgcagc tcacattttg tatatggccc atagggaaat gaagtgtgta tttttttataa  55680 agttcaagtg ttaacttaat ttggaattta ctatcaaatc tcagttgtta tgggcattta   55740
tagctattaa tacttcgtcc catgtgtccc atgaggaaac caaggaacag aaattaaagt   55800
tctttctgga gtcccctgaa tctcgttcct gttcttttgc accctgttaa ttacatagag   55860
acattcacag ctcttctgac cttatcagcg ttaaggaaaa cagaaaacca gcgtgctatt   55920
tgttctgtcc cttagtcaag ccttctcaac atatattttt cttccaagat tttgcatgtg   55980
cacagggatg cctatcctct acaagaaaca cattttaggc aaattataat taaatgctg    56040
```

```
tttacatctc ttcaccttta gaatttaaag aatgatcatt tcttagattg catctcagac  56100
acacccttcc cctagtctgg agagggcgag gcccatgggt actgcaaaca gcctgacgtt  56160
gtcaggggcg gtctcaacgg ctcattcacc acatctgcct cgcgaaggct aagccatgtg  56220
ctgttacccc tgctgcgctc tggctcattc taaggtacac gctattaacc ttgtgagaaa  56280
acaaagaggc cagccccacc cttcctgctc actctgagtc acgtgaaaa tgtttcagga   56340
tctcgggttc gaccatgagt cctgtccagg tccaggagga aattcggaag gaccacatgt  56400
tcactctgag atcccacttt catttccctc ctggttgagc agcattaata ctctggctag  56460
atttaaattc tggctttctc cagttagaac tgaaagttat gacaatgtaa tcaaaataga  56520
atgtgggttt acagctggcc ccctggcctg gtttgtgaac ataaaacaga aacagaaagt  56580
gtaagtggtg acatcatatt ctctcattca atgtgaaagg ccaccgaagt ctttccagaa  56640
ttatttttga gaataatatg aattttaaa aaatacctaa ttattttaaa tatcgtcttg    56700
cttgctcccc aaatacctac tgttttcaac ttggatatac gacatgatta agaatatct   56760
aatatttggg aatgcatact ttaaccttat aaactaccac tgtaaataga cagactcatt  56820
aaagtgaaag gacattttaa atcaattagt aagcaaatca attaggtggc aaagacaaga  56880
ttattttttcc ttatggtagt tgaagaataa tgcttaacct gtcattctaa ttaccaagca 56940
cggtgttctc tttggaagat catttcaaca aaacattatt ttcatccaga atttgaacct  57000
tgagattgca tggtatttta gaaatctatt ttagaaatct ttggcaaagg ttactattaa  57060
aacaatcaca ttcatggaaa atcagtataa gagcaactaa aataactcac aataccagta  57120
aaatcacttt gtcatcttct taagacttt aaagagcatt tgtaagtaac tgaatagaag   57180
gccaaagggt gtgtaggtag cccagaccat cagtgggcag ccagggccag ggcagggcc   57240
acggttgcag cctgcattct tctaaagggc agagcaaatt aaagttgaag caggagctaa  57300
aaaaaaaaaa aaaaatgttt caaagaattc caccaaccag aggatactac ctaggacagt  57360
ttgggcctaa cttatctgtg aaggcctcca gcttcctcca caccggtggc cacttttcat  57420
tcactctgaa cccttctttg tatggaggtc atttttattaa ttgagctgtg accaacatga  57480
cagaatttcc tgttttaggg cttttataat atagatagtt tatatctaat ttcagaatat  57540
attcactggg gaatggactt agcaaccact accacaacaa tgcaacaatg tgttttggaa  57600
caaatttacc aatctgaatt tccccctaga ttaggtcaca ggaacattgc agctgatgta  57660
cagctatgtt cctcctgaaa cttggagaca catcctcttg agctgggtta taatgggcca  57720
cccaaagctc gagttcctgt aatggataca ctcaggcagc agaacctacc accgtagtga  57780
ggacagcacc cagagccctc agaggccatc acaagtgcac cacagctgcc ttctctggca  57840
cgctcagagc tacacagtgt actctgggat tggaactctt tatttttttt tcagttgatt  57900
tgtaaataag attgcacaaa aatccatgca catcaactct ccaaatcaga atttgctgag  57960
ctaaaaagag cattaaatta gatgggctgg ctttcaaggg gtggggtgc aatagtggaa   58020
ctctgcacaa cagttcttta caagagaca agcaagcaca tcgcgtggaa atttccattc   58080
aactggaaat gtccaagcct gtttacctca attaattgtc cttgttcact tgtccagcct  58140
agcaattgtc cattagtaat ttgttataaa tgagacattt ggtattaaag catctctttg  58200
ggatactggt atggtttatt ataacattct gttagtagtg ttgtacaagc ttgagatgta  58260
ttaatacgaa atccaagctg catgagggct ttatttttca agcctacacc ttgctgaaat  58320
tctgaattaa aatatgattc tcagtacaaa tgaataaatc aacagaaatg gtaacgcatg  58380
tcaaatattc ttaaaaccca agaaagcctt gtaacttcct tcaatctaat gggaaatgca  58440
```

```
ggcaaataca agactgatgt ccttgagttt tattatcaag actcaagggc accagtaaaa  58500
tctagtttca ttggttggaa aaaaaatcct gataagcact gttaggcata ttaactttaa  58560
tgattacaat ttttaggaca ctctgtggcc tagacttaga aacacaacta atgtccagaa  58620
aaagattcct cttttattc catcatctga taggcctatt tttacacata cacaccaacc  58680
aaaagtagcc aagcaaacaa acaacatac tcacacccct tcgcctatta tcatctaggt  58740
gattttcaat gctcattgca atgaaaccta cttattgtgc atggcaccca ccccactga  58800 ggaatactgt agtttctttc cctttgaact tcattagtag agcacatggt tcattcactc  58860
ctgaagagtt cttcgtatgt cagaatatat atactacaac ataatttcca tcagagctct  58920
gaccacccgc ttatctattt tcataatgcc tgccactcca tcattagctg ttgtcatgta  58980
ggctatcaat aaatatatga caaataaaac agttagggaa tgagggaaat tgactagcag  59040
ccaaagacct aagccatcct ctgcttggac attagaaaac tgagttcact acagtcataa  59100
gatacacaaa ggcagaatgt aagccataca aaaatccatg tcaatcccaa tatgtgagta  59160
caactattga acaccatgta ctaatggatg agttggtaaa tcattcaatg tcttcatgag  59220
gtcaattaca gattattatt tagaccccaa agattccaaa gatggtattt cggtcagatc  59280
ttcatccttt gtaagcctag cagaaaatat ggcagttta ttgactacta ttctttgctg  59340
ggtgtggtat ttttaaactg agacatcagt gtgcctagca cagggcctca agcacacaga  59400
aaaattcctt gataataatt aaataaaatt tcagcaaaaa atatcatctt aaggctgtga  59460
aattatcttc ctgtgtggct aaaatagtga ataaaattca gcgcaatata aatcatagta  59520
caatttcatc actaaatttt ctgatcttga tcttgtcatt ttacattgga agtaaaaatg  59580
tgtcctcctt tttttctctg acagtgaaaa gtgtgtgtgt gttgtgtgcc cttttgcaca  59640
ccctgcctca cacttgctgg tctaattcct tccagcatga ttatgatata attaaatgac  59700
agaaatgttt acttccaagt ggaactaagc cagggtaact cagggtaggg cagctgcttg  59760
caccgaaaga ccaagactgc tagagaacta ggaaacaggc ggtgcaagaa ctccaggctc  59820
tcatggaaga gcgggaggct tctatgggc tgcagaaact ctttggtgct tggggaaaaa  59880
atgggttaaa tgctcttaaa aaagaaacct gggagaggta gtttccagat gcaggcccgt  59940
cttttctttt aaacagaggc agctccgaag agctggacat tgaaccctga gcaggaactg  60000
gaggccgtca gcgcagcttt gtttggcgag cggagctttg caagggtgta atgctgcacc  60060
agggagacgc tatctgcagg gaccggtgac gccgtgggtg tggaggggga ggcagtggct  60120
ggccctcttg gggtaaggta cgcccaggaa cagtttagaa taacgtgcgc gagtcaaagg  60180
gaagaagaag ctcctgcaga ccttctggc actgtgcagg gtttgctcct gtccaccgtg  60240
ccgtgttcct gtcctgggt atttgggtgt gtggcgtgtg gggaggggag aaggagcaag  60300
gcggcaggga gggatgagg accaccctgt ccatgggaca ggcctgggc cccgcacaca  60360 ccccaagccc cgcgtcccgc gtcctcactg tcctgggaca ccccccaccc caccccaccg  60420
ccacagccca gagcggtgcc aggaagccgc ctcgacgcag ccgtatcttg aggctccagc  60480
cccatcccca gggtaccacg ccacgtagag acactatttt tcacttcgtg tttgtcactc  60540
ctaaagcatg tgtgctagct gcaccaaccc tgggatgcct cggtgcatag ggtttatgtg  60600
cgtcctcctc cttccctctg agctggtccc ccgtgggaa ctgctgccca gactgacctg  60660
cgtccttccg cacgtgcagg aaaatgtcca cgtgcacttg tcagggtggg ggccacacgg  60720
gcaccaccac tgatcatctg tgggatcgag ttactgccca tgcagatccc acgtgcaggg  60780
```

```
cccagtcgct tggtgagag  agtggacgct gtggtgactc cacggtctgt ggctgtgctc  60840
aggaggacag agagggaca  tcctgagatg gtttgggcag cccgcggatc ctgtgcatgt  60900
ccccagagcg tccactttct ccatggagca gtggagtggc gttgctgaga cagaaagttc  60960
aggttctcca ctccccatgc agcccccact ccctgtctc  cggccaggca cgcgtctggg  61020
gtggagactc ccggtgcccg ggccctcca  gacctctttc cccacccag  ggagcaggcg  61080 ggtacttcta ttccgtttgg cttcagaagg gaaagagaa  cgtaagttca gggagttctc  61140
gtccattcct ctcccgtggg ccgggcaggc agcagggaca gccttcagga gccaggaggg  61200
gctcgagctg cgaggccctg gaatgaggca ggcatgggct gaggctggag ggaaagcccc  61260
gctaaggctg gcgggggcg  ggaaaactta ccaccagggg actcgagatg gggaaggaaa  61320
ggtcagaaga ggagaggcca ggcacggggt gtgggcggcc tgcagagctg gagcaggtgc  61380
tccgcccaga gccaggcatg cacactcaga gtaggtggcc tgtgcagcgg ggaagagggg  61440
cgggtcggcg tgctgctgaa gatgcaggag ctgcggcctg ctctgtgcgt gctgaaggtg  61500
tggtgagaag cacttacaaa aagaaatgga ctgtgttagg attgcacatt ttactttgtt  61560
tctcccaaat acgtgttctt tgaattttt  tccttccagg gccaggactg gagtgatggt  61620
tgagacaggc acgcactggg tcttgtctgc atttacattt tgagattttg ttcagcatgg  61680
attttatggc gttttttgt  ttgtttgttt gttcgttttc aaaatactgc acggtttatc  61740
gtgaagacag ggtcctttgc tgccgtctta agttttgggc caagaacgt  gccccaccct  61800 aggcccgggc ctgctggctt catagctctc atcattccca cggaacctta agacctgagg  61860
acagaaagga aggaaacaag cccagtagtc cgtgaaaatc cagggtcccg ccactccagg  61920
tgtctgcagc agagctgaac acacgtaggc tcttgccagg aggggcattt gtatgtgctg  61980
agcattcctt atattctcaa tatgacgcct ttgaaagatc tgtggtttgc aaatatttac  62040
tctcagtcca taacttatct ttccaacctc ttaccaggct cttttgctga ataaaagttt  62100
taaattttga agtctaatat attttttaatt ttttttatttt atggatcata cttttttgtgt  62160 caggtttgag aagtctgcac caaagtatgt cctgtggttt tcccttaggt catcttcaac  62220
aagtttcata gtattttgtt tagatgtaaa tctgtggccc attttgagtt agtttttgca  62280
caagagttga ggtcaaggtt cttttttttgc ctgtgatgtt cagtggctct ggcaccattt  62340
gttgaaaaca tgatagccaa tgtcaagact taatagttat aataatcagg agcttttgtt  62400 tcttttgtt  ttgtttttag taactgccag tcactgcttg tggtatacat acacaatgga  62460
atactattca gtcttaaaaa aaaaaaaga aggaaatcct gtcatttgca tacctggagg  62520
acattatgtt aagtgaaata agccaggcac caaagaaaa  acattgcatg atctcactcc  62580
ttcatggaat ctaaaaaatt gtattcagag aagcagagag tggaatggtg gttaccaggg  62640
gctgggaagg tgtgagcttg gggagatttg gtgaaaggac atagaatctc agttagacag  62700
gaggaataag ttaaagagat ctattgcaca tcatggtaac tgtagttagt gacaatgtat  62760
tgtatacatg aaaattgcta agagagtaga ttttaagtgt tctcaccaca ccaaaaaag   62820 gtatgtgcag taatacagtc attaattagc ttgatgtagc cattccacaa tggatacata  62880
tatcaaaaca tcatgttgta taccataaat atatactgtc tctttatgta aatttaaaaa  62940
taagataaaa taaatgttat tcacttgtcg tggatgtggt ggggacaggt gtgggatagc  63000
cctccctgta caactaggac ccaggggtga tctagtgaca ctagccattt atcaggacgt  63060
atgggtgcca gtcaggatga taaagcttcc ttttggccac tatactactt agaaatgccc  63120
tgcaaaaggt gcacatcaaa gattgaaagc tcaatcctgg atttaagtg  cttcaaaagt  63180
```

```
gcacttaatt gccacatttt tgtcaaacat tttcccaggt agtattttc ctcatgtaaa     63240 acaacagcaa tttaatttga acagaaagca ttttgaaaca tacttttggc agggttcctt    63300
gcagatcaga atggaaatga ttaacagggc aattatcaat catggactt tggcggcaga     63360 aggaactgta ttgtttggta cagtctgggc cagggccaca caccgtaacg agatactct    63420 attctgtgga cggttggagg gggctgtgct gagcagggta actgcatctt ttcctagact    63480
gttcacactg ctgccacgaa ggagtcttgt ttagactgga cctggctttc ttcttcgcaa    63540
tgagtgttgc agactcccga caaaggccag gtggtaaagt gtggtgtctg tgagcgagag    63600
cctgagatgc ctgagctgac ctgtcctcag ccacctgcca tcgtgcagag gtgagagcag    63660
cccctgaatt ctgcccctcg gtctctccat agctaaagca aaaccatcct tccgtgctcc    63720
caggacaagc aggctattac caaatcaccc actaaccctg ggcgaggagg ggccatcact    63780
gcacaattca tcagtgtctg tgacaggaag agattgtttt agactggttt tttttttttt    63840
atttgcaagc ttttttctct ctccaaaacg tgctgtcagt gtgttctaat ttactctgta    63900
aggaattctg gagctaatca taggctcaca aaaagcagca caggaaagtt tcccagataa    63960
catctatttc agtggctttc aaacatttt gaccttacca agtaagaaa tacattttaa     64020 tatcatggca cacatacagc tgtatctaaa ctttcataat actgccttta cgatatcact    64080
ctgatattgt ctattctttt ctgtttattt ttctttttgt tccttgttat gctggttgtg    64140
acccactcca gtgatttcac aatgcaggct gggtggtgtc ccacagtttg aaatcccaat    64200
ctagggcctt cctctcactg tacaaagtag gtaactgggg acattagtgg atcagtgatc    64260
aaaccaaagt tatttgatct taccaagtga tatcaggatg agaaagctgt tagagtgtca    64320
gatatgtgaa ggaacttggg tcattcctga tacctcaaag agaaaaaagg tagtccttga    64380
acacctccta cttgtaaagg atgcacaatc ctacatgccc ctccctttcc tttcctcccc    64440
tctgtacccc acccctgccc acattttctt cataagcagc tttggtgttt tggcttgttt    64500
gtttcccttg tctcctacct gtgacttat agccttttgg agactcacag caatagttgt    64560
atttaaactc agtgggtggc atccaaggct aaaaggaga ttgcctagac acaaaaccac     64620
ccaagggaga aagcaggaca gcatcttact atgattgttt cttgtttctt cctgtctcat    64680
aaggattatt acccagggtt ttcattttt tcatttcatg gttcattttc gctccagtgt     64740
agacatacaa tagaccactc gtccctgtgg ctccgggcag cagcctcatc tgagaccctc    64800
ctgagacatc tcgtgcaggg cagccgtagt gtgtggcttc cccagggctg ctctaacaga    64860
tcaccatcct tgccatggct taagaagctg cagatttatt tgcttacagc tctggaagcc    64920
agaagtccaa aatcaaggtg tcagtagagt ctctctctct gaaacctgct gaggatgatg    64980
cccctggcct ctccccagcc tctggtgttc ccagcagccc ttggcattcc ttgccttgta    65040
gatgcaaaac tccgatctcc acctctatcc tcacagtgag ttctcctgca tgtctgtctc    65100
tgtgccttca cattcctctc tgtgtgtctg tgtttccatc tccttatgag acacccatc     65160 actgaatcag ggcccactct ataccagtaa gacctcattt caactccatt acatcttcaa    65220
aaaccccatt ctcaaataag gttacttcac aagtgctgga ggttaggact tgaacatacc    65280
ttattgaaca atccaactga tgacacatag taatttatgc actcgttctt ggagacgttg    65340 actttatta gtagcattaa ccatggcaat gtcaccagca tcgctgacag cctgaagcat     65400
atgatctcca gaatgtattt caatcatcat gttcacttcc ttggtattct ttagacaata    65460
actcagcctt gaactccagt aaagggtttc cctgggattt tcttcttgac tcactccact    65520
```

```
gtggcctccc tcatccagga ctgtaacaga cgcctgacgt cagtggtcta gacctctctg   65580
ctgaatgtca tctttggtga atgtcttatg agaaaacaca tggttggtca ctcttagaag   65640
ggcatgaaag cctgtctgca gtataaccaa aacaggcaca tggcgaggca cactgtgcgc   65700
atgtgtgtac aattaatatc atggttttaa attattttca ggccaagggg agatctttgc   65760
tgcatctact gaagaaagcg aatcttttc ttcctgaaaa aaaatggcta cttattagtc    65820
gaatttgtgt tttaaaaata tgtgaactaa tataatgcag acatgcatta atgtttaaat   65880
atactggaag tttttggtaa aatgaaaccc attgtctctg ttgattactt tgatgagtca   65940
agaagtaaca tcctgggaat gattggccag tttaaatgag tgcctcaggt ttttggaata   66000
caagaaatca agaggaaggg attagaacat ataggttagc aagattggga tcctaaaata   66060
cagacccaaa tgaatggaac aaaatcaggg aatttattaa taacagggtc aaggccaaat   66120
cagtaacaaa tatcctgagt ggaagaaagg tggtttaaca aatgcccta tgaaagatag    66180
agattggctt accatgatga gatgtaagcc caagttatga ggttggcaca caaaaccaca   66240
aatgtcatag cttaaaacaa cacacacttc ttatctctgt ttctgtgggt cagggtctgg   66300
gttctcaggg actcacaaag tatgttttca tctggagctc caggtcctct tccaggctca   66360
taagggttct tggcagaatt cagtttcttg aggctgtagg actgaggtcc tggctcctag   66420
aggccaccct ctccataagc agttcttagc atggccgcct gcttctccag gcccagtggg   66480
aaagcatgtg cctccaggag ggctcagtcc attcttcatg gcttttacct ggttaagtca   66540
ggcccactca ggataacttc attttgtatt aaatcaaaac cagctgattt gggatgttaa   66600
ttacatctgc acaacttcaa ctttgccata taacctaacc atgggactga tatttatcat   66660
gcatttgggt caagttgcat taagagatat aataaagctg acaagcttc tgttgattag    66720
aagagttcag ttacaaggct acacttggga ggaatgttta caaactggaa tggtcagagg   66780
atggggaaga cacttgagaa aagtcaagtg acggatgaag gcaaatgtgg atatttatct   66840
gggagaaaac taagaggagt tataatagct gtcttcaaat atttaagg cttttattag     66900
gaagaggaat ttgcatatt ggattttgcc ttcagagaag tggagtcctg agatgctctt    66960
agccattcat tccagcctcc agggctcacc tgctgtcttc tgtccaggtt ctcggtagca   67020
gggcagtaca gccccatccg tgatcttcca tagtcaggca tattgtcaca ctcagtgagc   67080
ggagagtcaa ccgggaggaa ggcacagttt ctctggaatg acctacggaa tggtacgctc   67140
aaatgcaaat tctccttccc ttccccagtc cttgtcctc agatggtaat ttaggagctg    67200
aaggtcaggg caccagcagc ctttggaagc ctacaggaca acagtcagcc tggctagaaa   67260
aaaaaacaat gtcacaggca tgttgtgttt aatcacatga aggatatttg cattgttttc   67320
caactgatgc cagcagacac attgtcagtg gtatcatgcc tggggtatca gagttgacat   67380
tgggttgccc cttctctgag gcattcatgt aaatccttt aagtttataa aacctccatg    67440
tggctcctgc atgcttcatc atttgcatgt gtctcttttt ccaggggagg cagcatgggg   67500
agcaggatgc tggtgggctc caggtgcaga gagcagggtg ggcgtcagac cccaggtcca   67560
ctgtgcacgc cctcttgtag agcccgttcc gttgtccatg agatgaggag tgttcttatc   67620
tctaaagtat tatcatgaaa acctaacaat gtagaaagac taaagcacat gggtggtgct   67680
tcataaatag tatttctccc actttctgaa aactcctgct gaagtaactg cacaagaatc   67740
cttgaacatt tagaattctg gttttagcca taccataaag tcagtagtgc gtggtggaat   67800
tctgctaacg aaaattgcga aggatcaagg cagagtacag agctggtgtg tagcgggtac   67860
cttctgtctg ctggcactag gtattttaca cattaaatca gctcgttctc acatcagctc   67920
```

```
tttaaaaat aaggaaatga ggagccacag tggcccaact gatgcagtgg cagaagtaga    67980
atttgagctt gtgcagatgt gcctccgtgt tttgtctcct gagcatgctg ccccaagttt    68040
gacaatacca agatttgtac tggaacattc cctcccatcc ccaccccta gaagcccctc    68100 ttcctccctt agatttgaca catagtttga aaccactatt aactacctta tgagagccac    68160
tgtttgtgaa gtgctgacta tgtgccaggt cccgtgccgt gcaattttg tgaattatct    68220 cgtgtctaca gtgcctcaca atttctctgc tcaatacctc catgttactg ccgaggaaag    68280
ggaagctcag agagagtaag taatttgctc gagttaaaga gctggccagg acagccaggg    68340
gcttgcaccc cggagccttc atccactaca ctgtcagctg gtatctcaac cagccattac    68400
aggctgtaaa aaaattatat aagatagtct atggtaatgc agaaaagtga ggttattttg    68460
ctccctttcc ctttgaagaa aaaagccctg gaaagacata tcacttgagt atgggaaaaa    68520
atgaagctgt ggcttttctg tgagtcaatt ctttcctggc agcttcttgg aataagacca    68580
agtatagcag cagagttttc tgttttaatt tgagctgcag ggtgactttt tttcttctat    68640
gctttcatct ctctgtggct tcttttgcct cgttaatttc atgccctgcc caggcgggct    68700
actgtgctgc ccagtcaccc gggtctgggg cggccaccgc tggccagcag gcaggccctc    68760
cagaggcaga ggtggccacg cttaggtcgc tcccgctgtg gaggcggcac acttgggtgg    68820
cagcacagct gtgatgtggc ggcagctggc agccccatgg gaaagatgtg tgaagtgtgg    68880
ggtttgacga cccatgggag aacagacttt cttcctcttc ttgttttccc ttcaaagccg    68940
tgagtcaacc tcaaattctc tgtcttttt ctccacccccc tcgtgcctct ctccctcacg    69000
ctctgcatct ctcattgcaa gcttgcattt ttttgcacac aacactatct taatatttct    69060 ctttttctgca ggcaggaaat gagaagtcat ttttcagggt cattcaggaa gtcatccaga    69120
gttataatgg cccattatct actggtcaga gtttacttag gctttcacta cttccactgc    69180
ccacttgaaa cagggaaaaa tattttcccc ccgcgctgtg agtgtgctat ttagagctga    69240
ccacaagcgg ggggaagaga ggatggctcg gatgctgcat ttccactgag aacacaaggc    69300
tggcaaagct tgtctgctgc ccagcaagca cttcaggctc acaccatttt aggttcactt    69360
taagtagttt ctcaattgtt aaaaaaaaa caaaaaaaaa aaaacctgta ctctgaggat    69420
atgcttataa tcccatagct aacccagaat ttcttagaga actgatcaac atcagcagtg    69480
gcacttactg aaaatgcaca ttctcaggcc ctgcgtaggg cctactgagt tagaatatta    69540
gagagcaggt ctcagaaaca ttctatccgg cagtcttatt ctatgcaccc gaagggataa    69600
gagccatgct ttcatgaaac atgggttgtg tgtaaaatgt ttaaaaggta tggcaaaatg    69660
tgtttgattg gcaccaagga tttctggttc ctcctagaat cattaatcaa actttgaagg    69720
agaaataaga gagtcggcat tttcttgcac attctttgtg atgttgtgat gagttggaaa    69780
cttcccgatt gggtttatta gagcatgaac acccaggcac ccagcttcta gccagccctg    69840
tcaggcagag tctcctcgaa gatgtggaaa ggactgacca acagctgagg cctacaggaa    69900
cctgagcagg caaggggaga ggcaccccgg aaccaggagc aatggccttc ccaccctccc    69960
tcgtcctctc ctcttctcct tttggagttg caggccacag aaaggaagtg acatgagtca    70020
ctttgggcct tcttaattcc ttcatcaaag gcagcacagg tgtgtatgtg tgttggtggc    70080
taattgaggt aggcccacag aggagataac agatggacat actatttcct ttcttccatt    70140
ctgatataat tcagggtata aacacacaca cacacacaca cacacattct cacttctttg    70200
gcatctacca cacctgcccc agtgcccatt tctctcccac ctgaataaaa agccccaca    70260
```

```
aagcctgagg tacatggaaa ggagcagtgg tctggctccc aggagtgtga gaagcagcca    70320
tgttttcaga ggctgtattc cacttggact tggccctacg ctgaaggtag gagcggatgg    70380
gggaggcccc cttcgcacaa agagcccat gaaagagtgc acagtccagt ctataaaaca    70440
gacgcagaaa atgtgtgtag gacttcttcc tgaaaaagag cgtggtgcgt ccagtaccctc   70500
catgttcatg gaacttccca gtctgcagtt tacccttttg tgcaactccc ttttggtaaa    70560
gccctggtca cacttctggt tgttcagatt atacagggat aattccagag tgattttaaa    70620
gtcaactgcc aggcatccgc acttgcaaat tagatgcctg gcacatgctt gtgttaaggt    70680
aataattcat tacaatacaa attacagggg agttcctctg ggcatgcgac ctttcccgtc    70740
atttggcttt ccctgtgatt atcaggggag cttccatcgt gctgctaatg ggaccttaac    70800
catgtgtcaa cccatggctg taatgctgac actgttttct ttctggaatg aaaggccttc    70860
gcaattgaaa ccaaaatgtt atccaactca gtcctgtccc tttgacgatg aaaacatcaa    70920
gttctggaga ctggccatcc agcctccctg cctcatctcc cacgccctcc atcattttt     70980
gtctctactt acttatttat ttggctgtat tttacgtaca tcatgcaaaa atattcctct    71040
ttgtaaaaag tataatgatt tcaggaaatt agagggtaaa aagcaagaac catgctttca    71100
ctccactgtc aagagttgtg gaagaatcct tccagcattt tttctgtgta ttttacatac    71160
atacaaatat atgtacaaat aaaggtcgat catttaggtt ttgtttatat ttttgtatat    71220
atgagcttat gtcattcata catattgttt tgcctcttgc ttttttttaa cttaatttta    71280
ctttgcttga gagcttttg aactgaagta cgtgtaagtc agcctatgca tgtaatggct     71340
ccctcatctt ctgtgaggct gtcactaaaa aggggattta gcttgttctg ggctttgcag    71400
cccgtacact gggcactgtt catacgtact tctctgtgca cgcaaaggag ggcttgctag    71460
ggaggcctgg cagagggtgc cattcaaata ggattttcaa tggaggaatt tttaaatttt    71520
cagttatttg aataagtttt aatatatatc cagaacccca aatcatcaag tttgttttct    71580
tccacatctg tccttccatt tctgaactat tttaaggcca gtcatgtctc atccaagaaa    71640
tcccatcctt tcacacaaca ctatctccgt ttcatggtta tgaatctcta aaagcatgat    71700
ttttaaaaca taatcacaat gctgtcatcg aacttaaaaa ttagccataa atctcttatg    71760
ttacccaaca accagcctac tgacacatct ccagttgtct caaaaatgtg ttttccattg    71820
tggtttgtct gaaacatgat ccaaaagtca gacccacctc tcacctttcc ctaacctgcc    71880
ggagcccatg tttctttcca gccaggcttg gagaccacca cacggatttt gcttcttggg   71940
gcctccctct aaccagctat gcaggatgcc ctctttcctg tcaatacaag ctgctcaaag    72000
gactcattca gttcaaattc acctatgtga gcctaggtga tgctacttat ttatttattt    72060
atttatttat ttatttattt atttatttat tttgagatgg agtctcactc tgttgcccag    72120
gctggagttc agtggcataa tctgggctca ctgcaagctc tgcctcccgg gttcaagtga    72180
ttctcctgcc tcagcctcct cagtagctga gattacaggc acgtgccacc acgcccagct    72240
aattttata gttttagtag agacaggggt tcaccatgtt ggtcaggttg gtctcaaact    72300
cctgacctcg tgatccaccc acctcggctt cccaaagtgc ttcatgtttt caggagctgt    72360
acgtgcattt ttagttttga tgaccaggtc ctttttctgt ttttaaaga acttcaaatg    72420
atctccaggg tacacagcgc ttgtgtgctg atgaaaaagc tggcagtaca aaggccacca    72480
gccaaggtca cacagccaaa aagcccctga cctcgggccc cttccagac cctgggtctt     72540
ttgctgccac atgaatcttc ttcaaggtcc tatgtgtaga ttttcttgac ttggccatat    72600
tatttaggat tcagatataa taacaaaata gatgttaaag cataacatga aggcatttaa    72660
```

```
aagggtagaa agcacatgat ttactaaaac cataaatctt atgacctgaa agtttcacct    72720
aatctcttaa aaaataccgt actaaaccct gattgaaaat cagagctcag acatacagcc    72780
tgagatgcca aaaaatggcc aggcttgtct gttgagaaag ccatatgtaa ctaactgttt    72840
ggaaattcaa aatatatctt atcattttaa aaacatcttt cttctaaaga caatcatctt    72900
ggcttcagga atgaggctag taaaaagtga aatactccta cttgtggaag aaatcctcat    72960
tttaaccatg aagaactgaa aaatgcattc tgatgttgat ggacccaacc tatatttggg    73020
tattttatga tgtacacaat atacttttgt atatgagatt gttattaaat gtgactttgc    73080
tttttcaaga catacaatgt tcctccgggg gtcaggcact gtgtttagca ctttgtcctg    73140
acctcatctg acttctcagc tgtccctgag aggtaccagt gtgcaagatc gctgagttgg    73200
caagtgatag tgacaatatt ttcaccccaa tttctaattt aaagaccccg atttctagtt    73260
ttgttttgta ttggatttgc acaatttcac gttctgaaag aggatgccct caactttgca    73320
aaatgggcct tttgaatgaa aaggatcagt catgtcagga aaagcgctac aatgatgaaa    73380
tatgataaat aagtcagtct ttcatctgta attatctact atgggtaaa aagtgatgaa    73440 aactaccatc ttgaaaggtt ctggtgatag tggttcctaa tgcagtgaaa gatgtgtaag    73500
tcaaagattt gtaaccagcc agggaatgag aggcgaagcc atagctggtg gcgggggcca    73560
catctgggtg tggggaggcc acagttgggt tgggggtggg gcctgcagtt atccacaccc    73620
ctcccacctc ccttcgacag tacaggcttc tggttacct tccagagagt aaggccaggg    73680
agagttgaat aagttgagaa atgtcatgtc gaagctattg gtggaaagag ttccattaat    73740
tgacaataca agtccctact acattctaaa atctggtcct gactagtggc aagccgggcc    73800
caggagtagc acttaaacaa tggcaggctt gtgttgctgg caggatactt cagcctcaga    73860
ggagctgtgt gcagctgggg agactcacac tcagaggatt tcaaagcaga gggcatctcg    73920
tagagcaact tatccaaacc ctgacccact gtaaacacac acacacacac acacacacac    73980
acacacacac acacacaccc tgagagagag aaagagagag agataactaa agagagagaa    74040
ctaaagtttg gcaaaataat acatgctcta atgaaggttt attaatgatt aatctactcc    74100
tagcatttcc tagtccactc tatctcctta aaaaaaaatt ctggttgcag cccactaact    74160
tgattgtaca gctgcttaat ggatagcagg ctgtaatttt cagagaactg tttaatgcgg    74220
gctacctctg ttcttccatg ctgcttgtgg ttcctgctct gctcaggaca gaatggggag    74280
gaaaacaggc tctgcggcac aatattggca agtgaaattt tgtaaaccgg ccctccttc    74340 cttttgcatt tggtctgaaa attcaattag atgctgagtc ctacaatgta tttgagaagc    74400
ccaggagtgc cctagaggat gagactgggt ggctccctgt caggttgaac atttgcctta    74460
attactttgg caagatttgc atcagtggta ttagtccctg cctcacttgg aggcctgcac    74520
ttaagtggcc acattcaggc tccaatttcc tggtgatttc atagtgtagg gcacttgcaa    74580
tcaaaactag gcttaaagcc caaccctctt acatttacc cacccccaca aatgcagcaa    74640
ataaaatgac tctgattttc attccctaga cctcttttct atatttatta cattattgtt    74700
aagacagttt ttgaagaaag ctgtttatt taacaaaata gctttatgga atcaacttca    74760
tatatcttct ccgccagatc aaaacaagct cgtagtatta gatgtcaccg agcaccatga    74820
caggcagatg aacatcatcc ctgtgcccgg ctaatgatag ctcggcctgc cccggcgtca    74880
gccgctcctg gcagggccag cggcggtgt gggaccggca ccgtatctcc agcaattcgc    74940
agataacaaa tatggttctg atgatgttac taaagatctg tcccttttcaa gattggatta    75000
```

```
gacattagga atttggaggg cttttttattg ctagcattttt taagaataac caattagagt   75060
attgattcta aagtctgaaa gccacatgga cagagttcat gtaattggct actttatgtg   75120
cctcttccta gattgccctg catttttcaaa acaagagcct ttctatttta atcaaaagaa   75180
tccagaatga aatgaggctt tgaaaactca gcctatgttt gtcttgattt ccttaactga   75240
catctagaag aaaatatgag ctcaggggtc cgctgggttc cttccagcgc ctaagcctgt   75300
aagctcttcc tgctggaacc aagctttaaa tgcacttgtc agtcatgtcc catgagaata   75360
gatactgcct tccatgtttt tttgttctga tttccgtgtt tgaaatgatg aaaatcattt   75420
ttctgtgctt tttaaaaatg gaattgcttt tgtgttggga attgtgctgt tcatttttac   75480
tctacctcgt tttggaatca ctaatgtggc caatttatag ccaaaaatca gtatcgtaga   75540
gtgagcaatg aatggcatgg tgactgtgtg agcgaattca tgccctccct ccccaccgct   75600
cgccccgcgt ctcagtcctc agtgatggta aacagaatga ggaccttctc ccgaccgtga   75660
tgcgcctcag ccctacttcc cttgtccttt cctatcataa aatcttcttt catagaaatg   75720
gtcatttctg ttcatatctg tggactgtaa ataacaagga agtcattttt gaggtgaaaa   75780
ctgcacttag actcattcca attttgatgg aaactttttag ctggtggatg gcattttgtt   75840
ttgtcttagt tttgcaagga gttatcttaa tttagggaga tgaaactagt ctgtgatccg   75900
aggtctcact tccatacatt tctctcgggc agtgtggctg cctgaatcat gcctggatgc   75960
cacaggtgct tagccagctg gtcctgtcgt aactgtcact ggtagctcag ggagtgcaga   76020
ggtgccagca gacactatga aattggcctc gtaaagcatc agttatgttg tgatggtggc   76080
aaagctgcag gcgagatggg aagtgcagcc actgagaact cacagtagag cgtgtgtaac   76140
gtaaaaagat gaaacccatt gtacacagct gtgtactgcc tccttgaagt caaatttccc   76200
ccattaccaa ggaaaagttt tttctgaagg gggctgcttg acaggatgac atctggtgat   76260
atcatttatt cctttggaaa tcaatctgtg gaagtgagtt tccactgact gatgaggaga   76320
aaaatgaatt ggcttcaccc agcatccagc ttcttatcct gggagagata gctcttggtc   76380
tgtcatccac gcagctgcct ggtgcaagag ccaagtttgt gcagcctgca gagcactctt   76440
cctgagctgt gggctgccag gtcgggggc aggggggcc tcactgtgca gcctcctgcc   76500
acccactgat catctgggga gactggccta tcctgtcagg agacgcagtt gcccagacgt   76560
tttcaagggc ctaagatgta ggcagttgat ccacagattt ttggagagtc cttgagttgg   76620
agattacagg tgacctcaga ggagggagtg agaaacatctg ggtcatgggt ttctactagg   76680
agtccacagt gaaaacaaga agaggaattt acgacaagac agtccagcaa cttcctttct   76740
aacttctcct ttcacatatg ctggatactc caagactttg catttacatg gacatcacag   76800
atccactttg agagaagtag ggtaaaaaga aataaataca tagtgctttta ggtgtatttc   76860
tatacatctt aattgatatg ggattacatt ttcacttgtg tttactgtac agactctaga   76920
cagatcctgc tcttttgcag gtaaaacaaa tatttcttaa aacctagaaa gacccaaaac   76980
aatttaacag aaacattttg gaccatttg gaccttggca gttaggcccc agtgcagcag   77040
cggcaaccat aaacctctcc ataggtgctg aacccaggtg atccctggca ccggcagcct   77100
tatgtcaggg ctctccttatc gctggttttt atttctccta ataaaagtga ttaaaagatt   77160
catcttttaa agaaagcaag gacacagagg tggattctcc ctgacgctag cacagctcat   77220
gcccaagcca ctcctgcagg gctctggtct aagtgcaaaa gctggaaaag ctgcaggtcc   77280
cgcaagacac agagcaaccc tgcaagccag gtcaccttcc ctcttctctg ctgtccgact   77340
ggccctccac catgtgacat tcaaaagctc aagttactta acctctcaaa actcagcatc   77400
```

```
cttttctgta cagtggggaa gatactggac tgttgtgagg attaagtgag gagagtggcc    77460
caatgaggtt gacagttatt actgtcattg tcattatttg ccttctcaca ggcaggcgtg    77520
ccacagtcat tttactgaag ctgcttcagt gggtcctgaa ttaggccctg tcctttggga    77580
gagacagtcc tggttcaaca cacagctccc tgcccaggc agcttgggag tgtgggccag     77640
tttcgccttt agaaccacaa ttctctgata tgtgcaatga gagaattaat tatagactca    77700
aaggattgca tgcagacaca cacagataca aacacataca cacaacacac agagttacac    77760
acagacatgc tcacaataca cagaaataca cacagacaca cgcacacagc acacagagat    77820
acacacagac acacacacac acacacacag acatacgcac agatgggcac acacagagac    77880
acactcacag agacacacag atacacacag gcacacacac agagagacat acacacagcc    77940
cacagggata cacacagaca cacagagaca tacctacaac acacagagat acacacagtc    78000
acacacagag agacatacat acaatacaca gagatacaca cagagacaca gatcagacaca   78060 cagacagaca tacacacaga cacgggcaca cacagagaca cacagacaca cacaggcaca    78120
cacgtgcaga taaggtaata ttagctagtt caggaggaga aagagataaa gataaagtaa    78180
tattagctag ttcaggagga gtgaaagaag ccttgttttt ctccactttt tatagaagag    78240
aaagtgaaga ttcgatttga ggtgagttca gcacaaaagc gtatcccagg ccctctggct    78300
ccaactgcag ccctttctac ctcattccca gacccacct aagcctttc tcttcaaaat      78360 cttctcaggc acactgatac acatacctca gattttaat tctccggttg tgttcaccag     78420
gtgcttggtc atgattaaga attccgtgat gtgtacccca tgtgtttaaa tttgctgctg    78480
agttaacttt gtggcggcct gtggactaga cctctgcaca tgcaatgcag aacggcaggg    78540
ccagatttga aatcctgcta tcttttcggc tgccttgtaa aaataacatc aggcgatggg    78600
gatacgatgc cagaggtcac ctgtgataag ttctgtttat ggccatttta cttctaggaa    78660
gacaggaagt gtcaggatct cagggatcta ggaagccaaa atgttttcc actctgaaat     78720 aaagtgactg accaggagtt cccggccacg cagccctgtg ggaactgccg cacggccact    78780
tttatgaagt ggacacgtgt tggtcccact gaaaagaaac tccccaccca tggctccctc    78840
acgctgcagc agaggccctg ccacagcacc tgtcagcccc tgccagcttg caggggcgca    78900
ggcgcagagc ggtttgtgcc cttgctggag ccagggaagg gcacagggtc cctcctggag    78960
tcatgggagg tgcagccgag gttctatatt aaaatacaga ggctagcaca tgtgcttggg    79020
gaatgcagct acagtagtgg aatgaaagtg ctgtccgttc cttaccccc cagctcctca    79080 cctgtcctcc acacgcatat ccctggctcc cttccctag taaggagact gaattgaaat    79140
tgtggcttgc ccgaggctgc atacctgtgc tctttctgaa gcccaagtca ctggctctag   79200
aattctaacc tgtgaggaag ccactgagga tgtttgtcaa aatacatatt tctgtgcctt    79260
gccccagttc cacggcccag gaatctgcag ttttcacaag cacccccagg tgattctggt    79320
ggtgtctttg cacttcttca aggcagtact gcctggaacg cagaatccca gcctcctcta    79380
tcctccttgc ctaatggcct ggatgctctc agatctacag gggaagggaa ggtcacacag    79440
tcatcgcaat agtaacctca gctgataaat cctcccccat aaaacttatt ccccagtgtt    79500
ttttaatagg aaacaataaa actgtaacca gcccaaatat ccatcaaaga gaaaatggag    79560
aagtaaatca tcgcacattc acctggacca gatctattgt aaagccaata atactgaagc    79620
cccttccaag gccctgggag tcctaacagt gcactggcag tgtctataat ttatatttatg   79680 aaatttgcat aaggaaaaca ttttgtctca tttgtgcaat ttctccttct aaatatacgt    79740
```

```
gtcactttgt acctgatttc tataagaccc aggacctaca aaccctgtgt ctgcccctgc   79800
agccacccag ggaaggactg cacagcagca agacagattg ccatggagca tgttgtgccc   79860
aactagggac agcgcagata gattctgtaa tttgcctaac aatgtctata ggatgatccc   79920
atttgtcaaa aaaaaaaaag aactgggctt tattgatgtc acctaaatgc acctaaactt   79980
cttttttgcc ccatgctctt ctgtactctt gatctttccc caattttta aaacatgac    80040 actcattccc ttattttcc tacttagaaa agtgtagatg gttttatcat aggaagttca    80100 aaaaattaa aatataatga aaatactca aatagtgcct cacaacagta actactgcta     80160
acataaataa aatccatatt tcctctcata cagacccag agttgctttg cctgacagtg    80220
tagttgatgg agaaaataat ctttatcctt agcctccatc tggttgcaga ccataaagac   80280
agggaaaaaa tgagggtgtt ggtagcttcg ttagaaactg aaagctcact gatttttca    80340 aaacctaaat agcctgtgtt tctccaaata actaatttgc agccttcggc agccaggact   80400
ggcagggatg gggctagggg gactggggag aactgctctc tcctgagggt ggtctgaccc   80460
gacagcacgc atgaccttcc cacagtcagg aactgctcag agcgtgatg gcaactccat    80520 agaatgaaat actcttcagc cagtaaaatg tattttggga taaatatttg ctttaaaaaa   80580
ctttactata tgttgttaaa tgaaaaaaaa accttaaggc atcagaaatt atgtgcagta   80640
aaatctcact tttgtaaata aatatacctg tttactacgt atgcataaaa agaatcctga   80700
gaaatataag tactgtatgc atattgttgt taagtatttt ttctgtttgc ttatctataa   80760
ttctaatttt gcttcaaaga acaagttact ccggcaatat aaaaataaaa taactaattt   80820
gtcttgtcat caaacagata gtaagaacag gcaaacctgg ccctccacac tgccagcctt   80880
ttgtgattca aggcttcagt ttcctccact tgttaaaaag attcaacaaa gtagttgaaa   80940
tagtatgtga accagtaaac cctaaaaggt gtccagtgtt gtctgtgagc taattaagtg   81000
atttgattct gactccccga gtcttctgat ttcgaagcag tggggagtca gacaggagcc   81060
tcaggtggcc tctcctgaga ggccctggaa agtgatgaga acctggcctc tggcagctct   81120
tcataaacgt ccatgttttc cctctactct ctcactctt tcccagggcc tcaaacagaa    81180
gatgaaaatc aatttctaaa acagccctct gtgtgctctc tcgtatctct ccttttcaca   81240
catcgtggtg gtggctttct ctgtgttcct ctgttgattc agtctctgga attaacggat   81300
caggattcca tgcccagaat gctacaaaga ctgtgcttga gttctcccac atctcactca   81360
attacacaga agtttcagat tatgtaacag atgctgtgct gggttaggca gagccatctg   81420
acttgttttg ctttatttta gaccatgaga tgggtgagtt ttttcttttta atgccacatt   81480 cttttaagaa ttaaaaacct ccacttggct gtcagcattg gaaatcagag tgatggtgca   81540
agccctgatg aggacaatgt ccttgtctat gaaaaggtga aatcattgct tgaaatcgct   81600
aagcaggaca tgcagtccca gatggagggg ggaattcggg agctggttgg aaaagagtat   81660
ttggcacttt gcagccttga gaggtgcaga agagacaccg aggggttcac caccagagcc   81720
accattgtca gagaggcgtc cagctgtgtc cacctgggac tctgccttca gggcttcttg   81780
cctggctggg agctgcacag gcagactcct gggacggtgt gccgacagct ctgggcaccc   81840
ccttctagga tctgattcct gaggaatcac aatgtggatt tcacaatcac ttccagtgtc   81900
ttttgccaac ctctgtgaac agatgtgcaa ttaaaaaaaa aaaagaaag gggcccaatt    81960 ctcaacactg taagtggaaa ctttttaatg gaaaaggata ggctaatgaa ttgaatttga   82020
aatctgagac agaaccgatg catcaaatgt gctggtgttt acagataata caaggggggc   82080
tgcatcttat ggtttcaatc ctttttaaa ttttgttct gagagaccca gccagcagac     82140
```

```
tgccgccagt cttgtcagag atgtcagtgg tggccactct gaatggaaag cagcatctct    82200
cagcatctct gaggcactgc tcctcagcgg agactgtggt ggctttgcct ttcagcacgc    82260
atcctttcta cgatgcctga cagtgcccag ggaatgggca gagctgggag ctctgaagcc    82320
ctttcaccta aaccaccctg ggtcacctga cctagttttc ctcccaattt taattatgtc    82380
aggcacttca caaaggcctc cttggggaca ccatgagctc actgtcatca gattgctcca    82440
atcacagctg tggcttgcac acaaccgcca tctctgcccc agcagatgct gtgtgtaaac    82500
agttgtatta attacatctc aaaaacatgg ttcttgccag atcctcagga tttgggtgca    82560
gcctctgagg tgggtgggag ccctcgagg gagaaatgtc tgcaggaaat tcttcccta     82620 cgagaggtct gttttctaag ttatctaaga gctactgcag ctgtttactg cagagtgacc    82680
ctgctcaaag ctgtggtcac ccaaggcttt gaaagggac ctccacttcc gccctgggtg    82740
gagcaccgtg ctggagaccc acgcctgcca aggcctcatt gtcatctcca cacgccgtcc    82800
ttggggtggg ccactcctgg gacacgcaga caggaagccg gccacctgag ccactcggag    82860
gctctatcca gagtcagctg ccaagcctca cgtcacacat cactgttagt cttggagggc    82920
tggcggggcc ctgaagtcaa ttgaacactt ggatgacagg gaacttgcca ctgccagagg    82980
caatatgctc catttttttg acagttccaa caattttttct ttaaactgtc ataaaaaatt    83040
gctgctgtga ataccagtgt cggcgtccct gcctcacctt tacctggtgc ttttccacca    83100
cacaaaactg tttctcctcg tgctggcctt gggcttgcag acagctgatt cttctcctcc    83160
cgcggctgag cagcctcctc cgagcaaccc tctgacaact ctgctccttc tgacaacctc    83220
tgcaagggct gccagatgtg aacaaggggc cgggcagaa ggtatccagg aagactggaa     83280
actcgaggaa gcctgccctg tcctgtccac cagactttac gcttgcgtca ctgggctttg    83340
ggacctaagt cctcgtcatt tgttcctttt gcagttccta ctgttctcag cacttccttc    83400
cagcttactg aggtacactc agatgtgata tgccatcggt acagacacag ttctgctcca    83460
gcatttcccc gtgttctttc tgtcgctcta tttactgaat taccgtgagg atgtggagcg    83520
aggctgagtt ctgtattta acaccatttt aattctcacc tactgagaaa tccatcctct     83580
tatcactgtg cttttttttaa cctgtcacga atccatgaaa tcctatcagc cagcctgcat    83640
acttcctttt aaggtgcagt tgaatcagga gaaacttgcc gcacatgctg cgtccgggca    83700
cagcattggc tgaggctgct gccctgacct gtccgctttg tagtactgcc cagctatgaa    83760
acaggttagc cacacatgac ctgcatttag gagtaacaag tctgtctgta catgcacata    83820
cagcaacttt tttaaactgt ctatatttt tcctgagata ggtatttata atatctccat    83880
cttctttccc attttgaaac ttagaacaag tttgcctgtc aacagttctc cacagcatac    83940
tgtgtattct aggattttct aaggttgagc aacggaggtt cagcaatttt gacttaattt    84000
cttcccatcc cttttccacg cagcccagaa gccttggatc acgtggtgag gggaagaggt    84060
tgtgctatgt cgggaaactc tgtatcgaag ctcggctcag atcatgacat tctcttgact    84120
aaaaccctca gttccatca aacttgtcac tctggcatta aagcctgtca ctgtgtggct    84180
ctgaaaacct ctctgaacgt gttccctgcc tctgccctgc aggtccctgt gctccacaga    84240
agcccactta tgtgacccac ccccactcat caccaccttc cctcacccag agcctcagct    84300
ccccactccc acctgtaaga cccctactgg aaagattccc acctgcccct caagattaat    84360
ctccaaggac atttccaaat tcctctcccc atctctcagc cagatggctt tgctccctcc    84420
aggaacccca gccaccttcg acctccagca gggcactcca ctccacattc tcctggtctg    84480
```

```
tctggctcat cttacctgag ccatgctctc caggtgaagg actatgtcta actcaactct    84540
gctttaaaag cagctaacac attgctcttt gcatattgtt cactcactaa gttgaactgg    84600
acttggacat gcacactgaa ctgcagcgtc tgctgcttct tggtggccca gctcgtcaaa    84660
agaataagat ttcagcaaaa caatgtaaca attttttta ccaaaagtaa tgttaacaat     84720
atatggtttt cccctgatgt ttgcgtcaaa atgcttttg gaaaaaacat ttttcaactc     84780
tttagggtca gaattaagca atgaaattta tataccacat gtataatgtg tatgtttatc    84840
taagtatctg ttcatttata tatcttaaat agaaatttta aaattttt taaaactcct      84900 gataaacatt ctcaggaggc acactatgta actgttggtt gatataccta gctagatggt    84960
gaaatcagat tttgtttaaa gcatggagga gagggaaaaa ttaaatcttg cagattctgc    85020
agtccttaac atctttgaaa gaggaacatt tcagacaatg taataagaag gccacgtgct    85080
ttgacttctg tagattttaa aaatacttct gtatagtttc ttcttccttt gaagaagttt    85140
ggggagtttg ggaagatgga gaaagatata agaatagact ccccatatgg gtcatgaatt    85200 atcttttgc atcagaactc ttagtgcagt ttcagtattt tcttcctcag gagggtgagc     85260
tgcttccgaa tgtcctcccc ttctttgagg catcctctgt tggtgaactt tgagagcatc    85320
catttatgaa gttgatgacc tttcccagtc tctgcaagcc cttcagtgtg tgtcctctct    85380
gagcaaatct gaattgtgtg cttaatacat ggaaagggat ttgggagggt tgcttttaa     85440 actgatttct taattaatat tatgguttag ttaactagac agtctcattg cagaagtgca    85500
taaccataat atgtcttcaa atatatctcc cttcctaaca ccctgtaata acttttgta    85560 aagatacct tacagaatgt gatccaccat ttatgaacct gcagcattgc attcagagac    85620
taagtgaaaa gctggcagat tttcatttaa agcacaagct aaggaagaaa gctggtctag    85680
aaggagctac agaagggtaa tgcttaggga gggaatgatg tgcctgtggg tggtggtagt    85740
taaatctaac caaagaatga tgtcgtgggt gtttggatat tggatggtcc acattgggcc    85800
acattctttc aaacataaga gtctgtagaa atatgacctg taaaagactc ttaaatattc    85860
tggaaactgt ttcttccttg tcacatcctt atatatactt gaacctatgc ctaccagaca    85920
tgacatgtga ctattcatac agatttcatc atctctggtt taagaataaa ggatgctgca    85980
tagaaggctc acatctttta attcacaaga ctgaaactgt tctgaaatga cattgtttct    86040
aaaaattcat tacttgcatt atattcattt ttatttttcc atgccagaag ggtagaagtt    86100
cctgtgctca tattaagaaa cagcaatgtc aatcgaggcc caactcaaat ccaatttata    86160
ggagttataa agggcgtgtg cctgttttgt ctagaagcag tgttgggcag cactgagtag    86220
gatagaccac ctgttgctac cgataaagga gcagcttctc gaatgctcct gtctggtagg    86280
cactatcccg agtgctttgg cccctcatcc acaatctgtg tggcaaaagg cattgcaggc    86340
aattcagtga ggagaccgag gcatggagag caagtgccat ggaattccct aaggccgtgc    86400
agggagcagg ttgccaagct gggttgaaac cgtcctccgt aggctcccaa ctccgccgtc    86460
gctgctactg tgctggatga tgcctggtag atgcagatgt ggagccccat ggattctgag    86520
acaggccggg tttcagtcct gccctagctg cctattggct ggatgacctt gcaagttga    86580 ctttcgtgag cctcatttgt ctcatctctc aattaagaaa acctagagcc tatctgtggg    86640
ggttatctga aggattccag ggatgcatat ggcactgtct accgcatgcg gtaactgttt    86700
cacaaatgat gaggagcgat ttatgttctt agtggaaata tgtcggcgtg tgaagtccca    86760
aagctctgcc ctgcctggct tgatccagtg cctaggcact gcccctcttc ccctctctcc    86820
caacccactg taagaggcta ggctgcctca gtaactctga ggggcattga ctctttcat    86880
```

```
ccaaaaattc atgttactgc cccacatttt ttctgttgtt ttacaacgca gtaggaagtg     86940
ggcagactgt caggaaaagt gatttatagt catgtattgc ttgtgctttg gcttcatttg     87000
atccaatgca gatcagctgc actcagaaaa ctactcaagt gaaagagaaa aagtaactga     87060 aggggggaaat ctggatgagt aagaattcca gggataggaa tattaatagc aagcttttttg    87120 cctgatatag tcactttatg ctgcaggggt gcccctttat aaagtgcttg tacaatggat     87180
gtttgctttt gattttggat ttggagtcta atgaatgttc taaattatta ttagaggagc     87240
ttgcggttgt tacatgtctg cctttattgc ttattttttag ccatctcccc tgatgtcaaa    87300
tgctcaggca agaatgatac attcattttat aatgtggctc cttcagaaat ataccacata    87360 cctttttggtg tggtttgtgg ctgagaagag tggggaatgc acaagtggaa aactgcagaa    87420
agattatgcc ttcatcactt caagtatttg agatgaaact agatcatttg ctgttgctttt    87480 ttattctcat tctaagtgct tttcaaagtc agcgctaaga ttttaaaatg gttttctgtt    87540
gttggcagag agggaattac tctattactt tctgataaaa cagagtcttt catgatcaaa    87600
gagaaccagg ctctagtagt tccagtatcc taacgtggac actaattgtt tccctccttt    87660
tcttcatgaa aacagcttct gcacaaatga tagccttgtg aactagccat gggcacaact    87720
ggagaagcat ttagggagct ttagtgcaaa ttgagaccac ctacacatct gactctacag    87780
ggtttgacaa catccagggt gaatcacaaa acatcagtct aatcagggct tatatagaaa    87840
gagtgaaaga actctgatttt catcctaaag attatttata ttaaccattg ttccaaatgc    87900
attaactatt ttaatttagt tgttttgatt gttaaaaaaa acacatctgt ttggtagata    87960
agacataatt taagacaaat gttctatttg ataagcttttt agaaacaact tattttttatt   88020 ctttcctgtg agataactca gatgtggaga atgtgacaaa attttaagca taacatgaga    88080
agggctgaca cacatagatt tctgtgtgct tacttgaaaa caacaaaatt taagaatttg    88140
gtataggagt tgtatcaggt agtgcagagt ccccaggaga cctagagacc caggtctggg    88200
agcctagcgg caagggctga atgtgggatg acatcagcag aaactcacag ccactgctat    88260
tccaaaaacc cagcagcagc tcagtgcagg gcagtgctga tagtacagtg cctgcaatcc    88320
tggagtggat ttggatgtgt caggtacgca cacgctcact gctcccccag cagtacgttg    88380
aacagtgtgc gtccaggtgt ctgtagggcc cctcgcccta actcacaaaa ccattctggg    88440
tcagaagcca ccaatattgt catcatcctc ccttttctga gaaccctagt aagtccctcc    88500
agtggggcaa gcccacctttt tcccttcatt ctgtggcaat atgccttcat ttcctaatca    88560
gttttgccct gctcattcaa tgcaaaatgg atctgctttc cttgggcacc aatatgtcca    88620
gggattgttt atcaatcttc agttctgttt cctttacata tccctccaaa aatcaggcct    88680
gcactgcctg tgcactccac aatccacagg cctgaaggaa atgttatctt tgatgtagag    88740
acttaaagta aaactcttca aattaattat ttcatgcaaa aggctagtcc tgactctaat    88800
tctaagacat gtctcctaaa ctctggaagt ctgatgtatc ctattatcaa catttatcct    88860
taatgtgatg gtttatcatt tatcctcaaa gctgcattgt aaaatgtaca ctgtaaagtg    88920
tacattttaa agtcggtttt aaaaaatcat atttagagat cctggtaaaa atctatcaag    88980
tcaagacatt accttattac ccatggaatt gtcttcaact cttacagttc aaatattcct    89040
gaattggctt tcacaataaa catcctaaat atgtaagtag aaacatatat attgccaact    89100
ttgtgccttc ccaagcaaaa ttaaaataca ggaaagtca gtttgttttg cccataaata    89160
aatatatgtg tgtgtgtatg tgtgtgtata cacatacaca ctcagaaaag atagaagcag    89220
```

-continued

| | | | | |
|---|---|---|---|---|
| cagcatattt | tggcagcatc | tggtttattg | gaactcaaac | gttctgattg tgcatacaga | 89280 |
| ctagttaatg | tggtaacaat | tatgtatttc | ttccctgctc | cttgccttct ttccctcccc | 89340 |
| agtttttttc | ttcctgatag | taggtgtgta | cttttttcct | atttccattg gcaagccaca | 89400 |
| tgacaagcaa | aacgatcact | cgaagaatat | tgttccctca | atcaagaaaa atgcccattg | 89460 |
| ggttttgtta | tttgatgtta | tttgatgaca | gagacctatt | gtttttccat tttttctttt | 89520 |
| ttgttttccg | tggcacctat | ggaattaagc | aatataaaaa | atctattatt tcagatgttc | 89580 |
| acgtctaatg | aatttcatgt | gaaatactgg | cagtataacc | ccaaatagag gaaatttgtg | 89640 |
| aagagtggat | gctgcagggc | atgagacatc | tgcacagagt | tcatctcttc cagcatcttg | 89700 |
| catgtcccaa | gcactgccct | gccaggcaga | gaatgctgca | gatcacggca gtgaattcca | 89760 |
| gttgttcaga | gcacatttga | cttccaaatt | ctcaaggcca | cagatttgag gacagaacaa | 89820 |
| tatttgcatt | tgaaattgga | agattatttt | ttgcacaagt | gcctatatgc tatatagagt | 89880 |
| ttgcccactc | tgcattatct | tcccctgtt | ccccgttat | ctggcacaag ctattcaaaa | 89940 |
| gacacgccta | cttgtaaaat | aaatggtttg | caaactaagg | aaaatactta aatctcatgt | 90000 |
| aaatggtact | atactatgta | taaaaatgtg | aagaaacaca | gaacagctca tgaacacctc | 90060 |
| cactgctgta | taaagaacc | atctttttc | tggctcctat | tggatgcctt agaaaaatct | 90120 |
| gtatttcctc | tttagttatt | gtgtttgaaa | gatgaagttg | agacaaaagt tctattcttt | 90180 |
| ttaagttggc | agaacttctg | aaaggtgatt | tttagctgca | gtgtgactca ttccaaatgc | 90240 |
| agaaatctct | gaccctgagt | tagtctattt | gtcatgcaag | agcctagaaa agccctgagt | 90300 |
| gataagaaat | ggccataggc | cattcccaca | gaattttcaa | caaaaataga atcatgctta | 90360 |
| tgttctagtc | atgacttaga | acttataact | catgttcgga | actgtccatg ttcacgcaca | 90420 |
| ggggccgtat | cactccgcca | gagctgccct | gggtgccggt | gtgcagaggg gtccgagagt | 90480 |
| gactgtctct | tcctctgttg | tcgaatgtgt | gggttatctc | cataaatggc tgccatgagc | 90540 |
| atccttgttc | acacattttt | aggtacttga | gtgagtgtct | gtggaataat tttgggaagt | 90600 |
| gaaatctgtg | gtcagaggtt | tgtgagtttt | acatgctaca | ttttcagaag ttgagaaata | 90660 |
| gcagtaggct | gaaggcaagt | cgccatgcct | ggaattcatg | aacactagtt gaaagaactg | 90720 |
| gcgtgagtta | gtcatgacag | gagagatggg | gaagggagtt | gcaggtagga gggccatctt | 90780 |
| caaattctca | agtatagtc | actccaaacc | aaaattcgat | ttaatctgta ggactccatt | 90840 |
| ctcaaagcac | agtcactcca | aaccgaaatt | cgatttaatc | tgtaggactc caggtggcag | 90900 |
| aataagaggc | aatggatggg | tggaagcgaa | acagggccaa | agtttgactt catgtgcaac | 90960 |
| ttcctaagga | gtgatttgaa | ctccacaaac | atgaactaag | cacctcaaca caggctgggc | 91020 |
| aagttgctgt | tcttttggag | cttacatctt | agtggggaaa | gagaaatgcc tatgtaaaca | 91080 |
| tataaatcag | caggatacat | tgtgaggacg | gtcattgctc | agtgagactg caatagagtg | 91140 |
| atacgctgga | gggggctgca | agggagaagg | tgggagggac | agcatttagc agaatgagca | 91200 |
| gcacagtccc | ataggaagaa | gaatttattg | cctccttagg | caaataaatt cccaaacctt | 91260 |
| gaacatcaga | aaggaaatag | attaatgtgc | acagaggatt | aaattatgtg atctgcaaag | 91320 |
| tcatttaaaa | tctatttcca | cataaaacat | attaatgcaa | cctaaacaaa aggggtctgg | 91380 |
| ataccctcat | cttcttccca | agcatcaagt | cttttctatag | ttaaactgag atgcttttat | 91440 |
| tcttggaaaa | ttttaaggac | tatctacagc | aatggaagaa | tcgggtgttg ggatgtgttc | 91500 |
| ccaggtaata | atgactgcag | gctgatttgg | cccttgaggt | gtggcctcat ggccctctcc | 91560 |
| aaaaaaaatc | aaggacctgc | tacaaagcac | aaagccgact | gcaatgcttg ctgcttactg | 91620 |

```
gttagggcag ctcctctttg ccagcgacca agcagaaagc aagacaagac aggttctgaa    91680
gcagtaattc aaagccttcc tcgctttccc atgtgagtca ttgctagtca gaatattacc    91740
tttgcagaga ggcttaattc caaatttgct cttaaaggga tatcctctcc tggtttaggt    91800 ataaacttt t gactcacagg acaaattcta tcattccttt gggcctagga ttgcatttat    91860
ttccatgaca aaagggcctg tctggtgttt cagcaaatga aaacaaaaat ataaagccca    91920
tctccttttg aatgagctct aaaacagttc tccactggac ttcagaacaa gagggagctc    91980
tgggctgctg gctggttgtg catttgctgt gggttccctc cggcaggcga cctctccgcg    92040
ctgagaaggt tatccggata accaagtaag aaagtacatg aggaggcaca gaaagaaaaa    92100
tgtgagagat aacagcataa acacacagtg tatgttgtta tgaggcatca catgatgaga    92160
tactgctggg gagggaagaa gtgaggagat tcctaggaat cttatgagaa tttccagaga    92220
caacaagttt tgagcttttt tttaatttag aaaatttacc ttattttt aa aagaatatgt    92280 aacatatccc atgctataaa attctagaca tagtagattt aaaacagcat aatggaaaat    92340
ataaatatct attttctttt cctatttatg tattctgtgc cagtaggaat gtagccaaaa    92400
agagagaaaa ggggtctctg cagacatgga tgtctctgtg acttgatcac tgctaaccca    92460
agaagataat aaagcagaag catgtatcca ggttgctgca gccaagcctg cccggtctgc    92520
ggggcgtcct cacacatggg gcagctctcc caccccacac actgggaaag gcggacagag    92580
gctgggcaaa gccccaatt ttcgttggca ctgaccccga tgatttatag gcctttgttt    92640
cccatgttaa atgtcttacg atcattaaat tatttatagc tcaattagca tgtgtccaaa    92700
accaggaagt tcataggaga ctgtgtgact gggaattaag gagcaaagca actttccagt    92760
ctgtgattta ctgggtttcc attctgtttc ctgttcggat ccggaagtag aatttcaaat    92820
attgcttttc atgctttatt tgggaccgat tttagccccg ctctcctttc tcttgccatt    92880
cgctggccat tagccaccag cctctgcaca atgaccagct ggccctggc agatcttggg    92940 cccaggtgtg aagtcgctgg agaagcattt cagggccaag atgggagtga tttcattttc    93000
cattgacact atgcagaaat gaaggggatt caagtgcctt cagaaaagct tccttccagc    93060
gaatggagtt ttgggggttt tccagacttg caactgcttt tattcttgga agcatcattg    93120 ttgcttttc ccccttcca tttatatccc aggaactgat tcagaaacca tagaaattgg    93180
atttggaatc gctgaatgct agcagacagc tgactgcact cttcccaaga aaccctgcca    93240
gctgggttcg ggtatcgcgc ggtgtgtgct ctctctgcct ggcccgctga gtcctctaac    93300
tctaatggat tccttcttac accaaagtgc actagaacta aagtgttttg cttcattctt    93360
tagacatttt gtggtttagg gctcaatcag ccagggtatg atttgcaatc cacagtaacc    93420
ggtttcagag cagctgccca gcgaggcagg tttcatctcg cttgctagac gttttgtttt    93480
tttttttttc taaacctcac accttttatt tattagactt ggattccagt ttcctgagcc    93540
tgtttgtgcc actgattaga caggcttgaa gcagaaccca ccaggcttcc tgaataaaat    93600
gcagcagtga ttgtattagg gggttttaaa ttgctcaaaa tactgtctaa aaaacactaa    93660
aaatcatgtt actttctaga ttgaataaaa tcctatagaa atgaattcct ggacttgata    93720
tgtagcaagc tggcattggc tcgggagtga gtgggctcag ttaagtgagc taagatgaga    93780
tggtgcacag gcgagcaccc acctgaggag tgtttggatg ttatgatagc cagctcctct    93840
gtaaagacct gtccttctat gtcagcagcc cagcagataa atgacgtgta aataccacat    93900
ttaggagggc ttatgatgat gccaattaat ggagaccttt ttgaaacagg aaggaggtga    93960
```

-continued

| | |
|---|---|
| aacatattcc tttgcttcta catcactgtg tgccaggcac tgtttacagc atctcgttta | 94020 |
| accagcagtc accacctgac ggatggctga tgtggggtgg ggtcccaggg tgggattgcg | 94080 |
| tgatgggctt ggggtctctg gctgatgggt gccagagctg ggactggaac tcctggcgtg | 94140 |
| actgaggcag acacctgggc tacccagcct cacccacgac gccctcacta agtgacccac | 94200 |
| aggactcacc ggaagcaggg cagcaaggtc cccctacaga ggtccccact gcaaaccgat | 94260 |
| acccagctta gacagcagtt ctgcagtcgg cgtctcaccc cttcgggtct cattgtgact | 94320 |
| cactttgata gccacacgat ttaagggtgg ttcagtagtg atttgatgag tgctgtggct | 94380 |
| cagggtcatt cccctgccca agcatttcaa attccagaag ttcatgccct gcatggtggg | 94440 |
| tgaaaagtct caggccaacc atgagcacac agcagccagg cgactgaggc agctgcccgg | 94500 |
| ggtggcacgt tgctcaaacc catcatttgg agtcaaaaca aacagatgat tagctggggt | 94560 |
| ggtcactttc aatcaagagt tttcacatcg cctagacatg gcctcagaat caggcctggt | 94620 |
| gtggccaggg gctgatctca cagtagacag gaagtgtggc ccgagggcca tggctgcccc | 94680 |
| ctcagaaggc cctgtggagt ggctggccga gcctcagcag cctcctgtga agcgaggaag | 94740 |
| ggtcttcctg ccggcctctg gagatcagta tgggaatgca caagtaggaa acgctggatg | 94800 |
| ggaatccctc tgccctgtga taccaaggca gtgagtttgt agactatgga attgctgtcg | 94860 |
| gagggctctg taaccggcca aggtcacaca ggtagccatt ggtagagcag ggactggaat | 94920 |
| cccagacccc caacttccag gactgtgcac ctttctttat cccatacagc cttacagtca | 94980 |
| agtgccagtg caacacctga ttcccaggtt ccagccttg tcttttataa tgggaatcaa | 95040 |
| ccttatcttg acgatccaga gatagtcatc aaggaagatt aaattatccc cttagactca | 95100 |
| gagtgaccat atcattttcc ctccacacaa ggacactttt gagaatgaaa aggaggagat | 95160 |
| gtctgtacca gacgctggat gacaggcacc gacaggctgt ctgccagggg agcagcgatt | 95220 |
| cctgtatgtt gtagaaagtt tttcaaaagt caccttggaa agaggttttg ttccttaacc | 95280 |
| ttctgttaaa taggaagctc cgtgaatgaa acaactccc ttccctaaac attctagtaa | 95340 |
| tgacccaaca ctgccaagcc tgccagctct gcctcatggt cgtgttgact gtgtgagact | 95400 |
| atgtgagtgc ctgctacaca gtacgctttc agtaaacatg gtattgcctc gataatccca | 95460 |
| caaaaatgtc ctattcaaat cacctggcac ccaggaaatt tccttctttt ttttcccagg | 95520 |
| tgaaatatac agttgaaaac acctgacagc aattcccctc tcccatgtgt ttgcaggatg | 95580 |
| gtggttttgg ttcctccatc tttgatgtgt acaagtgtga tgttttcccc ccacagacaa | 95640 |
| gtaaaccaca ttctcttcac attcccaatg ttttgtcaat gtacctcctt caatagagga | 95700 |
| tcgataagga aaaaaatcat tgacaatctc aattagattc actatttcat ccaaaagcat | 95760 |
| agcttagaac tctagttttt gttcaacact cttgccctat gagtgcacag aactttaatt | 95820 |
| ctgatacaaa catccctgaa tgtttagctt tgacagagat tccaaggtga tttgataaga | 95880 |
| agcagggctg tgtttgggct ctgggagttt ttgatatggt ttcaagcccc atccaaaacc | 95940 |
| cacagacctc tagaaagtag gtgcctgcct tcctgcagca gccctggagc ctgctggggg | 96000 |
| ctttgagcag ctgctgccaa gccaggcctc acccgacact ctgatgggca cggccatggt | 96060 |
| ggcaggggct tggacgctgc caggtgactc taacttgtgg ccagggtggg aagcactgct | 96120 |
| ccacagaggt gccaaaacca ggttccttcc tgtgttctca catttcacag cctcaatgta | 96180 |
| aaaagtaaga catgggcact ctggaatatt acaaaaatat agaaaagcat gttatagtaa | 96240 |
| ataaaaggct cacagaattt tgtcatttag gaacaatgat tattaatata ttagtgtgtg | 96300 |
| tttttgctca ttaacagtat atcctgagat atttcctata ccatttaata ttttaaaaga | 96360 |

```
tgtttacact ggccacagta gctcatacct ataatcccaa cactttagag ggcaaggcag   96420
gaggatcact tgaggcttaa aaattagcca ggtgtagtgg cacatgcctg tagtcccagc   96480
tactcaggaa gctgaggctg gaggatcact tgagcccagg agttcaaggc tgcagtgagc   96540
tataattgca ccattgcact ccagcctagg tgacacagtg agaccctgtt tctaaaataa   96600
ataataaata aattaaaaca tttaaaaata catgatgttt aattattaga ggactcaatt   96660
ttatatctat gtatacaata atttttaagt ttcttaatat tggactttta gtaccttttt   96720
aaaaatacta tttttaaaaa aatctgtatt tctaactttt tataacaagg aacctttggc   96780
tttgagatga ctggggaatc cattctttcc tatagtatcc atgtccaatg gacttaaagt   96840
attaatcaat gtgtttatgt tttgttattt ttctggcatt acaaaaaatt ctaaatatat   96900
tgttaccgcc tgtataaata tcagcttttg agagaaggac attgtgtaga aataatgaaa   96960
cactgcaact tgtatttgta ttattctttt tttttttttt tttttttgaga tggagtctcg   97020 ccctgtcacc caggctggag tgcaatggtg cgatctctgc tcactgcaag ctccgcctcc   97080
caggttcaca ccattctcct gcctcagcct cctgagtagc tgggactaca ggtgcccgcc   97140
accgcgccgg ctaattttt tgtattttta gtagagacgg ggtttcacca tggtctcgat   97200
ctcctgacct catgatctgc cgcctcagc tcccaatgc actgggatta caggcattat   97260
attattcttt aaattcacat gagaatttag tatggcttca aaaatacca taagttaaaa   97320 tatcaccaag actctgttca gacaaaagta tcagaaaagt gagccaggca ctcacatagt   97380
ttatagttta taaaagtgag acaggcatga tctcttaacc tcactatagt cctgtgaata   97440
aggtttattt acatttcatt ttacctgcca ggattattgt aaaaacgcca agcacattgc   97500
ctacacaaac taaatattca gtcaatggct gctatttca tgagttcgtt ttaacatata   97560
tttattgtcc tctactggat ttaagaagtt atatttatta tcatctaaga ttttagctat   97620
tccttctctt aaaaatagat tttataatca atggcagtaa gggagagtaa ctcgcagttc   97680
tctgaatctc aagggttcc tggaagcctt cctgaaggta tagtgaaatt tcagcttcac   97740
attcccatcc atgagctccc tgcaaatatc ccggtctgct ctcaggaccc agtgacttac   97800
ctatgcagag gctgtagata gcacctggag cttcctgtgt gccctcctca aactcagcca   97860
atgccgtcat acagtagcag gcaggtgtct ttgctgggta gttggactgg atgtccctgg   97920
gattgcagaa ctggaatggg gagtgacatc aggaaactat aatcatcagg acaacatggt   97980
ttgccataac tttaagtttt aagcgaccgc agattatgcg gagagagatg catgcccaca   98040
gccatgcttc ccatgtaact ggagaggggt ctgaagtttg aaacaagtgt tcctaggcac   98100
gggttacagt gtttgttatc atcatacttg atttagaatg gggcacaaca tgtggattca   98160
tggtaactgt tacaacctta ctcatttaa tacctgaaaa catgctttcc ccatgctggg   98220
aatcgaaaga ttctcctagg aaaagaaagg cttgacaaca tcgattcaaa aagggcatgc   98280 atttcctca tttaaataac tctaatgtgc aagtagatcc cctgacctca agctcagaag   98340
agtccaggcc ttcacacctt ctctgcttct gctctgggc cagctattga gattcctgtg   98400
cccacgcaat gcgcacatcc cacccctggc cgctgtccac aagaaatcca gttgcaccaa   98460
gcaccccact ttttgcacct ctcatttatg tactcctaag agcctcacca caactcccctt   98520 ctaaaaacat gagttcctga ctgggaattc gatgctgccc aggcagcttt gctcagaggg   98580
agcagccttc tagaaatgtt tcaagtaaac tttcaagtat aactaaattc aaaaaaaaca   98640
catacacaca cacacacaca cacaagtcaa aggtgtgtaa tttggccaat atcacaaacc   98700
```

```
aattagccct ttgtaagtgg cacccagatc aggacagctg accataccag caccctagaa   98760
gcaccccgtg ctgcctcctg ggacagggct accaccatcc taaggccagc acgatgggcc   98820
agctttgcct gctgttgaat tttgcttaca tagaatcctc cagtaggtac tcctttgggt   98880
caggttcttt cactcaacat tatgtgttga tattttttcca tgctgtgctg caaaattgta   98940
tttcttgcat tccataactg ggcagttcca tcataggaga ataccacact gcgttcgtcc   99000
attctaccgc caatggacat atgggttctt tctcttttct tgcagttaca agtttatgaa   99060
tattgtccca cgtgtccctg gtgaacttttt gtttgcattt ctgttgggta cctcagagtg   99120
gcgttgctgg gtcagagggt actggtcgct ttagtagctt tgaaagatat tgccaaaaca   99180
ttttccagcg cagttatagc aaattataca ccaccagcag tagaaaacat ctcctaattg   99240
ctcacagtaa accccaaag attgccacat acatcttcca tatcaattac ttaactattc   99300
agcaaatttg aagggaaata tatttaatct ttttattcaa atagtttata aagtggaata   99360
gagatgtggg taaaagttgt cttgccacct ttttagatcg gtaaaagttt gttgaatgca   99420
ggcaagaaaa gatgagaaat aatggtaccc aatgaaagac atagcagtct acaaggaggg   99480
gcatttcccg gggtgggggg gacccacact ctgtaactcc cacattcaat tagcatgtta   99540
taggtaagct gcagaaaacg aggcagcttg tcaaagagga acggctcttg gccatggttg   99600
ctgccctagg aggatatttg atactagcag agctggggca accctggagg aaaccacctg   99660
gaatgatggg agaactcctc cagggaacat ggcccttttaa tagatctctg ttataaaaaa   99720
taatcccaaa gcagccacca gggcatactg ctgcgatcaa gtcctaggcg gtattccctt   99780
ctgcgccata gaccctgtgc agagtgccct caacgaagga gcaaggaaga ccaagtctcc   99840
cgagggtttg catatgtgta tgtgattctg cagtcatggt gaatgacaca gtcagggctg   99900
cggaaaagca ttggtaaagt gtatatttga ggcttcagaa gtttgaaaag gctagatttc   99960
ctaggccaaa acactgaaaa tttgcaatta gaacttcagt gctgatgctg ggaagactgg  100020
agttagtttg agacatgcac ctgtgcagaa ctgggccccc agaaaaggag aaggaaggga  100080
atccagacca gagtagggcc tgacaccact cagactcggc gtgtctataa attagaattg  100140
cgttacaatt acactttgac attttagtgg tttttaaagt gcccagcaca agttaatttt  100200
tcattaatga atcctttatt cataaaatgc ttagatggag attacccttt tgagcatttt  100260
gccagtgctt ctgaaattaa tggggacctc ctgttggagg acacagtctg ttgcaatagg  100320
tgaccactgc tctgaatcta tgtcacctct ccaggaccac gggcacaacc atcacctgag  100380
gcatgttgga gatgcagatg gtcaggccct cctagaatct cagaatctgc attttagcaa  100440
agtcctgggt aattcctatg tccattggag tttgagaagc actggtaatc tcaaatactt  100500
taaaagatta ctagagtaag ataggctcag taggtacctg aaggcaccat cccaaagacc  100560
agagtggtag aagcaggtgg accagcctct gaacacattt ctcccccact ccccggctgt  100620
gtggaaggtt gccacctttg gggtagtcat tcaacaaaca cgtgtcaact gtccactatg  100680
tgtcaggcca ccactgggca ctggctgtgg ctagctggat agacaccatt tctgccctcc  100740
agaaatgtca tgtccactgg cacatgacaa gtcactaagt cattcagagc catgggtgac  100800
agctccaggg gccgacaaag gagctgtgat ctcacagatc cacagagaag tgtcccaggg  100860
cgggcgggaa ccaggactgc acaggagggg gtgaagtgac ataagaag tcagcccatc  100920 agcctgaaat gctcccccaa atcttcccat tcagtgtttt ctcagtagca aactcgtggg  100980
aaaattggtt attttactta aaaaactcat actagaaagc tagtttaact ttaaaaataa  101040
attttaaaaa catttttatt aacaaatcct acctttcctc caaagtcaag gagaaaagaa  101100
```

```
tagaagtgaa caatggacca agtaagccta aaactctgct cttteccctg ctcattttac    101160 agttcaagtg ccattcaatt tatcctggca agaagaggaa ggcatcatca agaccttaat    101220
tttctaatac atctgatctg agaagaatgt gaaagctata aaattaattt ttgatcaata    101280
actacaggcc ttttgagaga gtgccctcct aatgaattga gtacctattt ctccatacac    101340
agtgtctatc atgacctaca aacccttttc ccatgaggtg taacagagag agattacagc    101400
cttggaactg gatgtcagac tctcctggtt taagacaata agccatgaca tagagcctga    101460
aaccaacaca atcttccgag tggttccaga aacatatagg ggataatgtt ggctctgatg    101520
ctgtacatcc ccaacaacca tcaactattt ggaaactaga atttcagcat aattggagtt    101580
ggtgttaccc tagcaaatgc tgtgggaaga gagtctcact gtgtatcttc tcctgtttaa    101640
agcctgaatt tgttcagaat gtaatatctc tgtttagcca ctctactgaa actgatctag    101700
gaaatgttca aaaaaaggta tcccaaggat ccctttgtag ctacatctgt gggattcccc    101760
tcgctctggc gtggcctggc ccctctgcat ttgacaatac ggtcctatgc ttttgtcttc    101820
ctgggctgcg tgaacccacc ctgccctggt tcacctctcc tcttgaccca tccttatcag    101880
tgtcttgaaa ggtccttcta ttggaggaca cattctgttg cagcaggtga ccactgcccc    101940
aaatctgttt cacctcccca gggccatggg cacaaccatc cctggagtgt gttagagatg    102000
cagttggcca ggtcctccaa aatctcagaa tctgcatttt tgcaaagtcc tgggtaactc    102060
ctatgtccat gagagtttga gaagtactgg tctcatgagt tcctgacata caaatagtgc    102120
tgaggccagt atgctgactg ggtagccaga tacaagtgaa aaccttcctg ttttttgcaa    102180
acctggatgg acccgaggcc gctgacgtgg gccaggacaa gctactcttt ttcagtgttt    102240
ctgttgcatc gctgtgtctc tctgtgatca ggtgctgccc tccctggcag gaggactgca    102300
gacaggatga ccaagagcac tctacacagc ctgctctcca gtgttggggg acgccaccca    102360
ccctcgtggt tcctgttcat ctgcctacac gtggagggcc caagagggct aatatgtgac    102420
tatctccact tcctggtacc ctgtgtgaat aacttcactt actaaaggga tgttgagcaa    102480 cttttattaat aatgaagaaa gcactttggt ttgacaaata atcactccat ttttcatttt    102540
gaaagttaac tcttgttagt agagaaagca atgtattaca accacaagga cgtttacatg    102600
gaaatgaacc atctgcaaag catcccccat tttccttttta aatcagccaa tgggtggtgg    102660
tgggagaaat attcaccaga gtatttaaca tctatccccc ttcctagact gtcagctcca    102720
tccgggcgga gactgttggt atctccacag cacacacagg gcctggcaca catccggggc    102780
tcagtgagca cttgctgaat ggtgaacaga ttagctctcc tgggaacgtt gttgacacat    102840
ctcataacac tggtttggag tggagggcat tcatcgggct gcatattcct atttttaatt    102900
gtattctcca ctggttacag cacctacagt tataaagaca ttgttaacat tgcttatagg    102960
aagacatttg atgaaatga gtccaaaggc attacggtta gaaactggcc aggtgtcatt    103020
tttgagagat tagataactg ttttccggta gagtgaattg cctgtttgtt gcaagttggg    103080
actttgctgg gctggtttac agggccaagg ggaaagagat aagtggatct tctagtgaga    103140
ggtcatctgt tttgaaagcc tggaagattc catgaactaa atccaagtct tacaacacag    103200
ggaagtgtgt catactgtgc agggatgaag tctccaattt agcatgaaaa caagagctcc    103260
tcacactgtc ctcttcagaa agcccataca atccaaactt ctgaatgctt agctgcttac    103320
aaccatacat agattgaggg ataaaactct gatatggaag agaaggtaaa cattttttgg    103380
cagacattcc caggaaaagg cggctctctt ctctcattgc tgctgctctt tcagaatcca    103440
```

```
tttcaacaga ggaggagtca atgggagccc cgtgcctctg gcagatatca tatggcgttt 103500
cagtggcatt gtgtgttacc cttcttaggt aacagctcag ccattagaag aatgtcctac 103560
acaccttctc attttctgtg atgagaggaa tgtgaggtac tgcccttcga gagctgtcat 103620
ttgtcctagt agccagcagc gtgactgtgc tgtcttctgc tctgtctccc tgtcagcctt 103680
ctgcccagcc accaccacta tagttttgtt ctctccattg gaactcctgg ttcagagaat 103740
taccataaaa aacagacccc tagacataca acactctatc acataatggt gactttgtct 103800
tctattttgg attactgagc tttcttgggt aacttccact aaatcgaagt taatattaga 103860
agaacttcct cttactagaa tcgaaaagca tttaagtgat gcagtcaagt ttgtaccata 103920
agtaattcag tcatttaaca aatatatatg gcctctgtgc gacagtgacc ttgactggga 103980
atgaagctgt cccatgtggg gcctgttctt caaaggcagt tccctgctgc ccagttcagt 104040
ccagtggatc tgggcatctc tctttaatcc gcattagggg ctctttactg attcttcact 104100
atccaaaaag acttggaggg gagacctgag cccacttctg gaaggaaatg ataacaattt 104160
atttagataa tctttgtgca acaagtcaat tcactgaaga gatctgctct ctaggagcct 104220
ctgtgacccc accataactg ggaaggctct acctctccag tcttcgggcc acatttctct 104280
ctggcctgct gtcttcccag cactctcagc cttgctcatg gagcactcta gtcctccgtc 104340
gaccttggcc tttggtaacg tgatttttca cctggcagct cccatctggt ctcactccct 104400
cttttttgtcc agtctgcatg acacagcctc acatcgttag tgttccctca ctcccctctt 104460
actgcccaac ctgcaaagtc catgcctggg ccagtgcagc atgtgtcctc aatgggctgc 104520
tggtggcagt gggggggaacc gcacagccac gctgtgtgct gctgaagaaa tgcacagcct 104580
cctaccctcg ccctcaagag gcagccatgg ctgcgcattt ctgcccttct gagctccgct 104640
cacttttggc agcagccgtt ccaacctgca tgggatcttc actctctcac agatgtgctg 104700
actcctcctg ctgcctcccc tctctgtgcc ttctcactct ctgttccctt tgcccttcct 104760
ccccttttct cctctgccta cctccaagcc atccatcaca ggacagctca agcatcagat 104820
cctctgggac acttttcctta gttgttcagt ctgatgaggt gtccctcatc ctctcttagc 104880
tgaaaatcag cagctgcctc aacttctttt ccagcatgtc tcatgagtat gccacaaca 104940
gcatctgtca caatgtgggg tagtggctga cttgcttttc tgccattcaa ctgagttccc 105000
tcagtgctgg ggccagcgtg cagtgtcttg tattcagtat atagctgatt aattgatgaa 105060
ttgattaatt aatggttcac actagcacag tgcaaccttc aatgcaaaga tctcatcaaa 105120
ataattcaca tggtgggata ttttagaagg atgaccaggc tagtttgtag taagaaaaaa 105180
tcaacaagac taggtcagga attcttttt tgtctacagg cttgctatag aagatattga 105240
aaatcatcta cctaattacc tttattttat caggttgtgt attaaatatc acgtctgggg 105300
gaagaaaatg tgatatgtga ttacagacct ttcctggtac aacatagtac gtttcagatt 105360
aactcaaggt attgtggtga tattgcggtc aaagccaggt gattaaagag tcattctttg 105420
aaacaaatat ctgtgcaatc aattaagaaa ttaatttgca aattttattt gcttagagta 105480
attgatatat cattccttt acaaacaaat ataagaaaa cttaactaaa aatactgcat 105540
atctctttca gattatatat cccagaaagg atatattttt ctcctttctg gtcttcctt 105600
ttggtgtagc atctgtagga aatgcatttc ttcatagcta agtgtacctc cttgtgaaat 105660
atcttcagag tctactggtg cacataagca attgctggca gcagcttgag ggtctccatc 105720
tcacatttat catatgcctt attgcatgag gctttgcaag aggaggtcta gagctacaat 105780
atctcatgga tatgaatgtc aattcaaatc ccagtggcag tttatgaggg ggaaagccta 105840
```

-continued

```
gaagagaaga aacctagagg aatcaagcag gaggggagag taataaaaga ctagagcagc   105900 aggttttttct taactcaaac tagaattaaa tctctgtgtg tgtgtgcatg tgaatgtgcc   105960
cgtatgtgca tgcatgcacg tgtgtaaatg gatgtgtgtg tgtgtgcatg tgtgtgcaag   106020
taagtgtgta tacgtgtgtg ggcatgtatt gtgtacatgt atgtgtgttt tatgcatctg   106080
tttgcaagta tgtgtgtatg cacataaaag tgtgaatgta catgtgtgct tggtgtatgt   106140
gtgtgtatta atgtatgcgt gtagttctag agtctagtta gagaaagtgc ataaagaaat   106200
agggaaatta acaagaaagc tatagcttaa attataggaa aaacttttct ccctatcagt   106260
catggtttta aaatgttcag acttgatatg tttcccagtg ctattgtcag aaaatgtccc   106320
tatgacattc catactactt caatcaaatc taaaacctttt gttccaacat gttttattga   106380
tatgagtata tttcaaattt ctaccaggtt tttggagagg tattttggcc ataaaattga   106440
ctaaattatt caaaataaaa aatgaataag cctgggccaa ggcttggaga cttgcttaac   106500
tcagttctta aattttcaga ttttcaaaat tacaaattta agctctaaaa tcatggtgct   106560
gtgtatgata ttcttttgatt gcaacttatg gttgaaaaac tatagagggc tttatgctaa   106620
gagttgtgga tcttaggatt ttcatgaaat ctgcattatc atcatctgca agtttagatg   106680
gggcataact gatccaaagg atggatccct cgggggcaat tcaactggct gattccagcc   106740
aagatgacaa cagtcaggat ccgttccctt ctgatcatcc attgggtgcc ctgatttcct   106800 ctacagcccct agctgaaaga ccagacacta tctcaggctg gctgccccac atgccttgct   106860
ccacaccaaa ttcacagtct ataaacctga gcctccagtg ctcctactac catactcact   106920
cgaacattcc cgattctgac ctggagatgt caacagctac ttgatgccac tctcttctat   106980 cttttctgtag ctaagccatc cccaagttttg tcgattcacc ctctttaacc cctgtcgggg   107040
tgtccattgt gccccttcac cctgccatct ccctggtgca ctgttttgca aagttcagca   107100
tacatgagcg tcacctggga accttaataa agtgcagatg ttgattcagc aaatctggga   107160
tgccctcggg ctgcatttcc agcaggctcc tggggatgtc cccgctgctg tgctgcagat   107220
gacactctca gtggtgggac tccaggctct gctgtcgcct cctaggggtt tctccacact   107280
ccctggaggc ctaatgggcc cttctccaca tggcagtaag atctgttttt gtgtttgtgt   107340
ttcaagttgg gagaaggaga ttatttaata ctaaaatgtg caacatggga ttgagaaaac   107400
taattattag tcataagttg agtatgcaac attgaaacca catgctttaa aaaattataa   107460
gaaaaaatca tagtatttga aagttacaag ctattatggc taactccatt tatctcagtt   107520
agagaagaag agtcacctgt caccagggca ctgccagaag ccaggctcat ttccaacagc   107580
actgggtgct ccagctttgg ggtgccagct cctcccataa agcaaacaca tacctaggga   107640
tgatatttct ttgcaagggc tctgccctac agcttgtaca tctcaagaag ttatgtaatt   107700
aaactgtctg ttttgagaaa attgtagatt cacacatact agctgtaaga aatgatgcgg   107760
ataaatccag cgtaccagct ttccccacgg agacgtcttg cagcgtcaca gccaggatga   107820
ggcattgacc caggcgaagt ccagagcacc tgtgcgctac agggcccctt gcactgtgct   107880
gtcacagaca cgcccacttc cagatgccat ctaggacccc ctccaaaaag cagaggcatt   107940
cttaaaaaca cacatctgca catgttcctc ttcatttgaa tctgtcagtg gcttctcagt   108000
gcctttcaaa tgaaatctaa agtccttaca agccttgcag caggaacctc tccatcccac   108060
ttcccctcac actctcagct tcatctctgc taggctctgt tcagccaggc agcctttcac   108120
agtccctctc ctcctgccct gccaggaagg tcccctgccc ccaactcttc cccacatgtg   108180
```

```
gcggggcccc gcttgtcctt agaagcccag ctgaactgct tcctgaagga accccctccag 108240 aacctctcag accaggtcag gtttctgcac tcttagatca tccccatggc ataatcacag 108300
ttgtgatgtt gtgatgattc agtgaatgtc tgtctcccca ctggatggta agcttcctga 108360
gggcaggaac agcattggtt ccagtcaatg ctatgtccca ggactgttcg tttttgcaca 108420
tactaatcct aaaaggacga tgacaacagc aaccacttac atgacctaga tgctcttctg 108480
ggtgttgtgc aaatattaac aatttaatcc ttgcaacaat ccacgaggga ggcattcttc 108540
tactcccact taacagacaa ggacagtgaa gctagtaaag agaagtcatt tgcccaaggg 108600
gaccccacta ctgttggcag agctgggtgc aaacgcaggc ttgtgaagcc aggacccatg 108660
cattcaaaga ccatgccagg tgcccccact gcacacctca tccccacata ccagtgaggg 108720
ggagagaaat gctcctgcac tgcctctgat taactgcttt cctagaagtc acacatataa 108780
aagggattta attctagtgg gattgaatct caatagtttc cttattaggt tgatttctgt 108840
taatagttta agtactggat atacatgaat tagaaaatct agattattag caaatgcaaa 108900
ctataaagta ttttataaat gttatcttgt ttgtcagggg atgagtgaga tattcattat 108960
acaaaaagta gtgtggattt tgaggtagaa ggtttactaa ggatcatacc gtagtatgaa 109020
atagccacaa acattcagtg aaaccaaaca ccccgctta acctcaaact aacactaaat 109080
aataaggaat agacttgggg gcagtgcaag tgtatttcta atggtgaaaa ccattcccca 109140
gtgaaaacta atgtaccatc tagttaataa gagctcctct gacccacgca catcaatact 109200
tacatcccaa tggtgatgtg acattttggg ttttgtattt cttttgcaaa ttgagctagc 109260
atttttgatg agtggcaggg ctctgctacc caacctttgg acagtttcca agcataaaat 109320
cacaattcca gataattctg tcacaaagat ctgggtctca ttaggaagga gaggaagctg 109380
ggagatgatc cagtccaacc tcccccaaac caaacatcac ggccttctca gttgtttcac 109440
caaccatcta aatgttttag taattctaaa aattgatgcg cttttccac gaaaggaagt 109500 gttaccacat tttccaagtg ggaggcatct atatccttac tccttcatcc tctccttccc 109560 acccctcac cccccaccac ccacacaaca tctgcaattc ttaaactaaa gcacaaattg 109620 ttacaaagt taattgcact tcaaaggaa tgcttgtata gaaactttct cggcttcaag 109680 gaaaataat acgctttgaa tggctgttca acagcataga aattagctga gtagaaggca 109740
ctcatatagc cattaggacc aatcctttct gccgccaaca ccccccttat aaagacttga 109800
cagtgggcca gaataaacaa cttcaggatg aattcagttg agacacaaag tacacacttc 109860
cagttttccc cttctctggt tactggcctc aataaccagg cagtcaactt aaaaagaaaa 109920
acaaaagctt gcttcagatt acagattgca gacttcttat aatatgtcca tttcaccagg 109980
ccccgctctc agccccggga aaggccactg gaaaccacct cacatggtag ggccttgcgg 110040
gagccagtaa taaccttatc tccgtcaaca tgttctgtca gattgaatgg ggcagccaga 110100
gaagccagag ttggcacagg aaccaaaaca aaggcttccc atcctcctgg agtgagcggt 110160
tgagcctgga ttggtgctta gacctataat gggtgcaagc agcgttcatt catagtggct 110220
ttctagaccc agggacttgg ccccagccct gctgctccac tcctcttctt gcttcattac 110280
cacgagtctc ctagaccacc gaacgatgcc tgcatttgaa agacacttct gctgatcaaa 110340
gcagctgatg tgtcccttttg cggttcattt ctaattgtcc ccaaggagga gaaattcaaa 110400
tagtttatta ctgagagtta agaaatcca ctgaaatatt ctttggtcta aaattactgt 110460
catggcggag cagcttcacc ttagtcattg cccttaaata tgaaagctat ttaagaaagt 110520
ttgcccttaa atatgaaagc tattttaaaa agtttaatga agaagagaa tcacaaaaca 110580
```

```
ttttcaaaaa gcaaagaaa acctaagaga aaagttgaaa gtaggaattt tttaaagaat   110640
atacgacgtg tgttctgtga ctcacccctg caagttattt gtgtgtattc ccttgcatag   110700
taattaataa tgaagcaaag catggcaatg atatcttttc ttgtctagta ttctagaaga   110760
ctccatgttt ttggaaaata tcactctagt tagatctcaa atatattcaa tcagaaaatg   110820
ggttttctac aagattctat atctgtagtc aatagcaaat ataattctat taagctagta   110880
ggatgtgata ggaaactaaa acctagggga gaccaaagca aggaaaaata cttcctcatc   110940
caaacttgag agcaatttac cgtcaggcct actattaata gatggaatac agattccatt   111000
ttcattactc aactgccata ttcattatta cactgtacag aaaagggaat cacatctgtt   111060
gaaaacttat atatgatgtt catgcatgca ttccagtaat tcaacaattt ttatttatct   111120
ttttattgct tgctaatttt tcaaaataat aagctaaaga aaacaaaatg tttgtgctgt   111180
tctcagatga catgttatct ctttaaagga caaaatgtgc tgtgaaataa tagaatgctt   111240
tcagcactca agtgtgagtg agtgctcata catgagagaa agccgtgggg actacagaag   111300
ccaagaagca gatctagctg gggaggcctt tgcagaggat gtagttgtgt ggagaggcca   111360
cacacgtgga attcccagga gggctgtgga ggcgggaat ctgcaggaaa gcactggggt   111420
gagaaacgtg atgagaaaca attattgtct taaaatatct gcagggctgt aaggtagaga   111480
agcaatacgt tgcatctgtg ttaagtcaaa caaaattatc aagggactgg tttcagctta   111540
acataaggaa caattatgtg atagggttgt caataacaag agtagactgc ttcttcacac   111600
actcctagtc actcagaatg gtccaggagg agtggacaac catttggtag agtatgggaa   111660
ggcaggggcc ctgggtggga gtggtgaggg taggagtga gtatcccaat ctagaagtaa   111720
attgtgccca gcacggagct gcaacactgc cctgcacaca aacacacaca aataacaatc   111780
cccagcccct gcatttccct ctccggtttc aggaccttgt atcttacttc aattccttta   111840
tttagctgat gatgaaatag gaagagctta gcactaagaa aatccttttg gagtttggcc   111900
ttgggggaaa atgaatcact ccaaccaggt ctgtcttcta gaaagtatag gatgaaaggg   111960
ctcctcatca catacttcct gacctcctgc taggcctttc cctaaaacag gggctggcaa   112020
agcacaacct gtgggtcacg cctagcctgc cacctgtttt tgcaaataaa gtttttattgg   112080
agcatgacta tatgtatttg cttacagtct gtggctgcgt tcacactatc ccagcagagt   112140
tgaataattg ggacagggac catatgatgg gtgaagctga aaacatttac tctctggctg   112200
tattcagagg aggtttactg agcccttctc tgagacatgg caagcgctgc ttcaggctca   112260
tgcttcacta gattcaggcc tgggcagta aagagccagc tcaggatagc actcccgact   112320
cactcatttt ttcaggcagg ggagccatct aatgtcaagt gcctacgtgc aggaactggt   112380
ctgttaatta gcagctctcc tcatggaagg gataatatat tctagaaaca ggagtgcggc   112440
cctattgcaa gaatgtcctg agccaaaatt aagattcttc tatggcagaa acttggctgg   112500
ggcttctcct gagttaactt ggtagttgtt agtgattttt gagtcagttt tccttgtca   112560
acgacccag gaatgagttt gggattacag ggtagccagg gaaagggaaa gcttcacgcc   112620
cgcccccggg acaaggtctg tcttcacact gctacatccc ttcacccact ttaaaatgaa   112680
acttaaaagg aggatttcag ttgagtagga agtgagaaga gggctcattt taaacaagc   112740
gttaaatgaa aacccacaca cactcagagc acacaaatcc aaccacgctt acaaaaccat   112800
cacagagggt caggcgaggc ccttttctaa atgaaaaga acaggggtgg agactgttct   112860
gagagcatgc tgggttccct gaagggaatt ctcagctgta tgtgccccgc acaggatccc   112920
```

```
tgctagacac aaggccagct gccttccttt caagccgcag acgcatccct gtgtccaggc  112980
gggctggtca gctgcggtca gcaccagctt ccccgctcca tggtgaggtc atcacaacat  113040
gtgagcagga gggcaggccg gcaacctctg agtgcttaga gaaagggacg ggattcctcc  113100
tgtgcaaccc ctctagtctc actcagactc aagtctgact aaggggccag gtgctttgac  113160
cagggactct cccctctcac ttccctccca ggagtcacag gtacatgagt ccttgtttta  113220
caaatgaaga aaacagaccc aacatgatta agatgttgcc ttcatagggg tggcaccagg  113280
attccaaacc atggactcca ctgagcccag tgcccactga catgtgccag taacagtgca  113340
gctgcctgtg gttctgtcga ctaaactgcc ggcagaggct ggctttccac cttcttttt  113400 tttttttcac tcttcaaaca ctttatgaca tgaacataaa ctactggctg catcgttctg  113460
ctgacaacat gacatgtttc tataacttga aaaagcaag cagtggactg ctcattggta  113520
aaattgagtc agtaatcttt taggaaggtt attttcttc cttttactgc ttctcatctg  113580
ttccccgcag taaagaggac aagatgacga cgactcaggg aacacctcca gcctgaagca  113640
gcaccatgcg agcttagacc ttagggtcgg cttagaaacc acaggcgggg cggcttgggc  113700
ccctcggaca ctccctctcg aagctgcttc tccccaagct accccaaagg cactgagcgc  113760
cctctgcccc ccagcaattc aattcactgg ctgtcctgct cctgtcagta ctgagagttg  113820
catgtttgac cctcggggga aaagtccaga ggccctgggg tgtccagcat gctctgaggt  113880
ccctgctgct gaccccttgc gctgtcagca ttcagagaca ttcacacagc acagcctccc  113940
aggctaacag ctgtcatgga acagtggagc agctagacgt ggccattctg tggcccagtg  114000
ctgcagaggt caaagggaca agcgcaggga gcatctttgc tttcagaaaa aaaaaaaaaa  114060
aaaagaagca cactggtgca ctgacctgct cctggtgtct ttgtgattgc tcttttcttt  114120 cgattttgg ttgtcttttt tttttgaaa gagggctttt tatgcttttt tcctaatgtt  114180
catgggtaaa ccaatgtaaa tgtgtgtatg tttatagaga tggctttaaa tcgcaattct  114240
gcagtagaga ttgatttttt aaaaacatg ggtaaaaatt gaagaaaaat tttaaagaa  114300 catttaaacc atcttgggct aggggtggat atgcaccacc ccacggaagc caaacaaaat  114360
ctctctgcag ataaacattt gcaaaagaa tttccaatcc caattttga gtcagagatc  114420 ttttatttcc ttgcaaatta catatctgtt tcaggatttt tgactataag aagaatgaat  114480
gaagatgtgt ttcttacaga taactatgaa caaaccagga aggataataa cttgtatccc  114540
ccaattcgaa tccagaggat gggaaggcat aaaaaaaaga aatggaagaa actttatttt  114600
tagtggtaaa tggtgggact atgtatttta cgtatggtga agtcaccaag cccaacactt  114660
ggcacttgta ggcaaggtag tcttctaatc tgaatgtgaa gtattatgtt ttcatttgct  114720
tggtaatgag gaatattggt gctttcgtcc cagttctcga gctgactgac ttctcttct  114780 gacgtgtgtt cctttagcac acctctacac tgcatggctc tgagatgtcc tgtgactgtt  114840
tcatgtgtaa agttgcctcc ccaaaggact cacatattcc ttcagggcag tgagtacttc  114900
tgattcatcc ttagcagcta ccttcgcgct actttactag atatgttgta gttgaattaa  114960
tgaacaaaag aacaagcaac tttggtgcct ggtgtgcatc tcagagcagg gtgggagtgag  115020 cctggccaaa gggtcatcat gcaacctctg tggctgactc catctggcca cggagcttct  115080
cagccatgct tggtattcac atgacttcta gggcgacagc tcaaccagca aataaacagc  115140
ttcatatggg aaatattact cagcctttgt catcaaggag tgagtcacgg gcctgaactg  115200
aatagaagat agaggagaaa aggtgtgtgg actgggtgag acagcgccca gcgaggtgaa  115260
ctcccggcag ccctgcctgt ctttacctgc acatcacctt gctagggtgc cttcggttgt  115320
```

```
gagggcctgt ctaggaagag aagagttgca ccctggcagg cagcactgag ctgtctcatg    115380
caaagctgag gaagaaagag tgagctgccc agtgagcctg ctggggtggt ggaggctggg    115440
ctgggctgtg cagtctgcag cccccagcag cccttggcac ctttctactg cctggtgctc    115500
accagctctc cagtaacaaa gagggacgtg aagtcagagg ggaagggagg tagcacaggg    115560
cagtcttgac tttgaacaaa gagctggctt cctgaagtca gctggccggg ttttgaagcc    115620
gattttccag cagtgatctt tgatgccaac cccatttagg aattctgtat ctcccctac     115680 cttctaccag atgtctctga gctcaccttt ggtgataatc atgcaatctc cgtcatcccc    115740
acgtccacac tgcccattc tgtcccaccc cgggttctgt ggtgctgtcg gctccccagc     115800
gagccaggaa gggagaggcc agctctgctg gggctcctgc cgccctggct ctgcactgcc    115860
cttctctggc aggtctgagg cgccactgga ggagccacac ggccctgaag cagcaaggca    115920
gatgccctgg acacagtgga ggcacagagt gcaagcaccg gcctggccca cagacttttg    115980
gaggggaagt ggtattattc agttcaaaag tatgcctgtg tgtaaagaga gagcccctga    116040
acatgagtaa gcaaaagtct cagcgcagag attagacaag tagaatgctg gcccgagagg    116100
aggcgtttac tcaccctctg tctaggaagg aaagccaggc ccagcacgct cactgctatc    116160
tatcctctca cacagaggga ttttgaatcg aagccagcat cctgtccttt ctccaatgtc    116220
ccctgctcag gagtcaggac tcagcaaggc ccaccccagc cacacacaga tacagttcca    116280
ggactcagaa ctcagcgagg cccaccccag ccacatgcag gtccagttcc aggattcagg    116340
acacagtgag gcccacccga gccacatcca ggtccagttc caggactcag gattcagtga    116400
ggcccacccc agccacacac aggtccagtt ccaggactca ggactcagcg aggcccaccc    116460
cagccacatg caggtccagt tccaggattc aggacacagt gaggcccacc ccagccatat    116520
ccaggttcag ttccaggtaa atcatctgcc ttcctccgtc caaagccttt gtttcctgtg    116580
tgtccttgtg tttaaaatgg aaacgttatg agaaactgcc tgccagggca aagggtgctg    116640
cccggcacac agtagggact caaaatgaaa ctattgtatt gaatacataa cagatcaacg    116700
ggtattgctt tctgaaatct tttttagccc aattttgttt cttatagtcc aataacaggt    116760
caaattcatt tctgatttac tagccattca gttgcccata aaaatggaa agtgatttaa     116820 gattattagt ttaaaaacca atgaaggtaa acagttatc attgaaggca cataggcaga    116880
aatagattgc aatagttgct gccatgtgaa gcctcagtgt catgctccat atttagagag    116940
atctatgatt tctgaggccc tttcatgtcc atgatctcag tactgctcac aactgccctg    117000
tgaaattcgc cgagctggcc ccatgtcaat cagagtacac tgagcactga gacccagcat    117060
gttgagataa ctggctagag atcatcccat aatggtacca tcacaatctt cacactgtag    117120
aagtttgatg atgtcactgg aagcatattc cacagtccct tgtgaactgg ccttcctgtg    117180
atcagaagca tcagtgaact cccaagaggg tgggaactcc caagaggtat tctcactcta    117240
cttagtgtat attttacaaa tcacaagctt ggctttggat tctttaatg gctagaagga     117300 gaatcatggg gttggaagtc caccagtttg ggtattctgt tccctaactc aaaataaaga    117360
gatgttattt tcaagtcttc tgcttgttaa cttaattaga gatacatgag tttgcagctg    117420
tgctgggcat gccgcagctt ggcatgttta gtccagaagg catattataa tgtacatgga    117480
agattgtcag aaattcaaaa ggactttttg agtatcacat gtgtattttc aagttccaat    117540
atagattcac attcagtttg acaggtatct ttggatgcct atcagttaag aactatttat    117600
tagttgtgga ataaaatagg gtaaaataag gaacaactga ggaaaaaaca taaaatttgc    117660
```

```
tttgtgaata aaagttgtct tcaaaattat gacttttttcc atcccacaaa agttttttgatt 117720
aaacccacaa tgaaaatttta aataagtgta tttactttgg tttaaccact tatttcatta 117780
tgactcacaa ctataggttt tctagttttcc attattacaa actattgtgt ggtttaaatc 117840
aatttcatag actagtctag ttctatagtc acaatttata aatttttttt atgtggtaaa 117900
ttgagtgtct tcatagatgt acatgattat ttctcaattt ttaaggaatg tatttttttaa 117960
gatagccttc tttagccttc tttaacactg attttttgtaa atttttttaca gatttttttta 118020
aatttttggt aatttttttag cataaagtaa tacatggtca ctatggaaaa cataaaaaca 118080
caaaaactat gaagagtaaa taagaaaaac acccagaaat ttaccattca gaaaaggtca 118140
ttgttaacaa cacggtgtat cttcctcctg tcatgcttcc gtgcatttga gcacatttga 118200
gatgtgtata catgttcact ttgagatttt agtatagcaa aagaaatgac cggtcctgat 118260
tcaatgaaac ctctggcaaa ctcgctatat tttccttaca tatttttaag ttcatccctat 118320
aaatgaacta tccattcatc ttatttgaga ttttcttaaa tctttcagca agaaagcggg 118380
aaaaaaatcc tcctctggcc tttaaagcct aattaaatat atgactaagc tagaaatatt 118440
ttataatgac caaccagaaa gtggcaagga ctgtcactct tcccatacag cccacctcct 118500
cctctatctc cctcaggcac acggaaacga gaaaggcaga gaaacccagg acaagtcatc 118560
caagactttg gtcacatggc catccattgc tttcacaaca aaaatataaa tccaacatgt 118620
gtgtgtgcat ttcataccag taggtccaat aagctatcta tatatacaca tatgtgtaca 118680
cacacacaca cacatcctta cagacactcc ccagcttact acagtttgac ttaagatttt 118740
ttgactttac gatggtgtga aagcaatgca cattcaatgg aaaccatact tctaatgttg 118800
aatttttttat cttttcttgg gttagttgat gtctgatatg ttactttctt gcgatgccag 118860
gcaatggctg ggagccagag ctcccagtca gccatgcaat caagaggcta aacagctgat 118920
actatacagt ggactgtgtc accagcattt tggggatatt gtgttttgtg tttttgaatc 118980
ctatcatgtc tacaaaatgc cattttcgac tgctattttc aatttagggt gggtttatca 119040
ggacataacc ctatggaaag ttgaggacca tctgtatatc tggtagggaa agatggataa 119100
caaattcata ggcaaataat aatttcatga ttattattaa gttattccta cttaataata 119160
agtagtgatc actgccaggg agcagagaat gcaggataat gtgacagatg taatggtggg 119220
tacttaagct aatgtagttg cagaacaggc ttttctagag ggtaggcctt taagcgtacc 119280
tcgaagatgc aaaggaagca aagatgcgaa gatctgggct ggggatggaa gcagagacaa 119340
cttggaggcc aaggggagag actgacaaca gcccagctca tacctcagca gcctttaatg 119400
catagctaag aaaacaacaa attaaaacaa ttatagttta cttagacgat tctaagtgtc 119460
taagtggatt tgggcaaatc tggagaaact tgttctaata ctgtgtctta ataagtaata 119520
tagatttgcc caggcttgtg ggcagagtgg tatacacccc ataatagcag aggaaggcca 119580
cagggcctac cctacaaaac cagaggcatt taaaaactta aggaggcag attgcttttta 119640
ttttcagtta aaataaagtg aggagtttct caagaaaaat aataacgaga ccaccggccc 119700
gccctagatg tccaacaaga atgcacagat aacttcgtat atccactttc ctgaacctgc 119760
ccctgacagc caagtggagc acaacaacag agatgaacct caaaactact gtgctgtgac 119820
ataaggcttg ctcaagagga cagtgtggtg tgagtccatc tatgttctaa agcaagcaaa 119880
gctattctgt agtgaaaatg gatcaggaca gcagttgcct ctggtgtatg ggggcaggga 119940
tcgactggga ggggcatgag ggatgacagt tagggtttcg atcatgacag gaattcgat 120000
tactccagca tgtgcatttg ttaaagctca tcaaatgcta cacttaagat taatcctctc 120060
```

```
acagtttgtg gatgttacct taaaaacaac aatgatgact gcaaactaat attgaactct 120120
ggttagtgat ataccaatgt gaagtatagt gatatctcta ctttacttta aaatgcatcc 120180
aaaggcagac tagaggacca tatctgacag acagaaaaat agatatgtga taaggtgaat 120240
gtagtaaaat gctaacataa ggatgtttgc ggtacaattc tttcagcttt tctatacatt 120300
tataaatcat aataaaattt taggacaaaa agttagtgct ttgaagtcct aagtcatagg 120360
gcctgctgct cttgatgcag tagaatttgt cttcagattt gcaaagggta aggcaaacca 120420
ctagcattt gtatggaact tgatgcaaat acttttaatt gtctggtttt caatgtata 120480
gacttaaagt aatatcaact ctttctttga atcaactact gaaataccta gtcttaaata 120540
aatatttta tgtaatcctt aaagtactat gtattcattt ttctttcttc tttcttttct 120600
ggtttgataa atattctata aagtaactgt gtttaatggc caacatttga gtaagtccat 120660
atgcagatcc aaacatctca gtttagacaa taacttaaga caatatagag tggctgacat 120720
cccctaacgt gggtccagat gcatgttatg ttatgtttct gttgcattct caatagttaa 120780
ctttaataaa agaaagtcaa aagcttatat attttttcaa tcttcaaaac atttctggga 120840
ggttgtctta gttaatttta tgttgctata cccatatcac agactgggta atttataaag 120900
aaaataaatg tatttggctc atggttctgg tggctgggaa gtccaagagc atggcattgg 120960
catctgcttg gcagctggtg agggccttca tgctgtgtca atctatggtg gaaggtcaag 121020
agagcatgca tgtgaggtgg tggggaagag aaaaagcggg tttaactcat cctttttatca 121080
gggactcact cccgtgatag ctaacccatt cttacatgaa tggcattaat ccattcctta 121140
gggcacagct ctcatgacct aattataata cctcttaaag tttccacctc tcaacactgt 121200
tgcattggtg attaagtttc caataaacgc actttggaaa acacattcaa accacagcag 121260
agatcaacgt tattgtcacc attttcatat ttgaggaaag catggcacag agagcttgga 121320
gaagtacttc aaggtcaccc aatgaggaag tggctaaaca aaaaccttat cttaaattaa 121380
ttaaaaacct cttgctcttt gcagttttgt cttaaatcta cctaatttgt gactgtaatt 121440
tttaagtaat ttactcatat aagtggtctc acattaaatt ttctcattgc tttatatttc 121500
taacatgaga tatttggtat aaggatggaa ccaagatcat accttgtttt aattagaaaa 121560
cctagaccaa gtcattgtga tcctcatcct agatttcagt taaatgctgc tgtctccttt 121620
tgggtatgtg acaggggaaa gcctcagaag aaacaaacct atgtgttttc ttttgatact 121680
ttagtaatta acccaggata gtattcaaga ttgacatgcc ttatattgaa tcaaatagca 121740
tatcaactgc cttcttattc tcaagtatag acatgttggg taattgggca tttaagtttc 121800
tttgcaattt tttccattat taacaaaatt aatgagcaac attctgcata aggtctgttt 121860
cctcagaata cgtttcccaa agtggaatca tcatgacgta gaatttaagc atacttactt 121920
gtttaaacaa attgtccagt tgcttcccaa aatgttttgt gaattaagat ttacatcaag 121980
aatatgtaat gttgttactg tctcccaaat acaggatctt tttctgaata taaaagttat 122040
acatgctaat tgtagacaat gaagggtcat tatcctcata gataatgaag tgcttctaat 122100
acttgtgctt ttattcattt attcaaaaag tgctaaataa gccctgaagg ggcttttggg 122160
gggtcatttg ggcttatttt agcacttttt gaataaaataa ataaaagcac aagtacagtt 122220
tttttaaaat actgttttct ataatagatt aatcttaaat ggcatgtttt cctttatttt 122280
actgacaaaa gttacttact ctgtgattga ataataaaaa ttctttggtt cagctgagag 122340
aaacttgcaa gctgacgtcc ttgattattt aaaatgaaag cagctgcctg ttttcatctc 122400
```

```
tctgcatcct gaggaaactc ttctgcaacg tgttccagcc ctaggttcta gctgaccctg   122460
ttcatctgtt tggcacgagg ggcccaacta acacttgcgg ctacctggac gacagccaat   122520
ctagttggaa tgagagttag aggccatagt ctgtcagctg ggaaagcagc ttttattcca   122580
aggtgtgcca accgaaaggc cacatgttat tgtcacaacc tggtacctac atcagtgctg   122640
acatctttaa gaaccttaga attgggaaat cagtttagcc ctatctgcat gtgtagccga   122700
caaccacaca attgttccaa cttgaggttg cattcagagc aacctcattt cccccatact   122760
cctgaggaaa agcagaccag agacgctggg tcaatccaga gttatggttg gaaaaatgat   122820
ggaataattc tgcccctggt gataggagag agggactcca tcttgtcaac tgtcatggtt   122880
cccatgtgaa agctatcatt atcactgaaa ttgaatgaga acacagaagg gaagaacagg   122940
gaaatcccca cagagttaaa gaggatgtga agattgcttc atgtttaatg tttgtgtaag   123000
tgctttgggt tggttatgtg ctgtctgaac atgtgctcat ttccatggct cattgagagg   123060
gcagacagtc caatgatact ctttagaatc attcccatgg ggaaggaaca agaagcctg    123120 taaaatagaa atgcacatgt aaaaagcatt gaagaaagtg ccagtgtatt gattttggcc   123180
atggtttgtg ctctaccacc tggttactgt gattgcagaa gtgcctttgc agatgaggaa   123240
gaacctggcc aaggctcaat ccaacatcca aagccagagg ccatatttct tcactcttaa   123300
gataatttgg gttcaaatta tagtcccttt acacactctc tgcctcaaaa ggcccaagac   123360
tctcttttgt tatgcttgcc taaacatgcc tttcaaagaa ctagttctgt aaatacaact   123420
ttattataaa cctctccttt gcttttaaaa atggatcacc acgtccattt ctatggtcca   123480
actttgtccc ttaatttaaa attttttctt ggattaagtt tgatgccttg aaacattagg   123540
aactcaagca tacaagattg tatgctggtg gtgagggaag taactgtgcc tccgcctgtg   123600
ctgggtggat caacatggag tgtggacgag catagggatg tgtgggtttc tcactagctg   123660
agagtgtttt taaatgttgt attttgatgt ttgttatttt ctgaatattc tacagttaga   123720
cctttgattt attctttgat gcattcattt gaataatatt tttaatctcc agccagttag   123780 gttttttaatt tacacttttg tccctgattt taggtgtagt gttgtgtaca ctactgccca   123840
gtgtatgtta tgtttgtaaa cattcattgc acgcacaaca atgtgactca caatatttt    123900 gagaagtaaa aagttcatta tatagttatt aactcaaccc tacagttata ttcgtgaaat   123960
accttgtgaa atttattttt tgcctactgg agctcttaca ggttaatcct gtcttcaaga   124020
ttttcataga attttcatct accacccacc cctttaaatt tcaacatttt tttattttgg   124080
cattttaatg caattcaatg cattataggg acaagctatc tcttattatg aattgcacct   124140
tatataaact taaagatctt ttatcacaaa tttctttgct gtgtccttta gtgagaattt   124200
gtattatcag tcactaaagc tcactaagtt agtaagcttt gcgcccagat gacctgggca   124260
ggaatgggtg agtctctgtg tggagagagt gaagaaactg ctaccttaa tacctggacc    124320 ttgagggatt gttttatttt agttttctg catttctcag tatttcatgt gatatctgtc    124380
tttttcttcc agtttgccaa ggcacgagta acaagctcac gcagttgggc acttttgaag   124440
atcattttct cagcctccag aggatgttca ataactgtga ggtggtcctt gggaatttgg   124500
aaattaccta tgtgcagagg aattatgatc tttccttctt aaaggttggt gactttgatt   124560
ttcctacaca aataaaattg gagaaaatct aagtggagaa aggcctgggc agaattccac   124620
ttgaagtgtg tttatttttg ctatggcaat gacaagtctt acagagctac aaacgagagt   124680
tttatgagaa agccattta ccagctaatg tcaagtaata actagaaaag gatatcaaat    124740
agaaacaggc taatctggag ttccatgtca tcatagacac tgacgtttat ccctgaccat   124800
```

-continued

```
tacctcagtc atgatgtgct gccatactcg ctcttaaaaa cttttttttaa aagccctgct 124860
ttgcaccatt tgcctattcc cttagtgtaa atactcctac tatagctgat ttcaaggtac 124920
caagtttcac tcagctggtc acagaattct tatttcacga taggcgctaa tgacccccata 124980
ggagccagct ctgaaggctt cagagtttca ctgaattttg gatggggttt acttagcctt 125040
cttctgtttt tcttttacct ttccttttta aataagaaat aatgcaagac agatacaaag 125100
taattctttt taatttccat tttcactgga gagtgttgaa ccccgtgagg catgagagca 125160
cagtgttcca gaacaatgct tactgctcat tatcacaggg gtcaaaggct aacgtgcagg 125220
gattgttgca gatcgtggac atgctgcctc ctgtgtccat gactgcaatc gtctacctat 125280
tttacagttg ttgagcactc gtgtgcatta gggttcaact gggcgtccta gggctccctg 125340
gacccatttt agaccttgag ttcttgagtt cctcaaaaga gaaatcacgc atttatgttt 125400
tctcttctta gaccatccag gaggtggctg gttatgtcct cattgccctc aacacagtgg 125460
agcgaattcc tttggaaaac ctgcagatca tcagaggaaa tatgtactac gaaaattcct 125520
atgccttagc agtcttatct aactatgatg caaataaaac cggactgaag gagctgccca 125580
tgagaaattt acagggtgag aggctgggat gccaaggctg ggggttcata aatgcagaca 125640
gcagttccga tggctcccag cgagcttgtc actcaattcc acctcggaga aggcttttat 125700
ttttacccag tacacgtgca ctgagtgccg gctgtgtgta agatactgca ggggaagtta 125760
ctgagaagat ggcagatact ggaatgggaa gatttaagcg gggtaccagt gtttacatgg 125820
acatgaaaaa atactgagag atagtaagaa atcgtaaaga ttctgagtaa aagagagtat 125880
gaccaaacaa gctgagcagg aatcgtgaat ctatgtgtgt aggcagtgaa taaactgcca 125940
gtcttattac ctggacctca aggataaaag acatacagta aaaatcaacc cacattgagg 126000
acagtttcga gagtcgcgct gctacacaga aagccctgtg taagttaagg atagagaatg 126060
aggtgttcta gaactttgaa tttttgtgag caggactcgt gaggttcctg tgagaggaaa 126120
caatgaagga tgatagaaaa gaagggaaat tgatttttaaa aaactggaga tagcagtgat 126180
tgtgcctcac tgtgcagtgg gtttgggggcc aggaatgtta aattggtaac ttcatttaac 126240
gcccacaacc tttcttcaaa gtaggcactg tacagatgcc ccttgactta tgatggcatc 126300
ctatctggct ggacccccgcc gagggtgaag gcgtcattag gtcggatttc agggctaatt 126360
gaatgtatat tgccttcaca ccatggcaaa gtcgaaaatc tgtgttaaat catgctaagc 126420
cggggactgg ctgtgctctg ccatcgtaca aataaataaa tggaagtcaa gtaactccct 126480
tgagggcccc agctagtgaa tggagaggcc agctatggcc accactctct gccccagggc 126540
gctcaacgcc cctcctgtgc catgcagttc tgacaggagg gcagtgctgg taggaaaggg 126600
gtgtgatgaa agggtgccc agcagaggga gtcatatccg gagtgacagg agcccaacag 126660
gggtgcagcg ctggaaccca agccagcacc tctggtcatg gctcctcagt tcaccgccta 126720
taaaattgtg tggttccccc acaccccttg ctgctcagag cagccgcgca catgcttgtg 126780
ctgtgcgtgc ctcctgtgag atggcctggt acaccggttc ctacagtgcg cctcacacgc 126840
tgtctcggag ggaggcagcc tgtgcgggtg cctggacctc cgagccagac cctctgggtt 126900
cctgcctggc cccgtccctc agcagccaga tggctcggga gcacattctc caatccctcc 126960
gtgtctctgt ttcgtcatct tcaaaaatgt ggatggcata gctgctaaaa aatggtgaca 127020
tacttcctag gtggtgcaga aaattaagtg actgtaggaa caggcctcag cagctccttc 127080
cacttccttg gtatgattgt tttttaaacc aaggctggga ttgtatagat gcagattagt 127140
```

```
taatgtgata ccattaatag ctaacctagt gcctgctgca gggtgagcct ccctaagcc  127200 accgggaagc ggctcctgca gcctccctca cgtgtgctgg ccctcctctg gcagtcattg  127260
cctgtggtgt gctgaaggcc cagctctgac tgtgcctctg tgctctcctc gccccgcccc  127320
ctgctctctc tcaggtcttt ggtctgttgt ccagctgcc acagcagcct ggacatccct  127380
gttggtgttt ccagccctgt cctctcctga gttccatcca cctgtgcatg gcttttcat  127440 gagtgttttc acggatggtt ctgctgtcat ctccaacctg ataaacaaag caccacgatt  127500
cagcccttat gaccccaagc ttccttcctc agttccttgc ttctgtgcat ccactgaaga  127560
agcctgttcc actgtttccc tgcactgggt ctcctgtctg caggaagcct tcagccctca  127620
cttccacact cctctaagat gtgtgcctgt gcccttctgg ggaagctcat tttcctagca  127680
gcctccagga tcttcagggg tgaatccctc cttcccacg ttggtactct gtacacacaa  127740
catgcccatt ccctgcctgg ggagctgggc attgcttcat gaatcagagg tcaatttttt  127800
ctctattaaa gtcacagatg ctcattgcac cattgtgaga atgaatgaag atagtgctta  127860
taaatcagcc agcaaggtac ccagcctcac tgtgtcaggg tctccctggg catgaggtgg  127920
ttagagtgtg tgacatgtct gtccccaagc ctgtcagctc ccagatcgaa gccagtggat  127980
ctcattcatc ctcgcagcgc ccacagcact tgcacagggt tttgtacaca taagtcattc  128040
tgtcaatgtt catgtttaat gtcatcagtg gaacactccc actttgtaaa gacttgaatg  128100
tgttcatccc tgacttttcc acatcttgtt agttcttctt tggaaacagc tgtacagttt  128160
caccatcctg tgcatccctg gagtctacct gtctctgtca tacattcaga ttcttcttgt  128220
ttcgtgtcac tctcatatcc ttttctctaa tgaaaagctc cgcctgggca tgcaaggtgg  128280
agccctggat gccagcccct cacctggcat ccagggctgt agcactcagg aactgcctcc  128340
ctgccctgcc tacccctac atcatgcgac cattccagtc cagccaatca gccccttggg  128400
acccagctta ccacatgcat atcatttatg ctgtgaccac tgactaaacc attctcttcc  128460
ttcctcccca tatttctaaa tttctaatca ttgctcaaag cccaattcag agaaaccct  128520 agctcctcca tggcaccatc attaacaatt ttatctggcc gccccccggg aagttcactg  128580
ggctaattgc gggactcttg ttcgcaccat ggcatctctt tagcagaaca taaatgcgaa  128640
gagcacatgc atccttcatg ggaatttaaa ggagctggaa agagtgctca ccgcagttcc  128700
attctcccgc agaaatcctg catggcgccg tgcggttcag caacaaccct gccctgtgca  128760
acgtggagag catccagtgg cgggacatag tcagcagtga ctttctcagc aacatgtcga  128820
tggacttcca gaaccacctg ggcagctgta agtgtcgcat acacactatc tctgcctcca  128880
gctcctatgg gggacagctc tacagcactg gggcagggga gagaagccat gtttagtaag  128940
tcacattaat cagaaacaaa aagtagtaag caaaatatct gaccactaga aaagcatgta  129000
tttaccacgg acatagagat cgtttttttg tggcgggtgg cagcccagct ggttggcagt  129060
gcaggccacc ggaggcagat cccctgcagg gacagcagag cacttgtgtc ctgagaagag  129120
ctgctgttca tggggctggc agcaccaggg cctctcctag cctgccctgc tgacactggc  129180
cagactccta catgcttctg agtctccaga ggctacccgg ccctcctgaa gcaccagggc  129240
tgaatccacc cccagctgag ggcatgaaca ctgccacatg gagtcacaca cacagctggg  129300
cactgccatg gagaggaagt ctgtccatgt ttccttgaat actggtggcc tggtccctgt  129360
cccattcccc agtgaggcag cctgtgggga agcctggcag ggaaccaggc gcaggtcagc  129420
gtggcgccct gactcaggcc agcactgatg ggggactctg agacgcaagc tcacactcac  129480
ccagctcccc tgggctgcgc ccgttcctga tcgcttggac tttctgttct ttagagtaag  129540
```

```
aagtgatcac catttcctgc ttctttgttt ctccacaact gtgcagtgga tgcctgtttg 129600
ttttctgccc tcagaacaaa aaaaaaaaaa aatagagctg acgtgaatct tcaaaatcat 129660
caactacagg gctttggatt tttgtgtatt tgttttattt tcatttatg gatggattgt 129720 gatgaaatgc ccgtaataca agattttcca tcttaaccat tgtaagttac aatgtcagtg 129780
gcattataca tccacatggg tgtgtggcca tcaccaccgt ccacacacag aactctttta 129840
tcttgcaaag ctgaaactct acccattaga cagtaactct ctgctctccc ttccttccca 129900
gcctctggcc ctggcaggca acagtccact tgatgtctct atgaatttga ctgctctggg 129960
gctctcatac aggtggaatc atgtagtatc tgtccttttg tgtctggctt atttcaccta 130020
gcaaaatgtc ccgaaggttt atccatgctg tagcacgtgt taagaatgtc cttcctcttc 130080
atggctgaat aatattccat tgtatgttga cactacattt tgtttgtcca ttcacctatc 130140
tacagacact ggggttgctt ccatctttg actgtttgaa taatgctgct gtgaacatgg 130200
gtattgaggc tctttgtttt atagacatat tattccacca gatacccatc ctgacaccta 130260
ctatgtttgc aagaaactga aagctttatt ttacattgca aaatttcata ttatgagatc 130320
aaggttagca tttcctcagc tgtctggtgg acaatgggga ggttaaactg tgcacatttt 130380
attttttttt aatgaacctg gaacggttat gggggccagtg tttgccatgg atcaggtcag 130440
gcagcccaca atggcaggtc tccatgttct gtacaacaac tgtgggaaag acccacagag 130500
aaagtgctgg aaaggggaat gatgggtagg ttcatgcagt aaaaagattc aaatactaca 130560
gggcattgaa ctataggcca atatagcatt gctttaagaa taaacaaaaa ataagacagt 130620
aagaataagc ctagcaaaat caaaagtcta taaagaactg acatttcaag ccaataagag 130680
aataattcct tattcaataa attgtctgga atgacttaac tattagggt gaaaatatca 130740 aagtgagaga actataaagg gtttttaaaa aggaattagg tatgttgggt tagtcgcatt 130800
ggagagtgca aattcaccat cgacctgata cctgaaattt cctccttacc atctagaggc 130860
aagttgggaa tgctgccagg ctcctgtggt aaaggaagct cctctcttga ctggtgcttt 130920
atggctacac gttcctgctc agaatggatc tcatttagtc ttcaccaaaa aaaaaaatct 130980
catgagatga tttaagtgtt ttatggacaa gatgtctaaa actcagaaaa atttcacagt 131040
gtgcctagct tttatgttta tgttgaagtt gggcattaga agttagaatg aatgggttta 131100
cttcagagaa aattaaatcc atcacccact ccttgtacta tgaattccaa atacatatta 131160
aatacatata ataaaatatt taatatatat gtaagtgcca gaaggaaaca taaatatgaa 131220
tattttgtaa tatcaagttg aagaaaagcc aaaatctgac atcataaaag aaactttca 131280 agtaaaatat gttaatggct accaggaaaa tattgtgcaa tgtctgattg ccatgaagag 131340
ggttaatatc cttgctatat cactctgtga agtcatcttt aaaagactaa gaaaagatg 131400 aatctcttaa taaaaacctg gcccagaaca tgagcagcct ctctctctca ctctcactgt 131460
ctctctttct gtcacacaca cacacgcaca catacacaca cacacacaaa tatggccaag 131520
aaataaagta aaatgttatt tctaatgtaa taagtaggtc aaaatagaaa aagaaagcat 131580
cacaccttcc tttgcaaagt atttgggttc cttttgcttt taaacacctg ggtcagctgg 131640
ggtgtcgaga aacagaaatt ctcacgttct gcttgtgggc atatatgtta ataaaaccaa 131700
gcttggcaat atgcctgcaa tatgtatcta aagcttcaaa gtatgtatag ctttgaccaa 131760
tcaatatcac atttcggaat aagagaaaaa gaaataatga aagtgaaaat cataagagat 131820
gtagaaacat attcttatac aagaattcct tgcagcctta tttataataa atttgtgaa 131880
```

```
caaattatat atctaaaaat aagagattgg ttgaaaaaat tatgcagcag ccatgctatt    131940
gataatcatg ttagatagaa gcatatttaa aggcatggaa aaattgccat gttttatatg    132000 ggttttaag gttataacac aatgtatagt gggattccaa ttcctgtata tacatagact    132060
tatatgtcta tattgattaa ctctggatga gtctcatgtc ttcttttgc tttcttctat    132120 tatccatatt ttatacgatg tgcctgcatt tcttttttgt aacagatggt caatactaga    132180
atcataaaca gatcttgttt gtttattggc aaatgtttcc cgttagaaaa agatgcatt    132240 ttcttttaaa tatttttatt ttatacaatg attacaagct tataatagaa atttgaaaat    132300
tatatgtgag tacagggtaa aaagttgaaa gaatgggatt gcacgctaca gatctagctg    132360
cttttagcac gcctgcgtag gaccttgctt tctctagacc tctgttgcag tctctctgcc    132420
tacctcctca caacgtccat ccccccgcggt cactgtcgtg atgccagcct ccccggcctt    132480
catgtctcta aggagcacca gcgcggcaat tagcgccctt tgccttggtg gtattctggc    132540
ttcacagtca catgggagat caatcgtcag cttttctgtt tgaaatctaa attcttcctg    132600
actgcagggg acctcgggac ccatgaacac ctctagtttta ctatgtcttc acagtaaaag    132660
atatctgcat gactggactc tttaacaaat ttggtggtta acctactctt tctatataga    132720
tatagcactt cgaccttcag acttctcaat actgataaaa agaaaacacg acagatgaca    132780
ggaaaacctt tgcagctata atttgtaatc ggccaattat aaaaactgca aaaattgacc    132840
agatagctaa ggttttacac agtcatgaaa gtgatctgca ctgttaacat ttcaccctct    132900
gtgcaccatt ctgtgcttct ctctggtttg gagtctagaa ggttttattt acaggctatg    132960
acttaacaat cccagaacgg ctgacacatg cagtcactca agactggaca cagcaaggaa    133020
gtagtgggtc catgccaaag gctcagccag acgagacact ctagctgtgg caggagatgc    133080
cagggaatgc tccaagccta agcagattgt aaacaaggaa cctcaaattc atgaaaaatt    133140
cttgcttatg tggcccatgt cagtaattac tctctgcctc agtttccgca gctgacatgt    133200
aaataaaagc agttcatggt tcatcttctt ttcttatcgg ggtctcaagt gattctacaa    133260
accagccagc caaacaatca gagaataagt tgaaagatt gtcttcattt attgaatgtg    133320
cttaactcag gcccgggaaa gggcgtcatc agtttctcat catttcactg agatatgcat    133380
ctattacttt tacatttcag gccaaaagtg tgatccaagc tgtcccaatg ggagctgctg    133440
gggtgcagga gaggagaact gccagaaacg taagtcagtg aacagcctca gacccatgtg    133500
tgaccgcccc tctcttcctt cacttgctta ggtgattgga tttgttttcc ctctgaagac    133560
tccaaagagt tactttatta cagggtcaga tgtgaaccag taggtgaagg acagtcttgc    133620
aaatctcacc gcatgcagtt aatccagggt gggctatttt gggagcttca gcctatcaca    133680
aataagtgaa catcagcagg ggctgggcgc ggtggctcac ccctataatc ccagcacttt    133740
gggaggcgga ggcggtcgga tcacgaggtc aggagatcga gccattctgg ttaacacagt    133800
gaaaccctgt ctctactaaa aatacaaaaa attagccggg cgtggtggcg gcgcctgta    133860 gtcccagcta ctcgggaggc tgaggcagga gaatggcatg aacctgggag gcggagcttg    133920
cagtgagccg agattgtgcc actgcattcc agcctgggcg acagagcgag actccgtctc    133980
aaaacaacaa caacaacaac aacaacaata agtgaacatc agcaagtacc ccagcccgt    134040 cctctgaaca cagcacactt tcccaggaat ggaagacttg ctcctgttga cagcagtcac    134100
cagacttctt gtttcctctc cctccctggc tttctttggt acccacctac acagaagcct    134160
gagcacgggt tctcatgggg acttttccat gtggaccctg ctttacgatg gagagggcca    134220
ttctcctagg tatggttgtc tggctcagcc tctcagtggc caaggaacct ggggacatga    134280
```

```
gctcaaaaac ggacactatg tccttaagct gaattgtggg ggggctgtta ggcccttcta  134340
aacactactt cccagcaggt atttttgttc tttgtatgtg ctttctgcat tgcccaagat  134400
gcatctaatt atttagcagg tctcaaagtc tagacttgat ctcatgagtt ctcttaagtg  134460
attaaaaata aatcaggaga aaaagaggc aatcagaaaa gggcatggtt tgacttagtt  134520
tgaatgtggt ttcgttggaa gcaaatgtgt cttcactttt tcatgaaaaa gtctgcaagt  134580
gctctgcgac atccctggga aatgatccta ccctcactct tcagctcaca gggaaccttt  134640
gctcttttc agtgaccaaa atcatctgtg cccagcagtg ctccgggcgc tgccgtggca  134700
agtcccccag tgactgctgc cacaaccagt gtgctgcagg ctgcacaggc cccgggaga  134760
gcgactgcct ggtaagatgc ccctccagca gcctccctgg agcaggctgg ggctgcaccc  134820
gcccacccca caccaggaca gaagacttcc tgtgggggag ctgtcaatta gcatttgtca  134880
taacagacag gatattgccc tctgcctggt gacaaagtat ctttagtatc ctgcctccac  134940
cactcactga gaccttggga aaatgatggg actaccatgc ctccatttcc ttacctgaca  135000
atgatgcata acaaagtctc tcccagttga atgcttaaat gatgagatgc ctgtgatgtc  135060
cgtcattagg acctgggcac agaacaagca ctaaatacta catgcaagta tttgtcatga  135120
atgtgccttt tgccagcag cacactctct ttattgtttg acttcggcta tacctctaga  135180
gacttgacac tgtgaggtcc ctaagagacc catggagagc cacacaggtc ttgctggctg  135240
gggctgggtt agggcctcct gacacggatc cctcggctcc tccaccactg ctcaggcacc  135300
tcctgagctg caccctgccc tcaagggtc ctgaagtact cactgtcgcc ccattgctcc  135360
agaaagtgcc agcagaagcc ttgctgcccc agcgggctct gagcagcact ggagggtaca  135420
ggtcagaagc gtcttggaag tcctggagac gccaaggctg gtggatgtga ctcctggagt  135480
gggagctggt gtgacgaagc ccttcctaag actaaatcca gagcactctg tggtttcaga  135540
gaagattcct aaattccaga gtttggaccc agacccagga attgtgactt ggttggcctg  135600
agctgtttct aatgtgagcc ccaggagaa gactgtgcgt ggggttggtc ctaggaaaag  135660
ccctcgctgt attgggtctg gctcctttac acggcattgt tctagcaagg cttctgccca  135720
ttcagcaata cattataaaa tataccctca attgtacttt ataagggaag cccaatgtcc  135780
tttataaggg aaattaaaca taatttcatt ccatagtcac cgctataatg tgtgaactcc  135840
atcatctata cgttagtaaa cagacgtatt tttatcataa tccataaatt atgataggtg  135900
ggacagtgca cctaagaaaa aaatggactt tttagagaag ggtctttctg actctgcaga  135960
gggcgccagc tgggttttcc cacactagtg gaacactagg ctgcaaagac agtaacttgg  136020
gctttctgac gggagtcaac accgtgctgc gcttcctccg tgtgtggcgc tgagtgtact  136080
tacctcactt gcccagcgtg tcctctctcc tccataggtc tgccgcaaat tccgagacga  136140
agccacgtgc aaggacacct gcccccact catgctctac aaccccacca cgtaccagat  136200
ggatgtgaac cccgagggca aatacagctt tggtgccacc tgcgtgaaga agtgtccccg  136260
tgagtcctcc tctgtgggcc ctctaactgg tcaggcatcc ttgtcccgct ctgtctcctg  136320
ctgagccctg gagtatccca tcttggagag tctttgggtg gatgtgtttg ccttgcttgg  136380
aggagcgac cctgtgcccg tccaggcaca caggcgaggg gaggggctgg cttgctaccg  136440
aggagcgggc aggtggtggc catctccacc catgggggct gctcagtgca cagggcagat  136500
ctgggtggca aggccacctc acaggagaaa cacctgctgc tcagccctca ccactcatcc  136560
agcagccaca gccgtgggta ttcagttgtc tgctgggcac aaagccgtgg gcatgccact  136620
```

```
gtttagtgct tgtgccaagc aggtatttaa tacaccgaaa tcagagagtc tatcagaaga   136680
cctgccttct tgagtggtta aaattctagt gaaagttatg cctcttagga gtattgcaga   136740
ggttttgttt ttgtttttat tttgttttgt tttaatggtt tgggtttgag ttttgcttgt   136800
ttgtacttac atttgtactg gtggctccag ggtttaggga aattgtgaca taaataatt    136860 cctgacagag aaagcaaaac tttgtctaat gaaagagttt tagaagccac tcttgatctc   136920
tagaagggga gattaactga gaaaaaaaat tgaaagaaca attatgaggg ggagatttta   136980
ccctgccaga tttgtgtaca tgaaaaattt tacattccgt atggaaaaaa aaacacaaa    137040 ataataagcc attataaggt aaatgacaaa caaagctaaa gaaaaatgtg ccacagtgat   137100
gacacagata tatctttgag atagggctta acagagcttt aaaatccata ggaaaacact   137160
tcgagcctga gataccaaga gcagatggtt cacagaagaa tcatcaatgt cctataaata   137220
tttttgagga tcttcttggg gaacttaaaa caggaacagg ccaggcacag tggctcattg   137280
gctcatgcct ttaatcccag cactttggga gactgaaggg gctggattgt ctgaggtcag   137340
gagtttggga ccagcctggc caacaggggtg aaacctcgtc tctactaaaa atacaaaaat   137400
tagccgggcg tggtggcgca cgcctgtaat cacagccgct caggaggctg aggcaggaga   137460
attgctttaa cccaggaggc ggaggttgca gtgagctgag atcacaccac tgcactccag   137520
cctgggtgac agagcaagac tccatctcag acaaacaaaa aaggaagaca tagagctcct   137580
aaaaataacg cagaagtctg ctattaatac aaatgaatta cttttaaaggt gagagcaggt   137640 ggaggagagg gctgaggtgc ctgctgggac gcaaaacagc tggcccctca agggacccag   137700
tgtttcctgc catgatgaaa cacctgtatt gtccacattg cggcctagaa tgttattaaa   137760
ctcttgaacg ggattccttc tctatttgca acctttcatt ctttgtcctt aaagtaaata   137820
aagccaaagg aggatggagc ctttccatca cccctcaaga ggacctggac cgcctgtgtg   137880
aggcccgagc acctggtgcc accgtcatca ccttcctttc atgctctctt ccccaggtaa   137940
ttatgtggtg acagatcacg gctcgtgcgt ccgagcctgt ggggccgaca gctatgagat   138000
ggaggaagac ggcgtccgca agtgtaagaa gtgcgaaggg ccttgccgca aaggtaggaa   138060
gcccgccggt gtgcggacga ggcttgttct cggctgctga ggctgggctc tcatgccacc   138120
tccaaaggaa cacatcttcc tcttctcatt aaaaaacaac tatacatatc gtttctttaa   138180
aacagaagat aaagctgtaa agctaggtta ggcaatggga aggcactgaa ggttgtgacg   138240
gggtgggggg ctctgatgag aacagtcaca gagccagccc cgctcagcag ctgccaggtg   138300
cccagccctg gggagaatcc agggaaggca gagctggaag cagtgcagct ccaagcggcc   138360
catgggaaat aatgaggaga acgcaaggtc agtgtgaggt gacagggatg gcatctccta   138420
caccgccgta gccccaaagt gtactatagg tcctggtgtc ccccttccc gcctgcactc     138480 tccccagccc cttcagtgtt tgttgagtga atgaaggatg atgtggcagt ggcggttccg   138540
gtgaccggaa ttccttcctg cttccctctg cctgtggatc cctagctatt cttaatccaa   138600
caaatgtgaa cggaatacac gtctctctta tctctgcagt gtgtaacgga ataggtattg   138660
gtgaatttaa agactcactc tccataaatg ctacgaatat taaacacttc aaaaactgca   138720
cctccatcag tggcgatctc cacatcctgc cggtggcatt tagggggtga gtcacaggtt   138780
cagttgcttg tataaagaaa aacaaaatct gcctttttaa ctggtagaga ttggtgatca   138840
ataatcaccc tgttgtttgt ttcagtgact ccttcacaca tactcctcct ctggatccac   138900
aggaactgga tattctgaaa accgtaaagg aaatcacagg tttgagctga attatcacat   138960
gaatataaat gggaaatcag tgttttagag agagaacttt tcgacatatt tcctgttccc   139020
```

```
ttggaataaa aacatttctt ctgaaatttt accgttaatg gctgatgttt tgatatttt   139080 caaaagtgca gtttctcctg caggcaaaag gggacacgtt aagtccaggc ttgggtcatt   139140
cactgcggtg taaacacgct ttctccctcc cgcccggccc cagccagctg ccttggtggc   139200
ccataacccc tgagggtaga gggaggggac aggggtaggt gacaggcagc ctgggcctca   139260
ggcttttgaa actggacgcc agagccttgt ggggccacgg gcaagcctcg ggtctatgac   139320
tgccgcctga gctccgcttc cttcctctct aaaatgggaa gattagacca aaataacaag   139380
actgttttaa ggttggaatc aaataaggaa aatttgtaaa gctccttgta tgtgatacca   139440
gatccacaat tggcagataa tcgcagcagg agcctcttcg gggtaatcag atacgcggcg   139500 cagcagggt ctcagggcca cagccagggg ggcggcggga acatgcgga atcgcagcgg    139560 aaggcgggag gcagctgtga actgtggctc ggcctgcgtc cgccctgcgc atgtacactc   139620
agagaagatg ataatgaaaa agaaagcaaa tccaattttc ccacttactg ttcatataat   139680
acagagtccc tgagagtcta gagtaatgtc tcatacaaaa aagaaactcc tacgtggtgt   139740
gtgtctgaag tctttcatct gccttacagg gttttttgctg attcaggctt ggcctgaaaa  139800
caggacggac ctccatgcct ttgagaacct agaaatcata cgcggcagga ccaagcaaca   139860
gtaagttgac cacagccaaa gcctggtaga ttacatttgc cttttagtt ggaaattagg    139920 cttaacagga gagttgctaa gatagggcac agagctcctg catctctcgc cggcattccc   139980
aaatgctatc tcacatgagc aggcacaggg agcaagactg cacgaccact ggcacaggct   140040
gtccgctaaa ccacagactt tcagcgctc gccagtgctt ctgcttctgt gtccactcca    140100
gatcccacat tgcacttagt tgtcaaatct tttcagtcca tttctaacct atattagctc   140160
ctgtgtcttt ccttgtcttt cacggccttg acacttacaa aacgtgtggg tcaggtactt   140220
tgcacactgt ctaaccatgt ctgttcagct ggtgttttct caggatgcaa ttgaggttat   140280
gcacatctta tcacagggac cagagagact ttttagcacc actcttcaag aatttccact   140340
ttttcagctt tgacagtgga atagacatgc aggtgctcac acacaagcat ctttaatatg   140400
gtaatggtaa tcatcagttt agtggtgtgg aggaggagat gggaatctct tagtgaaacc   140460
cgccttggaa gcagcctcgt tatgagaact gctgcccta cttgactctt aaagcactag    140520
ataatactgt gcaacattaa agagaataag agtgcgtgaa atatgcattg cctcccataa   140580
actcccttgg ctctgaatct ctgatactaa atatgtggct accgttgctt cccagaaagg   140640 ccttttgct ctgaattctc tggaatgctt tctttgacca agattcttat aaaaataaga    140700
gatttagagc aattttcttg gatggctggt atgagccagt tggcttagtt gtagggattt   140760
aaacaagata agggttactt acttttcaca tttaatgaga agtctggtga ttccagctcc   140820
tactgagaca gggtggccac acgttccagg gtgtgactca ctgaggcccc agacctgccc   140880
tgcaaggaaa acctggctct gccctggtgt cctggcctcc ctgggcatat gtgggggaga   140940
attcctaatg gtattggtta caggctccta tgcgagacca ctcatctgtg taggagaaag   141000 gaaaagatg ggggaaagaa gagcagcagg gagaggagaa gcctctggat gatactctaa    141060 cccctgcca tccaacacct gaacatcagt ctcttcatcc agtgctctca gctggcccag    141120
cccccagcct gggtcagat gagagcttcc tgcaaatgca gatctctttc ctgtggctcc    141180
ttctcaatta cagacagctc ctccacaagg tgcactctgg ccttgtgctc cctccccaaa   141240
ccagcccagc cctcccagcc tgcatcatcg tggtcctgta ggggctagag gttctcacac   141300
ccatcgtggt ctggcagagg ctggtggttc tcacacccat cgtggtccgg cagggcgtta   141360
```

```
gtggttctta tacccatcgt ggttcaggag gggctagtgg ttctcacacc catcgtggtc  141420 tggctgggc tagtggttct catgtccacc gcgtgctttc ctgctcctcc aggtggctga  141480
ggacatcccc ccttcggtct gaatgacttc catccagtca tctgatatac acattggacc  141540
acccaatagc atcctagtgt catgttggat ggtgaagaaa atgccacagt tactgctttc  141600
agggcctcac aaccttgggc atagcttttt ggaggaaggc cccacttccc aggcatccct  141660
cccagacctg gtcagaggcc cctgctcttt gcttccatgt tgcccacact cactgtgctc  141720
ttcacaccgg ctcaaaatga tctgcttacg gggttgtgtc accaccagat caagcgtcct  141780
ggagaggagg aaacatattt aacctgcaca gaatttggga cagagaacct ctagtgtttg  141840
ttcaataaat atatgaatgg atagagggac aggttgggtg gtggatagat ggatgaaccc  141900
acacctttga agtgtatttg gctgtttgag aggttagaat atgttctcaa tttccaggca  141960
aaatgaaaat ggagaaaata taatgacatt aaggcatttt attcatcctc cccatctgcc  142020
actgggttaa agatactaaa taaacaagga actatctttt gcctggagga actttaaaaa  142080
cacctgcagt tttcaaaagg tgcagtgtgt gcctcccaca gcatgaccta ccatcattgg  142140
aaagcagttt gtagtcaatc aaaggtggtc tggagaaaca aagttttcag ggatacattg  142200
tttttataat ttttcaccac atgatttttc ttctctccaa tgtagtggtc agttttctct  142260
tgcagtcgtc agcctgaaca taacatcctt gggattacgc tccctcaagg agataagtga  142320
tggagatgtg ataatttcag gaaacaaaaa tttgtgctat gcaaatacaa taaactggaa  142380
aaaactgttt gggacctccg gtcagaaaac caaaattata agcaacagag gtgaaaacag  142440
ctgcagtaag tcaccgcttt ctgtttagtt tatggagttg gttctaatgg gtcctttatt  142500
tgtatttaga atattgaagg gctattccca tttaaattac tttttttcagt tccttaagaa  142560 gcaaattaaa atcttaagat tcctaactgt gaaattacca tgtgaattcc attaaaactt  142620
tttccagatc attaccattc aatgggatga atttaccctg aggtttaggc taccaattat  142680
ttgtaatgta agtaactaaa tttagtatta gttatattac cttttagttg taggtcactc  142740
tctgctcatt tcagcctgta aagactacag ctacacacat acacacacag aggaatggaa  142800
tgagcacttt acatcaacac ttcctgttct ggctctagag cctcagcttt tgaagctggt  142860
gagagcctgg cctgtgctgg gccttggcca cgggcagcgt cagctttgag tcaagtgctg  142920
gtctggcctc cctagctttg agcctctgtc aattccctta atctgtttag gctttggctt  142980
cctcatccat agaatggaga tatgaatgat tcctacgccg tagtgctttg agagaattca  143040
gtgaaattcc tgtgtgtaaa acccttccat ggtgcctagc acacagcaca cagccaatgg  143100
cccaatggct cctatcagct gtgggatttg tcatcagaac accaccagct ctgctccagg  143160
ctgccctggg taccatcaaa acacaccctg tgcccagcag cacctgctcc tctgcacacc  143220
tggttccttc agcaggggca gtggccgtgg gagcacagaa aacatggagt cccatctggt  143280
ttaattgatg ccattgccaa aggggaggac tcacggcacc ccctctcggg tgccagggtg  143340
cctggctccc accaggagga agacctgtcc tccactgtca ggcacatttc agtcttccca  143400
gcagccagca caactacttt gtccttccag tcacggtcgg cctctgggaa gcccagtctg  143460
tgtcctcctc cttcagggct agccagcatg tctgtgtcac ccaaggtcat ggagcacagg  143520
gcccctcccg ggaaggtgcc gtctcctccg gcccctcggg tccctgctct gtcactgact  143580
gctgtgaccc actctgtctc cgcagaggcc acaggccagg tctgccatgc cttgtgctcc  143640
cccgagggct gctgggcccc ggagcccagg gactgcgtct cttgccggaa tgtcagccga  143700
ggcagggaat gcgtggacaa gtgcaacctt ctggagggt aggaggttat ttctttaatc  143760
```

```
cccttgcgtt gatcaaaaat aaggctccag gttgttgtta tagctttaca ggcattctgt    143820
ttgattttct cttccttta ttctttgccc ttggcttttg gaggttttgg gttttctgtg    143880
gggagacggg aagttgtttg attgcgttat ttttggcaaa tttaagcaca ataggaaata    143940
agcaagtatt attgcctaat ataatccaat aatttataga atctcttttc ctggaagtat    144000
cttaaatttt tctaagctac aaaaagttcc taagacaaat gagacagtca tcaatggttc    144060
atctagccaa caccgtggcc atttgggctt tctttgtag tgcccgattc ctggtgtgtg     144120
aaataaatt aacacaaatt atattgccaa gttaatatct gttttatgtg ccccagcat     144180
gtgttgaaca tcaaacagta ccagggactt taaatatacc cacggacaaa gaaataattc    144240
ataatgatgt ttgttgaatt tagttgcaat caataaaaag tgcagtttgt gaatgctctg    144300
aggttcttga tattgatgta aggctttgaa cgacaaatga ggacaaaaca taataggaa     144360
agtaaaactg aaggatagag gccaaggcca tgttttagaa gatttaaaga aaagggaaa    144420
tttggtgagc accataggaa ttacagatgg ctgtaggaat tcttcctgtt ttactctctg    144480
ggcatggacc acagcttgga tccagaaata tttaggagca ggataagagg accaagttca    144540
attctatagg aatcctttag ctgataggct cagaacaaat cacataattg atagtgctgc    144600
ttcaacttca agtaaggaat attgatgcaa tccttacagc tacaaatgga cagtggtctc    144660
atgttttcag ttttcaagtg tttcttaaga ggcaaggtga tgaaaacgcc cacgtgggga    144720
gccccatgtc cttccattag tgtagagaaa cctggtgtcc agcagcacct gctccctctg    144780
caagcccagc ccccttcagc aagggcagtg acccagagaa gaagcacaga agacacaacc    144840
ctgtatcaca ttttgtttaa tggtgccatt gaccaaaggg gaggatgaaa ggcacacact    144900
tttttgttgt tttttgagac agagtctcac gccatcaccc aggctggagt gcagtgatgt    144960
gatctcaact cactgcaacc tctgccccct gagttcaggt gattctcctg cctcagcctc    145020
ccaactagct ggaattacag gtgtgcacca ccatgtccag ctaattttt gtagttttag     145080
tagagacggg gtttcaccac gttggccagg ctggtctcaa actcctgacc tcaagtgatc    145140
tgcccgcctc ggcctcccaa agtgttggga ttataggcat aagccactgc acctagccaa    145200
ggcacacact ttggagaata aacactcctt gttcgctgct ggagggtaga actatgcttg    145260
actactaggc agagtccagt cttactgaca aacagccgta catctgttct gtcttttcaa    145320
tcaaacatca gcttcttgct taacattgat gtgtacatct tgagggatgt caaaatattg    145380
taagctaagt ttttcatacc tgtgttccac actcaccatt tttagtaata accattgagc    145440
gagttcattc tccctccttc cttttctat cacttaatct aaaattatca tttttccagc     145500
ttaattttga taaccatgaa tctggtatta gaggcaggga acacctcctc aggactatct    145560
tttcttttat catttggctt gcttacccaa tatgcaaaaa ctatgctgta gaaaaagcag    145620
aaaagatatc ttgattatga atgaagctcc tgtgtttact cagagagaag atgacccagg    145680
attcagttaa caaatcagc tgattatatt actatatagt cctggagtcc caactccttg      145740
accattacct caagttattt ggaattttga agaggtgatt tgtgttcctg caataatgtc    145800
tcaggggtgg gctgacgggt ttcctcttcc tcctctcagt gagccaaggg agtttgtgga    145860
gaactctgag tgcatacagt gccacccaga gtgcctgcct caggccatga acatcacctg    145920
cacaggacgg gtaagagccc cttgctgcta tccacgtcca tttcatggga agggccttca    145980
cagaagccga acagtgatga tggcccaggg catcctgtgt gggcaggacg gccatcagag    146040
ccacttccca gaggagacgg caggcgctga cagcgctgtc cgggcagggt gtcggtgaca    146100
```

-continued

```
ttagcacaca cattagcctg cgatgaacat tcactctttc tgctgacacc cccaaccttta  146160 tctaagctta tcaaatcctc acatttaacg gaggctgttt tcacctggtt tcccccatcc  146220
ctgacctagt cagcattgct ttatcgcttt catcaaacat cctcaaattc ttaacattag  146280
cttgtaatta attgaagaat ttttaaagaa attgctagca aaacttttta aactgcacaa  146340 cttttgtatct atatgttcaa taacatatag atacaatatt ctttacaata atctttttaaa  146400 gaatatgagt gagaattcgg gcccctctca caccaaatgt cctgatgttg ttaattctca  146460
atgttattat atagggagct ctgttttctt gtgagcttca acagccagtt ctaaatctac  146520
taactgaaaa cattttttag acattctcta aattgggcag aagatgacag gactgtgttt  146580
tgagggatag gctgccagcg tggctgctta caaagtaaag acttggttta taggtttgca  146640
tggtgttggg ttaaatttct gtcattaaaa taattggcga tattgacata gtcatctaat  146700
tatgctggct ctgggcacac acagcccttg agtggacaaa accaacatga gagaacttag  146760
ccaaggggaa agcctttccc tgctggtttt atttctgcta cttctgaagt gtgggggcaca  146820 caacctgagc agtgcttttta tttgagtccc aatgctttta tttgagttttt gcaaggttat  146880 tccaagtttt acaaatagaa ggtagcgtat gactcagtcc ttgatatgcc aaccactgca  146940
cagagacttg ccaccttcct gtcactggag aaacactcat gtgggttttc ttaaatttgc  147000
ctccctctga gcttcccttt aacttcaact ataatatgca agaaagacta tctgaccata  147060
aatacacatt tgggccaatc aagatggttt tgccaaggaa agatgcccac aatggttaag  147120
cagaatgcaa taatgtagag aatatcattt ctttcatgct ggtgtatatc atatgcattc  147180
aaaaacaggg agaacttcta agcaactaac agtgaccata tcaagcaggt gcaatcacag  147240
aataactggt tttctccttt aagaatttttt ctatcatttg gctttcccca ctcacacaca  147300
ctaaatattt taagtaaaaa gttacttcca ttttgaaaga gaaagaaag agacatgcat  147360 gaacattttt ctccaccttg gtgcagggac cagacaactg tatccagtgt gcccactaca  147420
ttgacggccc ccactgcgtc aagacctgcc cggcaggagt catgggagaa acaacacccc  147480
tggtctggaa gtacgcagac gccggccatg tgtgccacct gtgccatcca aactgcacct  147540
acgggtgagt ggaaagtgaa ggagaacaga acatttcctc tcttgcaaat tcagagatca  147600
aaaatgtctc ccaagttttc cggcaacaaa ttgccgaggt ttgtatttga gtcagttact  147660
taaggtgttt tggtccccac agccatgcca gtagcaactt gcttgtgagc aggcctcagt  147720
gcagtgggaa tgactctgcc atgcaccgtg tcccggccg ggcctgtgtt gtgcaatgct  147780
gcacatcaca acaggagggt aggggacaa aagagcacag gtcctggcag ctgccacagt  147840
ctccaggggc ttttgcgttt ctctccagat ttctaaggtt aacatgggga ttagctgttt  147900
tgcaatgaat aaaaggtaac attgcctgga atgttgctta aagacacttt tttaaagcta  147960
gttgattgtt aagctgttgc tacttaaatt aaaactactt tgggccagac gcagtggctc  148020
acgcctgtaa ttccagcact ttgggattcc aaggcaggca gatcacttga ggtcaggagc  148080
ttgagaccag gctggccaac atggtgaaac cccacctcta ctaaaaatac acctgtagtc  148140
ccagctactc aggaggctga ggcaggagaa ttgcttgaac ccgggaggca gaggttgcag  148200
tgagccaaga tctcgccact gcactccagc ctgagcacca agagcgaaac tctgtcgcaa  148260
aaaacaaaaa caaaaaaaaa agctactttg actggaatta gcagaagcac tctgattgtg  148320
tgtatcttat ttactggaat aataaagctg tcaatcaaac tggatcccac tcaacaatca  148380
gaaagagaag ttgagctgtc atatagtagt tcacacttac ttctgtttct caaaatcctc  148440
agctttgttt ggaactgtta ctcattcttt ctctgaatcc atctgtatga gttgtgtgcc  148500
```

```
cttgggcaag ggtcttacct tctctgtgcc tcactttctt ttctgtaaat tgggataata   148560
atgctgcata gctcacagga tttttatgac catgagttaa gatatgtcat atacttaaaa   148620
tggtgcctgg aaaatggtga atactgagtc aatgatagca tcattgatgg tgggatggtg   148680
atgaggaggt gggagtcaca atggtggtgt tgatggtggt gatggtggtg aggaggtggg   148740
agtcacagtg gtggtggtgt tgatggtggt gaggaggtgg gagtcacaat ggtggtggtg   148800
atggtgttga tggtggtgag gaggtgggag tcacaatggt ggtagtgatg atggtgttga   148860
tggtggtgag gaggtgagag tcacaatgtt ggtggtgttg gtggtggtgg tggtgaggag   148920
gtgggagtca caatggtggc agtgttggtg gtgaggaggt gggagtcaca atggtggtag   148980
tgatgatggt gttgatggtg gtgaggaggt gagagtcaca atgttggtgg tgttgatggt   149040
ggtgatggtg atgaggaggt gggagtcaca atggtggtga tgagggtggt gatgatgatg   149100
aggaggtggg agtcacaatg gtgtcagtgt tgatggtccg atggtgatga ggaggtggga   149160
gtcacaatgt tggtggtgtt gatggtggtg atgatgatga ggaggtggga gtcacaatgg   149220
tgtcagtgtt gatggtggcg atggtgatga ggaggtggga gtcacaatgg tggtggtgat   149280
gacggtgttg acagtggtga cgaggcggga gtcacaatgg tgtcggtggt gatggtggtg   149340
aggaggtggg agtcacaatg gtggtggtgg tgatggtggt gatggtggtg aggaggtggg   149400
agtcacaatg gtggtggtgt tgatggtggt gatggtggtg aggaggtggg agtcacaatg   149460
gtggtggtgt tgatggtggt gatggtggtg aggaggtggg agtcacagtg gtggtggtga   149520
tgagggtggt gatggtgatg aggaggtggg agtcacaacg ttggtggtga tgatggtgtt   149580
actggtggtg acgaggtggg agtcacaatg gtggtggtgg tgatggtggt gaggaggtgg   149640
gagtcacagt ggtggtggtg ttgatggtgg tgatggtggt gaggaggtgg gagtcacagt   149700
ggtggtggtg ttgatggtgg tgatggtggt gaggaggtga gagtcacaat ggtagtggcg   149760
atgatggtgt tggtggtgag gaggtggaag tcacggtggt ggcgatgatg gtggtgagga   149820
cgtgggagta acaacagtgg cagtgacggt gattgagaca tgatgatgat ttgtcaactt   149880
tctaggaaaa caatcatata atctccaaca gtgatatctt aatatctttt ccaaaagtat   149940
cagatcatat tataagggcc aagtttccag aataatatca gacataatga cagtggacat   150000
cagagcttgg catctaaagg taatgggaat agctctaatg tctcagcgtg aaaaacaaca   150060
tttgctatta gtctgagata ctaattatct agttaaggaa gtactcacct atacctagtt   150120
tttaactgtt ttttaaaatc tggaattgat tttgaatttt aacaaatatt tccctgggaa   150180
caatgtaaga ttcttcatat tttcgccttt gggtatacca acatgccagc tctgttggcc   150240
actttgtgag ctcgatgaag catggtataa aagatgcttt gctagtgttt cacgtaatct   150300
atttctataa gcaattttgg agctaagcct ctgaaacaga attatattat ctgtatagaa   150360
taaatgtttt atcttcccc ttttctttct tctggaatag atgtgcatca gtatctctgc   150420
atcaatatct ctatatcagt atctctgtgt cagtgagcat atgttgctgg gcttagggaa   150480
ggtccagaaa gtgattgggt tttggcattt tcaatacact tactttgtat aagaaatagt   150540
ttgccaaata tagaaagagg ggatttagtc aagatttaaa ttaaaaatgt tagtggtcat   150600
ttttctaatg tctttctatt ttttcccagg tcctaataaa tcttcactgt ctgactttag   150660
tctcccacta aaactgcatt tcctttctac aatttcaatt tctccctttg cttcaaataa   150720
agtcctgaca ctattcattt gacatatgga atttataaaa tattttcttt agtatgtgtg   150780
attacattcc tgattctgag ccttttttaga tgagtatata gtttgatata atcttgttat   150840
```

```
tgccacctgt gtcttctccc aaagccatta attatatagg aattcacgca tagaaatggg    150900 tttaatttt  aaaatacggc caagtgttga tgagagggaa aatttttta  atttctttca    150960 ctgagtattt atgacgtgca caacattcct gaatatattg tctctctcat ttctcagatg    151020
ggatgtattg ccttctccat ttctattgtt aaagaaacac ttacaggggt ttctttaaca    151080
acttgtgaac agcagcatca gagcccagac tacagcataa gcagctgctg attccaaaag    151140
ccctaccttc aaccgggca  ggtgcagcca cccagacgag ggggaggaac cctggaggaa    151200
tagctatttc ttttttttt  ttgtcgagac ggagtcttgt tctgtcaccc tggctggagt    151260
gcagtgccgt gatcttggct cactgcaacc tccacctccc aggttcaagc aattctcctg    151320
cttcagcctc ccgagtagct gggattacag acacctgcca ccgcctgg   ctaattttg    151380 tatttttagt acagacaggg tttcaccatg ttggccaggc ttgtcttgat ctcctgacaa    151440
gtgatccaca caccttggcc tcccaaagtg ctgagattac aggcgtgagc cactgcgccc    151500
agcaggaata tctattttta aatggaactg tgttttcata gtacacggtg aggagaaagt    151560
tgctttgaaa tctttatcct aataaaccaa ataatgaa   aatttgccta ttttaattat    151620
atgtaacaaa gtttagttac tgctataatt gcaaatatgt ataaattcct taccaaaaaa    151680
aaaagaatca agtgggagcc agagaataat ttttctgaca gaattaaata acatgctata    151740
gctgcttgag ttcatactca atagtcattt ctgcagagtt accgagggcc tcatcagcgt    151800
cagcaggagc ccctcgcctt ctgacgctct cacatccttc tctcctgcag ccccgtcctg    151860
ccactgtcct tgtccagctt ctcttcaagg gtcaactggt ctacctttcc ctacaagtct    151920
gtcacagctt cttgttagca atccctatgg ttgcccaaaa gcattttcag agcctgcata    151980
agactgcatc ttgtagaaaa tttgcagttt caatctgccc tccctctgcc gggtgttccc    152040
attgtattgc attcagcagg cagggagaga ctgctattag gtctgttcct gagtgactgc    152100
tttctgtctc agactgtttg gtgtctgtag gaggtagtgg ggtgggcagt aacgaggtct    152160
cctgtatatt ccacccctac gaagcctgtg tgtttggttt atgaactaag ctcaaaagca    152220 ccacagggt  aagactgcag tacatgacac catggaaaag agggagcacc cagaccccca    152280
aattaagaag agcagtgtag agaacagaga cctggagagc agagatagaa actgttagga    152340
tcagattata gtgttacacc agggctcccc aggcctctca catattgaaa tgtacttgtc    152400
catctttctc caggccagga aatgagagtc tcaaagccat gttattctgc cttttaaac    152460 tatcatcctg taatcaaagt aatgatggca gcgtgtccca ccagagcggg agcccagctg    152520
ctcaggagtc atgcttagga tggatccctt ctcttctgcc gtcagagttt cagctgggtt    152580
ggggtggatg cagccacctc catgcctggc cttctgcatc tgtgatcatc acggcctcct    152640
cctgccactg agcctcatgc cttcacgtgt ctgttccccc cgcttttcct ttctgccacc    152700
cctgcacgtg ggccgccagg ttcccaagag tatcctaccc atttccttcc ttccactccc    152760
tttgccagtg cctctcaccc caactagtag ctaaccatca cccccaggac tgacctcttc    152820
ctcctcgctg ccagatgatt gttcaaagca cagaatttgt cagaaacctg cagggactcc    152880
atgctgccag ccttctccgt aattagcatg gccccagtcc atgcttctag ccttggttcc    152940 ttctgccct  ctgttgaaa  ttctagagcc agctgtggga caattatctg tgtcaaaagc    153000
cagatgtgaa aacatctcaa taacaaactg gctgctttgt tcaatgctag aacaacgcct    153060
gtcacagagt agaaactcaa aaatatttgc tgagtgaatg aacaaatgaa taatgcata    153120 ataaataatt aaccaccaat ccaacatcca gacacatagt gatttaatt  atttaagagt    153180 agtttagcat atattgcttt atgatttaat taaaaatctc caaatatat  gccaagaag    153240
```

```
tagaatgaga aaaatgtata tttctctttc acttcctaca gatgcactgg gccaggtctt 153300
gaaggctgtc caacgaatgg gtaagtgttc acagctctgt gtcacatgga cctcgtcaag 153360
aatgaccaca ctgctgtggg tgaagatgct ttcctgcatt tctgactgtc ctctgtcctg 153420
atcaagtttc tatggctctg gccagccta ccctcagcca gggtttctgc agagactgcc 153480
cagctggttc cacgtggctc cacgtgccaa ctttgtcctc agtggaggga aagttggaca 153540
cacagtgctg gggctgctcc ctgctccgcc gttgctcgat gcatggcctg cctctgaatt 153600
ccttggttcc actggttttg ctgggtcctt ctgtgcctct agctcctctt tttttctgtc 153660
cacttacccc attggtccca tcacaagcct gtgtgtgagt ggcctttctg ttcgatgaca 153720
acctccagca taggggagtg tttctccttg ctttctttcc cagacacact gcccagcaaa 153780
ggcaaaaggg cttccttcaa catcagctct ggccagtttg ccagagcaaa gccctgagaa 153840
aagcaaggtt gaaaagtctt attcaaactc accaggaaag agtggtgtta ctctcgatgg 153900
cgtctagcca ggaatcatgg aattatacac cgagcacctg tttgccattt tggatgtttc 153960
caaacatgaa ccaaacttcc aggcccctct gccatctctg gtaacattta caaagtccct 154020
tcctcaccac tgcccttcct tcattttggc atgctcctcc gcccccgagt tgacagccat 154080
agctctctct cctgccacca gtgtcacatg atcgaggaag aaggcaactt caaaaagact 154140
gggtcccctt ccactcccat ctcttcagtg agctgctagg acacccagca gaacttcccc 154200
actccacact gcaatctcag ggatcttagt cacgggctt tccaccatgt ctccacctgg 154260
aaaccagtca tggccattcc ttcttacatc tgctcttttc catctttttc ttctcctcct 154320
gttcacccgc ccttactctt gtggcgccct atggatatgc gctccatagc aaatgattct 154380
ttatatctta cggtattcta gtgagctggc acatgtggct tctggtttcc tctctctgga 154440
actagacatg acctctgtgg gagggaggat taaatgcacc ctacagtctg aggctgcatg 154500
atgacatcac tcatcacaat gatgctttct atgtctgaat cctattcctt tataaccct 154560 ttcaagctcg ttcagagagt atttcacaca atccatgtgc tcatcttaaa agccaaggac 154620
ccagaggagt ctcagcattg ccaaaaagtc ccttcaccca gcctggccag aggcagtgcc 154680
tggtccatgt gtatggacta tggcacttca attgcatgga aatactcttg gaatgaacaa 154740 ataccaatc catgaaaaag cattattgaa gtctaagtta ttttttgaat catattttgt 154800
taatcaacaa attgaaaaat actcattata tggagaggtc cagataaagc ctcaattta 154860 aaaaatgagg aaaagtgtgc ctggtagggg actgggggaga gcttgagaaa gttggaaacg 154920
ttgccttaga agcctgtttt ttctcctttt agaagctaca tagtgtctca ctttccaaga 154980
tcattctaca agatgtcagt gcactgaaac atgcagggc gtgttgagtg ccaaggccat 155040
ggaatctgtc agcaacctca cccttccttg ttcctccacc tcattccagg cctaagatcc 155100
cgtccatcgc cactgggatg gtgggggccc tcctcttgct gctggtggtg gcctggga 155160 tcggcctctt catgcgaagg cgccacatcg ttcggaagcg cacgctgcgg aggctgctgc 155220
aggagaggga ggtgagtgcc agtcctgggt gggctcagga gccctcgcac cccgacagga 155280
acaagggcca gccccgagaa cgggccatta gcagttgtgt atgttagata cataattgta 155340
ttatgatgca gaaagaatct ctgaatgtgc agttatacccc agttggtgac atgttggtac 155400
atccatccga ggaaatggca atgtttctag gctgcaccct tcaatgtcca caaagctgtg 155460
tggcatctgc ttaggacccg gtgcctgtgt gtgcatagga gggaggccag gaagcctggc 155520
tgttgatccc atgctggcac tgtggcgaag gcgagagatt cctgctttgg aaaacaccat 155580
```

-continued

```
tgtccacaca gtggctttgt ccatgatgga cttcgccaca gcccagtcct gtgctggaag 155640
ccatgttctc tggaaagagc aacccagcgg ctcataagca taagcgcgtg tgatgtgccc 155700
caaccaaacg accgccatgc acaacttccc taccggagtt ttcaatccag ttaataggcg 155760
tggaaacaga catagaaatt gtgtttgttg aaaggtagct gttcagttaa agaacacctg 155820
tatcagagcc tgtgtttcta ccaacttctg tcaagctctg tagagaaggc gtacatttgt 155880
ccttccaaat gagctggcaa gtgccgtgtc ctggcaccca agcccatgcc gtggctgctg 155940 gtcccctgc tgggccatgt ctggcactgc tttccagcat ggtgagggct gaggtgaccc 156000
ttgtctctgt gttcttgtcc cccccagctt gtggagcctc ttacacccag tggagaagct 156060
cccaaccaag ctctcttgag gatcttgaag gaaactgaat tcaaaaagat caaagtgctg 156120
ggctccggtg cgttcggcac ggtgtataag gtaaggtccc tggcacaggc ctctgggctg 156180
ggccgcaggg cctctcatgg tctggtgggg agcccagagt ccttgcaagc tgtatatttc 156240
catcatctac tttactcttt gtttcactga gtgtttggga aactccagtg ttttcccaa 156300 gttattgaga ggaaatcttt tataaccaca gtaatcagtg gtcctgtgag accaattcac 156360
agaccaaagg cattttatg aaaggggcca ttgaccttgc catgggtgc agcacagggc 156420 gggaggaggg ccgcctctca ccgcacggca tcagaatgca gcccagctga aatgggctca 156480
tcttcgtttg cttcttctag atcctctttg catgaaatct gatttcagtt aggcctagac 156540
gcagcatcat taaattctgg atgaaatgat ccacacggac tttataacag gctttacaag 156600
cttgagattc ttttatctaa ataatcagtg tgattcgtgg agcccaacag ctgcagggct 156660 gcggggcgt cacagccccc agcaatatca gccttaggtg cggctccaca gccccagtgt 156720
ccctcacctt cggggtgcat cgctggtaac atccacccag atcactgggc agcatgtggc 156780
accatctcac aattgccagt taacgtcttc cttctctctc tgtcataggg actctggatc 156840
ccagaaggtg agaaagttaa aattcccgtc gctatcaagg aattaagaga agcaaacatct 156900 ccgaaagcca acaaggaaat cctcgatgtg agtttctgct ttgctgtgtg ggggtccatg 156960
gctctgaacc tcaggcccac cttttctcat gtctggcagc tgctctgctc tagaccctgc 157020
tcatctccac atcctaaatg ttcactttct atgtctttcc cttctagct ctagtgggta 157080 taactccctc cccttagaga cagcactggc ctctcccatg ctggtatcca ccccaaaagg 157140
ctggaaacag gcaattactg gcatctaccc agcactagtt tcttgacacg catgatgagt 157200
gagtgctctt ggtgagcctg gagcatgggt attgttttg gtatttttg gatgaagaaa 157260 tggaggcata agaaattgg ctgaccctta tatggctggg atagggttta agcccttgt 157320 tatttctgac tctgaaactt gcattcaatt cactccacca agttatctca tctttgaaat 157380
ggcttttttt aaaggtgcct agaatatgat ggcgtgcagt ctataaactg ttgcccacct 157440
tctgtacttt ctctcagaat aattcacatt cttctccagt gtctgttgat tgttactttg 157500
tggaataagt tcttggaaaa ttccacaaga ttattgttat cttcttacta ccaattctat 157560
tgaactttct ccaccttctc tgggccttcc ccagccagtg gtgggaagat gctggctgga 157620
gtctgacaga gcctcttcta cactggcctg ggcttgctgt gagttggtgg aaacctttgc 157680
tcttgtccca acacagagca agtgaaagag gaggtcaagg ggctcaggca gcggactagg 157740
gaagcagaat cgaggaaaag gaaaaatggc tgacttatta cctcaaaact ctagagaatt 157800
tagttgatct tacagccaag aaggacaaaa gccagagagt aatatcctcc gcctcatgtc 157860
taacccacag aatacatagc aagtaaagag aacatgggcc tttataaaaa tgtcttaaga 157920
tacaattttt taattggagg aaatctacag tttaattttc tctgggcagc ttttcttcct 157980
```

```
tttattatag tagggggaaat cccatgttga tatacttcta aatgaaagat gatgaattga  158040
tataatacaa taaaaaatct gtaaaattga tgatatactt atcaagaaaa attagctttc  158100
attttaacgg tttacaaatt gagtcaagtc ctagtaacaa aatgttaagt ctattaacat  158160
aaccacaaga aatacaggaa gacgggcaat ctgtgaagcc tttcacttac aatctctggc  158220
ccctcacctg tgctgtgtag gaaaatcttt gtgcacaatt tgcttcctta attcattttt  158280
tattcattca acacattcta ataaattata caaaatcatg ttgaaatgtg aatttcagtg  158340
gtatttataa atgcagtgtg aggagggttt ggatgtattc taagacaata gttgtgcttt  158400
gggaaggaag cagtgttcac tgaaaagtgc ccccaggacc ttttaattgg aggaaatatg  158460
cttctgtgga gttggaaatg gggtagaaga tagataaggt caaggcttaa aagttaagtg  158520
cacccaacat ctgaagcgtc catgggcctg gcatggtggc tttcgcctgt aatcccagca  158580 cttttgggagg ctgaggcagg aggatcccct gagcttagga gtttgagacc agcctgggca  158640
acatactgag acccagtctc tacaaaaaat aaaaaattag ctgggtgtgg tgtctcatgc  158700
ctgtagtccc agccactcag gagatgggaa gatggcttga gtccaggaga tctaggctgc  158760
agtgagctaa aatctcacca ctgcactcca gcctgggtga caaagcaaga ccctgctcaa  158820
aaaaatagtt agatataaat attaatatag ataccctatat atatctgaat atagatatct  158880
atatatactc tgtatatagt tatttagata tataaatata tatgatatat attagagag  158940 atatatattt agagagatat atatttagag atttatatat attttatata tatttagaga  159000
tatatatctc taaatatata tctctctcta aatatatata tatctctctc taaatatata  159060
tatatcccta aatatattaa ataaataaaa gaaataaaag aaagctcagt ttggcctcct  159120
gcttgtcctg tctcctcatc ccctcttccc cctccatcat tttatttcct tgccccatgt  159180
ttcttcactg cggccatgtc ccccctcctc tccaatgatg gatgtcatgt ctgctgcagt  159240
cagagggcga caagcctgga gtgttccctg aagcctgtgg tttgtggttt gtcctgcagc  159300
tcaggctgcc caggcctcac cagcaatcct ggcgggcagg gcaccacact gggatggaga  159360
gggggaagct ggaggaggca ctttctggta aagaaagcaa aagccagcag tgcccaggcc  159420
aatttcaaca gggagttaaa tagcaccta atcctgtggc aggacagctc atggggccat  159480
gtgtgctctt agaaagactc acatgcacgc atgcacggca gcaatgactc catactcacg  159540 ttccctgca gacaccaggc ccccacagcc ggcacacaca ctgcagcccc agttccatgt  159600
tgctagcagt ggcttagtga atgagtaaag ttcttaaaat gcaggggaca cctgcccttc  159660
attcataagg ctggacgtac acctctcctt aaggagttca agagctagtg aatcccaat  159720 tcatacggta gagccattca cagatgagag agacaagcca gaaggaagga accaaaagtc  159780
atgtcagcag ttaggacaaa ataacaggct ttcaaggtca caaagcctca gggacactcc  159840
tgcggtggga ctgggctagg agccatgggg gctccaactg tgcgctctgc ctgccagcct  159900
gtgggtgctg gggctccacg aagattgttg tggaatacca agcatgcttg ctgtaggtca  159960
cggtgcacgt ttactacttc caagacaaac agccgagaac aaaagctcgct ttagcttctg  160020 cgtacaccga acgggacaca cgactgaaca gcgttcccat tgtgcctgct gggtggggag  160080
gaagtgatgg cccagtgggt ctatcagatg ttagtaggat ggggcctggc ggggctccag  160140
gctctgtgtg gccgacaccc acgcccccg ctctgctccc cattcccagc cccaggtcag  160200
ccctgcgagg ccctgcagca gatgggctgc tcaaactgct ctggtttgca gatttttctt  160260
ccctctcaaa tgaatacaat atgttttcaa gtctcaacca gatcttgaga aaataggaag  160320
```

-continued

```
agccagaggg tttctttggt gttatggttg tacagcttcc cagactccgg gggagagatg  160380
tgatttgtgc tttctggcaa tcccatggcg tattaaattt tcataggctt tccagtttaa  160440
atttagggta ggcaatggaa gggaacgcaa aacagatttc taggtgtact gtgtgtgtgt  160500
ctcccacgtc taaagtctgt taactggagc acccaacagg ccccacaggc tgccttcaca  160560
cagaggacct ggggcgcctc cgacccattg gggtgagcag tgggccatgg agggagccag  160620
ggtcaggaga cctggttgtg ggcctgacct gaccctgctc agggtggcct caggtgggcc  160680
gttcacctcg tcagcctcag cttaccctct gactacagtg acctcagaca aaatacgctt  160740
cctggccctg tccagttctg acttttttata aacaagcact tatccaagtt aaagggatat  160800
tttcaatatc tactgagtcc acagatatta aatatctcct ctcttcttta aaattgtggc  160860
attatcttta gaatataaaa ggaaaataac acacactctc cttgaaaata gagagcctaa  160920
acactctgca ggaaatattt aaagctatag tttttgtttg tttgtcttga atgcaagtgg  160980
cctggacttt gacttgcttt gagtctttga ccttcatgac ttcagtacag ttcaaccctg  161040
acagttttga agtaggtatg tgcctagatc tgccctagtc cctgctggaa tgttgaagaa  161100
gcaaaggtcc aggccctcag agcacttgcc acgtacttgc caacagatac ggggcggaga  161160
cttgagtcaa cgtaagagca agtgtgtgcc gggtgatccg acactgcaga gcgccagcta  161220
gaccctaagc gtgtgctagg ggctgaccaa gccgttcttt cctcaaaaac ttggtgggga  161280
gggtattttt aaaatcacac aaatatttaa gtacagatta tgatgactgc ctcaaagcag  161340
tggctcttca gcttcatcaa gcttcagagt ccagagggtt tgttcatatg gaaggctagg  161400
cctgtctcct gcatttcacc ctcttggcct ggggcggga cccaagaatg tgtggctcta  161460
aaaggttccc aggcaatgct gaggctgctt tctgaaggaa aaactgcaag ataccaggag  161520
agtttcattt agattgaaga gtcgaggaag gctcctctga gaaagagtct gctaaggaag  161580
gaggaggtgg gttctgggga cagaggttct cccgtgggta agggtggagg gaagctctcc  161640
tggggagaag gtgggcagga ggaccagagg ctggagggag gagggcagtc agcctcgggg  161700
cttcccagga acagggacgg ccagggcagg gtttagggca aggaaagcgt gtgagcatat  161760
ttgtatttta gtaaatattt acagtttgcc ctccatgtct gcagtttcat atccatggat  161820
tcaatcaacc acaatgaaaa acgttgggga aaaaaattgc atcggtactg aacatatacg  161880
gacttttttt cttgtcatta ttccctaaac aatacagcat aacaattatt cacatagcat  161940
ttgcactgta ttaggtacta taggtaatca ggagatgctg tagatgggag gatgtctgta  162000
ggttacacac aaatgctgtg ccactttata tcagggcttt gagcatcctc acattttgat  162060
atttaaggga ggtcctggaa ccaattcccc agatactgag ggtccactgt ctgtgtcccc  162120
tcgccccacc ttgcctttgt ctcctgtctc ctatctccac cctgcctccc gccagcctgt  162180
tgctcctgac ctgcccgggc accctggagc agcaccctat ctcagagcct ggctcagtgt  162240
gttcacttct gcagagaaac taacttgccc aagtccacac tcaaaacata ggcattgctg  162300
agatgtgaaa agcagctgtg gatgctttct gctacagtct gtgtgttctt ttccatatct  162360
gaataaaagg tcaccaccat ttgtatttta aagagaaaga gaatttatgg gtggaaattg  162420
gggattccct cattctcagt cagacagaaa agagggcccc attgtgtgcc tgattgcaaa  162480
taaatttagc ttcctcagcc caagaatagc agaagggtta aaataaagtc tgtatttatg  162540
gctctgtcaa aggaaggccc ctgccttggc agccagccgg aattagcagg gcagcagatg  162600
cctgactcag tgcagcatgg atttcccata gggagcctgg gggcacagca cagagagacc  162660
acttctcttt agaaatgggt cccgggcagc caggcagcct ttagtcactg tagattgaat  162720
```

```
gctctgtcca tttcaaaacc tgggactggt ctattgaaag agcttatcca gctactcttt    162780
gcagaggtgc tgtgggcagg gtccccagcc caaatgccca cccatttccc agagcacagt    162840
cagggccaag cctggcctgt ggggaaggga ggcctttctc cctgctggct cggtgctccc    162900
cggatgcctt ctccatcgct tgtcctctgc agcacccaca gccagcgttc ctgatgtgca    162960
gggtcagtca ttacccaggg tgttccggac cccacacaga ttcctacagg ccctcatgat    163020
attttaaaac acagcatcct caaccttgag gcggaggtct cataacaaa  gatactatca    163080 gttcccaaac tcagagatca ggtgactccg actcctcctt tatccaatgt gctcctcatg    163140
gccactgttg cctgggcctc tctgtcatgg ggaatcccca gatgcaccca ggaggggccc    163200
tctcccactg catctgtcac ttcacagccc tgcgtaaacg tccctgtgct aggtcttttg    163260
caggcacagc ttttcctcca tgagtacgta ttttgaaact caagatcgca ttcatgcgtc    163320
ttcacctgga aggggtccat gtgccccctcc ttctggccac catgcgaagc cacactgacg    163380
tgcctctccc tccctccagg aagcctacgt gatggccagc gtggacaacc cccacgtgtg    163440
ccgcctgctg ggcatctgcc tcacctccac cgtgcagctc atcacgcagc tcatgccctt    163500
cggctgcctc ctggactatg tccgggaaca caaagacaat attggctccc agtacctgct    163560
caactggtgt gtgcagatcg caaaggtaat cagggaaggg agatacgggg aggggagata    163620
aggagccagg atcctcacat gcggtctgcg ctcctgggat agcaagagtt tgccatgggg    163680
atatgtgtgt gcgtgcatgc agcacacaca cattccttta ttttggattc aatcaagttg    163740
atcttcttgt gcacaaatca gtgcctgtcc catctgcatg tggaaactct catcaatcag    163800
ctacctttga agaattttct ctttattgag tgctcagtgt ggtctgatgt ctctgttctt    163860
atttctctgg aattctttgt gaatactgtg gtgatttgta gtggagaagg aatattgctt    163920
cccccattca ggacttgata acaaggtaag caagccaggc caaggccagg aggacccagg    163980
tgatagtggt ggagtggagc aggtgccttg caggaggccc agtgaggagg tgcaaggagc    164040
tgacagaggg cgcagctgct gctgctatgt ggctggggcc ttggctaagt gtccccctttt   164100 ccacaggctc gctccagagc cagggcgggg ctgagagagc agagtggtca ggtagccctg    164160
cctgggtgct ggagacaggc acagaacaac aagccaggta tttcacagct ggtgcggacc    164220
cagaaagact tctgcttttg ccccaaaccc ctcccatctc catcccagtc ttgcatcagt    164280
tatttgcact caacttgcta agtcctattt ttttctaaca atgggtatac atttcatccc    164340
attgacttta aaggatttgc aggcaggccc tgtctctgag aatacgccgt tgcccgtcat    164400
ctctctccga cagcagggca gggggtccag agatgtgcca gggaccagag ggagggagca    164460
gacacccacc cggcctgggc aggtcctcct cattgcttgc atccgcctgg ttagcagtgg    164520
cagtcagtcc tgccgagtca ttcgtgaggc gctcacccaa ctccaggcag atgtaaaagg    164580
tgacctacaa gaagacaaac aaaaacatct ggagcgctct tatgccagca tctgcccttg    164640
acaccaccag gcaggctgtt gctgggagcc gtggtgcttg ggtaagctcc ttcccatggc    164700
agagctcctg gacgcattg  tagaagcagg gaccacctcc caggataacc agatagcagc    164760
acaccctgca cagccccttt tactccagca tcatcgggca ttgatatctc agctgcagcc    164820
acaggcggcc cccagcaccc caggaagtgg ggagcgctca tgcttctctg agcacaaaaa    164880
tcactgaata tttttgccat tctcatggtc ataacccggg ccacagagta gaacactcct    164940
atcactgttg ttagacagtg gtcctgggag agggtcttgt gtgcctcgga tgccaggcc     165000 tcttttttatt gggaggtgct tgttatttct gtgtgtggct gcatttgttt cccaagactg    165060
```

```
ccacaacaaa tcatcaccaa cttggtagct caacatagca cagctttatt ccctcctggc   165120
tctggaggcc aggtgtctaa aaggccatgc tcccacaatg ttctgagga ggatccttcc    165180 tgcctctctg gcttctggtg gctccagcat ccctgggctg tggctgcacc tccccatgtc   165240
aacctccgtc ttcacaaggc cttttcctgt gtctctgcaa ccacaggccc ctctcctttc   165300
tcttaataaa gataccagtc attgagtttg aaaattgcta agagagtctg ttgtaaatct    165360
tcttagcaca aaaaaaaatg acagatatgt gaagtggtag atatattaat tagtttgatt   165420
tgatcactcc gctatgtgta taaatgtcaa acaaacatt gcactccata aatatatata    165480 ttaaaaaga tcccagtcat tgcatttagg acccacccta aatccaggat gatttcattt     165540
caagactttt aactagattt gcaaaacccc atttccaaat aaggtcacat tctgcagttt   165600
tgggtagacg tgaaatgtgg agacactgtg caacccactg tcttggggag ggggtggtca   165660
gcctggggca gatgttgctg ggtgtggagc tacatccact catgccctga cctggaaccc   165720
agacctgctt ccccagctct cctcctggtt atctgaagca gggaatggag agcactgccc    165780
tccttgccca ggcagtctct atcacctggt tttagtttct tcttagcaca tattgcccca   165840
gaatatctgg ttggtttatg gcttacttga gtttgtgcct acctgtccca accgggaggt   165900
gagccctggc tattccccaa acccggccct gcatgtggga gctgcccttc ctccgttcat   165960 cagaggggc caacagtcca cagctgttct taatcatctc ccagtaaccc ccagctccac    166020
aaaggtgact ccttacatgg tggagaggtg gtcgggccat ccgtgtgaaa tgtgtatgtg    166080
accgttttcc ttaaggggca cgtagtcttg gcaggtttcg ctcaatatag gatgagctca   166140
ggactccagt ggactgtgga ttcagatctg gattctggcg cattcgccgt gtgaacgggg   166200
gcacgttgct ggcctgtctg cgcctcgtct cccgactgtg gagtgtgttc tgccccttgt   166260
ctttctggga ggtagggagg gcagtgagcc ccttcgcatc gcccaccaca ggcccagcac   166320
atggctgatc cccactgagt gttctttttcc tcctttgatc ccctttggct gacctaggtt   166380
ggagcagcca ctaaaatata cccagaaaca tcttcctaat ctacatctgt gccaaccctc    166440
attccctggc gcagcatgac catcacatgc ccgccattgt tcctgatctc tgctgctcat    166500
gacctgctct ccagcgctcc ttctcatgct cacattccag ttggcctgac ctagataagt    166560
ggaggtttat ttgaccccaa aaattagcct tctacaaacg aatataatag tgtccattac    166620
agagaataaa cttagtgcgt gtcccattta agcagaagtt actgaaagcc tgagtttaag   166680
tttccagggc ctgaaagttt tccatgacag ttttctgcat aatattacct acaatttcaa    166740
tctgttattt aaagccattc ttgtgtttgt tgtactttga ttagctttat tttgatttga    166800
agtcctttta cattacgggc agttaacgct ttgtctctgt tagatttgct ttttagttca    166860
caagagaaac ctcattcctc tgtatttgaa tagttgcaat gatggaacag ctgtccctgg    166920
agggaaatga aaacagtgat tccccaaatt gtgacaatag aaatttgctc ttgggttact   166980
tacaatgtat ctgagtatta aaaattttc tttttaaacg tttgaagtaa aactacccag    167040
aaacacttag tggctgacca gaaactaaac tcctggcatc ctcaaaatgg gatttattgg   167100
cttataaatg tcctgtgttg actcacaaag gcacaaacta tctaggtaag ttttcttcta   167160
aatgttgatg ggagagctgg ccactgttat gcaagtttca ttgtcctgac taaactgcca   167220
aagagattac ataaaattat atcaactaga caaaggaaa aggaaaaaa aacagaggtg     167280 tcttgggagg aatccatatg agaccagtag accatgagag agacatccct tgccatctac    167340
aaggaaaatg gattttgttc tccatatgca aaaccatctc aggagcttgc ggagacacca   167400
cttgcttact agccagaaag agcaggtgcc tcctaaattc cccacacagg agctcacagt   167460
```

```
ggctttcatg cactgggatt aagttagact taagaaagcc tgtctactct tcctgggatt    167520
tacaagccag ctagtaaatc ccagaataaa tcacacggca cagtcatcca aagatcccgt    167580
catccgtgcc gtttggaaag ccctgctcct gtgccaccct ctccccgtgg agcctcccat    167640
gcccaggact gcagagtcct gccattcaga ctgcaactca tctcacattc ttccaaacta    167700
tttggacaac agagctttct catcacctaa tgcagattac agtctcacag aattgagtgt    167760
tcaggcagac actgatgtgg ttctgtagta cagcaaacaa tatcagttta cagtcctgag    167820
gccaggcctg gtgaacaacg cacggtagcg gtggggcagg gttctcagaa tgaaactggc    167880
ttacacatgg cactctctga ccacaactgt ataagcacca aactacactt agttccatct    167940
atgaggtaaa atttaatgca gatgaacatc aaagaaaacg tcaaaggctc ctttttacaa    168000
gtacgtgggc tacttaattt ggtccaagtc cattttaaaa agccctaggt gctttcacgg    168060
ctctgctact gacaagaagc cccagtgcct gtgagctgct aatgggaggg agaggaagat    168120
gagctgagtg ggccgggcta tcccgtccac accgggagac agggaaggag actccaagct    168180
ggtggtgcca gcacattcca ggccactcag gcctattcct aggtgccagg tcacgaaaac    168240
cacgctgaca gatcgtgctg tgtgcgtgtc atagcacaca agcaggactg tgagagagtg    168300
aaagtgacac tgggtggagc actgaggaag gccacagtg tgttggtgga gataggctgt    168360
catggagaag agaccctggc ttgctctaca ttgcttccaa tgcaactgca aggcaggtcc    168420
cagagggctc cggccttcgt catccaggtt tgctccctcc cctcatggct ttcccatcct    168480
cagatgagga ctcggcagag cctaccctg ctgactaact gtggcccag ggtggtgact    168540 cagccctgca cctcctgatc ccgtctgcac tgggccagag aggatgactt acccagcacg    168600
ttcacatcac acagctttgt ggattcctag gtccaaggac cagagatttc agttatgtga    168660
gttatttttt ttatttgttc ttgcgtattc cacaaagggt cgcagctaaa cttaacctaa    168720
tgatcacttt agtatatcac taaaaagaca aagctcacag tgctgttgaa gcacattcat    168780
catctttaga catttgact agttatttct taagcattta cctgctagtg ttaagcatca    168840
catgaaatac atatagaagt aagacaaaat ttcttatctc cccaagtttg ccaacaaata    168900
cagagcagga agggaagcag gtcagagcag gaggcgcagc tatagtgagg ccaccatgca    168960
aggcacaggg agggtgagct ccaagtttga atggaatggg tctgtcagcc aagcccctg    169020 gctctgggaa gatagcagtg aacaagccag atggcccctc accctccaga gccgtgagtc    169080
ctgcagacca aacagcgtga caggtccttt ccctgtccag gaggcctctg tgggtgagag    169140
ttggctgcgg acagggcgtg aaggcacttg agggtgggga agtgactctg actgggagat    169200
gctgaggaca gggaggaaac caccagataa gggacactgg ggaggagggg tggacccctc    169260
agggccaagc acatggagcc tcatcacaaa ggcaagatgg tggccaaatt caaggtcgct    169320
gcaaaaggaa tggagaagag agaatagatt tggcatttgg aggaaatggt gacaatcatg    169380
agcacctacc cgggactctc catgggtgct atctctacat aaactcattc caccctctga    169440
ttaatccatt ctacatatgg ggaaacaaag gcatgcggtg tttacgtcac ttgccaagat    169500
ctcaggattt gatccaggtg gcctggttcc atggtgcagc ctctcagcct gcatggatgc    169560
cccagctcag agcatgactc tcaggacagg gtcccagca gccctccctc cctgagcagc    169620
agggtgcccg tgctgcacca cttctgtcta ggaataggac attctgacac tttcctgcct    169680
cttccgaggt ctagcactta ctctatgcct gcctgggaag gtggcaagct ggcctgagga    169740
acagactctt ccatttttta gggagctcaa ggccacagat gctctgagat ctggagtcca    169800
```

```
gagacaggag cggaggcttc tcctggtgac cactctgctt aaaaacttca tcagatccgt   169860
agtttcagag ccccctgaa ccccatccct tacctctacc agttgcaggt gggtctctgg   169920
ggtggggctg ccctccccac cagcacccca agggctaaaa ggttgagggg agaacaccat   169980
catttgtaca gggggatc                                                 169998
```

```
<210> SEQ ID NO 25
<211> LENGTH: 1593
<212> TYPE: DNA
<213> ORGANISM: Homo sapiens
<220> FEATURE:
<221> NAME/KEY: CDS
<222> LOCATION: (245)...(1462)

<400> SEQUENCE: 25
```

```
ccggcgcagc gcggccgcag cagcctccgc ccccgcacg gtgtgagcgc cgccgcggc    60 cgaggcggcc ggagtcccga gctagccccg gcggccgccg ccgcccagac cggacgacag   120
gccacctcgt cggcgtccgc ccgagtcccc gcctcgccgc caacgccaca accaccgcgc   180 acggcccct gactccgtcc agtattgatc gggagagccg gagcgagctc ttcggggagc    240 agcg atg cga ccc tcc ggg acg gcc ggg gca gcg ctc ctg gcg ctg ctg   289
     Met Arg Pro Ser Gly Thr Ala Gly Ala Ala Leu Leu Ala Leu Leu
      1               5                  10                  15 gct gcg ctc tgc ccg gcg agt cgg gct ctg gag gaa aag aaa gtt tgc    337
Ala Ala Leu Cys Pro Ala Ser Arg Ala Leu Glu Glu Lys Lys Val Cys
              20                  25                  30 caa ggc acg agt aac aag ctc acg cag ttg ggc act ttt gaa gat cat    385
Gln Gly Thr Ser Asn Lys Leu Thr Gln Leu Gly Thr Phe Glu Asp His
          35                  40                  45 ttt ctc agc ctc cag agg atg ttc aat aac tgt gag gtg gtc ctt ggg    433
Phe Leu Ser Leu Gln Arg Met Phe Asn Asn Cys Glu Val Val Leu Gly
      50                  55                  60 aat ttg gaa att acc tat gtg cag agg aat tat gat ctt tcc ttc tta    481
Asn Leu Glu Ile Thr Tyr Val Gln Arg Asn Tyr Asp Leu Ser Phe Leu
  65                  70                  75 aag acc atc cag gag gtg gct ggt tat gtc ctc att gcc ctc aac aca    529
Lys Thr Ile Gln Glu Val Ala Gly Tyr Val Leu Ile Ala Leu Asn Thr
80                  85                  90                  95 gtg gag cga att cct ttg gaa aac ctg cag atc atc aga gga aat atg    577
Val Glu Arg Ile Pro Leu Glu Asn Leu Gln Ile Ile Arg Gly Asn Met
              100                 105                 110 tac tac gaa aat tcc tat gcc tta gca gtc tta tct aac tat gat gca    625
Tyr Tyr Glu Asn Ser Tyr Ala Leu Ala Val Leu Ser Asn Tyr Asp Ala
          115                 120                 125 aat aaa acc gga ctg aag gag ctg ccc atg aga aat tta cag gaa atc    673
Asn Lys Thr Gly Leu Lys Glu Leu Pro Met Arg Asn Leu Gln Glu Ile
      130                 135                 140 ctg cat ggc gcc gtg cgg ttc agc aac aac cct gcc ctg tgc aat gtg    721
Leu His Gly Ala Val Arg Phe Ser Asn Asn Pro Ala Leu Cys Asn Val
145                 150                 155 gag agc atc cag tgg cgg gac ata gtc agc agt gac ttt ctc agc aac    769
Glu Ser Ile Gln Trp Arg Asp Ile Val Ser Ser Asp Phe Leu Ser Asn
              160                 165                 170                 175 atg tcg atg gac ttc cag aac cac ctg ggc agc tgc caa aag tgt gat    817
Met Ser Met Asp Phe Gln Asn His Leu Gly Ser Cys Gln Lys Cys Asp
              180                 185                 190 cca agc tgt ccc aat ggg agc tgc tgg ggt gca gga gag gag aac tgc    865
Pro Ser Cys Pro Asn Gly Ser Cys Trp Gly Ala Gly Glu Glu Asn Cys
              195                 200                 205
```

-continued

| | |
|---|---|
| cag aaa ctg acc aaa atc atc tgt gcc cag cag tgc tcc ggg cgc tgc<br>Gln Lys Leu Thr Lys Ile Ile Cys Ala Gln Gln Cys Ser Gly Arg Cys<br>    210                         215                       220 | 913 |
| cgt ggc aag tcc ccc agt gac tgc tgc cac aac cag tgt gct gca ggc<br>Arg Gly Lys Ser Pro Ser Asp Cys Cys His Asn Gln Cys Ala Ala Gly<br>225                         230                       235 | 961 |
| tgc aca ggc ccc cgg gag agc gac tgc ctg gtc tgc cgc aaa ttc cga<br>Cys Thr Gly Pro Arg Glu Ser Asp Cys Leu Val Cys Arg Lys Phe Arg<br>240                         245                     250                       255 | 1009 |
| gac gaa gcc acg tgc aag gac acc tgc ccc cca ctc atg ctc tac aac<br>Asp Glu Ala Thr Cys Lys Asp Thr Cys Pro Pro Leu Met Leu Tyr Asn<br>                      260                       265                       270 | 1057 |
| ccc acc acg tac cag atg gat gtg aac ccc gag ggc aaa tac agc ttt<br>Pro Thr Thr Tyr Gln Met Asp Val Asn Pro Glu Gly Lys Tyr Ser Phe<br>              275                       280                       285 | 1105 |
| ggt gcc acc tgc gtg aag aag tgt ccc cgt aat tat gtg gtg aca gat<br>Gly Ala Thr Cys Val Lys Lys Cys Pro Arg Asn Tyr Val Val Thr Asp<br>290                         295                       300 | 1153 |
| cac ggc tcg tgc gtc cga gcc tgt ggg gcc gac agc tat gag atg gag<br>His Gly Ser Cys Val Arg Ala Cys Gly Ala Asp Ser Tyr Glu Met Glu<br>             305                       310                       315 | 1201 |
| gaa gac ggc gtc cgc aag tgt aag aag tgc gaa ggg cct tgc cgc aaa<br>Glu Asp Gly Val Arg Lys Cys Lys Lys Cys Glu Gly Pro Cys Arg Lys<br>320                         325                       330                       335 | 1249 |
| gtg tgt aac gga ata ggt att ggt gaa ttt aaa gac tca ctc tcc ata<br>Val Cys Asn Gly Ile Gly Ile Gly Glu Phe Lys Asp Ser Leu Ser Ile<br>                      340                       345                       350 | 1297 |
| aat gct acg aat att aaa cac ttc aaa aac tgc acc tcc atc agt ggc<br>Asn Ala Thr Asn Ile Lys His Phe Lys Asn Cys Thr Ser Ile Ser Gly<br>                355                       360                       365 | 1345 |
| gat ctc cac atc ctg ccg gtg gca ttt agg ggt gac tcc ttc aca cat<br>Asp Leu His Ile Leu Pro Val Ala Phe Arg Gly Asp Ser Phe Thr His<br>             370                       375                       380 | 1393 |
| act cct cct ctg gat cca cag gaa ctg gat att ctg aaa acc gta aag<br>Thr Pro Pro Leu Asp Pro Gln Glu Leu Asp Ile Leu Lys Thr Val Lys<br>385                         390                       395 | 1441 |
| gaa atc aca ggt ttg agc tga attatcacat gaatataaat gggaaatcag<br>Glu Ile Thr Gly Leu Ser<br>400                 405 | 1492 |
| tgttttagag agagaacttt tcgacatatt tcctgttccc ttggaataaa acatttctt | 1552 |
| ctgaaatttt accgttaaaa aaaaaaaaa aaaaaaaaa a | 1593 |

<210> SEQ ID NO 26
<211> LENGTH: 1868
<212> TYPE: DNA
<213> ORGANISM: Homo sapiens
<220> FEATURE:
<221> NAME/KEY: CDS
<222> LOCATION: (504)...(1721)

<400> SEQUENCE: 26

| | |
|---|---|
| gaaacaggc tgggcccggt ggctcactcc tgtaatccca gcactttggg aggttgaggt | 60 |
| gggcggatca cctgaggtca ggagtttgag accagccggc gggagtggcc ttgggtcccc | 120 |
| gctgctggtt ctcctccctc ctcctcgcat tctcctcctc ctctgctcct ccgatccct | 180 |
| cctccgccgc ctggtccctc tcctcccgc cctgcctccc cgcgcctcgg cccgcgcgag | 240 |
| ctagacgtcc gggcagcccc cggcgcaccg cggccgcagc agcctcctcc ccccgcacgg | 300 |
| tgtgagcgcc cgccgcggcc gaggcggccg gagtcccgag ctagccccgg cggccgccgc | 360 |

```
                                                              -continued cgcccagacc ggacgacagg ccacctcgtc ggcgtccgcc cgagtccccg cctcgccgcc    420
aacgccacaa ccaccgcgca cggcccctg actccgtcca gtattgatcg ggagagccgg     480
agcgagctct tcggggagca gcg atg cga ccc tcc ggg acg gcc ggg gca gcg   533
                          Met Arg Pro Ser Gly Thr Ala Gly Ala Ala
                           1               5                  10 ctc ctg gcg ctg ctg gct gcg ctc tgc ccg gcg agt cgg gct ctg gag    581
Leu Leu Ala Leu Leu Ala Ala Leu Cys Pro Ala Ser Arg Ala Leu Glu
             15                  20                  25 gaa aag aaa gtt tgc caa ggc acg agt aac aag ctc acg cag ttg ggc    629
Glu Lys Lys Val Cys Gln Gly Thr Ser Asn Lys Leu Thr Gln Leu Gly
             30                  35                  40 act ttt gaa gat cat ttt ctc agc ctc cag agg atg ttc aat aac tgt    677
Thr Phe Glu Asp His Phe Leu Ser Leu Gln Arg Met Phe Asn Asn Cys
         45                  50                  55 gag gtg gtc ctt ggg aat ttg gaa att acc tat gtg cag agg aat tat    725
Glu Val Val Leu Gly Asn Leu Glu Ile Thr Tyr Val Gln Arg Asn Tyr
         60                  65                  70 gat ctt tcc ttc tta aag acc atc cag gag gtg gct ggt tat gtc ctc    773
Asp Leu Ser Phe Leu Lys Thr Ile Gln Glu Val Ala Gly Tyr Val Leu
 75                  80                  85                  90 att gcc ctc aac aca gtg gag cga att cct ttg gaa aac ctg cag atc    821
Ile Ala Leu Asn Thr Val Glu Arg Ile Pro Leu Glu Asn Leu Gln Ile
                 95                 100                 105 atc aga gga aat atg tac tac gaa aat tcc tat gcc tta gca gtc tta    869
Ile Arg Gly Asn Met Tyr Tyr Glu Asn Ser Tyr Ala Leu Ala Val Leu
             110                 115                 120 tct aac tat gat gca aat aaa acc gga ctg aag gag ctg ccc atg aga    917
Ser Asn Tyr Asp Ala Asn Lys Thr Gly Leu Lys Glu Leu Pro Met Arg
         125                 130                 135 aat tta cag gaa atc ctg cat ggc gcc gtg cgg ttc agc aac aac cct    965
Asn Leu Gln Glu Ile Leu His Gly Ala Val Arg Phe Ser Asn Asn Pro
     140                 145                 150 gcc ctg tgc aac gtg gag agc atc cag tgg cgg gac ata gtc agc agt   1013
Ala Leu Cys Asn Val Glu Ser Ile Gln Trp Arg Asp Ile Val Ser Ser
155                 160                 165                 170 gac ttt ctc agc aac atg tcg atg gac ttc cag aac cac ctg ggc agc   1061
Asp Phe Leu Ser Asn Met Ser Met Asp Phe Gln Asn His Leu Gly Ser
                 175                 180                 185 tgc caa aag tgt gat cca agc tgt ccc aat ggg agc tgc tgg ggt gca   1109
Cys Gln Lys Cys Asp Pro Ser Cys Pro Asn Gly Ser Cys Trp Gly Ala
             190                 195                 200 gga gag gag aac tgc cag aaa ctg acc aaa atc atc tgt gcc cag cag   1157
Gly Glu Glu Asn Cys Gln Lys Leu Thr Lys Ile Ile Cys Ala Gln Gln
         205                 210                 215 tgc tcc ggg cgc tgc cgt ggc aag tcc ccc agt gac tgc tgc cac aac   1205
Cys Ser Gly Arg Cys Arg Gly Lys Ser Pro Ser Asp Cys Cys His Asn
     220                 225                 230 cag tgt gct gca ggc tgc aca ggc ccc cgg gag agc gac tgc ctg gtc   1253
Gln Cys Ala Ala Gly Cys Thr Gly Pro Arg Glu Ser Asp Cys Leu Val
235                 240                 245                 250 tgc cgc aaa ttc cga gac gaa gcc acg tgc aag gac acc tgc ccc cca   1301
Cys Arg Lys Phe Arg Asp Glu Ala Thr Cys Lys Asp Thr Cys Pro Pro
                 255                 260                 265 ctc atg ctc tac aac ccc acc acg tac cag atg gat gtg aac ccc gag   1349
Leu Met Leu Tyr Asn Pro Thr Thr Tyr Gln Met Asp Val Asn Pro Glu
             270                 275                 280 ggc aaa tac agc ttt ggt gcc acc tgc gtg aag aag tgt ccc cgt aat   1397
Gly Lys Tyr Ser Phe Gly Ala Thr Cys Val Lys Lys Cys Pro Arg Asn
         285                 290                 295
```

```
tat gtg gtg aca gat cac ggc tcg tgc gtc cga gcc tgt ggg gcc gac       1445
Tyr Val Val Thr Asp His Gly Ser Cys Val Arg Ala Cys Gly Ala Asp
    300             305                 310 agc tat gag atg gag gaa gac ggc gtc cgc aag tgt aag aag tgc gaa       1493
Ser Tyr Glu Met Glu Glu Asp Gly Val Arg Lys Cys Lys Lys Cys Glu
315                 320                 325                 330 ggg cct tgc cgc aaa gtg tgt aac gga ata ggt att ggt gaa ttt aaa       1541
Gly Pro Cys Arg Lys Val Cys Asn Gly Ile Gly Ile Gly Glu Phe Lys
                335                 340                 345 gac tca ctc tcc ata aat gct acg aat att aaa cac ttc aaa aac tgc       1589
Asp Ser Leu Ser Ile Asn Ala Thr Asn Ile Lys His Phe Lys Asn Cys
            350                 355                 360 acc tcc atc agt ggc gat ctc cac atc ctg ccg gtg gca ttt agg ggt       1637
Thr Ser Ile Ser Gly Asp Leu His Ile Leu Pro Val Ala Phe Arg Gly
        365                 370                 375 gac tcc ttc aca cat act ccc cct ctg gat cca cag gaa ctg gat att       1685
Asp Ser Phe Thr His Thr Pro Pro Leu Asp Pro Gln Glu Leu Asp Ile
    380                 385                 390 ctg aaa acc gta aag gaa atc aca ggt ttg agc tga attatcacat            1731
Leu Lys Thr Val Lys Glu Ile Thr Gly Leu Ser
395                 400                 405 gaatataaat gggaaatcag tgttttagag agagaacttt tcgacatatt tcctgttccc     1791
ttggaataaa aacatttctt ctgaaatttt accgttaaaa aaaaaaaaaa aaaaaaaaa      1851 aaaaaaaaaa aaaaaaa                                                    1868

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ggctagctcg ggactccggc                                                 20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tccggtctgg gcggcggcgg                                                 20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggttgtggcg ttggcggcga                                                 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 30
ggagggtcgc atcgctgctc                                                      20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
tggcaaactt tcttttcctc                                                      20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tgcacatagg taatttccaa                                                      20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
atggtcttta agaaggaaag                                                      20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cctggatggt ctttaagaag                                                      20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cacctcctgg atggtcttta                                                      20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ttgagggcaa tgaggacata                                                      20

<210> SEQ ID NO 37
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 37
gggttgttgc tgaaccgcac                                                      20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ttgggacagc ttggatcaca                                                      20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tctggcagtt ctcctctcct                                                      20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
tgggcacaga tgattttggt                                                      20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gttgtggcag cagtcactgg                                                      20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
caggtggcac caaagctgta                                                      20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
``` tagcattat ggagagtgag 20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
caagcctgaa tcagcaaaaa 20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
caggccaagc ctgaatcagc 20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gaaaactgac catgttgctt 20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
atcacttatc tccttgaggg 20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
agttttttcc agtttattgt 20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gagacgcagt ccctgggctc 20

<210> SEQ ID NO 50
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 50
caggtgatgt tcatggcctg                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
atgtagtggg cacactggat                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gcttggttgg gagcttctcc                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
actttgatct ttttgaattc                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tcaccttctg ggatccagag                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tttctcacct tctgggatcc                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
ggagatgttg cttctcttaa                                               20
```

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ccaagtagtt catgcccttt                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
tctgtgatct tgacatgctg                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ccaaaatctg tgatcttgac                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ccagcccaaa atctgtgatc                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gtttggccag cccaaaatct                                                    20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
aaaattgatt ccaatgccat                                                    20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gcttggatcc aaaggtcatc                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
cgggccattt tggagaattc                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
tgcattcttt catccccctg                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
gcaaatgcat tctttcatcc                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
agccacggtg gaattgttgc                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ggctgattgt gatagacagg                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tgctggtagt cagggttgtc                                               20

<210> SEQ ID NO 70

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
agtcctgctg gtagtcaggg                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ggtattctgc attttcagct                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctccgtggtc atgctccaat                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ttcctggcta gtcggtgtaa                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tacttcctgg ctagtcggtg                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gatgcgtttc tgtaaatgct                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
```
aaaaatcctc acatatactt                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
agcgacaatg aaaaactcca                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
agtaaaaatc aatagcgaca                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
actcagggta gcaagtgcta                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ttggatcttt agtgttttgc                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gcttatccta ctgtacctgc                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gaaaccactg gtccatcagt                                               20

<210> SEQ ID NO 83
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 83
agttattatt tgatgtgtca                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ctatgcccca aaggacctga                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
ggtgatggct aaaggagatt                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tcttccataa gtaacacaaa                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gcagagacac ttttgtgtg                                                20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tcacactact cataatgcta                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
tagctgaatc ttccaatctt                                               20
```

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
ccagtcaggt tacagggcac                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gactgaacat aactgtaggc                                          20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
atatagtttt attttcattg                                          20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
ggtcctgaga gcagaccggg                                          20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aggtcctgaa accggagagg                                          20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
gcaagataaa agagttctgt                                          20

<210> SEQ ID NO 96
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 96
aaatgttaac agtgcagatc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
gcatcttacc aggcagtcgc                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
gttccactag tgtgggaaaa                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
tgacctcaga caatccagcc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gtttggaaac atccaaaatg                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
aagttggtag aaacacaggc                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
aagtagtaaa cgtgcaccgt                                              20
```

```
<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gggacccaag gccactcccg                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gaatgcgagg aggagggagg                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
aggtggcctg tcgtccggtc                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
ccgatcaata ctggacggag                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tccggctctc ccgatcaata                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
gcatcgctgc tccccgaaga                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 109
ccgtcccgga gggtcgcatc                                          20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
ctttcttttc ctccagagcc                                          20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tcgtgccttg gcaaactttc                                          20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
agcttgttac tcgtgccttg                                          20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
tgcccaactg cgtgagcttg                                          20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
tcttcaaaag tgcccaactg                                          20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
agaaaatgat cttcaaaagt                                          20

<210> SEQ ID NO 116
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 116
atcctctgga ggctgagaaa                                             20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
cagttattga acatcctctg                                             20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
ggaccacctc acagttattg                                             20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
aaattcccaa ggaccacctc                                             20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ggtaatttcc aaattcccaa                                             20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ttcctctgca cataggtaat                                             20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
```
aagaaggaaa gatcataatt                                        20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
accagccacc tcctggatgg                                        20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
atgaggacat aaccagccac                                        20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
cactgtgttg agggcaatga                                        20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
tccaaaggaa ttcgctccac                                        20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ctgcaggttt tccaaaggaa                                        20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
cctctgatga tctgcaggtt                                        20

<210> SEQ ID NO 129
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 129
gctaaggcat aggaattttc                                               20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
agttagataa gactgctaag                                               20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
gtccggtttt atttgcatca                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
agctccttca gtccggtttt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
tttctcatgg gcagctcctt                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
caggatttcc tgtaaatttc                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
atgctctcca cattgcacag                                               20
```

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
actatgtccc gccactggat                                         20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
agtccatcga catgttgctg                                         20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
gtggttctgg aagtccatcg                                         20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139 tttggcagc tgcccaggtg                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
tggatcacac ttttggcagc                                         20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
gctcccattg ggacagcttg                                         20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tctcctgcac cccagcagct                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
ttctggcagt tctcctctcc                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
gatgattttg gtcagtttct                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
gcactgctgg gcacagatga                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
gggggacttg ccacggcagc                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
cagcagtcac tgggggactt                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
cctgcagcac actggttgtg                                              20

<210> SEQ ID NO 149

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
gcagaccagg cagtcgctct                                             20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
gcaggtgtcc ttgcacgtgg                                             20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
atgagtgggg ggcaggtgtc                                             20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ggttgtagag catgagtggg                                             20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
tacgtggtgg ggttgtagag                                             20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
catccatctg gtacgtggtg                                             20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
```
tcggggttca catccatctg 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
gcaccaaagc tgtatttgcc 20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
cttcacgcag gtggcaccaa 20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
cggggacact tcttcacgca 20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ccgtgatctg tcaccacata 20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
caggctcgga cgcacgagcc 20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
gtcggcccca caggctcgga 20

<210> SEQ ID NO 162
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 162
ccatctcata gctgtcggcc                    20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
ttacacttgc ggacgccgtc                    20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
aggcccttcg cacttcttac                    20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
cactttgcgg caaggcccctt                   20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
tattccgtta cacactttgc                    20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
aaattcacca atacctattc                    20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
gtgagtcttt aaattcacca                    20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
atattcgtag catttatgga                      20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
gtgcagtttt tgaagtgttt                      20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
gccactgatg gaggtgcagt                      20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
aatgccaccg gcaggatgtg                      20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
gtgaaggagt caccCctaaa                      20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
cagaggagga gtatgtgtga                      20

<210> SEQ ID NO 175
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 175
cagttcctgt ggatccagag                                      20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
ttcagaatat ccagttcctg                                      20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
ctttacggtt ttcagaatat                                      20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
cctgtgattt cctttacggt                                      20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
tgtgataatt cagctcaaac                                      20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
aaaacactga tttcccattt                                      20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
agttctctct ctaaaacact                                      20

-continued

```
<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
tttttattcc aagggaacag                                              20
```